(12) United States Patent
Gifford et al.

(10) Patent No.: US 12,364,741 B2
(45) Date of Patent: *Jul. 22, 2025

(54) IMMUNOGENIC COMPOSITIONS COMPRISING NUCLEIC ACIDS FOR RAS PEPTIDES AND THEIR USE FOR TREATING CANCER

(71) Applicant: Think Therapeutics, Inc., Newton, MA (US)

(72) Inventors: David Kenneth Gifford, Newton, MA (US); Brandon Carter, Cambridge, MA (US)

(73) Assignee: Think Therapeutics, Inc., Newton, MA (US)

( * ) Notice: Subject to any disclaimer, the term of this patent is extended or adjusted under 35 U.S.C. 154(b) by 390 days.

This patent is subject to a terminal disclaimer.

(21) Appl. No.: 17/815,086

(22) Filed: Jul. 26, 2022

(65) Prior Publication Data

US 2023/0051404 A1 Feb. 16, 2023

Related U.S. Application Data

(60) Division of application No. 17/551,679, filed on Dec. 15, 2021, now Pat. No. 11,464,837, which is a continuation of application No. 17/336,960, filed on Jun. 2, 2021, now Pat. No. 11,235,039, which is a
(Continued)

(51) Int. Cl.
*A61K 39/00* (2006.01)
*A61P 35/00* (2006.01)

(52) U.S. Cl.
CPC ...... *A61K 39/0005* (2013.01); *A61K 39/0011* (2013.01); *A61P 35/00* (2018.01); *C12Y 306/05002* (2013.01); *A61K 2039/585* (2013.01)

(58) Field of Classification Search
CPC . A61K 39/0005; A61K 2039/53; A61P 35/00; C12Y 306/05002
See application file for complete search history.

(56) References Cited

U.S. PATENT DOCUMENTS 5,443,956 A 8/1995 Carney
5,961,978 A 10/1999 Gaudernack et al.
(Continued)

FOREIGN PATENT DOCUMENTS

WO WO-97/33602 A1 9/1997
WO WO-99/63945 A2 12/1999
(Continued)

OTHER PUBLICATIONS

Betts et al., "Amino Acid Properties and Consequences of Substitutions," Chapter 14 in Bioinformatics for Geneticists, Wiley & Sons, Ltd., Apr. 18, 2003, pp. 289-316.
(Continued)

*Primary Examiner* — Elly-Gerald Stoica
(74) *Attorney, Agent, or Firm* — Wilmer Cutler Pickering Hale and Dorr LLP

(57) ABSTRACT

The present disclosure provides for methods, systems, and compositions of nucleic acid and peptide sequences. The present disclosure provides for a nucleic acid sequence encoding two or more amino acid sequences selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, and SEQ ID NO: 41. The present disclosure also provides for an immunogenic peptide composition comprising two or more peptides selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, and SEQ ID NO: 41. The present disclosure further provides for a nucleic acid sequence encoding one or more amino acid sequences selected from the group consisting of SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, and SEQ ID NO: 65. The present disclosure additionally provides for an immunogenic peptide composition comprising one or more peptides selected from the group consisting of SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, and SEQ ID NO: 65.

14 Claims, 10 Drawing Sheets

Specification includes a Sequence Listing.

Related U.S. Application Data continuation of application No. 17/100,630, filed on Nov. 20, 2020, now Pat. No. 11,058,751.

(56) References Cited

U.S. PATENT DOCUMENTS

| | | | |
|---|---|---|---|
| 6,602,510 | B1 | 8/2003 | Fikes et al. |
| 7,488,718 | B2 | 2/2009 | Scheinberg et al. |
| 7,756,644 | B2 | 7/2010 | Fridman et al. |
| 7,973,128 | B2 | 7/2011 | Kosmatopoulos et al. |
| 8,007,810 | B2 | 8/2011 | Fikes et al. |
| 8,465,747 | B2 | 6/2013 | Kosmatopoulos et al. |
| 8,653,237 | B2 | 2/2014 | Liu et al. |
| 8,741,576 | B2 | 6/2014 | Tangri et al. |
| 8,765,687 | B2 | 7/2014 | Scheinberg et al. |
| 8,900,600 | B2 | 12/2014 | Kosmatopoulos et al. |
| 9,340,577 | B2 | 5/2016 | Grey et al. |
| 9,913,884 | B2 | 3/2018 | Fikes et al. |
| 10,024,868 | B2 | 7/2018 | Kosmatopoulos et al. |
| 10,238,741 | B2 | 3/2019 | Creusot |
| 10,335,473 | B2 | 7/2019 | Eriksen |
| 10,456,457 | B2 | 10/2019 | Eriksen |
| 10,556,943 | B2 | 2/2020 | Knutson et al. |
| 10,596,239 | B2 | 3/2020 | Eriksen |
| 10,738,355 | B2 | 8/2020 | Sahin et al. |
| 10,835,585 | B2 | 11/2020 | Fritsch et al. |
| 11,058,751 | B1 | 7/2021 | Gifford et al. |
| 11,161,892 | B1 | 11/2021 | Gifford et al. |
| 11,222,711 | B2 | 1/2022 | Sahin et al. |
| 11,235,039 | B1 | 2/2022 | Gifford et al. |
| 11,464,842 | B1 | 10/2022 | Gifford et al. |
| 11,466,053 | B2 | 10/2022 | Tang et al. |
| 11,672,850 | B2 | 6/2023 | Gifford et al. |
| 2002/0155093 | A1 | 10/2002 | Houghton et al. |
| 2002/0164346 | A1 | 11/2002 | Nicolette |
| 2003/0220239 | A1 | 11/2003 | Simard et al. |
| 2003/0224036 | A1 | 12/2003 | Fikes et al. |
| 2004/0037843 | A1 | 2/2004 | Fikes et al. |
| 2004/0072240 | A1 | 4/2004 | Kosmatopoulos et al. |
| 2006/0018915 | A1 | 1/2006 | Ishioka et al. |
| 2006/0093617 | A1 | 5/2006 | Buyse et al. |
| 2007/0054262 | A1 | 3/2007 | Baker et al. |
| 2007/0098776 | A1 | 5/2007 | Fikes et al. |
| 2007/0224201 | A1 | 9/2007 | Wu et al. |
| 2011/0002963 | A1 | 1/2011 | Weinschenk et al. |
| 2011/0182926 | A1 | 7/2011 | La Monica et al. |
| 2011/0257890 | A1 | 10/2011 | Weinschenk et al. |
| 2014/0178421 | A1 | 6/2014 | Kosmatopoulos |
| 2016/0101170 | A1 | 4/2016 | Hacohen et al. |
| 2016/0125129 | A1 | 5/2016 | Sahin et al. |
| 2018/0066017 | A1 | 3/2018 | Hunt et al. |
| 2018/0102585 | A1 | 4/2018 | Forster |
| 2018/0117133 | A1 | 5/2018 | Chaplin et al. |
| 2018/0134804 | A1 | 5/2018 | Scheinberg et al. |
| 2018/0141998 | A1 | 5/2018 | Nguyen et al. |
| 2019/0175727 | A1 | 6/2019 | Huang et al. |
| 2019/0307868 | A1 | 10/2019 | Rooney |
| 2019/0322714 | A1 | 10/2019 | Petit et al. |
| 2020/0061166 | A1 | 2/2020 | Sahin et al. |
| 2020/0069782 | A1 | 3/2020 | Biskup et al. |
| 2020/0078454 | A1 | 3/2020 | Kosmatopoulos et al. |
| 2020/0105378 | A1 | 4/2020 | Abelin et al. |
| 2020/0237885 | A1 | 7/2020 | Levey et al. |
| 2021/0154280 | A1 | 5/2021 | Martin et al. |
| 2021/0177954 | A1 | 6/2021 | Juneja |
| 2021/0177955 | A1 | 6/2021 | Petit et al. |
| 2021/0196806 | A1 | 7/2021 | Yelensky et al. |
| 2021/0196809 | A1 | 7/2021 | Maianti et al. |
| 2021/0268086 | A1 | 9/2021 | Zhong et al. |
| 2021/0268091 | A1 | 9/2021 | Juneja |
| 2021/0275657 | A1 | 9/2021 | Juneja et al. |
| 2021/0290746 | A1 | 9/2021 | Sahin et al. |
| 2021/0389280 | A1 | 12/2021 | Wang |
| 2022/0160848 | A1 | 5/2022 | Gifford et al. |
| 2022/0194999 | A1 | 6/2022 | Krishna et al. |

FOREIGN PATENT DOCUMENTS

| | | |
|---|---|---|
| WO | WO-2005/042698 A2 | 5/2005 |
| WO | WO-2009/002418 A2 | 12/2008 |
| WO | WO-2013/177214 A2 | 11/2013 |
| WO | WO-2016/172722 A1 | 10/2016 |
| WO | WO-2016/187508 | 11/2016 |
| WO | WO-2017/075531 A1 | 5/2017 |
| WO | WO-2018/081459 A1 | 5/2018 |
| WO | WO-2018/081480 A1 | 5/2018 |
| WO | WO-2018/102585 A1 | 6/2018 |
| WO | WO-2018/187356 A2 | 10/2018 |
| WO | WO-2019/246286 | 12/2019 |
| WO | WO-2020/037239 A1 | 2/2020 |
| WO | WO-2020/123300 A2 | 6/2020 |
| WO | WO-2020/154617 A1 | 7/2020 |
| WO | WO-2020/252039 A1 | 12/2020 |
| WO | WO-2020/253643 A1 | 12/2020 |
| WO | WO-2021/055594 | 3/2021 |
| WO | WO-2021/087840 A1 | 5/2021 |
| WO | WO-2021/207152 A1 | 10/2021 |
| WO | WO-2022/036142 A2 | 2/2022 |
| WO | WO-2022/132596 A2 | 6/2022 |
| WO | WO-2022/171032 A1 | 8/2022 |
| WO | WO-2022/180219 A1 | 9/2022 |
| WO | WO-2023/170535 A2 | 9/2023 |
| WO | WO-2023/230014 A1 | 11/2023 |

OTHER PUBLICATIONS

Carter et al., "A pan-variant mRNA-LNP T cell vaccine protects HLA transgenic mice from mortality after infection with SARS-COV-2 Beta," bioRxiv preprint, posted Sep. 26, 2022. 38 pages. (https://www.biorxiv.org/content/10.1101/2022.09.23.509206v1).

Carter et al., "A pan-variant mRNA-LNP T cell vaccine protects HLA transgenic mice from mortality after infection with SARS-COV-2 Beta," Frontiers in Immunology, Mar. 9, 2023, vol. 14:1135815, pp. 1-9.

Chu et al., "A transformer-based model to predict peptide-HLA class I binding and optimize mutated peptides for vaccine design," Nature Machine Intelligence, vol. 4(3), Mar. 23, 2022, pp. 300-311 and figures. 15 pages.

Chu et al., "TransMut: a program to predict HLA-I peptide binding and optimize mutated peptides for vaccine design by the Transformer-derived self-attention model," Research Square, Sep. 30, 2021. 47 pages. (https://doi.org/10.21203/rs.3.rs-785618/v1).

Getentry Accession No. CU234118, DNA Data Bank of Japan. (Year 2015). 1,543 pages.

NCBI Database, GenBank Accession No. AB051004. (Year 2016). 1 page.

NCBI Database, GenBank Accession No. FRAP01000011. (Year 2016). 73 pages.

NCBI Database, GenBank Accession No. PYDT01000009. (Year 2019). 983 pages.

Racle et al., "Robust prediction of HLA class II epitopes by deep motif deconvolution of immunopeptidomes," Nature Biotechnology, Nov. 2019, vol. 37(11), pp. 1283-1286, Methods and Reporting Summary. 12 pages.

UniProt Accession No. A0A1M6V319-A0A1M6V319_PSETH. (Year 2017). 5 pages.

UniProt Accession No. A0A4S8INI8-A0A4S8INI8_MUSBA. (Year 2019). 6 pages.

UniProt Accession No. A4YTR3-A4YTR3_BRASO. (Year 2007). 5 pages.

Aurisicchio et al., "A novel minigene scaffold for therapeutic cancer vaccines," OncoImmunology, published online Jan. 16, 2014, vol. 3, e27529, pp. 1-13. 14 pages.

Fridman et al., "An efficient T-cell epitope discovery strategy using in silico prediction and the iTopia assay platform," OncoImmunology, published online Nov. 30, 2012, vol. 1:8, pp. 1258-1270 and Supplemental Material. 21 pages.

Zhang et al., "Epitope-based minigene vaccine targeting fibroblast activation protein α induces specific immune responses and anti-

(56) References Cited

OTHER PUBLICATIONS tumor effects in 4 T1 murine breast cancer model," International Immunopharmacology, available online Sep. 21, 2022, vol. 112, 109237, pp. 1-10.

Antunes et al., "General Prediction of Peptide-MHC Binding Modes Using Incremental Docking: A Proof of Concept," Scientific Reports, published online Mar. 12, 2018, vol. 8(1):4327-4339. 13 pages.

Badrinath et al., "A vaccine targeting resistant tumours by dual T cell plus NK cell attack," Nature, Jun. 30, 2022, vol. 606, pp. 992-998 and Methods. 31 pages.

Bear et al., "Biochemical and functional characterization of mutant KRAS epitopes validates this oncoprotein for immunological targeting," Nature Communications, published online Jul. 16, 2021, vol. 12(1):4365-4380. 16 pages.

Brito et al., "A cationic nanoemulsion for the delivery of next-generation RNA vaccines," Molecular Therapy, Dec. 2014, vol. 22(12), pp. 2118-2129.

Bulik-Sullivan et al., "Deep learning using tumor HLA peptide mass spectrometry datasets improves neoantigen identification," Nature Biotechnology (2019), published online Dec. 17, 2018, vol. 37, pp. 55-63 and Online Methods. 13 pages.

Dai et al., "Constrained Submodular Optimization for Vaccine Design," arXiv preprint, arXiv:2206.08336v2. https://arxiv.org/abs/2206.08336, version 2, Jan. 27, 2023. 24 pages.

Geall et al., "Nonviral delivery of self-amplifying RNA vaccines," Proc. Natl. Acad. Sci., Sep. 4, 2012, vol. 109(36), pp. 14604-14609.

Hie et al., "Learning the language of viral evolution and escape," Science, Jan. 15, 2021, vol. 371(6526):284-288. 5 pages.

Li et al., "Circular RNA cancer vaccines drive immunity in hard-to-treat malignancies," Theranostics, Aug. 29, 2022, vol. 12(14), pp. 6422-6436.

London et al., "Rosetta FlexPepDock web server—high resolution modeling of peptide-protein interactions," Nucleic Acids Research, published online May 27, 2011, vol. 39, Web Server issue: W249-253.

Parkhurst et al., "Improved induction of melanoma-reactive CTL with peptides from the melanoma antigen gp100 modified at HLA-A*0201-binding residues," The Journal of Immunology, Sep. 15, 1996, vol. 157(6), pp. 2539-2548.

Postigo-Fernandez et al., "A multi-epitope DNA vaccine enables a broad engagement of diabetogenic T cells for tolerance in Type 1 diabetes," Journal of Autoimmunity (2019), available online Nov. 17, 2018, vol. 98, pp. 13-23.

Slingluff et al., "Immunologic and clinical outcomes of a randomized phase II trial of two multipeptide vaccines for melanoma in the adjuvant setting," Clin. Cancer Res., Nov. 2007, vol. 13(21), pp. 6386-6395.

Wang et al., "A benchmark study of sequence alignment methods for protein clustering," BMC Bioinformatics, Dec. 31, 2018, vol. 19(Suppl 19):529, pp. 95-104.

Wang et al., "Direct Detection and Quantification of Neoantigens," Cancer Immunology Research, published online Sep. 16, 2019, vol. 7(11), pp. 1748-1754.

Bakker et al., "Analogues of CTL epitopes with improved MHC class-I binding capacity elicit anti-melanoma CTL recognizing the wild-type epitope," Int. J. Cancer, Jan. 27, 1997, vol. 70(3), pp. 302-309.

Gross et al., "High vaccination efficiency of low-affinity epitopes in antitumor immunotherapy," The Journal of Clinical Investigation, Feb. 2004, vol. 113(3), pp. 425-433.

International Search Report and Written Opinion mailed Apr. 2, 2024, in the International Application No. PCT/US23/74984. 11 pages.

Menez-Jamet et al., "Optimized tumor cryptic peptides: the basis for universal neo-antigen-like tumor vaccines," Ann. Transl. Med., Jul. 2016, 4(14):266, Review Article pp. 1-11.

Scardino et al., "HER-2/neu and hTERT cryptic epitopes as novel targets for broad spectrum tumor immunotherapy," The Journal of Immunology, Jun. 2002, 168(11):5900-6. 8 pages.

Tourdot et al., "A general strategy to enhance immunogenicity of low-affinity HLA-A2.1-associated peptides: implication in the identification of cryptic tumor epitopes," Eur. J. Immunol., Dec. 2000, vol. 30(12), pp. 3411-3421.

Valmori et al., "Enhanced generation of specific tumor-reactive CTL in vitro by selected Melan-A/MART-1 immunodominant peptide analogues," The Journal of Immunology, Feb. 15, 1998, 160(4):1750-8. 10 pages.

U.S. Appl. No. 17/243,096, Gifford et al.

U.S. Appl. No. 17/551,679, Gifford et al.

Abelin et al., "Defining HLA-II Ligand Processing and Binding Rules with Mass Spectrometry Enhances Cancer Epitope Prediction," Immunity, Oct. 15, 2019, vol. 51(4), pp. 766-779; e1-e17, and Update (Feb. 9, 2021, 54(2):388). 34 pages.

Alhadj-Ali et al., "Metabolic and immune effects of immunotherapy with proinsulin peptide in human new-onset type 1 diabetes," Science Translation Medicine, Aug. 9, 2017, vol. 9;9(402):eaaf7779. 9 pages.

Alvarez, B. et al., "NNAlign_MA; MHC Peptidome Deconvolution for Accurate MHC Binding Motif Characterization and Improved T-cell Epitope Predictions", Molecular & Cellular Proteomics, Dec. 2019, vol. 18(12), pages: cover, 2459-2477 (20 pages).

Asahara et al., "Phase I/II clinical trial using HLA-A24-restricted peptide vaccine derived from KIF20A for patients with advanced pancreatic cancer," Journal of Translational Medicine, Nov. 16, 2013, vol. 11:291. 13 pages.

Bae et al., "Myeloma-Specific Multiple Peptides Able to Generate Cytotoxic T Lymphocytes: A Potential Therapeutic Application in Muliple Myeloma and other Plasma Cell Disorders," Clinical Cancer Research, published online Jul. 2, 2012, vol. 18(17), pages.

Berzofsky et al., "Progress on new vaccine strategies for the immunotherapy and prevention of cancer," The Journal of Clinical Investigation, Jun. 2004, vol. 113(11), pp. 1515-1525.

Berzofsky et al., "Strategies for designing and optimizing new generation vaccines," Nature Reviews: Immunology, vol. 1(3), Dec. 2001, pp. 209-219.

Berzofsky, "Epitope selection and design of synthetic vaccines. Molecular approaches to enhancing immunogenicity and cross-reactivity of engineered vaccines," Annals of the New York Academy of Sciences, Aug. 12, 1993, vol. 690(1), pp. 256-264.

Bhasin, M. and Raghava, G.P.S., "Prediction of Promiscuous and High-Affinity Mutated MHC Binders", Hybridoma and Hybridomics, Nov. 4, 2003, vol. 22, 229-234, (8 pages).

Candia et al., "On Peptides and Altered Peptide Ligands: From Origin, Mode of Action and Design to Clinical Application (Immunotherapy)," International Archives of Allergy and Immunology, published online Sep. 20, 2016; vol. 170(4), pp. 211-233.

Chicz et al., "Predominant naturally processed peptides bound to HLA-DR1 are derived from MHC-related molecules and are heterogeneous in size," Nature, Aug. 27, 1992, vol. 358(6389), pp. 764-768.

Cleveland et al., "Routine large-scale production of monoclonal antibodies in a protein-free culture medium," Journal of Immunological Methods, Jan. 28, 1983, vol. 56, Issue 2, pp. 221-234.

Croft et al., "Most viral peptides displayed by class I MHC on infected cells are immunogenic," Proceedings of the National Academy of Sciences, Feb. 19, 2019, vol. 116(8), pp. 3112-3117.

Dai et al., "Machine learning optimization of peptides for presentation by class II MHCs," bioRxiv, posted Aug. 18, 2020 (https://doi.org/10.1101/2020.08.18.256081). 35 pages.

Dastagir et al., "Efficient Presentation of Multiple Endogenous Epitopes to Both CD4+ and CD8+ Diabetogenic T Cells for Tolerance," Molecular Therapy: Methods & Clinical Development, Mar. 2017, vol. 4, pp. 27-38.

Dey et al., "A Bioinformatics approach to designing a Zika virus vaccine," Computational Biology and Chemistry, available online Mar. 10, 2017, vol. 68, pp. 143-152.

Dyall et al., "Heteroclitic Immunization Induces Tumor Immunity," J. Exp. Med., Nov. 2, 1998, vol. 188(9), pp. 1553-1561.

Fong et al., "Altered peptide ligand vaccination with Flt3 ligand expanded dendritic cells for tumor immunotherapy," PNAS, Jul. 17, 2001, vol. 98(15), pp. 8809-8814.

(56) References Cited

OTHER PUBLICATIONS

Gibson et al., "Proinsulin multi-peptide immunotherapy induces antigen-specific regulatory T cells and limits autoimmunity in a humanized model," Clinical Experimental Immunology, Dec. 2015, vol. 182(3), pp. 251-260.
Guevara-Patino et al., "Optimization of a self antigen for presentation of multiple epitopes in cancer immunity," The Journal of Clinical Investigation, May 2006, vol. 116(5), pages: cover, 1382-1390.
Hollingsworth et al., "Turning the corner on therapeutic cancer vaccines," npj Vaccines, published online Feb. 8, 2019, vol. 4(7), pp. 1-10.
Hong et al., "Epitope-optimized alpha-fetoprotein genetic vaccines prevent carcinogen-induced murine autochthonous hepatocellular carcinoma," Hepatology, Apr. 2014, vol. 59(4), pp. 1448-1458.
Hoppes et al., "Altered Peptide Ligands Revisited: Vaccine Design through Chemically Modified HLA-A2-Restricted T Cell Epitopes," Journal of Immunology, published online Oct. 13, 2014, vol. 193, pp. 4803-4813. (12 pages).
Houghton et al., "Immunological validation of the EpitOptimizer program for streamlined design of heteroclitic epitopes," Vaccine, available online Jun. 4, 2007, vol. 25(29), pp. 5330-5342.
International Search Report and Written Opinion mailed Mar. 28, 2022, in the International Application No. PCT/US2021/060013. 14 pages.
International Search Report and Written Opinion mailed Oct. 14, 2022, in the International Application No. PCT/US22/26354. 21 pages.
Jain et al., "Synthetic Tumor-Specific Breakpoint Peptide Vaccine in Patients With Chronic Myeloid Leukemia and Minimal Residual Disease," Cancer, Sep. 1, 2009, vol. 115, pp. 3924-3934.
Jaravine et al., "Assessment of cancer and virus antigens for cross-reactivity in human tissues," Bioinformatics, Jan. 1, 2017, vol. 33, No. 1, pp. 104-111.
Jaravine et al., "Expitope 2.0: a tool to assess immunotherapeutic antigens for their potential cross-reactivity against naturally expressed proteins in human tissues," BMC Cancer, Dec. 28, 2017, vol. 17:892. 9 pages.
Jurtz, V et al., "NetMHCpan-4.0: Improved Peptide-MHC Class I Interaction Predictions Integrating Eluted Ligand and Peptide Binding Affinity Data", The Journal of Immunology, prepublished online Oct. 4, 2017, vol. 199, pp. 3360-3368 (9 pages).
Keogh et al., "Identification of new epitopes from four different tumor-associated antigens: Recognition of naturally processed epitopes correlates with HLA-A*0201-binding affinity," The Journal of Immunology, Jul. 15, 2001, vol. 167(2), pp. 787-796. 11 pages.
Klinger et al., "Multiplex identification of antigen-specific T cell receptors using a combination of immune assays and immune receptor sequencing," PLOS One, Oct. 28, 2015, vol. 10(10), e0141561. 21 pages.
Kranz et al., "Systemic RNA delivery to dendritic cells exploits antiviral defence for cancer immunotherapy," Nature, Jun. 16, 2016, vol. 534(7607), pp. 396-401, and Methods. 16 pages.
Kreiter, et al., "Increased antigen presentation efficiency by coupling antigens to MHC class I trafficking signals," The Journal of Immunology, Jan. 2008, vol. 180(1), pp. 309-318, and Corrections. 12 pages.
Krienke, C. et al., "A noninflammatory mRNA vaccine for treatment of experimental autoimmune encephalomyelitis", Science, Jan. 8, 2021, vol. 371, pp. 145-153 (10 pages).
Liu et al. "Computationally Optimized SARS-CoV-2 MHC Class I and II Vaccine Formulations Predicted to Target Human Haplotype Distributions," Cell Systems, Aug. 26, 2020, vol. 11(2), pp. 131-144, e1-e6, Supplementary Table. 23 pages.
Liu et al., "Maximum n-times Coverage for COVID-19 Vaccine Design," arXiv (arXiv:2101.10902v1), submitted Jan. 24, 2021. 13 pages.
Liu et al., "Predicted Cellular Immunity Population Coverage Gaps for SARS-CoV-2 Subunit Vaccines and their Augmentation by Compact Peptide Sets," bioRxiv, posted Oct. 21, 2020, 29 pages. (https://www.biorxiv.org/content/10.1101/2020.08.04.200691v2).
Liu et al., "Predicted Cellular Immunity Population Coverage Gaps for SARS-CoV-2 Subunit Vaccines and their Augmentation by Compact Peptide Sets," Cell Systems, Journal Pre-proof, Nov. 26, 2020. (https://doi.org/10.1016/j.cels.2020.11.010). 36 pages.
Longmate et al., "Population coverage by HLA class-I restricted cytotoxic T-lymphocyte epitopes," Immunogenetics (2001), published online Dec. 19, 2000, vol. 52, pp. 165-173.
Maa et al., "Biopharmaceutical Powders: Particle Formation and Formulation Considerations," Current Pharmaceutical Biotechnology, Nov. 2000, vol. 1, No. 3, pp. 283-302.
Mahanty et al., "Immunogenicity of infectious pathogens and vaccine antigens," BMC Immunology, published online May 29, 2015, vol. 16(1), pp. 1-6.
Mashiba et al., "Identification of CTL epitopes in hepatitis C virus by a genome-wide computational scanning and a rational design of peptide vaccine," Immunogenetics, published online Jan. 16, 2007, vol. 59, pp. 197-209.
Merriam-Webster, "Prevent", available online at https://www.merriam-webster.com/dictionary/prevent. 10 pages. Accessed on Sep. 24, 2021.
Mösch et al., "Machine Learning for Cancer Immunotherapies Based on Epitope Recognition by T Cell Receptors," Frontiers in Genetics, Nov. 19, 2019, vol. 10, Article 1141. 17 pages.
Nair et al., "A simple practice guide for dose conversion between animals and human," Journal of Basic and Clinical Pharmacy, Article Review, Mar.-May 2016, vol. 7, Issue 2, pp. 27-31.
Ng et al., "In silico-guided sequence modifications of K-ras epitopes improve immunological outcome against G12V and G13D mutant KRAS antigens," PeerJ, published Jul. 20, 2018, 6:e5056. doi: 10.7717/peerj.5056. 21 pages.
Nielsen et al., "NNAlign: a platform to construct and evaluate artificial neural network models of receptor-ligand interactions," Nucleic Acids Research, published online Apr. 12, 2017, vol. 45, pp. W344-W349.
Nielsen et al., "The role of the proteasome in generating cytotoxic T-cell epitopes: insights obtained from improved predictions of proteasomal cleavage," Immunogenetics, published online Mar. 3, 2005, vol. 57, pp. 33-41.
Nielsen, M. and Lund, O., "NN-align. An artificial neural network-based alignment algorithm for MHC class II peptide binding prediction", BMC Bioinformatics, Sep. 18, 2009, vol. 10:296, pp. 1-10 (10 pages).
Nielsen, M. et al., "Quantitative Predictions of Peptide Binding to Any HLA-DR Molecule of Known Sequence: NetMHCIIpan", PLoS Computational Biology, Jul. 4, 2008, vol. 4(7):e1000107, pp. 1-10 (10 pages).
O'Donnell, T.J. et al., "MHCflurry 2.0: Improved Pan-Allele Prediction of MHC Class I-Presented Peptides by Incorporating Antigen Processing", Cell Systems, Jul. 22, 2020, vol. 11, pages: cover, 42-48 (15 pages).
O'Donnell, T.J. et al., "MHCflurry: Open-Source Class I MHC Binding Affinity Prediction", Cell Systems, Jul. 25, 2018, vol. 7, pages: cover, 129-132 (9 pages).
Ogishi et al., "Quantitative Prediction of the Landscape of T Cell Epitope Immunogenicity in Sequence Space," Frontiers in Immunology, Apr. 16, 2019, vol. 10, Article 827. 20 pages.
Park et al., "Accurate structure prediction of peptide-MHC complexes for identifying highly immunogenic antigens," Mol. Immunol., Nov. 2013, vol. 56(0):81-90. NIH Author Manuscript. 25 pages.
Reynisson et al., "NetMHCpan-4.1 and NetMHCIIpan-4.0: improved predictions of MHC antigen presentation by concurrent motif deconvolution and integration of MS MHC eluted ligand data," Nucleic Acids Research, published online May 14, 2020; vol. 48(W1), pp. W449-W454.
Rist et al., "HLA peptide length preferences control CD8+ T cell responses," The Journal of Immunology, published online Jun. 7, 2013, vol. 191(2), pp. 561-571. 12 pages.
Rosenberg et al., "Immunologic and therapeutic evaluation of a synthetic peptide vaccine for the treatment of patients with metastatic melanoma," Nature Medicine, Mar. 1998, vol. 4(3), pp. 321-327.

(56) References Cited

OTHER PUBLICATIONS

Sahin et al., "Personalized RNA mutanome vaccines mobilize poly-specific therapeutic immunity against cancer," Nature, Jul. 13, 2017, vol. 547(7662), pp. 222-226, and Methods. 19 pages.

Schipper et al., "Minimal Phenotype Panels, A Method for Achieving Maximum Population Coverage with a Minimum of HLA Antigens," Human Immunology, vol. 51, Dec. 1996, pp. 95-98.

Sette et al., "Peptides and Methods for Creating Synthetic Peptides With Modulated Binding Affinity for HLA Molecules," U.S. Appl. No. 09/226,775, filed Jan. 6, 1999—not published, abandoned. 133 pages.

Sette et al., "The Relationship Between Class I Binding Affinity and Immunogenicity of Potential Cytotoxic T Cell Epitopes," The Journal of Immunology, Dec. 15, 1994, vol. 153, pp. 5586-5592.

Shimokawa, C. et al., "CD8+ regulatory T cells are critical in prevention of autoimmune-mediated diabetes", Nature Communications, Apr. 22, 2020, vol. 11:1922, pp. 1-9 (9 pages).

Sim et al., "Correction—High-affinity oligoclonal TCRs define effective adoptive T cell therapy targeting mutant KRAS-G12D," Proc. Natl. Acad. Sci. USA, Nov. 3, 2020, vol. 117(44), pp. 27743-27744.

Sim et al., "High-affinity oligoclonal TCRs define effective adoptive T cell therapy targeting mutant KRAS-G12D," Proc. Natl. Acad. Sci. USA, first published May 27, 2020, vol. 117(23), pp. 12826-12835.

Slansky et al., "Enhanced antigen-specific antitumor immunity with altered peptide ligands that stabilize the MHC-peptide-TCR complex," Immunity, Oct. 2000, vol. 13(4), pp. 529-538.

Slota et al., "ELISpot for measuring human immune responses to vaccines," Expert Review of Vaccines, Mar. 2011, vol. 10(3), pp. 299-306. NIH Author Manuscript. 14 pages.

Soria-Guerra et al., "An overview of bioinformatics tools for epitope prediction: implications on vaccine development," Journal of Biomedical Informatics (2015), available online Nov. 10, 2014, vol. 53, pp. 405-414.

Takahashi et al., "Induction of Broadly Cross-Reactive Cytotoxic T Cells Recognizing an HIV-1 Envelope Determinant," Science, Jan. 17, 1992, vol. 255(5042), pp. 333-336.

Tangri et al., "Structural Features of Peptide Analogs of Human Histocompatibility Leukocyte Antigen Class I Epitopes That Are More Potent and Immunogenic than Wild-Type Peptide," Journal of Experimental Medicine, Sep. 17, 2001, vol. 194(6), pp. 833-846.

Tapia-Calle et al., "A PBMC-Based System to Assess Human T Cell Responses to Influenza Vaccine Candidates In Vitro," Vaccines, Nov. 13, 2019, vol. 7(4):181. 26 pages.

Toussaint, N.C. et al., "A Mathematical Framework for the Selection of an Optimal Set of Peptides for Epitope-Based Vaccines", PLoS Computational Biology, Dec. 26, 2008, vol. 4(12):e1000246, pp. 1-10 (10 pages).

Trolle et al., "The length distribution of class I-restricted T cell epitopes is determined by both peptide supply and MHC allele-specific binding preference," The Journal of Immunology, Feb. 15, 2016, vol. 196(4), 1480-1487. HSS Author Manuscript. 21 pages.

Vita et al., "The Immune Epitope Database (IEDB): 2018 update," Nucleic Acids Research (2019), published online Oct. 24, 2018, vol. 47, database issue D339-D343. 5 pages.

Woodham et al., "Nanobody-Antigen Conjugates Elicit HPV-Specific Antitumor Immune Responses," Cancer Immunology Research, Jul. 2018, vol. 6(7); pp. 870-880.

Zaremba et al., "Identification of an enhancer agonist cytotoxic T lymphocyte peptide from human carcinoembryonic antigen," Cancer Research, Oct. 15, 1997, vol. 57(20), pp. 4570-4577.

Zhang et al., "Cancer vaccines: Targeting KRAS-driven cancers," Expert Review of Vaccines, published online Mar. 14, 2020, vol. 19(2), pp. 163-173. 12 pages.

Zirlik et al., "Cytotoxic T cells generated against heteroclitic peptides kill primary tumor cells independent of the binding affinity of the native tumor antigen peptide," Blood, Dec. 1, 2006, Vo. 108, No. 12, pp. 3865-3870.

Fikes et al., "Design of multi-epitope, analogue-based cancer vaccines," Expert Opinion on Biological Therapy, published online Mar. 3, 2005, vol. 3:6, pp. 985-993. 10 pages.

Bell et al., "Dynamics-Based Peptide—MHC Binding Optimization by a Convolutional Variational Autoencoder: A Use-Case Model for CASTELO," Journal of Chemical Theory and Computation, Nov. 18, 2021, vol. 17, pp. 7962-7971.

Xiao et al., "In silico design of MHC class I high binding affinity peptides through motifs activation map," BMC Bioinformatics, published Dec. 31, 2018, vol. 19(Suppl 19):516. 12 pages.

Factoring of disease presentation type probabilities and for each
presentation, probability of targets presented

| Disease | Target 1<br>KRAS G12D | Target 2<br>KRAS G12V | ... | Target m<br>KRAS G12R |
|---|---|---|---|---|
| Presentation 1<br>0.032<br>(Pancreas) | 0.328 | 0.226 | | 0.151 |
| Presentation 2<br>0.082<br>(Colon and rectum) | 0.279 | 0.214 | | 0.093 |
| ... | | | | |
| Presentation 3<br>0.127<br>(Bronchus and lung) | 0.019 | 0.038 | | 0.000 |

FIG. 5

```
 1  def merge_multi(lists):
 2      values = []
 3
 4      # While any list in lists has elements remaining
 5      while max(map(lambda l: len(l), lists)) > 0:
 6          # Find list with largest value at its head.
 7          cur_max = None
 8          cur_max_idx = None
 9          for idx, l in enumerate(lists):
10              if not l:  # List is empty.
11                  continue
12              if cur_max is None or l[0] > cur_max:
13                  cur_max = l[0]
14                  cur_max_idx = idx
15          # Pop that value from list l.
16          values.append((lists[cur_max_idx].pop(0), cur_max_idx))
17
18      return values
```

FIG. 9

IMMUNOGENIC COMPOSITIONS COMPRISING NUCLEIC ACIDS FOR RAS PEPTIDES AND THEIR USE FOR TREATING CANCER

This application is a divisional of U.S. patent application Ser. No. 17/551,679, filed on Dec. 15, 2021, now U.S. Pat. No. 11,464,837, issued on Oct. 11, 2022; which is a continuation of U.S. patent application Ser. No. 17/336,960, filed on Jun. 2, 2021, now U.S. Pat. No. 11,235,039, issued on Feb. 1, 2022; which is a continuation of U.S. Patent Application No. 17/100,630, filed on Nov. 20, 2020, now U.S. Pat. No. 11,058,751, issued on Jul. 13, 2021. The specifications of each of the foregoing are incorporated by reference herein in their entireties. This patent disclosure contains material that is subject to copyright protection. The copyright owner has no objection to the facsimile reproduction of the patent document or the patent disclosure as it appears in the U.S. Patent and Trademark Office patent file or records, but otherwise reserves any and all copyright rights.

INCORPORATION BY REFERENCE

All documents cited herein are incorporated herein by reference in their entirety.

SEQUENCE LISTING

The instant application contains a Sequence Listing which has been submitted electronically in XML format and is hereby incorporated by reference in its entirety. The XML file, originally created on Sep. 13, 2022, is named 2215269_00123US1_SL.xml and is 1,337,255 bytes in size.

TECHNICAL FIELD

The present invention relates generally to compositions, systems, and methods of peptide vaccines. More particularly, the present invention relates to compositions, systems, and methods of designing peptide vaccines to treat or prevent disease optimized based on predicted population immunogenicity.

BACKGROUND

The goal of a peptide vaccine is to train the immune system to recognize and expand its capacity to engage cells that display foreign peptides to improve the immune response to cancerous cells or pathogens. A peptide vaccine can also be administered to someone who is already diseased to increase their immune response to a causal cancer, other diseases, or pathogen. There exists a need for compositions, systems, and methods of peptide vaccines based on prediction of the foreign peptides that will be displayed at a later time to protect a host from cancer, other disease, or pathogen infection.

SUMMARY OF THE INVENTION

In one aspect, the invention provides for a nucleic acid sequence encoding two or more amino acid sequences selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, and SEQ ID NO: 41.

In some embodiments, the nucleic acid sequence is an immunogenic composition. In some embodiments, the nucleic acid sequence is administered in a construct for expression in vivo. In some embodiments, the in vivo administration of the nucleic acid sequence is configured to produce one or more peptides that are displayed by an HLA class I molecule. In some embodiments, the one or more peptides is a modified or unmodified fragment of a mutated KRAS protein. In some embodiments, the mutated KRAS protein is selected from the group consisting of KRAS G12D, KRAS G12V, and KRAS G12R. In some embodiments, the nucleic acid sequence is administered in an effective amount to a subject to prevent cancer. In some embodiments, the nucleic acid sequence is administered in an effective amount to a subject to treat cancer.

In another aspect, the invention provides for an immunogenic peptide composition comprising two or more peptides selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, and SEQ ID NO: 41.

In some embodiments, a peptide in the immunogenic peptide composition is displayed by an HLA class I molecule. In some embodiments, a peptide in the immunogenic peptide composition is a modified or unmodified fragment of a mutated KRAS protein. In some embodiments, the mutated KRAS protein is selected from the group consisting of KRAS G12D, KRAS G12V, and KRAS G12R. In some embodiments, the immunogenic peptide composition is administered in an effective amount to a subject to prevent cancer. In some embodiments, the immunogenic peptide composition is administered in an effective amount to a subject to treat cancer. In some embodiments, the immunogenic peptide composition comprises at least three peptides selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, and SEQ ID NO: 41.

In another aspect, the invention provides for a nucleic acid sequence encoding one or more amino acid sequences selected from the group consisting of SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO:

53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, and SEQ ID NO: 65.

In some embodiments, the nucleic acid sequence is an immunogenic composition. In some embodiments, the nucleic acid sequence is administered in a construct for expression in vivo. In some embodiments, the in vivo administration of the nucleic acid sequence is configured to produce one or more peptides that are displayed by an HLA class II molecule. In some embodiments, the one or more peptides is a modified fragment of a mutated KRAS protein. In some embodiments, the mutated KRAS protein is selected from the group consisting of KRAS G12D, KRAS G12V, KRAS G12R, KRAS G12C, and KRAS G13D. In some embodiments, the nucleic acid sequence is administered in an effective amount to a subject to prevent cancer. In some embodiments, the nucleic acid sequence is administered in an effective amount to a subject to treat cancer.

In another aspect, the invention provides for an immunogenic peptide composition comprising one or more peptides selected from the group consisting of SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, and SEQ ID NO: 65.

In some embodiments, a peptide in the immunogenic peptide composition is displayed by an HLA class II molecule. In some embodiments, a peptide in the immunogenic peptide composition is a modified or unmodified fragment of a mutated KRAS protein. In some embodiments, the mutated KRAS protein is selected from the group consisting of KRAS G12D, KRAS G12V, KRAS G12R, KRAS G12C, and KRAS G13D. In some embodiments, the immunogenic peptide composition is administered in an effective amount to a subject to prevent cancer. In some embodiments, the immunogenic peptide composition is administered in an effective amount to a subject to treat cancer. In some embodiments, the immunogenic peptide composition comprises at least two peptides selected from the group consisting of SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, and SEQ ID NO: 65.

BRIEF DESCRIPTION OF THE DRAWINGS

The following figures depict illustrative embodiments of the invention.

FIG. 5 shows probabilities of disease presentations for pancreas, colon/rectum, and bronchus/lung and respective probabilities of target presentations for KRAS G12D, KRAS G12V, and KRAS G12R targets.

FIG. 9 shows an example Python implementation of the MERGEMULTI function for combined vaccine design procedures.

DETAILED DESCRIPTION

Figure 1:
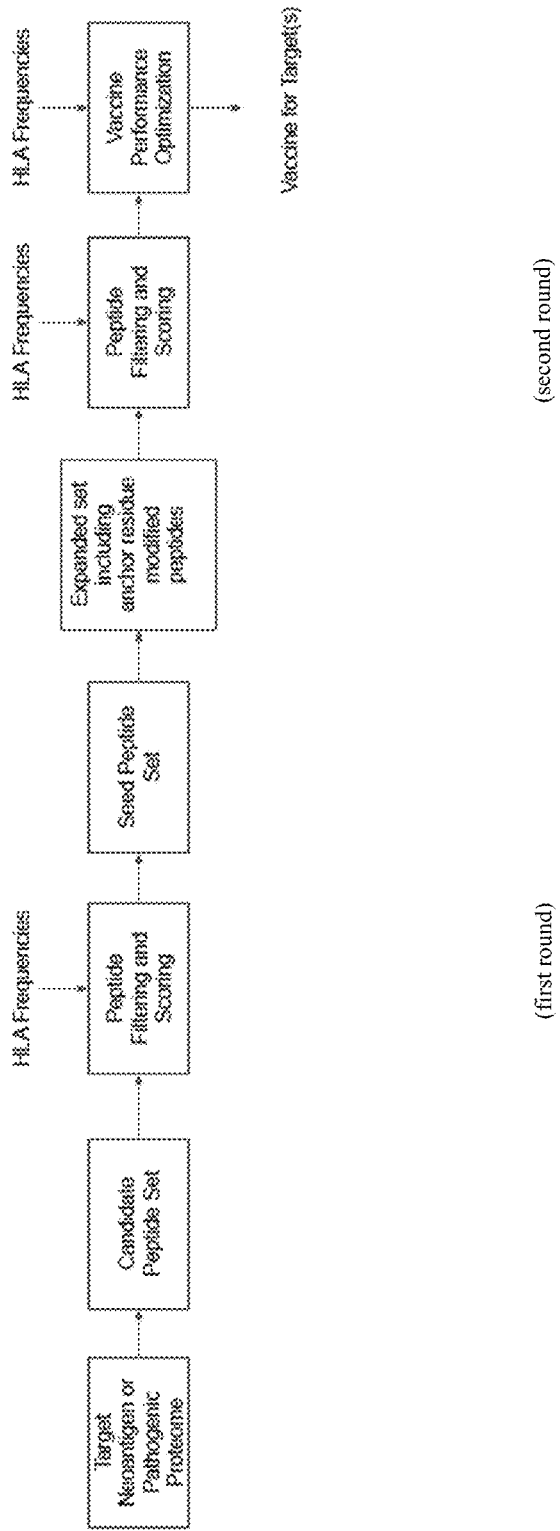
FIG. 1 is a flow chart of a vaccine optimization method.

In some embodiments, the disclosure provides for peptide vaccines that incorporate peptide sequences that will be displayed by Major Histocompatibility Complex (MHC) molecules on cells and train the immune system to recognize cancer or pathogen diseased cells. In some embodiments, a peptide vaccine is a composition that consists of one or more peptides. In some embodiments, a peptide vaccine is an mRNA or DNA construct administered for expression in vivo that encodes for one or more peptides.

Peptide display by an WIC molecule is necessary, but not sufficient, for a peptide to be immunogenic and cause the recognition of the resulting peptide-WIC complex by an individual's T cells to trigger T cell activation, expansion, and immune memory. In some embodiments, experimental data from assays such as the ELISPOT (Slota et al., 2011) or the Multiplex Identification of Antigen-Specific T Cell Receptors Using a Combination of Immune Assays and Immune Receptor Sequencing (MIRA) assay (Klinger et al., 2015) can be combined with machine learning based predictions of peptide display by an WIC molecule. In some embodiments, the MHCflurry or NetMHCpan computational methods (known in the art) are used to predict MHC class I display of a peptide by an HLA allele (see Table 1). In some embodiments, the NetMHCIIpan computational method (known in the art) is used to predict WIC class II display of a peptide by an HLA allele (see Table 2).

A peptide is displayed by an MHC molecule when it binds within the groove of the WIC molecule and is transported to the cell surface where it can be recognized by a T cell receptor. In some embodiments, a peptide that is part of the normal proteome in a healthy individual is a self-peptide, and a peptide that is not part of the normal proteome is a foreign peptide. Foreign peptides can be generated by mutations in normal self-proteins in tumor cells that create epitopes called neoantigens, or by pathogenic infections. In some embodiments, a neoantigen is any subsequence of a human protein, where the subsequence contains one or more altered amino acids or protein modifications that do not appear in a healthy individual.

For example, KRAS gene mutations are the most frequently mutated oncogenes in cancer, but they have been very difficult to treat with small molecule therapeutics. The KRAS protein is part of a signaling pathway that controls cellular growth, and point mutations in the protein can cause constitutive pathway activation and uncontrolled cell growth. Single amino acid KRAS mutations result in minor changes in protein structure, making it difficult to engineer small molecule drugs that recognize a mutant specific binding pocket and inactivate KRAS signaling. KRAS oncogenic mutations include the mutation of position 12 from glycine to aspartic acid (G12D), glycine to valine (G12V), glycine to arginine (G12R), or glycine to cystine (G12C); or the mutation of position 13 from glycine to aspartic acid (G13D). The corresponding foreign peptides contain these mutations.

A challenge for the design of peptide vaccines is the diversity of human MHC alleles that each have specific preferences for the peptide sequences they will display. The Human Leukocyte Antigen (HLA) loci, located within the MHC, encode the HLA class I and class II molecules. There are three classical class I loci (HLA-A, HLA-B, and HLA-C) and three loci that encode class II molecules (HLA-DR, HLA-DQ, and HLA-DP). An individual's HLA type describes the alleles they carry at each of these loci. Peptides of length of between about 8 and about 11 residues can bind to HLA class I (or MHC class I) molecules whereas those of length of between about 13 and about 25 bind to HLA class II (or MHC class II) molecules (Rist et al., 2013; Chicz et al., 1992). Human populations that originate from different geographies have differing frequencies of HLA alleles, and these populations exhibit linkage disequilibrium between HLA loci that result in population specific haplotype frequencies. In some embodiments, methods are disclosed for creating effective vaccines that includes consideration of the HLA allelic frequency in the target population, as well as linkage disequilibrium between HLA genes to achieve a set of peptides that is likely to be robustly displayed.

The present disclosure provides for compositions, systems, and methods of vaccine designs that produce immunity to multiple targets. In some embodiments, a target is a neoantigen protein sequence, a pathogen proteome, or any other undesired protein sequence that is non-self and is expected to be bound and displayed by an MHC molecule. When a target is present in an individual it may result in multiple peptide sequences that are displayed by a variety of HLA alleles. Therefore, in this disclosure, "foreign peptide" refers to an amino acid sequence encoding a fragment of a target protein/peptide (or a full protein/peptide), the target protein/peptide consisting of: a neoantigen protein, a pathogen proteome, or any other undesired protein that is non-self and is expected to be bound and displayed by an MHC molecule.

In some embodiments, peptide-MHC immunogenicity data or computational predictions of peptide-MHC immunogenicity can be included and combined with scores for peptide display in the methods disclosed herein. One way of combining the scores is using immunogenicity data for peptides assayed for immunogenicity in diseased or vaccinated individuals, and assigning peptides to the HLA allele that displayed them in the individual by choosing the HLA allele that computational methods predict has the highest likelihood of display. For peptides that are not experimentally assayed, computational predictions of display can be used.

Since immunogenicity may vary from individual to individual, one method to increase the probability of vaccine efficacy is to use a diverse set of foreign peptides (e.g., at least two peptides) to increase the chances that some subset of them will be immunogenic in a given individual. Prior research using mouse models has shown that most MHC displayed peptides are immunogenic, but immunogenicity varies from individual to individual as described in Croft et al. (2019). In some embodiments, experimental peptide-HLA immunogenicity data are used to determine which foreign peptides and their modifications will be effective immunogens in a vaccine.

Considerations for the design of peptide vaccines are outlined in Liu et al., Cell Systems 11, Issue 2, p. 131-146 (Liu et al., 2020) and (Liu et al., 2020b) which are incorporated by reference herein.

Certain foreign peptides may not bind with high affinity to a wide range of HLA molecules. To increase the binding of foreign peptides to HLA molecules, their amino acid composition can be altered to change one or more anchor residues or other residues. Anchor residues are amino acids that interact with an HLA molecule and have the largest influence on the affinity of a peptide for an HLA molecule. Peptides with altered anchor residues are called heteroclitic peptides. In some embodiments, heteroclitic peptides include foreign peptides with residue modifications at non-anchor positions. In some embodiments, heteroclitic peptides include foreign peptides with residue modifications that include unnatural amino acids and amino acid derivatives. Modifications to create heteroclitic peptides can improve the binding of peptides to both MHC class I and MHC class II molecules, and the modifications required can be both peptide and MHC class specific. Since peptide anchor residues face the MHC molecule groove, they are less visible than other peptide residues to T cell receptors. Thus, heteroclitic peptides have been observed to induce a T cell response where the stimulated T cells also respond to unmodified peptides. It has been observed that the use of heteroclitic peptides in a vaccine can improve a vaccine's effectiveness (Zirlik et al., 2006). In some embodiments, the immunogenicity of heteroclitic peptides are experimentally determined and their ability to activate T cells that also recognize the corresponding base (also called seed) peptide of the heteroclitic peptide is performed as is known in the art. In some embodiments, these assays of the immunogenicity and cross-reactivity of heteroclitic peptides are performed when the heteroclitic peptides are displayed by specific HLA alleles.

Peptide Vaccines to Induce Immunity to One or more Targets

In some embodiments, a method is provided for formulating peptide vaccines using a single vaccine design for a one or more targets. In some embodiments, a single target is a foreign protein with a specific mutation (e.g., KRAS G12D). In some embodiments, multiple targets can be used (e.g. both KRAS G12D and KRAS G13D).

Figure 2:
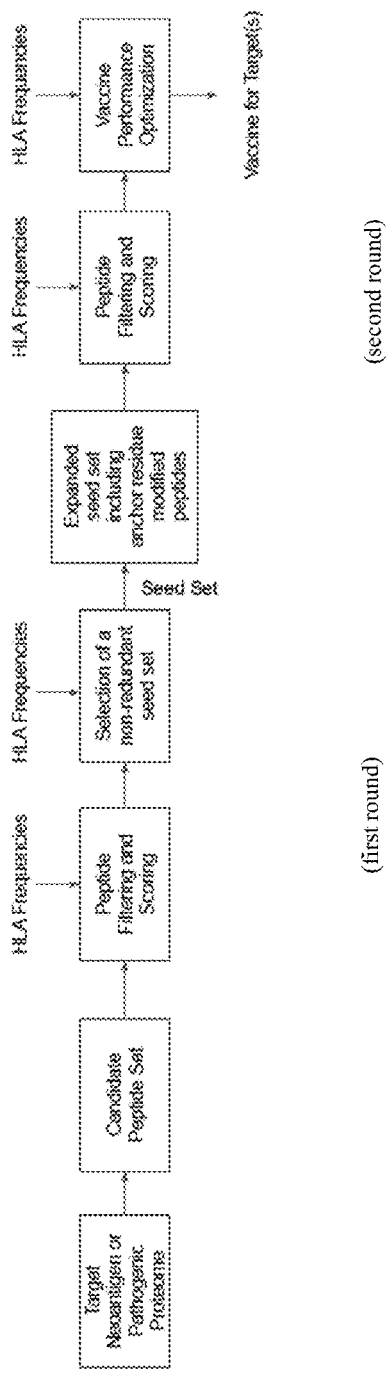
FIG. 2 is a flow chart of vaccine optimization method with seed set compression.

In some embodiments, the method includes extracting peptides to construct a candidate set from all target proteome sequences (e.g., entire KRAS G12D protein) as described in Liu et al. (2020). FIGS. 1 and 2 depict flow charts for example vaccine design methods that can be used for MHC class I or MHC class II vaccine design. In some embodiments, extracted foreign peptides are of amino acid length of between about 8 and about 10 (e.g., for MHC class I binding (Rist et al., 2013)). In some embodiments, the extracted foreign peptides presented by MHC class I molecules are longer than 10 amino acid residues, such as 11 residues (Trolle et al., 2016). In some embodiments, extracted foreign peptides are of length between about 13 and about 25 (e.g., for class II binding (Chicz et al., 1992)). In some embodiments, sliding windows of various size ranges described herein are used over the entire proteome. In some embodiments, other foreign peptide lengths for MHC class I and class II sliding windows can be utilized. In some embodiments, computational predictions of proteasomal cleavage are used to filter or select peptides in the candidate set. One computational method for predicting proteasomal cleavage is described by Nielsen et al. (2005). In some embodiments, peptide mutation rates, glycosylation, cleavage sites, or other criteria can be used to filter peptides as described in Liu et al. (2020).

As shown in FIGS. 1-2, in some embodiments, the next step of the method includes scoring the foreign peptides in the candidate set for binding to all considered HLA alleles as described in Liu et al. (2020) and Liu et al. (2020b). Scoring can be accomplished for human HLA molecules, mouse H-2 molecules, swine SLA molecules, or MHC molecules of any species for which prediction algorithms are available or can be developed. Thus, vaccines targeted at non-human species can be designed with the method. Scoring metrics can include the affinity for a foreign peptide to an HLA allele in nanomolar, eluted ligand, presentation, and other scores that can be expressed as percentile rank or any other metric. The candidate set may be further filtered to exclude peptides whose predicted binding cores do not contain a particular pathogenic or neoantigen target residue of interest or whose predicted binding cores contain the target residue in an anchor position. The candidate set may also be filtered for foreign peptides of specific lengths, such as length 9 for MHC class I, for example. In some embodiments, scoring of foreign peptides is accomplished with experimental data or a combination of experimental data and computational prediction methods.

The criteria used for scoring peptide-HLA binding during the scoring procedure can accommodate different goals during the candidate identification and vaccine design phases. For example, a foreign peptide with peptide-HLA binding affinities of 500 nM may be displayed by an individual that is diseased, but at a lower frequency than a foreign peptide with a 50 nM peptide-HLA binding affinity. Thus, during the scoring of a candidate set to qualify potential immune system targets, 500 nM or other less constrained affinity criteria than 50 nM may be utilized. During the combinatorial design phase of a vaccine, a more constrained affinity criteria may be used, such a 50 nM, to increase the probability that a vaccine peptide will be found and displayed by HLA molecules. In some embodiments, peptides are selected that have peptide-HLA binding affinities of between about 50 nM and about 500 nM. Alternatively, combined models that incorporate peptide immunogenicity can be used to qualify foreign peptides for improvement and score their modified versions for vaccine inclusion. In some embodiments, experimental observations of the immunogenicity of peptides in the context of their display by HLA alleles can be used to score peptides for vaccine inclusion. In some embodiments, computational predictions of the immunogenicity of a peptide in the context of display by HLA alleles can used for scoring such as the methods of Ogishi et al. (2019).

In some embodiments, the method further includes running the OptiVax-Robust algorithm as described in Liu et al. (2020) using the HLA haplotype frequencies of a population on the scored candidate set to construct a seed set (also referred to as base set herein) of foreign peptides (FIG. 2). In some embodiments, HLA diplotype frequencies can be provided to OptiVax. OptiVax-Robust includes algorithms to eliminate peptide redundancy that arises from the sliding window approach with varying window sizes, but other redundancy elimination measures can be used to enforce minimum edit distance constraints between foreign peptides in the candidate set. The size of the seed set is determined by a point of diminishing returns of population coverage as a function of the number of foreign peptides in the seed set. Other criteria can also be used, including a minimum number of vaccine foreign peptides, maximum number of vaccine foreign peptides, and desired predicted population coverage. One alternative criterion is a minimum number of expected peptide-HLA hits in each individual, where a peptide-HLA hit is the potential immunogenic display of a peptide by a single HLA allele as described as in Liu et al. (2020b). In alternate embodiments, the method further includes running the OptiVax-Unlinked algorithm as described in Liu et al. (2020) instead of OptiVax-Robust.

The OptiVax-Robust method uses binary predictions of foreign peptide binding to HLA alleles, and these binary predictions can be generated as described in Liu et al. (2020). The OptiVax-Unlinked method uses the probability of foreign peptide binding to HLA alleles and can be generated as described in Liu et al. (2020). Either method can be used for the purposes described herein, and thus we will the term "OptiVax" refers to either the Robust or Unlinked method. In some embodiments, the observed probability of peptide-HLA immunogenicity in experimental assays can be used as the probability of peptide-HLA binding in EvalVax-Unlinked and OptiVax-Unlinked. In some embodiments, the HLA haplotype or HLA allele frequencies of a population provided to OptiVax for vaccine design describe the world's population. In alternative embodiments, the HLA haplotype or HLA allele frequencies of a population provided to OptiVax for vaccine design are specific to a geographic region. In alternative embodiments, the HLA haplotype or HLA allele frequencies of a population provided to OptiVax for vaccine design are specific to an ancestry. In alternative embodiments, the HLA haplotype or HLA allele frequencies of a population provided to OptiVax for vaccine design are specific to a race. In alternative embodiments, the HLA haplotype or HLA allele frequencies of a population provided to OptiVax for vaccine design are specific to individuals with risk factors such as genetic indicators of risk, age, exposure to chemicals, alcohol use, chronic inflammation, diet, hormones, immunosuppression, infectious agents, obesity, radiation, sunlight, or tobacco use. In alternative embodiments, the HLA haplotype or HLA allele frequencies of a population provided to OptiVax for vaccine design are specific to individuals that carry certain HLA alleles. In alternative embodiments, the HLA diplotypes provided to OptiVax for vaccine design describe a single individual, and are used to design an individualized vaccine.

In some embodiments, the seed set of foreign peptides that results from OptiVax application to the candidate set of target peptides describes a set of unmodified foreign peptides that represent a possible compact vaccine design (Seed Set in FIG. 2). In some embodiments, the seed set is based upon filtering candidate peptides by predicted or observed affinity or immunogenicity with respect to HLA molecules (Seed Set in FIG. 1). However, to improve the display of the foreign peptides in a wide range of HLA haplotypes as possible, some embodiments include modifications of the seed (or base) set. In some embodiments, experimental assays can be used to ensure that a modified seed (or base) peptide activates T cells that also recognize the seed peptide.

For a given foreign peptide, the optimal anchor residue selection may depend upon the HLA allele that is binding to and displaying the foreign peptide and the class of the HLA allele (MHC class I or class II). A seed peptide set can become an expanded set by including anchor residue modified peptides of either MHC class I or II peptides (FIGS.

1-2). Thus, one aspect of vaccine design is considering how to select a limited set of heteroclitic peptides that derive from the same foreign peptide for vaccine inclusion given that different heteroclitic peptides will have different and potentially overlapping population coverages.

In some embodiments, all possible anchor modifications for each base set foreign peptide are considered. There are two anchor residues in peptides bound by MHC class I molecules, typically at positions 2 and 9 for 9-mer peptides. At each anchor position, 20 possible amino acids are attempted in order to select the best heteroclitic peptides. Thus, for MHC class I binding, 400 (i.e., 20 amino acids by 2 positions=$20^2$) minus 1 heteroclitic peptides are generated for each base foreign peptide. There are four anchor residues in peptides bound by MHC class II molecules, typically at positions 1, 4, 6, and 9 of the 9-mer binding core. Thus, for MHC class II binding there are 160,000 (i.e., 20 amino acids by 4 positions=$20^4$) minus 1 heteroclitic peptides generated for each base foreign peptide. Other methods, including Bayesian optimization, can be used to select optimal anchor residues to create heteroclitic peptides from each seed (or base) set peptide. Other methods are presented in "Machine learning optimization of peptides for presentation by class II MHCs" by Dai et al. (2020), incorporated in its entirety herein. In some embodiments, the anchor positions are determined by the HLA allele that presents a peptide, and thus the set of heteroclitic peptides includes for each set of HLA specific anchor positions, all possible anchor modifications.

In some embodiments, for all of the foreign peptides in the seed set, new peptide sequences with all possible anchor residue modifications (e.g., MHC class I or class II) are created resulting in a new heteroclitic base set (Expanded set in FIGS. 1-2) that includes all of the modifications. In some embodiments, the heteroclitic base set (Expanded set in FIGS. 1-2) also includes the original seed (or base) set (Seed Peptide Set in FIGS. 1-2). In some embodiments, the heteroclitic base set includes amino acid substitutions or non-natural amino acid analogs at non-anchor residues. The heteroclitic base set is scored for HLA affinity or other metrics as described herein (another round of Peptide Filtering and Scoring as shown in FIGS. 1-2). The scoring predictions may be further updated for pairs of heteroclitic peptide and HLA allele, eliminating pairs where a heteroclitic peptide is predicted to be displayed by an allele but the seed (or base) peptide from which it was derived is not predicted to be displayed by the allele. The scoring predictions may also be filtered to ensure that predicted binding cores of the heteroclitic peptide displayed by a particular HLA allele align exactly in position with the binding cores of the respective seed (or base) set foreign peptide for that HLA allele. In some embodiments the scoring predictions are filtered for an HLA allele to ensure that the heteroclitic peptides considered for that HLA allele are only modified at anchor positions determined by that HLA allele. In some embodiments, heteroclitic peptides are included in experimental assays such as MIRA (Klinger et al., 2015) to determine their immunogenicity with respect to specific HLA alleles. In some embodiments, the methods of Liu et al. (2020b), can be used to incorporate MIRA data for heteroclitic peptides into a model of peptide-HLA immunogenicity. In some embodiments, the immunogenicity of heteroclitic peptides are experimentally determined and their ability to activate T cells that also recognize the corresponding seed (or base) peptide of the heteroclitic peptide is performed as is known in the art. In some embodiments, these assays of the immunogenicity and cross-reactivity of heteroclitic peptides are performed when the heteroclitic peptides are displayed by specific HLA alleles. In some embodiments, computational predictions of the immunogenicity of a heteroclitic peptide in the context of display by HLA alleles can used for scoring such as the methods of Ogishi et al. (2019).

In some embodiments, the next step involves inputting heteroclitic base set (also referred to as Expanded set as shown in FIGS. 1-2) to OptiVax to select a compact set of vaccine peptides that maximizes vaccine performance (Vaccine Performance Optimization; FIGS. 1-2). Vaccine performance is the population coverage of a vaccine, or the expected number peptide-HLA hits produced by a vaccine, or a function of population coverage and expected number of peptide-HLA hits desired. In some embodiments, the vaccine immunogenicity metric is a metric that describes the overall immunogenic properties of a vaccine with two or more peptides In some embodiments, the methods described herein are included for running OptiVax. In some embodiments, population coverage means the proportion of a subject population that presents one or more immunogenic peptides that activate T cells responsive to a seed foreign peptide. The metric of population coverage is computed using the HLA haplotype frequency in a given population such as a representative human population. In some embodiments, the metric of population coverage is computed using marginal HLA frequencies in a population. Maximizing population coverage means selecting a foreign peptide set that collectively results in the greatest fraction of the population that has at least a minimum number (e.g., 1, 2, 3, 4, 5, 6, 7, or 8) of immunogenic peptide-HLA bindings based on proportions of HLA haplotypes in a given population (e.g., representative healthy or diseased human population). In some embodiments, this process includes the OptiVax selection of heteroclitic peptides (as described in this disclosure) that activate T cells that respond to their corresponding seed (or base) peptide and the heteroclitic base peptides to improve population coverage. In some embodiments, the seed (or base) foreign peptides are always included in the final vaccine design to guard against the possibility that heteroclitic peptides will not produce immunity that reacts with the native seed (or base) foreign peptides. In some embodiments, peptides are only considered as candidates for a vaccine design if they have been observed to be immunogenic in clinical data or animal models.

In some embodiments, a candidate vaccine peptide is eliminated from vaccine inclusion if it activates T cells that recognize self-peptides (e.g., this can be achieved at the first and/or second round of Peptide Filtering and Sorting as shown in FIGS. 1-2). Testing a vaccine peptide for its ability to activate T cells that recognize self-peptides can be experimentally accomplished by the vaccination of animal models followed by ELISPOT or other immunogenicity assay or with human tissue protocols. In both cases, models with HLA alleles that present the vaccine peptide are used. In some embodiments, human primary blood mononuclear cells (PBMCs) are stimulated with a vaccine peptide, the T cells are allowed to grow, and then T cell activation with a self-peptide is assayed as described in Tapia-Calle et al. (2019) or other methods as known in the art. In some embodiments, computational predictions of the ability of a peptide to activate T cells that also recognize self-peptides can be utilized. These predictions can be based upon the modeling of the outward facing residues from the peptide-HLA complex and their interactions with other peptide residues. In some embodiments, a candidate vaccine peptide is eliminated from vaccine inclusion or experimentally tested for cross-reactivity if it is predicted to activate T cells that also recognize self-peptides based upon the structural similarity of the peptide-WIC complex of the candidate peptide and the peptide-WIC complex of a self-peptide. One method for the prediction of peptide-MHC structure is described by Park et al. (2013).

In some embodiments, a candidate heteroclitic vaccine peptide is eliminated from vaccine inclusion if it does not activate T cells that recognize its corresponding seed foreign peptide (second round of Peptide Filtering and Scoring, FIGS. 1-2). Testing a candidate heteroclitic peptide for its ability to activate T cells that recognize its corresponding seed (or base) foreign peptide can be experimentally accomplished by the vaccination of animal models followed by ELISPOT or other immunogenicity assay or with human tissue protocols. In both cases, models with HLA alleles that present the heteroclitic peptide are used. In some embodiments, human PBMCs are stimulated with the heteroclitic peptide, the T cells are allowed to grow, and then T cell activation with the seed (or base) foreign peptide is assayed as described in Tapia-Calle et al. (2019) or using other methods known in the art. In some embodiments, computational predictions of the ability of a heteroclitic peptide to activate T cells that also recognize the corresponding seed (or base) foreign peptide can be utilized. These predictions can be based upon the modeling of the outward facing residues from the peptide-HLA complex and their interactions with other peptide residues. In some embodiments, the structural similarity of the peptide-MHC complex of a heteroclitic peptide and the peptide-MHC complex of the corresponding seed (or base) foreign is used to qualify heteroclitic peptides for vaccine inclusion or to require experimental immunogenicity testing before vaccine inclusion.

Figure 3:
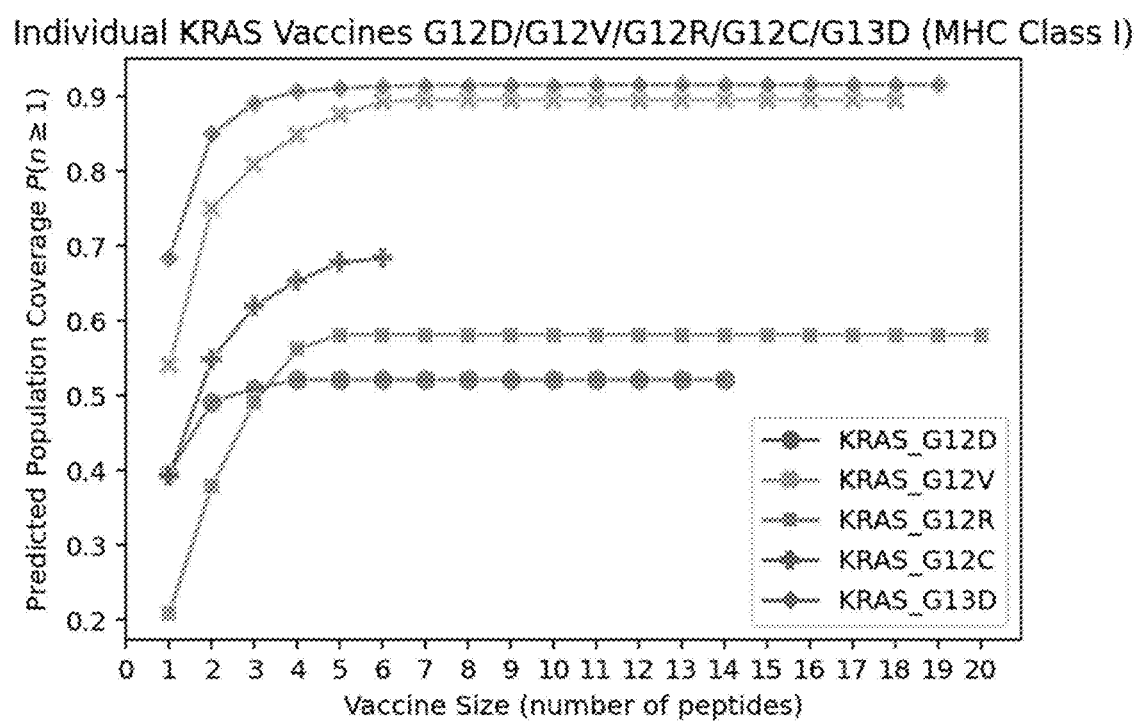
FIG. 3 shows predicted population coverage for single target MHC class I vaccines by vaccine size for KRAS G12D, KRAS G12V, KRAS G12R, KRAS G12C, and KRAS G13D targets.
Figure 4:
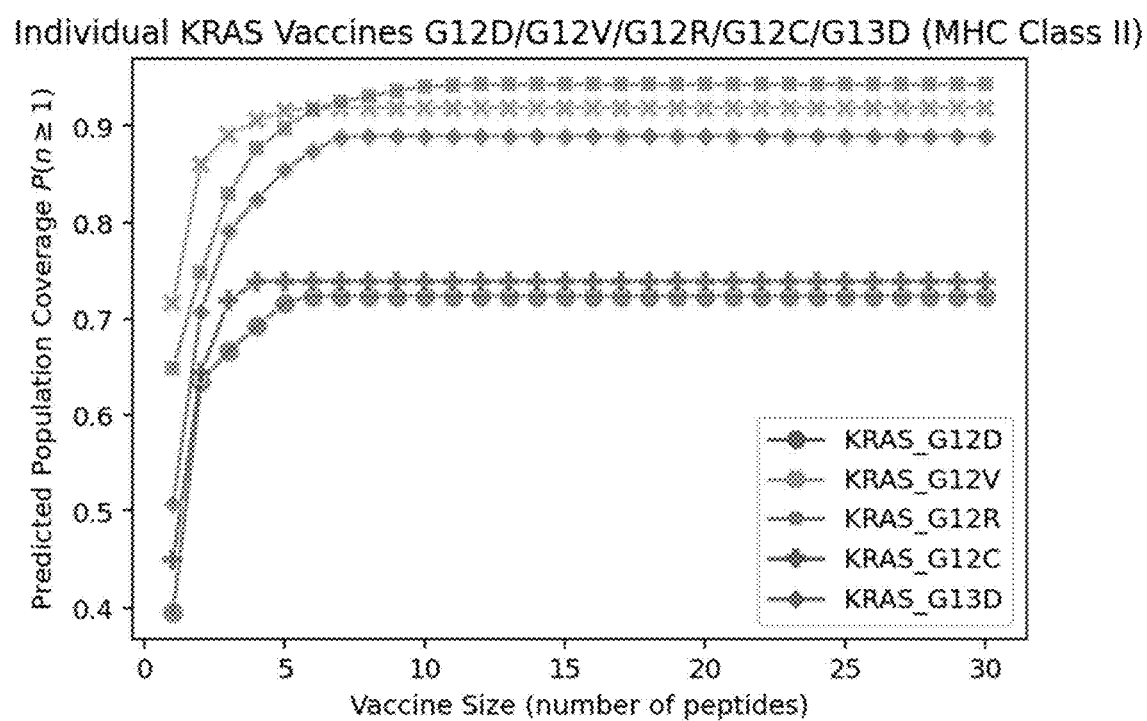
FIG. 4 shows predicted population coverage for single target MHC class II vaccines by vaccine size for KRAS G12D, KRAS G12V, KRAS G12R, KRAS G12C, and KRAS G13D targets.

FIG. 3 (MHC class I) and FIG. 4 (MHC class II) show the predicted population coverage of OptiVax-Robust selected single target-specific vaccines with differing number of peptides designed for the KRAS mutations G12D, G12V, G12R, G12C, and G13D. FIGS. 4-5 show that as the number of peptides increases for a vaccine, its predicted population coverage increases. The population coverage shown in FIGS. 4-5 are of those individuals that have the specific mutation that the vaccine is designed to cover. An increase in peptide count will also typically cause the average number of peptide-HLA hits in each individual to increase in the population.

OptiVax can be used to design a vaccine to maximize the fraction/proportion of the population whose HLA molecules are predicted to bind to and display at least p peptides from the vaccine. In some embodiments, this prediction includes experimental immunogenicity data to directly predict at least p peptides will be immunogenic. The number p is input to OptiVax, and OptiVax can be run multiple times with varying values for p to obtain a predicted optimal foreign peptide set for different peptide counts p. Larger values of p will increase the redundancy of a vaccine at the cost of more peptides to achieve a desired population coverage. In some embodiments, it may not be possible to achieve a given population coverage given a specific heteroclitic base set. In some embodiments, the number p is a function of the desired size of a vaccine.

The methods described herein can be used to design separate vaccine formulations for MHC class I and class II based immunity.

In some embodiments, this procedure is used to create a vaccine for an individual. In some embodiments, the foreign peptides present in the individual are determined by sequencing the individual's tumor RNA or DNA, and identifying mutations that produce foreign peptides. One embodiment of this is described in U.S. Pat. No. 10,738,355B2. In some embodiments, peptide sequencing methods are used to identify foreign peptides in the individual. One embodiment of this is described in US20110257890A1. In some embodiments, the foreign peptides used for the individual's vaccine are selected when a foreign peptide or foreign peptide encoding RNA observed in a specimen from the individual is present at a predetermined level. The foreign peptides in the individual are used to construct a vaccine as described in the disclosure herein. For vaccine design OptiVax is provided a diplotype comprising the HLA type of the individual. In an alternative embodiment, the HLA type of an individual is separated into multiple diplotypes with frequencies that sum to one, where each diplotype comprises one or more HLA alleles from the individual and a notation that the other allele positions should not be evaluated. The use of multiple diplotypes will cause OptiVax's objective function to increase the chance that immunogenic peptides will be displayed by all of the constructed diplotypes.

Figure 10:
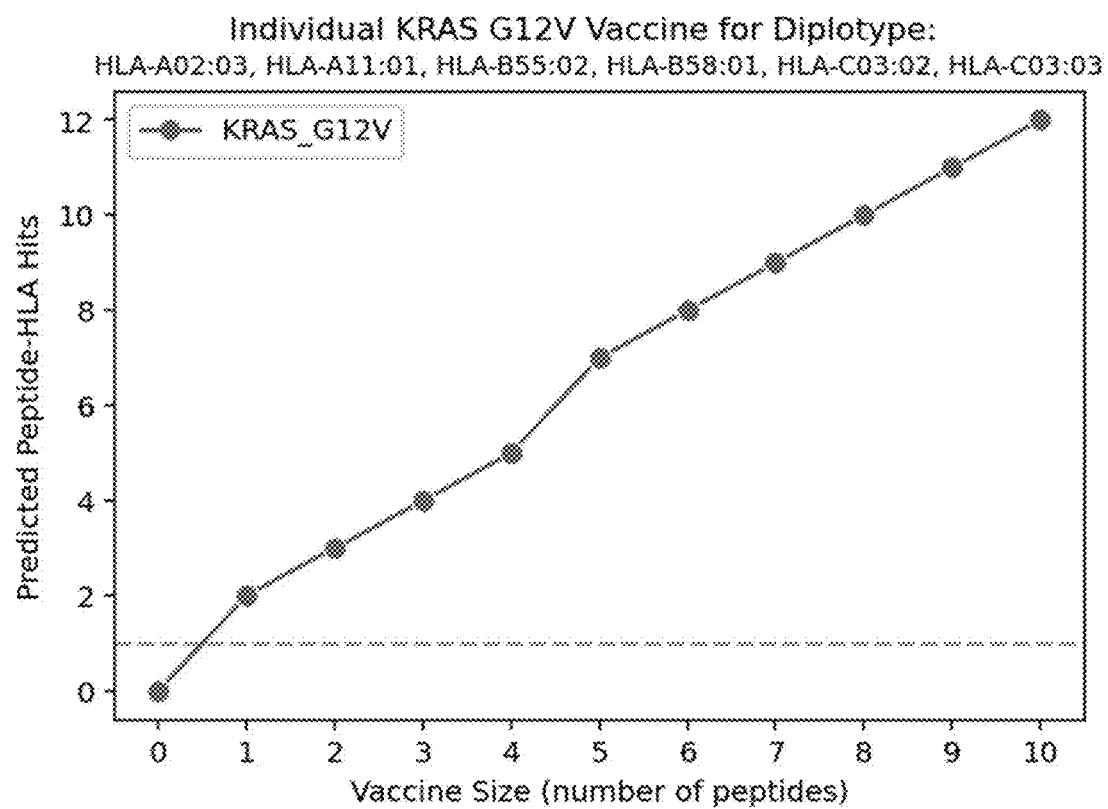
FIG. 10 shows predicated peptide-HLA hits by vaccine size for a KRAS G12V vaccine for the HLA diplotype HLA-A02:03, HLA-A11:01, HLA-B55:02, HLA-B58:01, HLA-C03:02, HLA-O03:03.

FIG. 10 shows the vaccine performance (predicted number of peptide-HLA hits) of ten example G12V MHC class I vaccines for a single individual with the MHC class I HLA diplotype HLA-A02:03, HLA-A11:01, HLA-B55:02, HLA-B58:01, HLA-O03:02, HLA-C03:03. OptiVax was used to design ten G12V MHC class I vaccines for this HLA diplotype with peptide counts ranging from 1 to 10. For the results in FIG. 10, OptiVax was run with six synthetic diplotypes, each equally weighted, each with one HLA allele from the individual's HLA diplotype, and the other allele positions marked to not be evaluated. The 10 peptide vaccine in FIG. 10 comprises SEQ ID NO: 3 (GAVGVGKSL), SEQ ID NO: 4 (LMVVGAVGV), SEQ ID NO: 7 (VVGAVGVGK), SEQ ID NO: 14 (GPVGVGKSV), SEQ ID NO: 69 (LMVVGAVGI), SEQ ID NO: 72 (LMVVGAVGL), SEQ ID NO: 131 (GAVGVGKSM), SEQ ID NO: 138 (GPVGVGKSA), SEQ ID NO: 142 (VTGAVGVGK), and SEQ ID NO: 198 (VAGAVGVGM). Two peptides, SEQ ID NO: 3 (GAVGVGKSL) and SEQ ID NO: 131 (GAVGVGKSM), are predicted to bind two of the HLA alleles with an affinity of 50 nM or less.

MHC Class I Vaccine Design Procedure

In some embodiments, MHC class I vaccine design procedures consist of the following computations steps.

In some embodiments, the inputs for the computation are:

$P_{1 \ldots n}$: Peptide sequence (length n) containing the neoantigen or pathogenic target(s) of interest (e.g., KRAS G12D, KRAS G12V, KRAS G12R, KRAS G12C, KRAS G13D). $P_i$ denotes the amino acid at position i.

t: Position of target mutation in P, $t \in [1, \ldots n]$ (e.g., t=12 for KRAS G12D).

$\tau_1$: Threshold for potential presentation of peptides by MHC for peptide-MHC scoring (e.g., 500 nM binding affinity)

$\tau_2$: Threshold for predicted display of peptides by MHC for peptide-MHC scoring (e.g., 50 nM binding affinity)

$\mathcal{H}$: Set of HLA alleles (for HLA-A, HLA-B, HLA-C loci)

F: $\mathcal{H}^3 \to \mathbb{R}$: Population haplotype frequencies (for OptiVax optimization and coverage evaluation).

N: Parameter for EvalVax and OptiVax objective function. Specifies minimum number of predicted per-individual hits for population coverage objective to consider the individual covered. Default=1 (computes $P(n \geq 1)$ population coverage).

In some embodiments, Peptide-HLA Scoring Functions used are:

SCOREPOTENTIAL: $P \times \mathcal{H} \to \mathbb{R}$: Scoring function mapping a (peptide, HLA allele) pair to a prediction of peptide-HLA display. If predicted affinity$\leq \tau_1$, then returns 1, else returns 0. Options include MHCflurry, NetMHCpan, PUFFIN, ensembles, or alternative metrics or software may be used, including models calibrated against immunogenicity data.

SCOREDISPLAY: $P \times \mathcal{H} \to \mathbb{R}$: Scoring function mapping a (peptide, HLA allele) pair to a prediction of peptide-HLA display. If predicted affinity$\leq \tau_2$, then returns 1, else returns 0. Options include MHCflurry, NetMHCpan, PUFFIN, ensembles, or alternative metrics or software may be used, including models calibrated against immunogenicity data.

Next, from the seed protein sequence (P), a set $\mathcal{P}$ of windowed native peptides spanning the protein sequence(s) is constructed. In some embodiments, 9-mers are produced, but this process can be performed with any desired window lengths and the resulting peptide sets combined.

$$\mathcal{P} = \{P_{j \ldots j+8} | j \in [t-8 \ldots, t], j \neq \{t-7, t\}\}$$

The second condition $j \neq \{t-7, t\}$ excludes peptides where the mutation at t is in positions P2 or P9 of the windowed 9-mer peptide (i.e., the anchor positions).

Next, each peptide sequence in $\mathcal{P}$ is scored against all HLA alleles in $\mathcal{H}$ for potential presentation using SCOREPOTENTIAL (with threshold $\tau_1$=500 nM) and store results in a $|\mathcal{P}| \times |\mathcal{H}|$ matrix S:

$$S[p, h] = \text{SCOREPOTENTIAL}(p, h) \forall p \in \mathcal{P}, h \in \mathcal{H}$$

Note that S is a binary matrix where 1 indicates the HLA is predicted to potentially present the peptide, and 0 indicates no potential presentation.

Define Base Set of Peptides $B \subseteq \mathcal{P}$:

$$B = \{p \in \mathcal{P} \, | \, \exists h \text{ s.t. } S[p, h]=1\}$$

Thus, B contains the native peptides that are predicted to be potentially presented by at least 1 HLA.

Create a Set of all Heteroclitic Peptides B' Stemming from Peptides in B:

$$B' = \bigcup_{b \in B} \text{ANCHOR-MODIFIED}(b)$$

where ANCHOR-MODIFIED(b) returns a set of all 399 anchor-modified peptides stemming from b (with all possible modifications to the amino acids at P2 and P9).

Next, all heteroclitic candidate peptides in B' are scored against all HLA alleles in $\mathcal{H}$ for predicted display using SCOREDISPLAY (with threshold $\tau_2$=50 nM), and store results in binary $|B'| \times |\mathcal{H}|$ matrix $S'_1$:

$$S'_1[b', h] = \text{SCOREDISPLAY}(b', h) \forall b' \in B', h \in \mathcal{H}$$

Next, an updated scoring matrix $S'_2$ is computed for heteroclitic peptides conditioned on the potential presentation of the corresponding base peptides by each HLA:

$$S'_2[b', h] = \begin{cases} S'_1[b', h], & \text{if } S[b, h] = 1 \\ 0, & \text{otherwise} \end{cases} \forall b' \in B', h \in \mathcal{H}$$

where each heteroclitic peptide $b' \in B'$ is a mutation of base peptide $b \in B$. This condition enforces that if h was not predicted to potentially present b, then all heteroclitic peptides b' derived from b will not be displayed by h (even if h would otherwise be predicted to display b').

In some embodiments, OptiVax-Robust is used to design a final peptide set from the union of base peptides and heteroclitic peptides $B \cup B'$ (with corresponding scoring matrices S and $S'_2$ for B and B', respectively). Let $V_k$ denote the compact set of vaccine peptides output by OptiVax containing k peptides. Note that $V_{k+1}$ is not necessarily a superset of $V_k$. (In alternate embodiments, OptiVax can be used to augment the base set B with peptides from B' using scoring matrix $S'_2$ to return set $\mathcal{A}_k$, and the final vaccine set $V_{k+|B|}$ consists of peptides $B \cup \mathcal{A}_k$.)

In some embodiments, this procedure is repeated independently for each target of interest, and the resulting independent vaccine sets can be merged into a combined vaccine as described below.

MHC Class II Vaccine Design Procedure

In some embodiments, MHC class II vaccine design procedures consist of the following computations steps.

In some embodiments, the inputs for the computation are:

$P_{1 \ldots n}$: Peptide sequence(s) (length n) containing the neoantigen(s) of interest (e.g., KRAS G12D, KRAS G12V, KRAS G12R, KRAS G12C, KRAS G13D). $P_i$ denotes the amino acid at position i.

t: Position of target mutation in P, $t \in [1, \ldots, n]$ (e.g., t=12 for KRAS G12D).

$\tau_1$: Threshold for potential presentation of peptides by MHC for peptide-MHC scoring (e.g., 500 nM binding affinity)

$\tau_2$: Threshold for predicted display of peptides by MHC for peptide-MHC scoring (e.g., 50 nM binding affinity)

$\mathcal{H}$: Set of HLA alleles (for HLA-DR, HLA-DQ, HLA-DP loci)

F: $\mathcal{H}^3 \to \mathbb{R}$: Population haplotype frequencies (for OptiVax optimization and coverage evaluation).

N: Parameter for EvalVax and OptiVax objective function. Specifies minimum number of predicted per-individual hits for population coverage objective to consider the individual covered. Default=1 (computes $P(n \geq 1)$ population coverage).

In some embodiments, Peptide-HLA Scoring Functions used are:

SCOREPOTENTIAL: $P \times \mathcal{H} \to \mathbb{R}$: Scoring function mapping a (peptide, HLA allele) pair to a prediction of peptide-HLA display. If predicted affinity$\leq \tau_1$, then returns 1, else returns 0. Options include NetMHCIIpan, PUFFIN, ensembles, or alternative metrics or software may be used, including models calibrated against immunogenicity data.

SCOREDISPLAY: $P \times \mathcal{H} \to \mathbb{R}$: Scoring function mapping a (peptide, HLA allele) pair to a prediction of peptide-HLA display. If predicted affinity$\leq \tau_2$, then returns 1, else returns 0. Options include NetMHCIIpan, PUFFIN, ensembles, or alternative metrics or software may be used, including models calibrated against immunogenicity data.

FindCore: $P \times \mathcal{H} \to [1, \ldots, n]$: Function mapping a (peptide, HLA allele) pair to a prediction of the 9-mer binding core. The core may be specified as the offset position (index) into the peptide where the core begins.

Next, from the seed protein sequence (P), a set $\mathcal{P}$ of peptides spanning the protein sequence are constructed. Here, we extract all windowed peptides of length 13-25 spanning the target mutation, but this process can be performed using any desired window lengths (e.g., only 15-mers).

$$\mathcal{P} = \bigcup_{k \in [13, \ldots, 25]} \mathcal{P}_k$$

$$\mathcal{P}_k = \{P_j \ldots _{j+(k-1)} | j \in [t-(k-1), \ldots, t]\}$$

where $\mathcal{P}_k$ contains all sliding windows of length k, which are combined to form $\mathcal{P}$. Note that here (unlike MHC class I), no peptides are excluded based on binding core or anchor residue positions (for MHC class II, filtering is performed in Paragraph 0063).

Next, each peptide sequence in P is scored against all HLA alleles in $\mathcal{H}$ for potential presentation using SCOREPOTENTIAL (with threshold $\tau_1$=500 nM) and store results in $|\mathcal{P}| \times |\mathcal{H}|$ matrix $S_1$:

$$S_1[p, h] = \text{ScorePotential}(p, h) \forall p \in \mathcal{P}, h \in \mathcal{H}$$

Note that $S_1$ is a binary matrix where 1 indicates the HLA is predicted to potentially present the peptide, and 0 indicates no potential presentation.

For each (peptide, HLA allele) pair (p, h), identify/predict the 9-mer binding core using FINDCORE. The predicted binding core is recorded in a matrix C:

$$C[p, h] = \text{FindCore}(p, h) \forall p \in \mathcal{P}, h \in \mathcal{H}$$

Next, an updated scoring matrix $S_2$ is computed for native peptides in $\mathcal{P}$:

$$S_2[p, h] = \begin{cases} S_1[p, h], & \text{if } C[p, h] \text{ specifies } P_t \text{ at} \\ & \text{a non-anchor position} \\ & \text{inside core} \\ 0, & \text{otherwise} \end{cases} \forall p \in \mathcal{P}, h \in \mathcal{H}$$

where $P_t$ is the target residue of interest (e.g., the mutation site of KRAS G12D). This condition enforces the target residue to fall within the binding core at a non-anchor position for all (peptide, HLA allele) pairs with non-zero scores in $S_2$, and allows the binding core to vary by allele per peptide (as the binding cores of a particular peptide may differ based on the HLA allele presenting the peptide). Thus, for each pair (p, h), if the predicted binding core C[p, h] specifies the target residue $P_t$ at an anchor position (P1, P4, P6, or P9 of the 9-mer core), or if $P_t$ is not contained within the binding core, then $S_2[p, h]$=0. In an alternate embodiment, $P_t$ can be located outside of the core or inside the core in a non-anchor position.

Next, OptiVax-Robust is run with peptides $\mathcal{P}$ and scoring matrix $S_2$ to identify a non-redundant base set of peptides B $\subseteq$ P. (In alternate embodiments, B can be chosen as the entire set $\mathcal{P}$ rather than identifying a non-redundant base set.)

Next, a set of all heteroclitic peptides B' is created stemming from peptides in B:

$$B' = \bigcup_{b \in B} \{\text{ANCHOR} - \text{MODIFIED}(b, c) \forall c \mid \exists h \text{ s.t. } S_2[b, h] = 1\}$$

where ANCHOR-MODIFIED(b,c) returns a set of all $20^4-1$ anchor-modified peptides stemming from b with all possible modifications to the amino acids at P1, P4, P6, and P9 of the 9-mer binding core c. Thus, for each base peptide b, the heteroclitic set B' contains all anchor-modified peptides b' with modifications to all unique cores of b identified for any HLA alleles that potentially present b with a valid core position as indicated by scoring matrix $S_2$.

Next, all heteroclitic candidate peptides in B' are scored against all HLA alleles in $\mathcal{H}$ for predicted display using SCOREDISPLAY (with threshold $\tau_2$=50 nM), and store results in binary $|B'| \times |\mathcal{H}|$ matrix $S'_1$:

$$S'_1[b', h] = \text{ScoreDisplay}(b', h) \forall b' \in B', h \in \mathcal{H}$$

For each (heteroclitic peptide, HLA allele) pair (b',h), identify/predict the 9-mer binding core using FINDCORE. The predicted binding core is recorded in a matrix C':

$$C'[b', h] = \text{FindCore}(b', h) \forall b' \in B', h \in \mathcal{H}$$

An updated scoring matrix $S'_2$ is computed for heteroclitic peptides conditioned on the identified binding cores of a heteroclitic and base peptides occurring at the same offset by a particular HLA:

$$S'_2[b', h] = \begin{cases} S'_1[b', h], & \text{if } C'[b', h] = C[b, h] \\ 0, & \text{otherwise} \end{cases} \forall b' \in B', h \in \mathcal{H}$$

where each heteroclitic peptide b' ∈ B' is a mutation of base peptide b ∈ B. This condition enforces the binding core of the heteroclitic peptide b' to be at the same relative position as the base peptide b, and, implicitly, enforces that the target residue Pt still falls in a non-anchor position within the 9-mer binding core (Step 3).

An updated scoring matrix $S'_3$ is computed for heteroclitic peptides conditioned on the potential presentation of the corresponding base peptides by each HLA:

$$S'_3[b', h] = \begin{cases} S'_2[b', h], & \text{if } S[b, h] = 1 \\ 0, & \text{otherwise} \end{cases} \forall b' \in B', h \in \mathcal{H}$$

where each heteroclitic peptide b' ∈ B' is a mutation of base peptide b ∈ B. This condition enforces that if h was not predicted to display b, then all heteroclitic peptides b' derived from b will not be displayed by h (even if h would otherwise be predicted to display b').

OptiVax-Robust is used to design a final peptide set from the union of base peptides and heteroclitic peptides B ∪ B' (with corresponding scoring matrices $S_2$ and $S'_3$ for B and B', respectively). Let $V_k$ denote the compact set of vaccine peptides output by OptiVax containing k peptides. Note that $V_{k+1}$ is not necessarily a superset of $V_k$. (In alternate embodiments, OptiVax can be used to augment the base set B with peptides from B' using scoring matrix $S'_2$ to return set $\mathcal{A}_k$, and the final vaccine set $V_{k+|B|}$ consists of peptides B ∪ $\mathcal{A}_k$.)

In some embodiments, this procedure is repeated independently for each single target of interest, and the resulting independent vaccine sets can be merged into a combined vaccine as described below.

Methods for Combining Multiple Vaccines

The above described methods will produce an optimized foreign peptide set for one or more targets. In some embodiments, a method is provided for designing separate vaccines for WIC class I and class II based immunity for multiple targets (e.g., two or more targets such as KARS G12D and KRAS G12V).

In some embodiments, a method is disclosed for producing a combined peptide vaccine for multiple targets by using a table of presentations for a disease that is based upon empirical data from sources such as the Cancer Genome Atlas (TCGA). FIG. 5 shows one embodiment for factoring disease presentation type probabilities (pancreatic cancer, colon/rectum cancer, and bronchus/lung cancer) by probability, for each disease presentation, of target presented for various KRAS mutation targets (KRAS G12D, KRAS G12V, and KRAS G12R). A presentation is a unique set of targets that are presented by one form of a disease (e.g., distinct type of cancer as shown in FIG. 5). For each presentation, FIG. 5 shows an example of the probability of that presentation, and the probability that a given target is observed. For a given presentation, there can be one or more targets, each having a probability. In some embodiments, the method for multi-target vaccine design will allocate peptide resources for inducing disease immunity based on the presentation and respective target probabilities as shown in FIG. 5, for example. In some embodiments, presentations correspond to the prevalence of targets in different human populations or different risk groups. The probability of a target in a population is computed by summing for each possible presentation the probability of that presentation times the probability of the target in that presentation.

Figure 6:
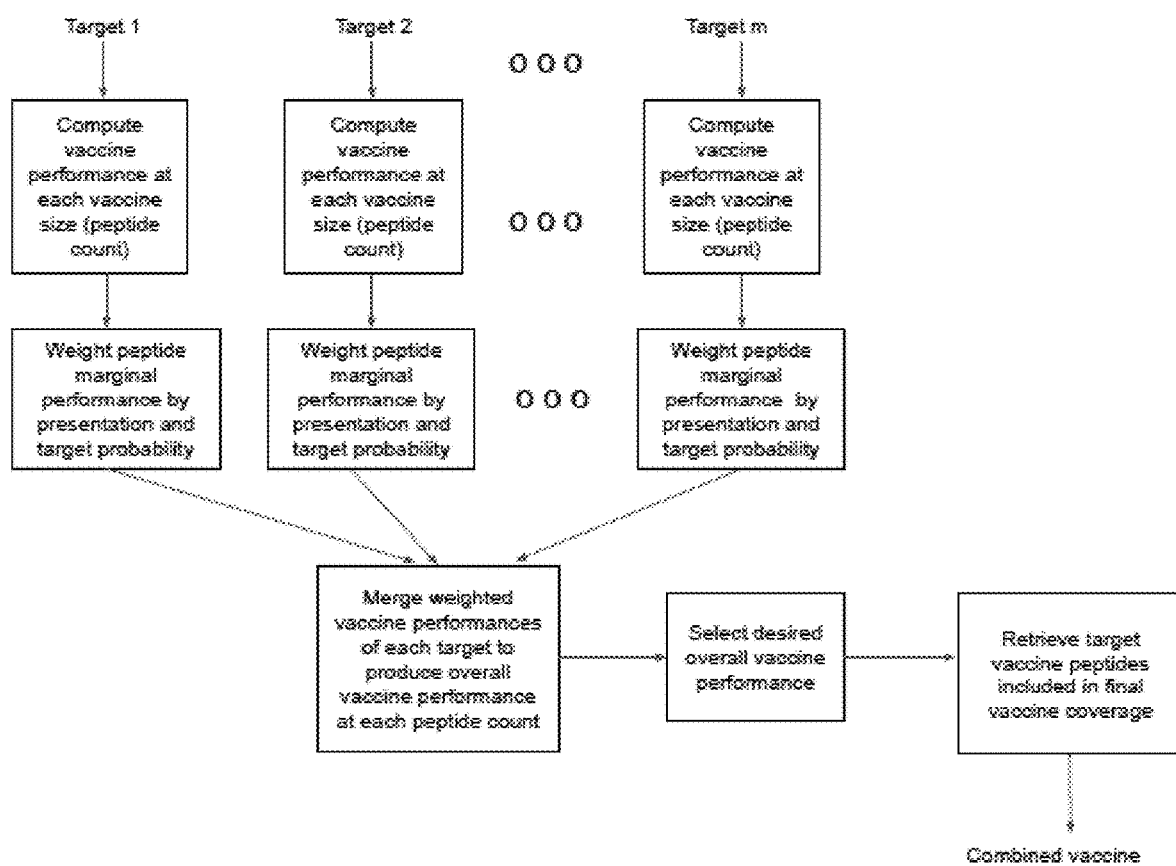
FIG. 6 is a flow chart for multiple target (combined) vaccine optimization methods.

Referring to FIG. 6, in some embodiments, the method first includes designing an individual peptide vaccine for each target to create a combined vaccine design for multiple targets. This initially results in sets of target-specific vaccine designs. In some embodiments, the marginal vaccine performance of each target-specific vaccine at size k is defined by vaccine performance at size k minus the vaccine performance of the vaccine at size k minus one (see FIGS. 3-4). The composition of a vaccine may change as the number of peptides used in the vaccine increases, and thus for computing contributions to a combined vaccine the marginal vaccine performance of each target-specific vaccine is used instead of a specific set of peptides.

In some embodiments, the weighted marginal vaccine performance of a target-specific vaccine design for each target specific vaccine size is computed as shown in FIG. 6. For a given target specific vaccine size, its weighted vaccine performance is computed by multiplying its vaccine performance times the probability of the target in the population (e.g., by using values as shown in FIG. 5). The marginal weighted vaccine performance for a target specific vaccine is its weighted coverage at size k minus its coverage a size k minus one (e.g., see FIGS. 3-4). The marginal weighted vaccine performance of a target specific vaccine of size one is its weighted vaccine performance. The marginal weighted vaccine performances for all vaccines are combined into a single list, and the combined list is sorted from largest to least by the weighted marginal vaccine performances of the target specific vaccines as shown in FIG. 6. The combined vaccine of size n is then determined by the first n elements of this list. The peptides for the combined vaccine are determined by the individual peptide target vaccines whose sizes add to n and whose weighted vaccine performances sums to the same sum as the first n elements of the sorted list. This maximizes the vaccine performance of the combined vaccine of size n.

In some embodiments, the combined multiple target vaccine can be designed on its overall predicted coverage for the disease described depending on the presentation table used (e.g., see FIG. 5), by its predicted coverage for a specific indication, and/or by its predicted coverage for a specific target by adjusting the weighting used for vaccine performance accordingly. Once a desired level of coverage is selected, the peptides of the combined vaccine are determined by the contributions of target-specific designs. For example, if the combined vaccine includes a target-specific vaccine of size k, then the vaccine peptides for this target at size k are used in the combined vaccine.

Figure 7:
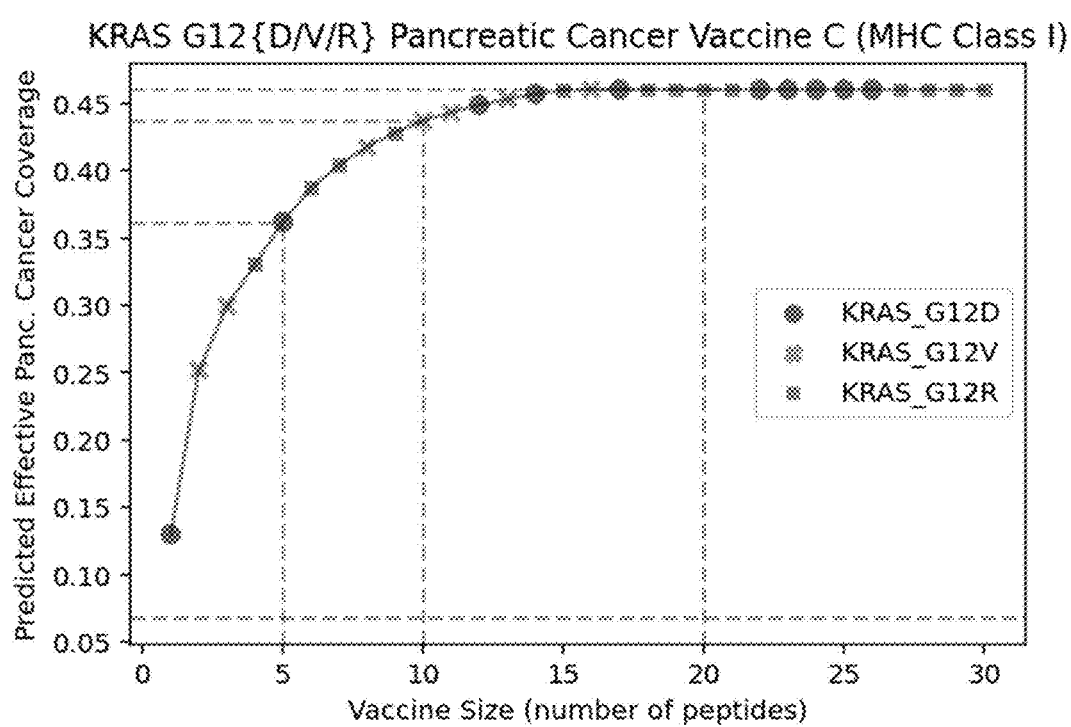
FIG. 7 shows predicted population coverage for pancreatic cancer multiple target (combined) MHC class I vaccines by vaccine size for KRAS G12D, KRAS G12V, and KRAS G12R targets.
Figure 8:
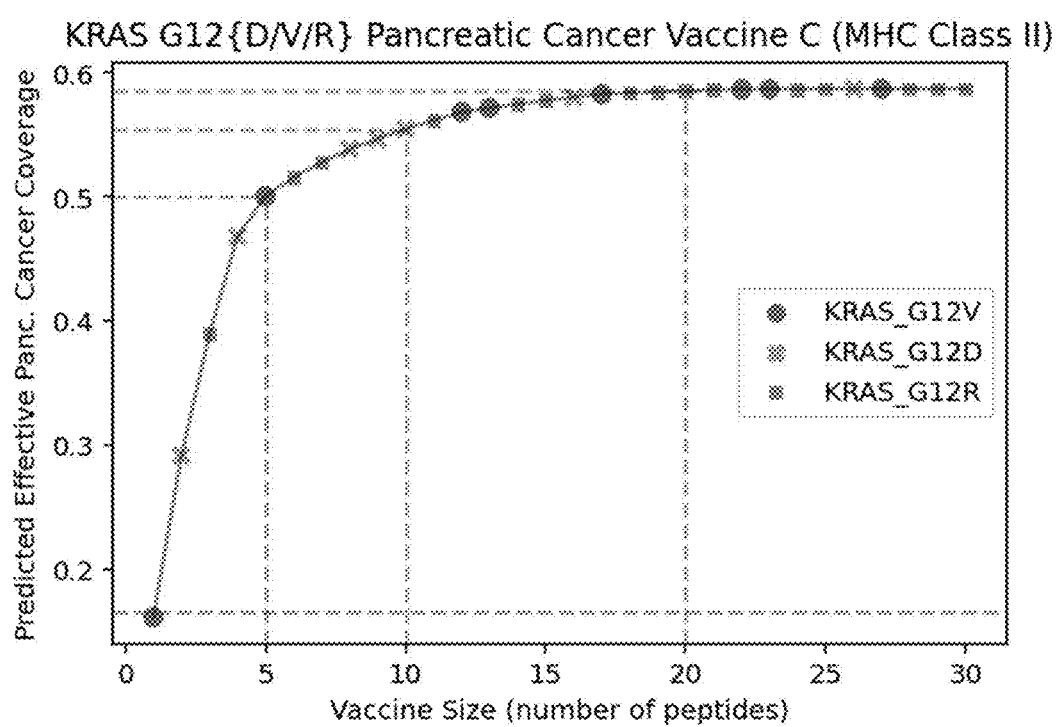
FIG. 8 shows predicted population coverage for pancreatic cancer multiple target (combined) MHC class II vaccines by vaccine size for KRAS G12D, KRAS G12V, and KRAS G12R targets.

As an example of one embodiment, FIG. 5 shows three mutations (KRAS G12D, G12V, and G12R) and their respective probabilities of occurring in an individual with pancreatic cancer. FIG. 3 (MHC class I) and FIG. 4 (MHC class II) show the population coverage of target-specific vaccines for the KRAS G12D, G12V, G12R, G12C, and G13D targets using the methods for vaccines described herein. The marginal population coverage of each target-specific vaccine at a given vaccine size is the improvement in coverage at that size and the size less one. The coverage with no peptides is zero. The marginal coverage of each target-specific vaccine is multiplied by the probability of the target in the population as determined by the proportions as shown in FIG. 5 for the pancreas (pancreatic cancer). These weighted marginal coverages of all target-specific vaccines are sorted to determine the best target-specific compositions, and the resulting list describes the composition of a combined vaccine at each size k by taking the first k elements of the list. As an example of one embodiment, FIGS. 7 (MHC Class I) and FIG. 8 (MHC Class II) show the target specific contributions at each vaccine size for a combined KRAS vaccine for the three mutations KRAS G12D, G12V, and G12R. The methods for combined vaccine protocol described herein was used to compute the examples in FIGS. 7 and 8. At each combined vaccine size, different components of the target-specific vaccines are utilized. Table 1 (below) contains the peptides present in independent (single target) and combined (multiple target) MHC class I vaccine designs for the KRAS G12D, G12V, G12R, G12C, and G13D targets. Table 2 (below) contains the contains the peptides present in independent (single target) MHC class II vaccine designs for the KRAS G12D, G12V, G12R, G12C, and G13D targets, and any subset of the individual/single target vaccines can be combined to create an MHC class II vaccine for two or more multiple targets. For alternate embodiments, Sequence Listing provides heteroclitic peptides useful in MHC class I vaccines for the KRAS G12D, G12V, G12R, G12C, and G13D targets.

Combined Vaccine Design Procedure

In some embodiments, the procedure described herein is used to combine individual compact vaccines optimized for different targets into a single optimized combined vaccine.

In some embodiments, the computational inputs for the procedure are:

$\mathcal{T}$ : Set of neoantigen or pathogenic targets of interest (e.g., KRAS G12D, KRAS G12V, KRAS G12R)

V: Vaccine sets optimized individually for each target. Let $V_{t,k}$ denote the optimal vaccine set of exactly k peptides for target $t \in \mathcal{T}$ (e.g., as computed by the procedures describe above). Note that $V_{t,k+1}$ may not necessarily be a superset of $V_{t,k}$.

W: $\mathcal{T} \to [0,1]$: Target weighting function mapping each target $t \in \mathcal{T}$ to a probability or weight of t in a particular presentation of interest (e.g., pancreatic cancer; see Exhibit A, Table 1 for example).

PopulationCoverage: $V \to [0,1]$: Function mapping a peptide set into population coverage (e.g., EvalVax). This function may also take as input additional parameters, including HLA haplotype frequencies and a minimum per-individual number of peptide-HLA hits N (here, we compute coverage as $P(n \geq 1)$ using EvalVax-Robust).

For each target t (individually) and vaccine size (peptide count) k, the unweighted population coverage $c_{t,k}$ is computed:

$c_{t,k}$=PopulationCoverage($V_{t,k}$)∀ $t \in \mathcal{T}$, k

Note that for each target t, $c_{t,k}$ is generally monotonically increasing and concave down for increasing values of k (each additional peptide increases coverage but with decreasing returns).

For each target t (individually), the marginal coverage $m_{t,k}$ is computed of the k-th peptide added to the vaccine set:

$$m_{t,k} = \begin{cases} c_{t,k} & \text{if } k = 1 \\ c_{t,k} - c_{t,k-1}, & \text{otherwise} \end{cases} \forall t \in \mathcal{T}, k$$

Note that for each target t, $m_{t,k}$ should be a monotonically decreasing function in k (by Step 1 above).

The weighted marginal population coverage $\tilde{m}_{t,k}$ is computed using weights of each target in W:

$$\tilde{m}_{t,k} = W(t) \cdot m_{t,k} \ \forall \ t \in \mathcal{T}, k$$

The weighted marginal population coverage gives the effective marginal coverage of the k-th peptide in the vaccine weighted by the prevalence of the target in the presentation (by multiplication with the probability/weight of the target in the presentation).

The individual vaccines are combined into a combined vaccine via the MERGEMULTI procedure called on the weighted marginal population coverage lists $\tilde{m}_t = [\tilde{m}_{t,k}, k \in 1,2,\ldots]$. FIG. 9 shows an example Python implementation of the MERGEMULTI function. This procedure takes as input multiple sorted (descending) lists and merges them into a single sorted (descending) list. Let M indicate the output of MERGEMULTI where each element $M_k$ contains both the marginal weighted coverage and source (target) of the k-th peptide in the combined vaccine. The combined vaccine contains peptides from different targets. In particular, the combined vaccine with k peptides contains $C_{t,k} = \Sum_{j \leq k} \mathbb{1}\{M_k \text{ from } t\}$ peptides from target t. Note that $C_{t,k} \in [0, \ldots, k]$ and $\Sum_t C_{t,k} = k$ ($C_{t,k}$ gives the distribution of the k peptides in the combined vaccine across the targets).

The optimal combined vaccine set $\hat{V}_k$ is defined as:

$$\hat{V}_k = \bigcup v_{t,C_{t,k}}$$

Thus, the combined vaccine with k peptides is the combination of the optimal individual ($C_{t,k}$)-peptide vaccines. The marginal weighted coverage values of the combine vaccine $M_k$ can be cumulatively summed over k to give the overall effective (target-weighted) population coverage of the combined vaccine containing k peptides as $\Sum_{j \leq K} M_k$ (taking into account both the probabilities/weights of the targets in the presentation and the expected population coverage of peptides based on HLA display). The final vaccine size k can vary based upon the specific population coverage goals of the vaccine.

MHC Class I Peptide Sequences

In some embodiments, a peptide vaccine (single target or combined multiple target vaccine) comprises about five, ten, or twenty MHC class I peptides with each peptide consisting of 8 or more amino acids. In some embodiments, an MHC class I peptide vaccine is intended for one or more of the KRAS G12D, G12V, and G12R targets. In some embodiments, the amino acid sequence of a first peptide in a five-peptide combined vaccine comprises SEQ ID NO: 1. GADGVGKSM (SEQ ID NO: 1). In some embodiments, the amino acid sequence of a second peptide in a five-peptide combined vaccine comprises SEQ ID NO: 2. LMVVGADGV (SEQ ID NO: 2). In some embodiments, the amino acid sequence of a third peptide in a five-peptide combined vaccine comprises SEQ ID NO: 3. GAVGVGKSL (SEQ ID NO: 3). In some embodiments, the amino acid sequence of a fourth peptide in a five-peptide combined vaccine comprises SEQ ID NO: 4. LMVVGAVGV (SEQ ID NO: 4). In some embodiments, the amino acid sequence of a fifth peptide in a five-peptide combined vaccine comprises SEQ ID NO: 5. VTGARGVGK (SEQ ID NO: 5). An example combined vaccine for the KRAS G12D, G12V, and G12R targets with five peptides (SEQ ID NO: 1 to SEQ ID NO: 5) is predicted to have a weighted population coverage of 0.3620.

In some embodiments, any one of the peptides (peptides 1-5) in the five-peptide vaccine comprise an amino acid sequence 80, 81, 82, 83, 84, 85, 86, 87, 88, 89, 90, 91, 92, 93, 94, 95, 96, 97, 98 or 99% identical to SEQ ID NO: 1, SEQ ID NO: 2, SEQ ID NO: 3, SEQ ID NO: 4, or SEQ ID NO: 5.

In some embodiments, the amino acid sequence of peptides 1 to 5 in a ten-peptide combined vaccine comprise SEQ ID NO: 1, SEQ ID NO: 2, SEQ ID NO: 3, SEQ ID NO: 4, and SEQ ID NO: 5. In some embodiments, the amino acid sequence of a sixth peptide in a ten-peptide combined vaccine comprises SEQ ID NO: 6. VMGAVGVGK (SEQ ID NO: 6). In some embodiments, the amino acid sequence of a seventh peptide in a ten-peptide combined vaccine comprises SEQ ID NO: 7. VVGAVGVGK (SEQ ID NO: 7). In some embodiments, the amino acid sequence of an eight peptide in a ten-peptide combined vaccine comprises SEQ ID NO: 8. GARGVGKSY (SEQ ID NO: 8). In some embodiments, the amino acid sequence of a ninth peptide in a ten-peptide combined vaccine comprises SEQ ID NO: 9. GPRGVGKSA (SEQ ID NO: 9). In some embodiments, the amino acid sequence of a tenth peptide in a ten-peptide combined vaccine comprises SEQ ID NO: 10. LMVVGARGV (SEQ ID NO: 10). An example combined vaccine for the KRAS G12D, G12V, and G12R targets with ten peptides (SEQ ID NO: 1 to SEQ ID NO: 10) is predicted to have a weighted population coverage of 0.4374.

In some embodiments, any one of the peptides (peptides 1-10) in the ten-peptide vaccine comprise an amino acid sequence 80, 81, 82, 83, 84, 85, 86, 87, 88, 89, 90, 91, 92, 93, 94, 95, 96, 97, 98 or 99% identical to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10.

In some embodiments, the amino acid sequence of peptides 1 to 10 in a twenty-peptide combined vaccine comprise SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10. In some embodiments, the amino acid sequence of an $11^{th}$ peptide in a twenty-peptide combined vaccine comprises SEQ ID NO: 11. GADGVGKSL (SEQ ID NO: 11). In some embodiments, the amino acid sequence of a $12^{th}$ peptide in a twenty-peptide combined vaccine comprises SEQ ID NO: 12. GADGVGKSY (SEQ ID NO: 12). In some embodiments, the amino acid sequence of a $13^{th}$ peptide in a twenty-peptide combined vaccine comprises SEQ ID NO: 13. GYDGVGKSM (SEQ ID NO: 13). In some embodiments, the amino acid sequence of a $14^{th}$ peptide in a twenty-peptide combined vaccine comprises SEQ ID NO: 14. GPVGVGKSV (SEQ ID NO: 14). In some embodiments, the amino acid sequence of a $15^{th}$ peptide in a twenty-peptide combined vaccine comprises SEQ ID NO: 15. LTVVGAVGV (SEQ ID NO: 15). In some embodiments, the amino acid sequence of a $16^{th}$ peptide in a twenty-peptide combined vaccine comprises SEQ ID NO: 16. VVGAVGVGR (SEQ ID NO: 16). In some embodiments, the amino acid sequence of a $17^{th}$ peptide in a twenty-peptide combined vaccine comprises SEQ ID NO: 17. GARGVGKSM (SEQ ID NO: 17). In some embodiments, the amino acid sequence of an $18^{th}$ peptide in a twenty-peptide combined vaccine comprises SEQ ID NO: 18. GPRGVGKSV (SEQ ID NO: 18). In some embodiments, the amino acid sequence of a $19^{th}$ peptide in a twenty-peptide combined vaccine comprises SEQ ID NO: 19. LLVVGARGV (SEQ ID NO: 19). In some embodiments, the amino acid sequence of a 20th peptide in a twenty-peptide combined vaccine comprises SEQ ID NO: 20. VAGARGVGM (SEQ ID NO: 20). An example combined vaccine for the KRAS G12D, G12V, and G12R targets with twenty peptides (SEQ ID NO: 1 to SEQ ID NO: 20) is predicted to have a weighted population coverage of 0.4604.

In some embodiments, any one of the peptides (peptides 1-20) in the twenty-peptide vaccine comprise an amino acid sequence 80, 81, 82, 83, 84, 85, 86, 87, 88, 89, 90, 91, 92, 93, 94, 95, 96, 97, 98 or 99% identical to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, or SEQ ID NO: 20

Table 1 shows MHC class I peptide sequences described herein including the respective SEQ ID NO, amino acid sequence corresponding to the SEQ ID NO, KRAS protein target (with specific mutation), the seed amino acid sequence (i.e., the amino acid sequence of the wild type KRAS fragment), the amino acid substitution (if any) for heteroclitic peptides at positions 2 and 9, and notes detailing embodiments in which the peptide may be included in a 5, 10, or 20 combined peptide vaccine as described herein. Table 1 also includes additional peptide sequences comprising SEQ ID NOs: 21-41. In some embodiments, any combination of peptides listed in Table 1 (SEQ ID NOs: 1-41) may be used to create a combined peptide vaccine having between about 2 and about 40 peptides. In some embodiments, any one of the peptides (peptides 1-41; SEQ ID NOs: 1-41) in the combined vaccine comprises an amino acid sequence 80, 81, 82, 83, 84, 85, 86, 87, 88, 89, 90, 91, 92, 93, 94, 95, 96, 97, 98 or 99% identical to any of SEQ ID NOs: 1-41.

TABLE 1

Example KRAS Vaccine Peptides (MHC class I)

| SEQ ID NO | Sequence corresponding to SEQ ID | Target | Seed | Heteroclitic Modification P2 | Heteroclitic Modification P9 | Note |
|---|---|---|---|---|---|---|
| SEQ ID NO: 1 | GADGVGKSM | KRAS G12D | GADGVGKSA | — | A9M | Individual KRAS G12D (MHCflurry); Combined (5 peptide) (MHCflurry); Combined (10 peptide) (MHCflurry); Combined (20 peptide) (MHCflurry) |
| SEQ ID NO: 2 | LMVVGADGV | KRAS G12D | LVVVGADGV | V2M | — | Individual KRAS G12D (MHCflurry); Individual KRAS G12D (NetMHCpan); Combined (5 peptide) (MHCflurry); Combined (10 peptide) (MHCflurry); Combined (20 peptide) (MHCflurry) |
| SEQ ID NO: 3 | GAVGVGKSL | KRAS G12V | GAVGVGKSA | — | A9L | Individual KRAS G12V (MHCflurry); Combined (5 peptide) (MHCflurry); Combined (10 peptide) (MHCflurry); Combined (20 peptide) (MHCflurry) |
| SEQ ID NO: 4 | LMVVGAVGV | KRAS G12V | LVVVGAVGV | V2M | — | Individual KRAS G12V (MHCflurry); Individual KRAS G12V (NetMHCpan); Combined (5 peptide) (MHCflurry); Combined (10 peptide) (MHCflurry); Combined (20 peptide) (MHCflurry) |
| SEQ ID NO: 5 | VTGARGVGK | KRAS G12R | VVGARGVGK | V2T | — | Individual KRAS G12R (MHCflurry); Combined (5 peptide) (MHCflurry); Combined (10 peptide) (MHCflurry); Combined (20 peptide) (MHCflurry) |

TABLE 1-continued

Example KRAS Vaccine Peptides (MHC class I)

| SEQ ID NO | Sequence corresponding to SEQ ID | Target | Seed | Heteroclitic Modification P2 | Heteroclitic Modification P9 | Note |
|---|---|---|---|---|---|---|
| SEQ ID NO: 6 | VMGAVGVGK | KRAS G12V | VVGAVGVGK | V2M | — | Individual KRAS G12V (MHCflurry); Combined (10 peptide) (MHCflurry); Combined (20 peptide) (MHCflurry) |
| SEQ ID NO: 7 | VVGAVGVGK | KRAS G12V | VVGAVGVGK | — | — | Individual KRAS G12V (MHCflurry); Individual KRAS G12V (NetMHCpan); Combined (10 peptide) (MHCflurry); Combined (20 peptide) (MHCflurry) |
| SEQ ID NO: 8 | GARGVGKSY | KRAS G12R | GARGVGKSA | — | A9Y | Individual KRAS G12R (MHCflurry); Combined (10 peptide) (MHCflurry); Combined (20 peptide) (MHCflurry) |
| SEQ ID NO: 9 | GPRGVGKSA | KRAS G12R | GARGVGKSA | A2P | — | Individual KRAS G12R (MHCflurry); Combined (10 peptide) (MHCflurry); Combined (20 peptide) (MHCflurry) |
| SEQ ID NO: 10 | LMVVGARGV | KRAS G12R | LVVVGARGV | V2M | — | Individual KRAS G12R (MHCflurry); Individual KRAS G12R (NetMHCpan); Combined (10 peptide) (MHCflurry); Combined (20 peptide) (MHCflurry) |
| SEQ ID NO: 11 | GADGVGKSL | KRAS G12D | GADGVGKSA | — | A9L | Individual KRAS G12D (MHCflurry); Combined (20 peptide) (MHCflurry) |
| SEQ ID NO: 12 | GADGVGKSY | KRAS G12D | GADGVGKSA | — | A9Y | Individual KRAS G12D (MHCflurry); Combined (20 peptide) (MHCflurry) |
| SEQ ID NO: 13 | GYDGVGKSM | KRAS G12D | GADGVGKSA | A2Y | A9M | Individual KRAS G12D (MHCflurry); Combined (20 peptide) (MHCflurry) |
| SEQ ID NO: 14 | GPVGVGKSV | KRAS G12V | GAVGVGKSA | A2P | A9V | Combined (20 peptide) (MHCflurry) |
| SEQ ID NO: 15 | LTVVGAVGV | KRAS G12V | LVVVGAVGV | V2T | — | Individual KRAS G12V (NetMHCpan); Combined (20 peptide) (MHCflurry) |
| SEQ ID NO: 16 | VVGAVGVGR | KRAS G12V | VVGAVGVGK | — | K9R | Individual KRAS G12V (MHCflurry); Individual KRAS G12V (NetMHCpan); Combined (20 peptide) (MHCflurry) |
| SEQ ID NO: 17 | GARGVGKSM | KRAS G12R | GARGVGKSA | — | A9M | Combined (20 peptide) (MHCflurry) |
| SEQ ID NO: 18 | GPRGVGKSV | KRAS G12R | GARGVGKSA | A2P | A9V | Combined (20 peptide) (MHCflurry) |

TABLE 1-continued

Example KRAS Vaccine Peptides (MHC class I)

| SEQ ID NO | Sequence corresponding to SEQ ID | Target | Seed | Heteroclitic Modification P2 | Heteroclitic Modification P9 | Note |
|---|---|---|---|---|---|---|
| SEQ ID NO: 19 | LLVVGARGV | KRAS G12R | LVVVGARGV | V2L | — | Individual KRAS G12R (NetMHCpan); Combined (20 peptide) (MHCflurry) |
| SEQ ID NO: 20 | VAGARGVGM | KRAS G12R | VVGARGVGK | V2A | K9M | Individual KRAS G12R (MHCflurry); Combined (20 peptide) (MHCflurry) |
| SEQ ID NO: 21 | LTVVGADGV | KRAS G12D | LVVVGADGV | V2T | — | Individual KRAS G12D (NetMHCpan) |
| SEQ ID NO: 22 | LLVVGADGV | KRAS G12D | LVVVGADGV | V2L | — | Individual KRAS G12D (NetMHCpan) |
| SEQ ID NO: 23 | LMVVGADGL | KRAS G12D | LVVVGADGV | V2M | V9L | Individual KRAS G12D (NetMHCpan) |
| SEQ ID NO: 24 | VMGAVGVGR | KRAS G12V | VVGAVGVGK | V2M | K9R | Individual KRAS G12V (NetMHCpan) |
| SEQ ID NO: 25 | VMGARGVGK | KRAS G12R | VVGARGVGK | V2M | — | Individual KRAS G12R (NetMHCpan) |
| SEQ ID NO: 26 | GACGVGKSL | KRAS G12C | GACGVGKSA | — | A9L | Individual KRAS G12C (MHCflurry) |
| SEQ ID NO: 27 | LMVVGACGV | KRAS G12C | LVVVGACGV | V2M | — | Individual KRAS G12C (MHCflurry); Individual KRAS G12C (NetMHCpan) |
| SEQ ID NO: 28 | LTVVGACGV | KRAS G12C | LVVVGACGV | V2T | — | Individual KRAS G12C (MHCflurry); Individual KRAS G12C (NetMHCpan) |
| SEQ ID NO: 29 | VTGACGVGK | KRAS G12C | VVGACGVGK | V2T | — | Individual KRAS G12C (MHCflurry) |
| SEQ ID NO: 30 | VVGACGVGR | KRAS G12C | VVGACGVGK | — | K9R | Individual KRAS G12C (MHCflurry) |
| SEQ ID NO: 31 | AADVGKSAM | KRAS G13D | AGDVGKSAL | G2A | L9M | Individual KRAS G13D (MHCflurry); Individual KRAS G13D (NetMHCpan) |
| SEQ ID NO: 32 | AEDVGKSAM | KRAS G13D | AGDVGKSAL | G2E | L9M | Individual KRAS G13D (MHCfluriy) |
| SEQ ID NO: 33 | AYDVGKSAM | KRAS G13D | AGDVGKSAL | G2Y | L9M | Individual KRAS G13D (MHCfluriy) |
| SEQ ID NO: 34 | DAGKSALTV | KRAS G13D | DVGKSALTI | V2A | I9V | Individual KRAS G13D (MHCflurry) |
| SEQ ID NO: 35 | GAGDVGKSM | KRAS G13D | GAGDVGKSA | — | A9M | Individual KRAS G13D (MHCfluriy) |
| SEQ ID NO: 36 | LQVVGACGV | KRAS G12C | LVVVGACGV | V2Q | — | Individual KRAS G12C (NetMHCpan) |
| SEQ ID NO: 37 | VMGACGVGK | KRAS G12C | VVGACGVGK | V2M | — | Individual KRAS G12C (NetMHCpan) |
| SEQ ID NO: 38 | VMGACGVGR | KRAS G12C | VVGACGVGK | V2M | K9R | Individual KRAS G12C (NetMHCpan) |
| SEQ ID NO: 39 | AADVGKSAL | KRAS G13D | AGDVGKSAL | G2A | — | Individual KRAS G13D (NetMHCpan) |

TABLE 1-continued

Example KRAS Vaccine Peptides (MHC class I)

| SEQ ID NO | Sequence corresponding to SEQ ID | Target | Seed | Heteroclitic Modification P2 | Heteroclitic Modification P9 | Note |
|---|---|---|---|---|---|---|
| SEQ ID NO: 40 | ASDVGKSAL | KRAS G13D | AGDVGKSAL | G2S | — | Individual KRAS G13D (NetMHCpan) |
| SEQ ID NO: 41 | ASDVGKSAM | KRAS G13D | AGDVGKSAL | G2S | L9M | Individual KRAS G13D (NetMHCpan) |

Additional amino acid sequences of WIC class I heteroclitic peptides are provided in Sequence Listings (SEQ ID NOs: 67-1522). In some embodiments, any combination of WIC class I peptides disclosed herein (SEQ ID NOs: 1-41 and 67-1522) may be used to create a combined peptide vaccine having between about 2 and about 40 peptides. In some embodiments, any one of the peptides (SEQ ID NOs: 1-41 and 67-1522) in the combined vaccine comprises or contains an amino acid sequence 80, 81, 82, 83, 84, 85, 86, 87, 88, 89, 90, 91, 92, 93, 94, 95, 96, 97, 98 or 99% identical to any of SEQ ID NOs: 1-41 or 67-1522.

MHC Class II Peptide Sequences

In some embodiments, a peptide vaccine (single target or combined multiple target vaccine) comprises about 2 to 40 MHC class II peptides with each peptide consisting of about 20 amino acids. In some embodiments, an MHC class II peptide vaccine is intended for one or more of the KRAS G12D, G12V, G12R, G12C, and G13D targets.

Table 2 summarizes MHC class II peptide sequences described herein including the respective SEQ ID NO, amino acid sequence corresponding to the SEQ ID NO, the amino acid sequence corresponding to the peptide's binding core, the KRAS protein target (with specific mutation), the seed amino acid sequence (i.e., the amino acid sequence of the wild type KRAS fragment), the seed amino acid sequence of the binding core, and the amino acid substitution (if any) for heteroclitic peptides at positions 1, 4, 6, and 9. Table 2 includes peptide sequences comprising SEQ ID NOs: 42-66. SEQ ID NOs: 42-65 (Table 2) encode for recombinant peptides. In some embodiments, any combination of peptides listed in Table 2 (SEQ ID NOs: 42-66) may be used to create a single target (individual) or combined peptide vaccine having between about 2 and about 40 peptides. In some embodiments, any one of the peptides (peptides 42-66; SEQ ID NOs: 42-66) in the combined vaccine comprises an amino acid sequence 80, 81, 82, 83, 84, 85, 86, 87, 88, 89, 90, 91, 92, 93, 94, 95, 96, 97, 98 or 99% identical to any of SEQ ID NOs: 42-66.

TABLE 2

Example KRAS Vaccine Peptides (MHC class II)

| SEQ ID NO | Sequence corresponding to SEQ ID | Core | Target | Seed | Seed Core | Heteroclitic Modification P1 | Heteroclitic Modification P4 | Heteroclitic Modification P6 | Heteroclitic Modification P9 | Note |
|---|---|---|---|---|---|---|---|---|---|---|
| SEQ ID NO: 42 | EYKFVVFGSDGAGKS | FVVFG SDGA | KRAS G12D | EYKLVVVGADGVGKS | LVVVGADGV | L1F | V4F | A6S | V9A | Individual KRAS G12D (NetMHCIIpan) |
| SEQ ID NO: 43 | EYKFVVIGNDGAGKSALTIQLIQN | FVVIG NDGA | KRAS G12D | EYKLVVVGADGVGKSALTIQLIQN | LVVVGADGV | L1F | V4I | A6N | V9A | Individual KRAS G12D (NetMHCIIpan) |
| SEQ ID NO: 44 | EYKFVVLGADGAGKS | FVVLG ADGA | KRAS G12D | EYKLVVVGADGVGKS | LVVVGADGV | L1F | V4L | — | V9A | Individual KRAS G12D (NetMHCIIpan) |
| SEQ ID NO: 45 | MTEYKFVVSGADGIGKSALT | FVVSG ADGI | KRAS G12D | MTEYKLVVVGADGVGKSALT | LVVVGADGV | L1F | V4S | — | V9I | Individual KRAS G12D (NetMHCIIpan) |
| SEQ ID NO: 46 | MTEYKFVVYGSDGIGKSALT | FVVYG SDGI | KRAS G12D | MTEYKLVVVGADGVGKSALT | LVVVGADGV | L1F | V4Y | A6S | V9I | Individual KRAS G12D (NetMHCIIpan) |
| SEQ ID NO: 47 | EYKFVVIGRVGHGKS | FVVIG RVGH | KRAS G12V | EYKLVVVGAVGVGKS | LVVVGAVGV | L1F | V4I | A6R | V9H | Individual KRAS G12V (NetMHCIIpan) |

TABLE 2-continued

Example KRAS Vaccine Peptides (MHC class II)

| SEQ ID NO | Sequence corresponding to SEQ ID | Core | Target | Seed | Seed Core | Heteroclitic Modification P1 | Heteroclitic Modification P4 | Heteroclitic Modification P6 | Heteroclitic Modification P9 | Note |
|---|---|---|---|---|---|---|---|---|---|---|
| SEQ ID NO: 48 | EYKFVVLGTVGHGKS | FVVLG TVGH | KRAS G12V | EYKLVVVGAVGVGKS | LVVVGAVGV | L1F | V4L | A6T | V9H | Individual KRAS G12V (NetMHCIIpan) |
| SEQ ID NO: 49 | EYKFVVYGNVGMGKS | FVVYG NVGM | KRAS G12V | EYKLVVVGAVGVGKS | LVVVGAVGV | L1F | V4Y | A6N | V9M | Individual KRAS G12V (NetMHCIIpan) |
| SEQ ID NO: 50 | EYKIVVAGNVGIGKS | IVVAG NVGI | KRAS G12V | EYKLVVVGAVGVGKS | LVVVGAVGV | L1I | V4A | A6N | V9I | Individual KRAS G12V (NetMHCIIpan) |
| SEQ ID NO: 51 | TEYKIVVMGNVGYGK | IVVMG NVGY | KRAS G12V | TEYKLVVVGAVGVGK | LVVVGAVGV | L1I | V4M | A6N | V9Y | Individual KRAS G12V (NetMHCIIpan) |
| SEQ ID NO: 52 | MTEYKFVVFGSRGVGKSALT | FVVFG SRGV | KRAS G12R | MTEYKLVVVGARGVGKSALT | LVVVGARGV | L1F | V4F | A6S | — | Individual KRAS G12R (NetMHCIIpan) |
| SEQ ID NO: 53 | MTEYKFVVIGNRGVGKSALT | FVVIG NRGV | KRAS G12R | MTEYKLVVVGARGVGKSALT | LVVVGARGV | L1F | V4I | A6N | — | Individual KRAS G12R (NetMHCIIpan) |
| SEQ ID NO: 54 | MTEYKFVVIGVRGDGKSALT | FVVIG VRGD | KRAS G12R | MTEYKLVVVGARGVGKSALT | LVVVGARGV | L1F | V4I | A6V | V9D | Individual KRAS G12R (NetMHCIIpan) |
| SEQ ID NO: 55 | MTEYKFVVMGSRGAGKSALT | FVVM GSRGA | KRAS G12R | MTEYKLVVVGARGVGKSALT | LVVVGARGV | L1F | V4M | A6S | V9A | Individual KRAS G12R (NetMHCIIpan) |
| SEQ ID NO: 56 | VVVIARGVPKSLLTI | IARGV PKSL | KRAS G12R | VVVGARGVGKSALTI | GARGVGKSA | G1I | — | G6P | A9L | Individual KRAS G12R (NetMHCIIpan) |
| SEQ ID NO: 57 | EYKFVVFGNCGAGKS | FVVFG NCGA | KRAS G12C | EYKLVVVGACGVGKS | LVVVGACGV | L1F | V4F | A6N | V9A | Individual KRAS G12C (NetMHCIIpan) |
| SEQ ID NO: 58 | EYKFVVSGACGVGKS | FVVSG ACGV | KRAS G12C | EYKLVVVGACGVGKS | LVVVGACGV | L1F | V4S | — | — | Individual KRAS G12C (NetMHCIIpan) |
| SEQ ID NO: 59 | EYKFVVSGNCGLGKS | FVVSG NCGL | KRAS G12C | EYKLVVVGACGVGKS | LVVVGACGV | L1F | V4S | A6N | V9L | Individual KRAS G12C (NetMHCIIpan) |
| SEQ ID NO: 60 | EYKLVVMGPCGAGKS | LVVM GPCGA | KRAS G12C | EYKLVVVGACGVGKS | LVVVGACGV | — | V4M | A6P | V9A | Individual KRAS G12C (NetMHCIIpan) |
| SEQ ID NO: 61 | KLVIVGICKVGHSAL | IVGICK VGH | KRAS G12C | KLVVVGACGVGKSAL | VVGACGVGK | V1I | A4I | G6K | K9H | Individual KRAS G12C (NetMHCIIpan) |

TABLE 2-continued

Example KRAS Vaccine Peptides (MHC class II)

| SEQ ID NO | Sequence corresponding to SEQ ID | Core | Target | Seed | Seed Core | Heteroclitic Modification P1 | Heteroclitic Modification P4 | Heteroclitic Modification P6 | Heteroclitic Modification P9 | Note |
|---|---|---|---|---|---|---|---|---|---|---|
| SEQ ID NO: 62 | EYKFVVFGNGDLGKS | FVVFG NGDL | KRAS G13D | EYKLVVVGAGDVGKS | LVVVGAGDV | L1F | V4F | A6N | V9L | Individual KRAS G13D (NetMHCIIpan) |
| SEQ ID NO: 63 | EYKFVVMGNGDSGKS | FVVM GNGDS | KRAS G13D | EYKLVVVGAGDVGKS | LVVVGAGDV | L1F | V4M | A6N | V9S | Individual KRAS G13D (NetMHCIIpan) |
| SEQ ID NO: 64 | EYKFVVSGSGDVGKS | FVVSG SGDV | KRAS G13D | EYKLVVVGAGDVGKS | LVVVGAGDV | L1F | V4S | A6S | — | Individual KRAS G13D (NetMHCIIpan) |
| SEQ ID NO: 65 | EYKIVVMGRGDMGKS | IVVMG RGDM | KRAS G13D | EYKLVVVGAGDVGKS | LVVVGAGDV | L1I | V4M | A6R | V9M | Individual KRAS G13D (NetMHCIIpan) |
| SEQ ID NO: 66 | YKLVVVGAGDVGKSA | — | KRAS G13D | — | — | — | — | — | — | Individual KRAS G13D (NetMHCIIpan) |

In some embodiments, any combination of MHC class I and/or MHC class II peptides disclosed herein (SEQ ID NOs: 1-1522) may be used to create a single target (individual) or combined peptide vaccine having between about 2 and about 40 peptides. In some embodiments, any one of the peptides (peptides 1-1522; SEQ ID NOs: 1-1522) in the combined vaccine comprises an amino acid sequence 80, 81, 82, 83, 84, 85, 86, 87, 88, 89, 90, 91, 92, 93, 94, 95, 96, 97, 98 or 99% identical to any of SEQ ID NOs: 1-1522.

mRNA and DNA Vaccines

In some embodiments, vaccine peptides are encoded as mRNA or DNA molecules and are administered for expression in vivo as is known in the art. One example of the delivery of vaccines by mRNA is found in Kranz et al. (2016), incorporated herein by reference. In one embodiment, a construct comprises 10 peptides, including a five-peptide MHC class I combined pancreatic cancer vaccine (targets: KRAS G12D, G12V, G12R) and a five-peptide MHC class II combined pancreatic cancer vaccine (targets: KRAS G12D, G12V, G12R), as optimized by the procedure described herein. Peptides are prepended with a secretion signal sequence at the N-terminus and followed by an MHC class I trafficking signal (MITD) (Kreiter et al., 2008; Sahin et al., 2017). The MITD has been shown to route antigens to pathways for HLA class I and class II presentation (Kreiter et al., 2008). Here we combine all peptides of each MHC class into a single construct using non-immunogenic glycine/serine linkers from Sahin et al. (2017), though it is also plausible to construct individual constructs containing single peptides with the same secretion and MITD signals as demonstrated by Kreiter et al. (2008).

In some embodiments, the amino acid sequence encoded by the mRNA vaccine comprises SEQ ID NO: 1523. Underlined amino acids correspond to the signal peptide (or leader) sequence. Bolded amino acids correspond to MHC class I (9 amino acids in length; 5 peptides) and MHC class II (13-25 amino acids in length; 5 peptides) peptide sequences. Italicized amino acids correspond to the trafficking signal.

(SEQ ID NO: 1523)
MRVTAPRTLILLLSGALALTETWAGSGGSGGGGSGGGADGVGKSMGGSGG

GGSGGLMVVGADGVGGSGGGGSGGGAVGVGKSLGGSGGGGSGGLMVVGAV

GVGGSGGGGSGGVTGARGVGKGGSGGGGSGGEYKFVVLGTVGHGKSGGSG

GGGSGGEYKIVVAGNVGIGKSGGSGGGGSGGEYKFVVFGSDGAGKSGGSG

GGGSGGMTEYKFVVSGADGIGKSALTGGSGGGGSGGMTEYKFVVIGNRGV

GKSALTGGSLGGGGSG*IVGIVAGLAVLAVVVIGAVVATVMCRRKSSGGKG*

*GSYSQAASSDSAQGSDVSLTA*.

In some embodiments, the vaccine is an mRNA vaccine comprising a nucleic acids sequence encoding the amino acid sequence consisting of SEQ ID NO: 1523. In some embodiments, the nucleic acid sequence of the mRNA vaccine encodes for an amino acid sequence 80, 81, 82, 83, 84, 85, 86, 87, 88, 89, 90, 91, 92, 93, 94, 95, 96, 97, 98 or 99% identical to SEQ ID NO: 1523.

In some embodiments, the vaccine is a DNA vaccine comprising a nucleic acids sequence encoding the amino acid sequence consisting of SEQ ID NO: 1523. In some embodiments, the nucleic acid sequence of the DNA vaccine encodes for an amino acid sequence 80, 81, 82, 83, 84, 85, 86, 87, 88, 89, 90, 91, 92, 93, 94, 95, 96, 97, 98 or 99% identical to SEQ ID NO: 1523.

In some embodiments, one or more MHC class I and/or MHC class II peptides disclosed herein (SEQ ID NO: 1-1522) can be encoded in one or more mRNA or DNA molecules and administered for expression in vivo. In some embodiments between about 2 and about 40 peptide sequences are encoded in one or more mRNA constructs. In some embodiments, between about 2 and about 40 peptide sequences are encoded in one or more DNA constructs (i.e., nucleic acids encoding the amino acids sequences comprising on or more of SEQ ID NOs: 1-1522). In some embodiments, the amino acid sequence of the mRNA vaccine or the nucleic acid sequence of the DNA vaccine encodes for an amino acid sequence 80, 81, 82, 83, 84, 85, 86, 87, 88, 89, 90, 91, 92, 93, 94, 95, 96, 97, 98 or 99% identical to any of SEQ ID NOs: 1-1522.

Non-Limiting Embodiments of the Subject Matter

In one aspect, the invention provides for a nucleic acid sequence encoding two or more amino acid sequences selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, and SEQ ID NO: 41.

In some embodiments, the nucleic acid sequence is an immunogenic composition. In some embodiments, the nucleic acid sequence is administered in a construct for expression in vivo. In some embodiments, the in vivo administration of the nucleic acid sequence is configured to produce one or more peptides that are displayed by an HLA class I molecule. In some embodiments, the one or more peptides is a modified or unmodified fragment of a mutated KRAS protein. In some embodiments, the mutated KRAS protein is selected from the group consisting of KRAS G12D, KRAS G12V, and KRAS G12R. In some embodiments, the nucleic acid sequence is administered in an effective amount to a subject to prevent cancer. In some embodiments, the nucleic acid sequence is administered in an effective amount to a subject to treat cancer.

In another aspect, the invention provides for an immunogenic peptide composition comprising two or more peptides selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, and SEQ ID NO: 41.

In some embodiments, a peptide in the immunogenic peptide composition is displayed by an HLA class I molecule. In some embodiments, a peptide in the immunogenic peptide composition is a modified or unmodified fragment of a mutated KRAS protein. In some embodiments, the mutated KRAS protein is selected from the group consisting of KRAS G12D, KRAS G12V, and KRAS G12R. In some embodiments, the immunogenic peptide composition is administered in an effective amount to a subject to prevent cancer. In some embodiments, the immunogenic peptide composition is administered in an effective amount to a subject to treat cancer. In some embodiments, the immunogenic peptide composition comprises at least three peptides selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, and SEQ ID NO: 41.

In another aspect, the invention provides for a nucleic acid sequence encoding one or more amino acid sequences selected from the group consisting of SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, and SEQ ID NO: 65.

In some embodiments, the nucleic acid sequence is an immunogenic composition. In some embodiments, the nucleic acid sequence is administered in a construct for expression in vivo. In some embodiments, the in vivo administration of the nucleic acid sequence is configured to produce one or more peptides that are displayed by an HLA class II molecule. In some embodiments, the one or more peptides is a modified fragment of a mutated KRAS protein. In some embodiments, the mutated KRAS protein is selected from the group consisting of KRAS G12D, KRAS G12V, KRAS G12R, KRAS G12C, and KRAS G13D. In some embodiments, the nucleic acid sequence is administered in an effective amount to a subject to prevent cancer. In some embodiments, the nucleic acid sequence is administered in an effective amount to a subject to treat cancer.

In another aspect, the invention provides for an immunogenic peptide composition comprising one or more peptides selected from the group consisting of SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, and SEQ ID NO: 65.

In some embodiments, a peptide in the immunogenic peptide composition is displayed by an HLA class II molecule. In some embodiments, a peptide in the immunogenic peptide composition is a modified or unmodified fragment of a mutated KRAS protein. In some embodiments, the mutated KRAS protein is selected from the group consisting of KRAS G12D, KRAS G12V, KRAS G12R, KRAS G12C, and KRAS G13D. In some embodiments, the immunogenic peptide composition is administered in an effective amount to a subject to prevent cancer. In some embodiments, the immunogenic peptide composition is administered in an effective amount to a subject to treat cancer. In some embodiments, the immunogenic peptide composition comprises at least two peptides selected from the group consisting of SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, and SEQ ID NO: 65.

Compositions

In some embodiments, the foreign peptides (e.g., peptide vaccine) are administered in a pharmaceutical composition comprising the peptides and a pharmaceutically acceptable carrier. In some embodiments, the pharmaceutical composition is in the form of a spray, aerosol, gel, solution, emulsion, or suspension.

The composition is preferably administered to a subject with a pharmaceutically acceptable carrier. Typically, in some embodiments, an appropriate amount of a pharmaceutically acceptable salt is used in the formulation, which in some embodiments can render the formulation isotonic.

In certain embodiments, the foreign peptides are provided as an immunogenic composition comprising any one of the foreign peptides described herein and a pharmaceutically acceptable carrier. In certain embodiments, the immunogenic composition further comprises an adjuvant. In certain embodiments, the foreign peptides are conjugated with other molecules to increase their effectiveness as is known by those practiced in the art. For example, peptides can be coupled to antibodies that recognize cell surface proteins on antigen presenting cells to enhance vaccine effectiveness. One such method for increasing the effectiveness of peptide delivery is described in Woodham, et al. (2018).

In some embodiments, the pharmaceutically acceptable carrier is selected from the group consisting of saline, Ringer's solution, dextrose solution, and a combination thereof. Other suitable pharmaceutically acceptable carriers known in the art are contemplated. Suitable carriers and their formulations are described in Remington's Pharmaceutical Sciences, 2005, Mack Publishing Co. The pH of the solution is preferably from about 5 to about 8, and more preferably from about 7 to about 7.5. The formulation may also comprise a lyophilized powder. Further carriers include sustained release preparations such as semipermeable matrices of solid hydrophobic polymers, which matrices are in the form of shaped articles, e.g., films, liposomes or microparticles. It will be apparent to those persons skilled in the art that certain carriers may be more preferable depending upon, for instance, the route of administration and concentration of peptides being administered.

The phrase pharmaceutically acceptable carrier as used herein means a pharmaceutically acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier is acceptable in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as butylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. The term carrier denotes an organic or inorganic ingredient, natural or synthetic, with which the active ingredient is combined to facilitate the application. The components of the pharmaceutical compositions also are capable of being comingled with the compounds of the present invention, and with each other, in a manner such that there is no interaction which would substantially impair the desired pharmaceutical efficiency. The composition may also include additional agents such as an isotonicity agent, a preservative, a surfactant, and, a divalent cation, preferably, zinc.

The composition can also include an excipient, or an agent for stabilization of a foreign peptide composition, such as a buffer, a reducing agent, a bulk protein, amino acids (such as e.g., glycine or praline) or a carbohydrate. Bulk proteins useful in formulating foreign peptide compositions include albumin. Typical carbohydrates useful in formulating foreign peptides include but are not limited to sucrose, mannitol, lactose, trehalose, or glucose.

Surfactants may also be used to prevent soluble and insoluble aggregation and/or precipitation of foreign peptides or proteins included in the composition. Suitable surfactants include but are not limited to sorbitan trioleate, soya lecithin, and oleic acid. In certain cases, solution aerosols are preferred using solvents such as ethanol. Thus, formulations including foreign peptides can also include a surfactant that can reduce or prevent surface-induced aggregation of foreign peptides by atomization of the solution in forming an aerosol. Various conventional surfactants can be employed, such as polyoxyethylene fatty acid esters and alcohols, and polyoxyethylene sorbitol fatty acid esters. Amounts will generally range between 0.001% and 4% by weight of the formulation. In some embodiments, surfactants used with the present disclosure are polyoxyethylene sorbitan mono-oleate, polysorbate 80, polysorbate 20. Additional agents known in the art can also be included in the composition.

In some embodiments, the pharmaceutical compositions and dosage forms further comprise one or more compounds that reduce the rate by which an active ingredient will decay, or the composition will change in character. So called stabilizers or preservatives may include, but are not limited to, amino acids, antioxidants, pH buffers, or salt buffers. Nonlimiting examples of antioxidants include butylated hydroxy anisole (BHA), ascorbic acid and derivatives thereof, tocopherol and derivatives thereof, butylated hydroxy anisole and cysteine. Nonlimiting examples of preservatives include parabens, such as methyl or propyl p-hydroxybenzoate and benzalkonium chloride. Additional nonlimiting examples of amino acids include glycine or proline.

The present invention also teaches the stabilization (preventing or minimizing thermally or mechanically induced soluble or insoluble aggregation and/or precipitation of an inhibitor protein) of liquid solutions containing foreign peptides at neutral pH or less than neutral pH by the use of amino acids including proline or glycine, with or without divalent cations resulting in clear or nearly clear solutions that are stable at room temperature or preferred for pharmaceutical administration.

In one embodiment, the composition is a pharmaceutical composition of single unit or multiple unit dosage forms. Pharmaceutical compositions of single unit or multiple unit dosage forms of the invention comprise a prophylactically or therapeutically effective amount of one or more compositions (e.g., a compound of the invention, or other prophylactic or therapeutic agent), typically, one or more vehicles, carriers, or excipients, stabilizing agents, and/or preservatives. Preferably, the vehicles, carriers, excipients, stabilizing agents and preservatives are pharmaceutically acceptable.

In some embodiments, the pharmaceutical compositions and dosage forms comprise anhydrous pharmaceutical compositions and dosage forms. Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprise a primary or secondary amine are preferably anhydrous if substantial contact with moisture and/or humidity during manufacturing, packaging, and/or storage is expected. An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Suitable vehicles are well known to those skilled in the art of pharmacy, and non-limiting examples of suitable vehicles include glucose, sucrose, starch, lactose, gelatin, rice, silica gel, glycerol, talc, sodium chloride, dried skim milk, propylene glycol, water, sodium stearate, ethanol, and similar substances well known in the art. Saline solutions and aqueous dextrose and glycerol solutions can also be employed as liquid vehicles. Whether a particular vehicle is suitable for incorporation into a pharmaceutical composition or dosage form depends on a variety of factors well known in the art including, but not limited to, the way in which the dosage form will be administered to a patient and the specific active ingredients in the dosage form. Pharmaceutical vehicles can be sterile liquids, such as water and oils, including those of petroleum, animal, vegetable or synthetic origin, such as peanut oil, soybean oil, mineral oil, sesame oil and the like.

The invention also provides that a pharmaceutical composition can be packaged in a hermetically sealed container such as an ampoule or sachette indicating the quantity. In one embodiment, the pharmaceutical composition can be supplied as a dry sterilized lyophilized powder in a delivery device suitable for administration to the lower airways of a patient. The pharmaceutical compositions can, if desired, be presented in a pack or dispenser device that can contain one or more unit dosage forms containing the active ingredient. The pack can for example comprise metal or plastic foil, such as a blister pack. The pack or dispenser device can be accompanied by instructions for administration.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for administration may be in the form of powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouthwashes and the like, each containing a predetermined amount of a compound of the present invention (e.g., peptides) as an active ingredient.

A liquid composition herein can be used as such with a delivery device, or they can be used for the preparation of pharmaceutically acceptable formulations comprising foreign peptides that are prepared for example by the method of spray drying. The methods of spray freeze-drying foreign peptides/proteins for pharmaceutical administration disclosed in Maa et al., Curr. Pharm. Biotechnol., 2001, 1, 283-302, are incorporated herein. In another embodiment, the liquid solutions herein are freeze spray dried and the spray-dried product is collected as a dispersible foreign peptide-containing powder that is therapeutically effective when administered to an individual.

The compounds and pharmaceutical compositions of the present invention can be employed in combination therapies, that is, the compounds and pharmaceutical compositions can be administered concurrently with, prior to, or subsequent to, one or more other desired therapeutics or medical procedures (e.g., foreign peptide vaccine can be used in combination therapy with another treatment such as chemotherapy, radiation, pharmaceutical agents, and/or another treatment). The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, the compound of the present invention may be administered concurrently with another therapeutic or prophylactic).

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The current invention provides for dosage forms comprising foreign peptides suitable for treating cancer or other diseases. The dosage forms can be formulated, e.g., as sprays, aerosols, nanoparticles, liposomes, or other forms known to one of skill in the art. See, e.g., Remington's Pharmaceutical Sciences; Remington: The Science and Practice of Pharmacy supra; Pharmaceutical Dosage Forms and Drug Delivery Systems by Howard C., Ansel et al., Lippincott Williams & Wilkins; 7th edition (Oct. 1, 1999).

Generally, a dosage form used in the acute treatment of a disease may contain larger amounts of one or more of the active ingredients it comprises than a dosage form used in the chronic treatment of the same disease. In addition, the prophylactically and therapeutically effective dosage form may vary among different conditions. For example, a therapeutically effective dosage form may contain peptides that has an appropriate immunogenic action when intending to treat cancer or other disease. On the other hand, a different effective dosage may contain foreign peptides that has an appropriate immunogenic action when intending to use the peptides of the invention as a prophylactic (e.g., vaccine) against cancer or another disease/condition. These and other ways in which specific dosage forms encompassed by this invention will vary from one another and will be readily apparent to those skilled in the art. See, e.g., Remington's Pharmaceutical Sciences, 2005, Mack Publishing Co.; Remington: The Science and Practice of Pharmacy by Gennaro, Lippincott Williams & Wilkins; 20th edition (2003); Pharmaceutical Dosage Forms and Drug Delivery Systems by Howard C. Ansel et al., Lippincott Williams & Wilkins; 7th edition (Oct. 1, 1999); and Encyclopedia of Pharmaceutical Technology, edited by Swarbrick, J. & J.C. Boylan, Marcel Dekker, Inc., New York, 1988, which are incorporated herein by reference in their entirety.

The pH of a pharmaceutical composition or dosage form may also be adjusted to improve delivery and/or stability of one or more active ingredients. Similarly, the polarity of a solvent carrier, its ionic strength, or tonicity can be adjusted to improve delivery. Compounds such as stearates can also be added to pharmaceutical compositions or dosage forms to alter advantageously the hydrophilicity or lipophilicity of one or more active ingredients to improve delivery. In this regard, stearates can also serve as a lipid vehicle for the formulation, as an emulsifying agent or surfactant, and as a delivery enhancing or penetration-enhancing agent. Different salts, hydrates, or solvates of the active ingredients can be used to adjust further the properties of the resulting composition.

Compositions can be formulated with appropriate carriers and adjuvants using techniques to yield compositions suitable for immunization. The compositions can include an adjuvant, such as, for example but not limited to, alum, poly IC, MF-59, squalene-based adjuvants, or liposomal based adjuvants suitable for immunization.

In some embodiments, the compositions and methods comprise any suitable agent or immune modulation which could modulate mechanisms of host immune tolerance and release of the induced antibodies. In certain embodiments, an immunomodulatory agent is administered in at time and in an amount sufficient for transient modulation of the subject's immune response so as to induce an immune response which comprises antibodies against for example tumor neoantigens (i.e., tumor-specific antigens (TSA)).

Expression Systems

In certain aspects, the invention provides culturing a cell line that expresses any one of the foreign peptides of the invention in a culture medium comprising any of the foreign peptides described herein.

Various expression systems for producing recombinant proteins/peptides are known in the art, and include, prokaryotic (e.g., bacteria), plant, insect, yeast, and mammalian expression systems. Suitable cell lines, can be transformed, transduced, or transfected with nucleic acids containing coding sequences for the foreign peptides of the invention in order to produce the molecule of interest. Expression vectors containing such a nucleic acid sequence, which can be linked to at least one regulatory sequence in a manner that allows expression of the nucleotide sequence in a host cell, can be introduced via methods known in the art. Practitioners in the art understand that designing an expression vector can depend on factors, such as the choice of host cell to be transfected and/or the type and/or amount of desired protein to be expressed. Enhancer regions, which are those sequences found upstream or downstream of the promoter region in non-coding DNA regions, are also known in the art to be important in optimizing expression. If needed, origins of replication from viral sources can be employed, such as if a prokaryotic host is utilized for introduction of plasmid DNA. However, in eukaryotic organisms, chromosome integration is a common mechanism for DNA replication. For stable transfection of mammalian cells, a small fraction of cells can integrate introduced DNA into their genomes. The expression vector and transfection method utilized can be factors that contribute to a successful integration event. For stable amplification and expression of a desired protein, a vector containing DNA encoding a protein of interest is stably integrated into the genome of eukaryotic cells (for example mammalian cells), resulting in the stable expression of transfected genes. A gene that encodes a selectable marker (for example, resistance to antibiotics or drugs) can be introduced into host cells along with the gene of interest in order to identify and select clones that stably express a gene encoding a protein of interest. Cells containing the gene of interest can be identified by drug selection wherein cells that have incorporated the selectable marker gene will survive in the presence of the drug. Cells that have not incorporated the gene for the selectable marker die. Surviving cells can then be screened for the production of the desired protein molecule.

A host cell strain, which modulates the expression of the inserted sequences, or modifies and processes the nucleic acid in a specific fashion desired also may be chosen. Such modifications (for example, glycosylation and other post-translational modifications) and processing (for example, cleavage) of peptide/protein products may be important for the function of the peptide/protein. Different host cell strains have characteristic and specific mechanisms for the post-translational processing and modification of proteins and gene products. As such, appropriate host systems or cell lines can be chosen to ensure the correct modification and processing of the foreign protein expressed. Thus, eukaryotic host cells possessing the cellular machinery for proper processing of the primary transcript, glycosylation, and phosphorylation of the gene product may be used.

Various culturing parameters can be used with respect to the host cell being cultured. Appropriate culture conditions for mammalian cells are well known in the art (Cleveland W L, et al., J Immunol Methods, 1983, 56(2): 221-234) or can be determined by the skilled artisan (see, for example, Animal Cell Culture: A Practical Approach 2nd Ed., Rickwood, D. and Hames, B. D., eds. (Oxford University Press: New York, 1992)). Cell culturing conditions can vary according to the type of host cell selected. Commercially available medium can be utilized.

Foreign peptides of the invention can be purified from any human or non-human cell which expresses the polypeptide, including those which have been transfected with expression constructs that express foreign peptides of the invention. For protein recovery, isolation and/or purification, the cell culture medium or cell lysate is centrifuged to remove particulate cells and cell debris. The desired polypeptide molecule is isolated or purified away from contaminating soluble proteins and polypeptides by suitable purification techniques. Non-limiting purification methods for proteins include: size exclusion chromatography; affinity chromatography; ion exchange chromatography; ethanol precipitation; reverse phase HPLC; chromatography on a resin, such as silica, or cation exchange resin, e.g., DEAE; chromatofocusing; SDS-PAGE; ammonium sulfate precipitation; gel filtration using, e.g., Sephadex G-75, Sepharose; protein A sepharose chromatography for removal of immunoglobulin contaminants; and the like. Other additives, such as protease inhibitors (e.g., PMSF or proteinase K) can be used to inhibit proteolytic degradation during purification. Purification procedures that can select for carbohydrates can also be used, e.g., ion-exchange soft gel chromatography, or HPLC using cation- or anionexchange resins, in which the more acidic fraction(s) is/are collected.

Methods of Treatment

In one embodiment, the subject matter disclosed herein relates to a preventive medical treatment started after following diagnosis of cancer in order to prevent the disease from worsening or curing the disease. In one embodiment, the subject matter disclosed herein relates to prophylaxis of subjects who are believed to be at risk for cancer or have previously been diagnosed with cancer (or another disease). In one embodiment, said subjects can be administered the peptide vaccine described herein or pharmaceutical compositions thereof. The invention contemplates using any of the foreign peptides produced by the systems and methods described herein. In one embodiment, the foreign peptide vaccines described herein can be administered subcutaneously via syringe or any other suitable method know in the art.

The compound(s) or combination of compounds disclosed herein, or pharmaceutical compositions may be administered to a cell, mammal, or human by any suitable means. Non-limiting examples of methods of administration include, among others, (a) administration though oral pathways, which includes administration in capsule, tablet, granule, spray, syrup, or other such forms; (b) administration through non-oral pathways such as intraocular, intranasal, intraauricular, rectal, vaginal, intraurethral, transmucosal, buccal, or transdermal, which includes administration as an aqueous suspension, an oily preparation or the like or as a drip, spray, suppository, salve, ointment or the like; (c) administration via injection, including subcutaneously, intraperitoneally, intravenously, intramuscularly, intradermally, intraorbitally, intracapsularly, intraspinally, intrasternally, or the like, including infusion pump delivery; (d) administration locally such as by injection directly in the renal or cardiac area, e.g., by depot implantation; (e) administration topically; as deemed appropriate by those of skill in the art for bringing the compound or combination of compounds disclosed herein into contact with living tissue; (f) administration via inhalation, including through aerosolized, nebulized, and powdered formulations; and (g) administration through implantation.

As will be readily apparent to one skilled in the art, the effective in vivo dose to be administered and the particular mode of administration will vary depending upon the age, weight and species treated, and the specific use for which the compound or combination of compounds disclosed herein are employed. The determination of effective dose levels, that is the dose levels necessary to achieve the desired result, can be accomplished by one skilled in the art using routine pharmacological methods. Typically, human clinical applications of products are commenced at lower dose levels, with dose level being increased until the desired effect is achieved. Alternatively, acceptable in vitro studies can be used to establish useful doses and routes of administration of the compositions identified by the present methods using established pharmacological methods. Effective animal doses from in vivo studies can be converted to appropriate human doses using conversion methods known in the art (e.g., see Nair AB, Jacob S. A simple practice guide for dose conversion between animals and human. Journal of basic and clinical pharmacy. 2016 March; 7(2):27.)

Methods of Prevention

In some embodiments, the foreign peptides prepared using methods of the invention can be used as a vaccine to promote an immune response against cancer (e.g., against tumor neoantigens). In some embodiments, the invention provides compositions and methods for induction of immune response, for example induction of antibodies to tumor neoantigens. In some embodiments, the antibodies are broadly neutralizing antibodies. In some embodiments, the foreign peptides prepared using methods of the invention can be used as a vaccine to promote an immune response against a pathogen.

The compositions, systems, and methods disclosed herein are not to be limited in scope to the specific embodiments described herein. Indeed, various modifications of the compositions, systems, and methods in addition to those described will become apparent to those of skill in the art from the foregoing description.

What is claimed:

1. An immunogenic composition comprising one or more polynucleotides encoding at least one amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 23, SEQ ID NO: 24, SEQ ID NO: 25, SEQ ID NO: 26, SEQ ID NO: 27, SEQ ID NO: 28, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, and SEQ ID NO: 41.

2. The immunogenic composition of claim 1, wherein the one or more polynucleotides are contained in a construct for in vivo expression of at least one peptide encoded by the one or more polynucleotides.

3. The immunogenic composition of claim 2, wherein an administration of the one or more polynucleotides causes the at least one peptide encoded by the one or more polynucleotides to be displayed by an HLA class I molecule in a subject.

4. The immunogenic composition of claim 1, wherein the immunogenic composition comprises one or more polynucleotides encoding at least two amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 23, SEQ ID NO: 24, SEQ ID NO: 25, SEQ ID NO: 26, SEQ ID NO: 27, SEQ ID NO: 28, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, and SEQ ID NO: 41.

5. The composition of claim 4, wherein the one or more polynucleotides are contained in a construct for in vivo expression in a subject of at least two peptides encoded by the one or more polynucleotides.

6. The composition of claim 5, wherein an administration of the one or more polynucleotides causes the at least two peptides encoded by the one or more polynucleotides to be displayed by a HLA class I molecule in the subject.

7. The composition of claim 6, wherein the administration of the one or more polynucleotides causes:
   a first peptide of the at least two peptides to be displayed by a first plurality of HLA class I alleles; and
   a second peptide of the at least two peptides to be displayed by a second plurality of HLA class I alleles,
   wherein the first plurality of HLA class I alleles and the second plurality of HLA class I alleles differ by at least one HLA class I allele.

8. A method of treating cancer in a subject in need thereof, the method comprising administering to the subject an effective amount of the immunogenic composition of claim 1, wherein the at least one amino acid sequence is selected based on a mutated KRAS protein that is expressed in the subject and is associated with the cancer.

9. An immunogenic composition comprising at least one peptide selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 23, SEQ ID NO: 24, SEQ ID NO: 25, SEQ ID NO: 26, SEQ ID NO: 27, SEQ ID NO: 28, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, and SEQ ID NO: 41.

10. The immunogenic composition of claim 9, wherein the at least one peptide is capable of being displayed by an HLA class I molecule present in a subject.

11. The immunogenic composition of claim 9, wherein the immunogenic composition comprises at least two peptides selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 23, SEQ ID NO: 24, SEQ ID NO: 25, SEQ ID NO: 26, SEQ ID NO: 27, SEQ ID NO: 28, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, and SEQ ID NO: 41.

12. The immunogenic composition of claim 11, wherein the at least two peptides are capable of being displayed by an HLA class I molecule present in a subject.

13. The immunogenic composition of claim 12, wherein:
   a first peptide of the at least two peptides is capable of being displayed by a first plurality of HLA class I alleles; and
   a second peptide of the at least two peptides is capable of being displayed by a second plurality of HLA class I alleles, wherein the first plurality of HLA class I alleles and the second plurality of HLA class I alleles differ by at least one HLA class I allele.

14. A method of treating cancer in a subject in need thereof, the method comprising administering to the subject an effective amount of the immunogenic composition of claim 9, wherein the at least one peptide is selected based on a mutated KRAS protein that is expressed in the subject and is associated with the cancer.

* * * * *

SEQUENCE LISTING

```
Sequence total quantity: 1523
SEQ ID NO: 1            moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 1
GADGVGKSM                                                                 9

SEQ ID NO: 2            moltype = AA  length = 9
FEATURE                 Location/Qualifiers
source                  1..9
                        organism = synthetic construct
                        mol_type = protein
                        note = Seed: LVVVGADGV (KRAS G12D)
SEQUENCE: 2
LMVVGADGV                                                                 9

SEQ ID NO: 3            moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 3
GAVGVGKSL                                                                 9
```

| | | |
|---|---|---|
| SEQ ID NO: 4<br>FEATURE<br>source<br><br>SEQUENCE: 4<br>LMVVGAVGV | moltype = AA   length = 9<br>Location/Qualifiers<br>1..9<br>organism = synthetic construct<br>mol_type = protein<br>note = Seed: LVVVGAVGV (KRAS G12V) | <br><br><br><br><br>9 |
| SEQ ID NO: 5<br>FEATURE<br>source<br><br>SEQUENCE: 5<br>VTGARGVGK | moltype = AA   length = 9<br>Location/Qualifiers<br>1..9<br>organism = synthetic construct<br>mol_type = protein<br>note = Seed: VVGARGVGK (KRAS G12R) | <br><br><br><br><br>9 |
| SEQ ID NO: 6<br>FEATURE<br>source<br><br>SEQUENCE: 6<br>VMGAVGVGK | moltype = AA   length = 9<br>Location/Qualifiers<br>1..9<br>organism = synthetic construct<br>mol_type = protein<br>note = Seed: VVGAVGVGK (KRAS G12V) | <br><br><br><br><br>9 |
| SEQ ID NO: 7<br>FEATURE<br>source<br><br>SEQUENCE: 7<br>VVGAVGVGK | moltype = AA   length = 9<br>Location/Qualifiers<br>1..9<br>organism = Homo sapiens<br>mol_type = protein<br>note = Native (KRAS G12V) | <br><br><br><br><br>9 |
| SEQ ID NO: 8<br>FEATURE<br>source<br><br>SEQUENCE: 8<br>GARGVGKSY | moltype = AA   length = 9<br>Location/Qualifiers<br>1..9<br>organism = synthetic construct<br>mol_type = protein<br>note = Seed: GARGVGKSA (KRAS G12R) | <br><br><br><br><br>9 |
| SEQ ID NO: 9<br>FEATURE<br>source<br><br>SEQUENCE: 9<br>GPRGVGKSA | moltype = AA   length = 9<br>Location/Qualifiers<br>1..9<br>organism = synthetic construct<br>mol_type = protein<br>note = Seed: GARGVGKSA (KRAS G12R) | <br><br><br><br><br>9 |
| SEQ ID NO: 10<br>FEATURE<br>source<br><br>SEQUENCE: 10<br>LMVVGARGV | moltype = AA   length = 9<br>Location/Qualifiers<br>1..9<br>organism = synthetic construct<br>mol_type = protein<br>note = Seed: LVVVGARGV (KRAS G12R) | <br><br><br><br><br>9 |
| SEQ ID NO: 11<br>FEATURE<br>source<br><br>SEQUENCE: 11<br>GADGVGKSL | moltype = AA   length = 9<br>Location/Qualifiers<br>1..9<br>organism = synthetic construct<br>mol_type = protein<br>note = Seed: GADGVGKSA (KRAS G12D) | <br><br><br><br><br>9 |
| SEQ ID NO: 12<br>FEATURE<br>source<br><br>SEQUENCE: 12 | moltype = AA   length = 9<br>Location/Qualifiers<br>1..9<br>organism = synthetic construct<br>mol_type = protein<br>note = Seed: GADGVGKSA (KRAS G12D) | |

```
GADGVGKSY                                                                              9

SEQ ID NO: 13           moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 13
GYDGVGKSM                                                                              9

SEQ ID NO: 14           moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 14
GPVGVGKSV                                                                              9

SEQ ID NO: 15           moltype = AA  length = 9
FEATURE                 Location/Qualifiers
source                  1..9
                        organism = synthetic construct
                        mol_type = protein
                        note = Seed: LVVVGAVGV (KRAS G12V)
SEQUENCE: 15
LTVVGAVGV                                                                              9

SEQ ID NO: 16           moltype = AA  length = 9
FEATURE                 Location/Qualifiers
source                  1..9
                        organism = synthetic construct
                        mol_type = protein
                        note = Seed: VVGAVGVGK (KRAS G12V)
SEQUENCE: 16
VVGAVGVGR                                                                              9

SEQ ID NO: 17           moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 17
GARGVGKSM                                                                              9

SEQ ID NO: 18           moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 18
GPRGVGKSV                                                                              9

SEQ ID NO: 19           moltype = AA  length = 9
FEATURE                 Location/Qualifiers
source                  1..9
                        organism = synthetic construct
                        mol_type = protein
                        note = Seed: LVVVGARGV (KRAS G12R)
SEQUENCE: 19
LLVVGARGV                                                                              9

SEQ ID NO: 20           moltype = AA  length = 9
FEATURE                 Location/Qualifiers
source                  1..9
                        organism = synthetic construct
                        mol_type = protein
                        note = Seed: VVGARGVGK (KRAS G12R)
SEQUENCE: 20
VAGARGVGM                                                                              9

SEQ ID NO: 21           moltype = AA  length = 9
FEATURE                 Location/Qualifiers
source                  1..9
                        organism = synthetic construct
                        mol_type = protein
```

```
                           note = Seed: LVVVGADGV (KRAS G12D)
SEQUENCE: 21
LTVVGADGV                                                                   9

SEQ ID NO: 22              moltype = AA  length = 9
FEATURE                    Location/Qualifiers
source                     1..9
                           organism = synthetic construct
                           mol_type = protein
                           note = Seed: LVVVGADGV (KRAS G12D)
SEQUENCE: 22
LLVVGADGV                                                                   9

SEQ ID NO: 23              moltype = AA  length = 9
FEATURE                    Location/Qualifiers
source                     1..9
                           organism = synthetic construct
                           mol_type = protein
                           note = Seed: LVVVGADGV (KRAS G12D)
SEQUENCE: 23
LMVVGADGL                                                                   9

SEQ ID NO: 24              moltype = AA  length = 9
FEATURE                    Location/Qualifiers
source                     1..9
                           organism = synthetic construct
                           mol_type = protein
                           note = Seed: VVGAVGVGK (KRAS G12V)
SEQUENCE: 24
VMGAVGVGR                                                                   9

SEQ ID NO: 25              moltype = AA  length = 9
FEATURE                    Location/Qualifiers
source                     1..9
                           organism = synthetic construct
                           mol_type = protein
                           note = Seed: VVGARGVGK (KRAS G12R)
SEQUENCE: 25
VMGARGVGK                                                                   9

SEQ ID NO: 26              moltype = AA  length = 9
FEATURE                    Location/Qualifiers
source                     1..9
                           organism = synthetic construct
                           mol_type = protein
                           note = Seed: GACGVGKSA (KRAS G12C)
SEQUENCE: 26
GACGVGKSL                                                                   9

SEQ ID NO: 27              moltype = AA  length = 9
FEATURE                    Location/Qualifiers
source                     1..9
                           organism = synthetic construct
                           mol_type = protein
                           note = Seed: LVVVGACGV (KRAS G12C)
SEQUENCE: 27
LMVVGACGV                                                                   9

SEQ ID NO: 28              moltype = AA  length = 9
FEATURE                    Location/Qualifiers
source                     1..9
                           organism = synthetic construct
                           mol_type = protein
                           note = Seed: LVVVGACGV (KRAS G12C)
SEQUENCE: 28
LTVVGACGV                                                                   9

SEQ ID NO: 29              moltype = AA  length = 9
FEATURE                    Location/Qualifiers
source                     1..9
                           organism = synthetic construct
                           mol_type = protein
                           note = Seed: VVGACGVGK (KRAS G12C)
SEQUENCE: 29
VTGACGVGK                                                                   9

SEQ ID NO: 30              moltype = AA  length = 9
FEATURE                    Location/Qualifiers
source                     1..9
```

```
                        organism = synthetic construct
                        mol_type = protein
                        note = Seed: VVGACGVGK (KRAS G12C)
SEQUENCE: 30
VVGACGVGR                                                                        9

SEQ ID NO: 31           moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 31
AADVGKSAM                                                                        9

SEQ ID NO: 32           moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 32
AEDVGKSAM                                                                        9

SEQ ID NO: 33           moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 33
AYDVGKSAM                                                                        9

SEQ ID NO: 34           moltype = AA  length = 9
FEATURE                 Location/Qualifiers
source                  1..9
                        organism = synthetic construct
                        mol_type = protein
                        note = Seed: DVGKSALTI (KRAS G13D)
SEQUENCE: 34
DAGKSALTV                                                                        9

SEQ ID NO: 35           moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 35
GAGDVGKSM                                                                        9

SEQ ID NO: 36           moltype = AA  length = 9
FEATURE                 Location/Qualifiers
source                  1..9
                        organism = synthetic construct
                        mol_type = protein
                        note = Seed: LVVVGACGV (KRAS G12C)
SEQUENCE: 36
LQVVGACGV                                                                        9

SEQ ID NO: 37           moltype = AA  length = 9
FEATURE                 Location/Qualifiers
source                  1..9
                        organism = synthetic construct
                        mol_type = protein
                        note = Seed: VVGACGVGK (KRAS G12C)
SEQUENCE: 37
VMGACGVGK                                                                        9

SEQ ID NO: 38           moltype = AA  length = 9
FEATURE                 Location/Qualifiers
source                  1..9
                        organism = synthetic construct
                        mol_type = protein
                        note = Seed: VVGACGVGK (KRAS G12C)
SEQUENCE: 38
VMGACGVGR                                                                        9

SEQ ID NO: 39           moltype = AA  length = 9
```

```
FEATURE                 Location/Qualifiers
source                  1..9
                        organism = synthetic construct
                        mol_type = protein
                        note = Seed: AGDVGKSAL (KRAS G13D)
SEQUENCE: 39
AADVGKSAL                                                                9

SEQ ID NO: 40           moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 40
ASDVGKSAL                                                                9

SEQ ID NO: 41           moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 41
ASDVGKSAM                                                                9

SEQ ID NO: 42           moltype = AA  length = 15
FEATURE                 Location/Qualifiers
source                  1..15
                        organism = synthetic construct
                        mol_type = protein
                        note = Seed: EYKLVVVGADGVGKS (KRAS G12D)
SEQUENCE: 42
EYKFVVFGSD GAGKS                                                        15

SEQ ID NO: 43           moltype = AA  length = 24
FEATURE                 Location/Qualifiers
source                  1..24
                        organism = synthetic construct
                        mol_type = protein
                        note = Seed: EYKLVVVGADGVGKSALTIQLIQN (KRAS G12D)
SEQUENCE: 43
EYKFVVIGND GAGKSALTIQ LIQN                                              24

SEQ ID NO: 44           moltype = AA  length = 15
FEATURE                 Location/Qualifiers
source                  1..15
                        organism = synthetic construct
                        mol_type = protein
                        note = Seed: EYKLVVVGADGVGKS (KRAS G12D)
SEQUENCE: 44
EYKFVVLGAD GAGKS                                                        15

SEQ ID NO: 45           moltype = AA  length = 20
FEATURE                 Location/Qualifiers
source                  1..20
                        organism = synthetic construct
                        mol_type = protein
                        note = Seed: MTEYKLVVVGADGVGKSALT (KRAS G12D)
SEQUENCE: 45
MTEYKFVVSG ADGIGKSALT                                                   20

SEQ ID NO: 46           moltype = AA  length = 20
FEATURE                 Location/Qualifiers
source                  1..20
                        organism = synthetic construct
                        mol_type = protein
                        note = Seed: MTEYKLVVVGADGVGKSALT (KRAS G12D)
SEQUENCE: 46
MTEYKFVVYG SDGIGKSALT                                                   20

SEQ ID NO: 47           moltype = AA  length = 15
FEATURE                 Location/Qualifiers
source                  1..15
                        organism = synthetic construct
                        mol_type = protein
                        note = Seed: EYKLVVVGAVGVGKS (KRAS G12V)
SEQUENCE: 47
EYKFVVIGRV GHGKS                                                        15
```

```
SEQ ID NO: 48           moltype = AA  length = 15
FEATURE                 Location/Qualifiers
source                  1..15
                        organism = synthetic construct
                        mol_type = protein
                        note = Seed: EYKLVVVGAVGVGKS (KRAS G12V)
SEQUENCE: 48
EYKFVVLGTV GHGKS                                                       15

SEQ ID NO: 49           moltype = AA  length = 15
FEATURE                 Location/Qualifiers
source                  1..15
                        organism = synthetic construct
                        mol_type = protein
                        note = Seed: EYKLVVVGAVGVGKS (KRAS G12V)
SEQUENCE: 49
EYKFVVYGNV GMGKS                                                       15

SEQ ID NO: 50           moltype = AA  length = 15
FEATURE                 Location/Qualifiers
source                  1..15
                        organism = synthetic construct
                        mol_type = protein
                        note = Seed: EYKLVVVGAVGVGKS (KRAS G12V)
SEQUENCE: 50
EYKIVVAGNV GIGKS                                                       15

SEQ ID NO: 51           moltype = AA  length = 15
FEATURE                 Location/Qualifiers
source                  1..15
                        organism = synthetic construct
                        mol_type = protein
                        note = Seed: TEYKLVVVGAVGVGK (KRAS G12V)
SEQUENCE: 51
TEYKIVVMGN VGYGK                                                       15

SEQ ID NO: 52           moltype = AA  length = 20
FEATURE                 Location/Qualifiers
source                  1..20
                        organism = synthetic construct
                        mol_type = protein
                        note = Seed: MTEYKLVVVGARGVGKSALT (KRAS G12R)
SEQUENCE: 52
MTEYKFVVFG SRGVGKSALT                                                  20

SEQ ID NO: 53           moltype = AA  length = 20
FEATURE                 Location/Qualifiers
source                  1..20
                        organism = synthetic construct
                        mol_type = protein
                        note = Seed: MTEYKLVVVGARGVGKSALT (KRAS G12R)
SEQUENCE: 53
MTEYKFVVIG NRGVGKSALT                                                  20

SEQ ID NO: 54           moltype = AA  length = 20
FEATURE                 Location/Qualifiers
source                  1..20
                        organism = synthetic construct
                        mol_type = protein
                        note = Seed: MTEYKLVVVGARGVGKSALT (KRAS G12R)
SEQUENCE: 54
MTEYKFVVIG VRGDGKSALT                                                  20

SEQ ID NO: 55           moltype = AA  length = 20
FEATURE                 Location/Qualifiers
source                  1..20
                        organism = synthetic construct
                        mol_type = protein
                        note = Seed: MTEYKLVVVGARGVGKSALT (KRAS G12R)
SEQUENCE: 55
MTEYKFVVMG SRGAGKSALT                                                  20

SEQ ID NO: 56           moltype = AA  length = 15
FEATURE                 Location/Qualifiers
source                  1..15
                        organism = synthetic construct
                        mol_type = protein
                        note = Seed: VVVGARGVGKSALTI (KRAS G12R)
```

-continued

```
SEQUENCE: 56
VVVIARGVPK SLLTI                                                        15

SEQ ID NO: 57           moltype = AA  length = 15
FEATURE                 Location/Qualifiers
source                  1..15
                        organism = synthetic construct
                        mol_type = protein
                        note = Seed: EYKLVVVGACGVGKS (KRAS G12C)
SEQUENCE: 57
EYKFVVFGNC GAGKS                                                        15

SEQ ID NO: 58           moltype = AA  length = 15
FEATURE                 Location/Qualifiers
source                  1..15
                        organism = synthetic construct
                        mol_type = protein
                        note = Seed: EYKLVVVGACGVGKS (KRAS G12C)
SEQUENCE: 58
EYKFVVSGAC GVGKS                                                        15

SEQ ID NO: 59           moltype = AA  length = 15
FEATURE                 Location/Qualifiers
source                  1..15
                        organism = synthetic construct
                        mol_type = protein
                        note = Seed: EYKLVVVGACGVGKS (KRAS G12C)
SEQUENCE: 59
EYKFVVSGNC GLGKS                                                        15

SEQ ID NO: 60           moltype = AA  length = 15
FEATURE                 Location/Qualifiers
source                  1..15
                        organism = synthetic construct
                        mol_type = protein
                        note = Seed: EYKLVVVGACGVGKS (KRAS G12C)
SEQUENCE: 60
EYKLVVMGPC GAGKS                                                        15

SEQ ID NO: 61           moltype = AA  length = 15
FEATURE                 Location/Qualifiers
source                  1..15
                        organism = synthetic construct
                        mol_type = protein
                        note = Seed: KLVVVGACGVGKSAL (KRAS G12C)
SEQUENCE: 61
KLVIVGICKV GHSAL                                                        15

SEQ ID NO: 62           moltype = AA  length = 15
FEATURE                 Location/Qualifiers
source                  1..15
                        organism = synthetic construct
                        mol_type = protein
                        note = Seed: EYKLVVVGAGDVGKS (KRAS G13D)
SEQUENCE: 62
EYKFVVFGNG DLGKS                                                        15

SEQ ID NO: 63           moltype = AA  length = 15
FEATURE                 Location/Qualifiers
source                  1..15
                        organism = synthetic construct
                        mol_type = protein
                        note = Seed: EYKLVVVGAGDVGKS (KRAS G13D)
SEQUENCE: 63
EYKFVVMGNG DSGKS                                                        15

SEQ ID NO: 64           moltype = AA  length = 15
FEATURE                 Location/Qualifiers
source                  1..15
                        organism = synthetic construct
                        mol_type = protein
                        note = Seed: EYKLVVVGAGDVGKS (KRAS G13D)
SEQUENCE: 64
EYKFVVSGSG DVGKS                                                        15

SEQ ID NO: 65           moltype = AA  length = 15
FEATURE                 Location/Qualifiers
source                  1..15
                        organism = synthetic construct
```

```
                    mol_type = protein
                    note = Seed: EYKLVVVGAGDVGKS (KRAS G13D)
SEQUENCE: 65
EYKIVVMGRG DMGKS                                               15

SEQ ID NO: 66       moltype = AA  length = 15
FEATURE             Location/Qualifiers
source              1..15
                    organism = Homo sapiens
                    mol_type = protein
                    note = Native (KRAS G13D)
SEQUENCE: 66
YKLVVVGAGD VGKSA                                               15

SEQ ID NO: 67       moltype = AA  length = 9
FEATURE             Location/Qualifiers
source              1..9
                    organism = synthetic construct
                    mol_type = protein
                    note = Seed: LVVVGACGV (KRAS G12C)
SEQUENCE: 67
LLVVGACGV                                                       9

SEQ ID NO: 68       moltype = AA  length = 9
FEATURE             Location/Qualifiers
source              1..9
                    organism = synthetic construct
                    mol_type = protein
                    note = Seed: LVVVGAVGV (KRAS G12V)
SEQUENCE: 68
LLVVGAVGV                                                       9

SEQ ID NO: 69       moltype = AA  length = 9
FEATURE             Location/Qualifiers
source              1..9
                    organism = synthetic construct
                    mol_type = protein
                    note = Seed: LVVVGAVGV (KRAS G12V)
SEQUENCE: 69
LMVVGAVGI                                                       9

SEQ ID NO: 70       moltype = AA  length = 9
FEATURE             Location/Qualifiers
source              1..9
                    organism = synthetic construct
                    mol_type = protein
                    note = Seed: LVVVGACGV (KRAS G12C)
SEQUENCE: 70
LMVVGACGI                                                       9

SEQ ID NO: 71       moltype = AA  length = 9
FEATURE             Location/Qualifiers
source              1..9
                    organism = synthetic construct
                    mol_type = protein
                    note = Seed: LVVVGACGV (KRAS G12C)
SEQUENCE: 71
LLVVGACGI                                                       9

SEQ ID NO: 72       moltype = AA  length = 9
FEATURE             Location/Qualifiers
source              1..9
                    organism = synthetic construct
                    mol_type = protein
                    note = Seed: LVVVGAVGV (KRAS G12V)
SEQUENCE: 72
LMVVGAVGL                                                       9

SEQ ID NO: 73       moltype = AA  length = 9
FEATURE             Location/Qualifiers
source              1..9
                    organism = synthetic construct
                    mol_type = protein
                    note = Seed: LVVVGACGV (KRAS G12C)
SEQUENCE: 73
LMVVGACGL                                                       9

SEQ ID NO: 74       moltype = AA  length = 9
FEATURE             Location/Qualifiers
```

```
                        -continued source                  1..9
                        organism = synthetic construct
                        mol_type = protein
                        note = Seed: LVVVGACGV (KRAS G12C)
SEQUENCE: 74
LLVVGACGL                                                                       9

SEQ ID NO: 75           moltype = AA  length = 9
FEATURE                 Location/Qualifiers
source                  1..9
                        organism = synthetic construct
                        mol_type = protein
                        note = Seed: LVVVGACGV (KRAS G12C)
SEQUENCE: 75
LIVVGACGV                                                                       9

SEQ ID NO: 76           moltype = AA  length = 9
FEATURE                 Location/Qualifiers
source                  1..9
                        organism = synthetic construct
                        mol_type = protein
                        note = Seed: LVVVGAVGV (KRAS G12V)
SEQUENCE: 76
LLVVGAVGI                                                                       9

SEQ ID NO: 77           moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 77
ATDVGKSAL                                                                       9

SEQ ID NO: 78           moltype = AA  length = 9
FEATURE                 Location/Qualifiers
source                  1..9
                        organism = synthetic construct
                        mol_type = protein
                        note = Seed: LVVVGACGV (KRAS G12C)
SEQUENCE: 78
LMVVGACGA                                                                       9

SEQ ID NO: 79           moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 79
AIDVGKSAL                                                                       9

SEQ ID NO: 80           moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 80
AVDVGKSAL                                                                       9

SEQ ID NO: 81           moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 81
AFDVGKSAL                                                                       9

SEQ ID NO: 82           moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 82
AADVGKSAV                                                                       9
```

```
SEQ ID NO: 83          moltype = AA   length = 9
FEATURE                Location/Qualifiers
source                 1..9
                       organism = synthetic construct
                       mol_type = protein
                       note = Seed: LVVVGAVGV (KRAS G12V)
SEQUENCE: 83
LMVVGAVGA                                                                   9

SEQ ID NO: 84          moltype = AA   length = 9
FEATURE                Location/Qualifiers
source                 1..9
                       organism = synthetic construct
                       mol_type = protein
                       note = Seed: AGDVGKSAL (KRAS G13D)
SEQUENCE: 84
AADVGKSAI                                                                   9

SEQ ID NO: 85          moltype = AA   length = 9
FEATURE                Location/Qualifiers
source                 1..9
                       organism = synthetic construct
                       mol_type = protein
                       note = Seed: AGDVGKSAL (KRAS G13D)
SEQUENCE: 85
AFDVGKSAM                                                                   9

SEQ ID NO: 86          moltype = AA   length = 9
FEATURE                Location/Qualifiers
source                 1..9
                       organism = synthetic construct
                       mol_type = protein
                       note = Seed: GADGVGKSA (KRAS G12D)
SEQUENCE: 86
GTDGVGKSL                                                                   9

SEQ ID NO: 87          moltype = AA   length = 9
FEATURE                Location/Qualifiers
source                 1..9
                       organism = synthetic construct
                       mol_type = protein
                       note = Seed: AGDVGKSAL (KRAS G13D)
SEQUENCE: 87
AYDVGKSAL                                                                   9

SEQ ID NO: 88          moltype = AA   length = 9
FEATURE                Location/Qualifiers
source                 1..9
                       organism = synthetic construct
                       mol_type = protein
                       note = Seed: GADGVGKSA (KRAS G12D)
SEQUENCE: 88
GSDGVGKSL                                                                   9

SEQ ID NO: 89          moltype = AA   length = 9
FEATURE                Location/Qualifiers
source                 1..9
                       organism = synthetic construct
                       mol_type = protein
                       note = Seed: AGDVGKSAL (KRAS G13D)
SEQUENCE: 89
ATDVGKSAM                                                                   9

SEQ ID NO: 90          moltype = AA   length = 9
FEATURE                Location/Qualifiers
source                 1..9
                       organism = synthetic construct
                       mol_type = protein
                       note = Seed: LVVVGAVGV (KRAS G12V)
SEQUENCE: 90
LLVVGAVGL                                                                   9

SEQ ID NO: 91          moltype = AA   length = 9
FEATURE                Location/Qualifiers
source                 1..9
                       organism = synthetic construct
                       mol_type = protein
                       note = Seed: AGDVGKSAL (KRAS G13D)
SEQUENCE: 91
```

```
AIDVGKSAM                                                                 9

SEQ ID NO: 92          moltype = AA  length = 9
FEATURE                Location/Qualifiers
source                 1..9
                       organism = synthetic construct
                       mol_type = protein
                       note = Seed: AGDVGKSAL (KRAS G13D)
SEQUENCE: 92
ALDVGKSAL                                                                 9

SEQ ID NO: 93          moltype = AA  length = 9
FEATURE                Location/Qualifiers
source                 1..9
                       organism = synthetic construct
                       mol_type = protein
                       note = Seed: AGDVGKSAL (KRAS G13D)
SEQUENCE: 93
AWDVGKSAL                                                                 9

SEQ ID NO: 94          moltype = AA  length = 9
FEATURE                Location/Qualifiers
source                 1..9
                       organism = synthetic construct
                       mol_type = protein
                       note = Seed: LVVVGAVGV (KRAS G12V)
SEQUENCE: 94
LIVVGAVGV                                                                 9

SEQ ID NO: 95          moltype = AA  length = 9
FEATURE                Location/Qualifiers
source                 1..9
                       organism = synthetic construct
                       mol_type = protein
                       note = Seed: AGDVGKSAL (KRAS G13D)
SEQUENCE: 95
ATDVGKSAI                                                                 9

SEQ ID NO: 96          moltype = AA  length = 9
FEATURE                Location/Qualifiers
source                 1..9
                       organism = synthetic construct
                       mol_type = protein
                       note = Seed: AGDVGKSAL (KRAS G13D)
SEQUENCE: 96
AVDVGKSAM                                                                 9

SEQ ID NO: 97          moltype = AA  length = 9
FEATURE                Location/Qualifiers
source                 1..9
                       organism = synthetic construct
                       mol_type = protein
                       note = Seed: GADGVGKSA (KRAS G12D)
SEQUENCE: 97
GIDGVGKSL                                                                 9

SEQ ID NO: 98          moltype = AA  length = 9
FEATURE                Location/Qualifiers
source                 1..9
                       organism = synthetic construct
                       mol_type = protein
                       note = Seed: GADGVGKSA (KRAS G12D)
SEQUENCE: 98
GVDGVGKSL                                                                 9

SEQ ID NO: 99          moltype = AA  length = 9
FEATURE                Location/Qualifiers
source                 1..9
                       organism = synthetic construct
                       mol_type = protein
                       note = Seed: AGDVGKSAL (KRAS G13D)
SEQUENCE: 99
ATDVGKSAV                                                                 9

SEQ ID NO: 100         moltype = AA  length = 9
FEATURE                Location/Qualifiers
source                 1..9
                       organism = synthetic construct
                       mol_type = protein
```

```
                        note = Seed: AGDVGKSAL (KRAS G13D)
SEQUENCE: 100
ASDVGKSAV                                                                                9

SEQ ID NO: 101          moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 101
GPRGVGKSL                                                                                9

SEQ ID NO: 102          moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 102
ASDVGKSAI                                                                                9

SEQ ID NO: 103          moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 103
AFDVGKSAF                                                                                9

SEQ ID NO: 104          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 104
GTDGVGKSM                                                                                9

SEQ ID NO: 105          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 105
GSDGVGKSM                                                                                9

SEQ ID NO: 106          moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 106
AIDVGKSAV                                                                                9

SEQ ID NO: 107          moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 107
AVDVGKSAI                                                                                9

SEQ ID NO: 108          moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 108
AIDVGKSAI                                                                                9

SEQ ID NO: 109          moltype = AA   length = 9
FEATURE                 Location/Qualifiers
source                  1..9
```

```
                            organism = synthetic construct
                            mol_type = protein
                            note = Seed: LVVVGACGV (KRAS G12C)
SEQUENCE: 109
LLVVGACGA                                                                    9

SEQ ID NO: 110              moltype = AA  length = 9
FEATURE                     Location/Qualifiers
source                      1..9
                            organism = synthetic construct
                            mol_type = protein
                            note = Seed: AGDVGKSAL (KRAS G13D)
SEQUENCE: 110
AADVGKSAF                                                                    9

SEQ ID NO: 111              moltype = AA  length = 9
FEATURE                     Location/Qualifiers
source                      1..9
                            organism = synthetic construct
                            mol_type = protein
                            note = Seed: AGDVGKSAL (KRAS G13D)
SEQUENCE: 111
AVDVGKSAV                                                                    9

SEQ ID NO: 112              moltype = AA  length = 9
FEATURE                     Location/Qualifiers
source                      1..9
                            organism = synthetic construct
                            mol_type = protein
                            note = Seed: GADGVGKSA (KRAS G12D)
SEQUENCE: 112
GLDGVGKSL                                                                    9

SEQ ID NO: 113              moltype = AA  length = 9
FEATURE                     Location/Qualifiers
source                      1..9
                            organism = synthetic construct
                            mol_type = protein
                            note = Seed: GARGVGKSA (KRAS G12R)
SEQUENCE: 113
GPRGVGKSM                                                                    9

SEQ ID NO: 114              moltype = AA  length = 9
FEATURE                     Location/Qualifiers
source                      1..9
                            organism = synthetic construct
                            mol_type = protein
                            note = Seed: AGDVGKSAL (KRAS G13D)
SEQUENCE: 114
AWDVGKSAM                                                                    9

SEQ ID NO: 115              moltype = AA  length = 9
FEATURE                     Location/Qualifiers
source                      1..9
                            organism = synthetic construct
                            mol_type = protein
                            note = Seed: AGDVGKSAL (KRAS G13D)
SEQUENCE: 115
ALDVGKSAM                                                                    9

SEQ ID NO: 116              moltype = AA  length = 9
FEATURE                     Location/Qualifiers
source                      1..9
                            organism = synthetic construct
                            mol_type = protein
                            note = Seed: GADGVGKSA (KRAS G12D)
SEQUENCE: 116
GADGVGKSV                                                                    9

SEQ ID NO: 117              moltype = AA  length = 9
FEATURE                     Location/Qualifiers
source                      1..9
                            organism = synthetic construct
                            mol_type = protein
                            note = Seed: AGDVGKSAL (KRAS G13D)
SEQUENCE: 117
AMDVGKSAL                                                                    9

SEQ ID NO: 118              moltype = AA  length = 9
```

```
FEATURE             Location/Qualifiers
source              1..9
                    organism = synthetic construct
                    mol_type = protein
                    note = Seed: GAVGVGKSA (KRAS G12V)
SEQUENCE: 118
GAVGVGKSY                                                                    9

SEQ ID NO: 119      moltype = AA   length = 9
FEATURE             Location/Qualifiers
source              1..9
                    organism = synthetic construct
                    mol_type = protein
                    note = Seed: AGDVGKSAL (KRAS G13D)
SEQUENCE: 119
AFDVGKSAI                                                                    9

SEQ ID NO: 120      moltype = AA   length = 9
FEATURE             Location/Qualifiers
source              1..9
                    organism = synthetic construct
                    mol_type = protein
                    note = Seed: VVGAVGVGK (KRAS G12V)
SEQUENCE: 120
VTGAVGVGR                                                                    9

SEQ ID NO: 121      moltype = AA   length = 9
FEATURE             Location/Qualifiers
source              1..9
                    organism = synthetic construct
                    mol_type = protein
                    note = Seed: GADGVGKSA (KRAS G12D)
SEQUENCE: 121
GIDGVGKSM                                                                    9

SEQ ID NO: 122      moltype = AA   length = 9
FEATURE             Location/Qualifiers
source              1..9
                    organism = synthetic construct
                    mol_type = protein
                    note = Seed: LVVVGAVGV (KRAS G12V)
SEQUENCE: 122
LQVVGAVGV                                                                    9

SEQ ID NO: 123      moltype = AA   length = 9
FEATURE             Location/Qualifiers
source              1..9
                    organism = synthetic construct
                    mol_type = protein
                    note = Seed: GADGVGKSA (KRAS G12D)
SEQUENCE: 123
GADGVGKSI                                                                    9

SEQ ID NO: 124      moltype = AA   length = 9
FEATURE             Location/Qualifiers
source              1..9
                    organism = synthetic construct
                    mol_type = protein
                    note = Seed: GADGVGKSA (KRAS G12D)
SEQUENCE: 124
GVDGVGKSM                                                                    9

SEQ ID NO: 125      moltype = AA   length = 9
FEATURE             Location/Qualifiers
source              1..9
                    organism = synthetic construct
                    mol_type = protein
                    note = Seed: LVVVGADGV (KRAS G12D)
SEQUENCE: 125
LMVVGADGI                                                                    9

SEQ ID NO: 126      moltype = AA   length = 9
FEATURE             Location/Qualifiers
source              1..9
                    organism = synthetic construct
                    mol_type = protein
                    note = Seed: AGDVGKSAL (KRAS G13D)
SEQUENCE: 126
AIDVGKSAF                                                                    9
```

-continued

```
SEQ ID NO: 127              moltype = AA   length = 9
FEATURE                     Location/Qualifiers
source                      1..9
                            organism = synthetic construct
                            mol_type = protein
                            note = Seed: GADGVGKSA (KRAS G12D)
SEQUENCE: 127
GADGVGKSF                                                                  9

SEQ ID NO: 128              moltype = AA   length = 9
FEATURE                     Location/Qualifiers
source                      1..9
                            organism = synthetic construct
                            mol_type = protein
                            note = Seed: AGDVGKSAL (KRAS G13D)
SEQUENCE: 128
AYDVGKSAF                                                                  9

SEQ ID NO: 129              moltype = AA   length = 9
FEATURE                     Location/Qualifiers
source                      1..9
                            organism = synthetic construct
                            mol_type = protein
                            note = Seed: GADGVGKSA (KRAS G12D)
SEQUENCE: 129
GLDGVGKSM                                                                  9

SEQ ID NO: 130              moltype = AA   length = 9
FEATURE                     Location/Qualifiers
source                      1..9
                            organism = synthetic construct
                            mol_type = protein
                            note = Seed: AGDVGKSAL (KRAS G13D)
SEQUENCE: 130
AFDVGKSAV                                                                  9

SEQ ID NO: 131              moltype = AA   length = 9
FEATURE                     Location/Qualifiers
source                      1..9
                            organism = synthetic construct
                            mol_type = protein
                            note = Seed: GAVGVGKSA (KRAS G12V)
SEQUENCE: 131
GAVGVGKSM                                                                  9

SEQ ID NO: 132              moltype = AA   length = 9
FEATURE                     Location/Qualifiers
source                      1..9
                            organism = synthetic construct
                            mol_type = protein
                            note = Seed: GARGVGKSA (KRAS G12R)
SEQUENCE: 132
GPRGVGKSI                                                                  9

SEQ ID NO: 133              moltype = AA   length = 9
FEATURE                     Location/Qualifiers
source                      1..9
                            organism = synthetic construct
                            mol_type = protein
                            note = Seed: AGDVGKSAL (KRAS G13D)
SEQUENCE: 133
ATDVGKSAF                                                                  9

SEQ ID NO: 134              moltype = AA   length = 9
FEATURE                     Location/Qualifiers
source                      1..9
                            organism = synthetic construct
                            mol_type = protein
                            note = Seed: GADGVGKSA (KRAS G12D)
SEQUENCE: 134
GMDGVGKSL                                                                  9

SEQ ID NO: 135              moltype = AA   length = 9
FEATURE                     Location/Qualifiers
source                      1..9
                            organism = synthetic construct
                            mol_type = protein
                            note = Seed: GADGVGKSA (KRAS G12D)
```

```
SEQUENCE: 135
GTDGVGKSI                                                                          9

SEQ ID NO: 136           moltype = AA   length = 9
FEATURE                  Location/Qualifiers
source                   1..9
                         organism = synthetic construct
                         mol_type = protein
                         note = Seed: AGDVGKSAL (KRAS G13D)
SEQUENCE: 136
AVDVGKSAF                                                                          9

SEQ ID NO: 137           moltype = AA   length = 9
FEATURE                  Location/Qualifiers
source                   1..9
                         organism = synthetic construct
                         mol_type = protein
                         note = Seed: AGDVGKSAL (KRAS G13D)
SEQUENCE: 137
AGDVGKSAM                                                                          9

SEQ ID NO: 138           moltype = AA   length = 9
FEATURE                  Location/Qualifiers
source                   1..9
                         organism = synthetic construct
                         mol_type = protein
                         note = Seed: GAVGVGKSA (KRAS G12V)
SEQUENCE: 138
GPVGVGKSA                                                                          9

SEQ ID NO: 139           moltype = AA   length = 9
FEATURE                  Location/Qualifiers
source                   1..9
                         organism = synthetic construct
                         mol_type = protein
                         note = Seed: GADGVGKSA (KRAS G12D)
SEQUENCE: 139
GTDGVGKSV                                                                          9

SEQ ID NO: 140           moltype = AA   length = 9
FEATURE                  Location/Qualifiers
source                   1..9
                         organism = synthetic construct
                         mol_type = protein
                         note = Seed: AGDVGKSAL (KRAS G13D)
SEQUENCE: 140
ASDVGKSAF                                                                          9

SEQ ID NO: 141           moltype = AA   length = 9
FEATURE                  Location/Qualifiers
source                   1..9
                         organism = synthetic construct
                         mol_type = protein
                         note = Seed: GADGVGKSA (KRAS G12D)
SEQUENCE: 141
GSDGVGKSV                                                                          9

SEQ ID NO: 142           moltype = AA   length = 9
FEATURE                  Location/Qualifiers
source                   1..9
                         organism = synthetic construct
                         mol_type = protein
                         note = Seed: VVGAVGVGK (KRAS G12V)
SEQUENCE: 142
VTGAVGVGK                                                                          9

SEQ ID NO: 143           moltype = AA   length = 9
FEATURE                  Location/Qualifiers
source                   1..9
                         organism = synthetic construct
                         mol_type = protein
                         note = Seed: GADGVGKSA (KRAS G12D)
SEQUENCE: 143
GSDGVGKSI                                                                          9

SEQ ID NO: 144           moltype = AA   length = 9
FEATURE                  Location/Qualifiers
source                   1..9
                         organism = synthetic construct
```

```
                              mol_type = protein
                              note = Seed: AGDVGKSAL (KRAS G13D)
SEQUENCE: 144
AWDVGKSAF                                                              9

SEQ ID NO: 145                moltype = AA  length = 9
FEATURE                       Location/Qualifiers
source                        1..9
                              organism = synthetic construct
                              mol_type = protein
                              note = Seed: GAGDVGKSA (KRAS G13D)
SEQUENCE: 145
GAGDVGKSY                                                              9

SEQ ID NO: 146                moltype = AA  length = 9
FEATURE                       Location/Qualifiers
source                        1..9
                              organism = synthetic construct
                              mol_type = protein
                              note = Seed: GADGVGKSA (KRAS G12D)
SEQUENCE: 146
GSDGVGKSF                                                              9

SEQ ID NO: 147                moltype = AA  length = 9
FEATURE                       Location/Qualifiers
source                        1..9
                              organism = synthetic construct
                              mol_type = protein
                              note = Seed: GADGVGKSA (KRAS G12D)
SEQUENCE: 147
GTDGVGKSF                                                              9

SEQ ID NO: 148                moltype = AA  length = 9
FEATURE                       Location/Qualifiers
source                        1..9
                              organism = synthetic construct
                              mol_type = protein
                              note = Seed: AGDVGKSAL (KRAS G13D)
SEQUENCE: 148
AMDVGKSAM                                                              9

SEQ ID NO: 149                moltype = AA  length = 9
FEATURE                       Location/Qualifiers
source                        1..9
                              organism = synthetic construct
                              mol_type = protein
                              note = Seed: GADGVGKSA (KRAS G12D)
SEQUENCE: 149
GVDGVGKSI                                                              9

SEQ ID NO: 150                moltype = AA  length = 9
FEATURE                       Location/Qualifiers
source                        1..9
                              organism = synthetic construct
                              mol_type = protein
                              note = Seed: AGDVGKSAL (KRAS G13D)
SEQUENCE: 150
ALDVGKSAV                                                              9

SEQ ID NO: 151                moltype = AA  length = 9
FEATURE                       Location/Qualifiers
source                        1..9
                              organism = synthetic construct
                              mol_type = protein
                              note = Seed: AGDVGKSAL (KRAS G13D)
SEQUENCE: 151
AYDVGKSAI                                                              9

SEQ ID NO: 152                moltype = AA  length = 9
FEATURE                       Location/Qualifiers
source                        1..9
                              organism = synthetic construct
                              mol_type = protein
                              note = Seed: GAVGVGKSA (KRAS G12V)
SEQUENCE: 152
GAVGVGKSF                                                              9

SEQ ID NO: 153                moltype = AA  length = 9
FEATURE                       Location/Qualifiers
```

```
source                          1..9
                                organism = synthetic construct
                                mol_type = protein
                                note = Seed: AGDVGKSAL (KRAS G13D)
SEQUENCE: 153
ALDVGKSAI                                                                        9

SEQ ID NO: 154                  moltype = AA  length = 9
FEATURE                         Location/Qualifiers
source                          1..9
                                organism = synthetic construct
                                mol_type = protein
                                note = Seed: LVVVGADGV (KRAS G12D)
SEQUENCE: 154
LLVVGADGL                                                                        9

SEQ ID NO: 155                  moltype = AA  length = 9
FEATURE                         Location/Qualifiers
source                          1..9
                                organism = synthetic construct
                                mol_type = protein
                                note = Seed: GADGVGKSA (KRAS G12D)
SEQUENCE: 155
GIDGVGKSF                                                                        9

SEQ ID NO: 156                  moltype = AA  length = 9
FEATURE                         Location/Qualifiers
source                          1..9
                                organism = synthetic construct
                                mol_type = protein
                                note = Seed: GADGVGKSA (KRAS G12D)
SEQUENCE: 156
GMDGVGKSM                                                                        9

SEQ ID NO: 157                  moltype = AA  length = 9
FEATURE                         Location/Qualifiers
source                          1..9
                                organism = synthetic construct
                                mol_type = protein
                                note = Seed: GADGVGKSA (KRAS G12D)
SEQUENCE: 157
GIDGVGKSI                                                                        9

SEQ ID NO: 158                  moltype = AA  length = 9
FEATURE                         Location/Qualifiers
source                          1..9
                                organism = synthetic construct
                                mol_type = protein
                                note = Seed: GADGVGKSA (KRAS G12D)
SEQUENCE: 158
GVDGVGKSF                                                                        9

SEQ ID NO: 159                  moltype = AA  length = 9
FEATURE                         Location/Qualifiers
source                          1..9
                                organism = synthetic construct
                                mol_type = protein
                                note = Seed: GADGVGKSA (KRAS G12D)
SEQUENCE: 159
GIDGVGKSV                                                                        9

SEQ ID NO: 160                  moltype = AA  length = 9
FEATURE                         Location/Qualifiers
source                          1..9
                                organism = synthetic construct
                                mol_type = protein
                                note = Seed: GADGVGKSA (KRAS G12D)
SEQUENCE: 160
GVDGVGKSV                                                                        9

SEQ ID NO: 161                  moltype = AA  length = 9
FEATURE                         Location/Qualifiers
source                          1..9
                                organism = synthetic construct
                                mol_type = protein
                                note = Seed: GAGDVGKSA (KRAS G13D)
SEQUENCE: 161
GAGDVGKSL                                                                        9
```

```
SEQ ID NO: 162          moltype = AA   length = 9
FEATURE                 Location/Qualifiers
source                  1..9
                        organism = synthetic construct
                        mol_type = protein
                        note = Seed: LVVVGADGV (KRAS G12D)
SEQUENCE: 162
LIVVGADGV                                                                   9

SEQ ID NO: 163          moltype = AA   length = 9
FEATURE                 Location/Qualifiers
source                  1..9
                        organism = synthetic construct
                        mol_type = protein
                        note = Seed: VVGAVGVGK (KRAS G12V)
SEQUENCE: 163
VAGAVGVGY                                                                   9

SEQ ID NO: 164          moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 164
AYDVGKSAV                                                                   9

SEQ ID NO: 165          moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 165
GARGVGKSF                                                                   9

SEQ ID NO: 166          moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 166
AWDVGKSAI                                                                   9

SEQ ID NO: 167          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 167
GGDGVGKSL                                                                   9

SEQ ID NO: 168          moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 168
GPRGVGKSF                                                                   9

SEQ ID NO: 169          moltype = AA   length = 9
FEATURE                 Location/Qualifiers
source                  1..9
                        organism = synthetic construct
                        mol_type = protein
                        note = Seed: VVGAVGVGK (KRAS G12V)
SEQUENCE: 169
VAGAVGVGL                                                                   9

SEQ ID NO: 170          moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 170
```

```
                                            -continued

GSVGVGKSY                                                                    9

SEQ ID NO: 171           moltype = AA  length = 9
FEATURE                  Location/Qualifiers
source                   1..9
                         organism = synthetic construct
                         mol_type = protein
                         note = Seed: GACGVGKSA (KRAS G12C)
SEQUENCE: 171
GACGVGKSY                                                                    9

SEQ ID NO: 172           moltype = AA  length = 9
FEATURE                  Location/Qualifiers
source                   1..9
                         organism = synthetic construct
                         mol_type = protein
                         note = Seed: AGDVGKSAL (KRAS G13D)
SEQUENCE: 172
AGDVGKSAV                                                                    9

SEQ ID NO: 173           moltype = AA  length = 9
FEATURE                  Location/Qualifiers
source                   1..9
                         organism = synthetic construct
                         mol_type = protein
                         note = Seed: AGDVGKSAL (KRAS G13D)
SEQUENCE: 173
ALDVGKSAF                                                                    9

SEQ ID NO: 174           moltype = AA  length = 9
FEATURE                  Location/Qualifiers
source                   1..9
                         organism = synthetic construct
                         mol_type = protein
                         note = Seed: AGDVGKSAL (KRAS G13D)
SEQUENCE: 174
AGDVGKSAI                                                                    9

SEQ ID NO: 175           moltype = AA  length = 9
FEATURE                  Location/Qualifiers
source                   1..9
                         organism = synthetic construct
                         mol_type = protein
                         note = Seed: GAGDVGKSA (KRAS G13D)
SEQUENCE: 175
GAGDVGKSF                                                                    9

SEQ ID NO: 176           moltype = AA  length = 9
FEATURE                  Location/Qualifiers
source                   1..9
                         organism = synthetic construct
                         mol_type = protein
                         note = Seed: GACGVGKSA (KRAS G12C)
SEQUENCE: 176
GPCGVGKSA                                                                    9

SEQ ID NO: 177           moltype = AA  length = 9
FEATURE                  Location/Qualifiers
source                   1..9
                         organism = synthetic construct
                         mol_type = protein
                         note = Seed: DVGKSALTI (KRAS G13D)
SEQUENCE: 177
DVGKSALTF                                                                    9

SEQ ID NO: 178           moltype = AA  length = 9
FEATURE                  Location/Qualifiers
source                   1..9
                         organism = synthetic construct
                         mol_type = protein
                         note = Seed: AGDVGKSAL (KRAS G13D)
SEQUENCE: 178
AWDVGKSAV                                                                    9

SEQ ID NO: 179           moltype = AA  length = 9
FEATURE                  Location/Qualifiers
source                   1..9
                         organism = synthetic construct
                         mol_type = protein
```

```
                           note = Seed: LVVVGAVGV (KRAS G12V)
SEQUENCE: 179
LLVVGAVGA                                                                    9

SEQ ID NO: 180         moltype = AA   length = 9
FEATURE                Location/Qualifiers
source                 1..9
                       organism = synthetic construct
                       mol_type = protein
                       note = Seed: GADGVGKSA (KRAS G12D)
SEQUENCE: 180
GYDGVGKSL                                                                    9

SEQ ID NO: 181         moltype = AA   length = 9
FEATURE                Location/Qualifiers
source                 1..9
                       organism = synthetic construct
                       mol_type = protein
                       note = Seed: VVGARGVGK (KRAS G12R)
SEQUENCE: 181
VAGARGVGL                                                                    9

SEQ ID NO: 182         moltype = AA   length = 9
FEATURE                Location/Qualifiers
source                 1..9
                       organism = synthetic construct
                       mol_type = protein
                       note = Seed: GARGVGKSA (KRAS G12R)
SEQUENCE: 182
GSRGVGKSY                                                                    9

SEQ ID NO: 183         moltype = AA   length = 9
FEATURE                Location/Qualifiers
source                 1..9
                       organism = synthetic construct
                       mol_type = protein
                       note = Seed: AGDVGKSAL (KRAS G13D)
SEQUENCE: 183
AMDVGKSAV                                                                    9

SEQ ID NO: 184         moltype = AA   length = 9
FEATURE                Location/Qualifiers
source                 1..9
                       organism = synthetic construct
                       mol_type = protein
                       note = Seed: AGDVGKSAL (KRAS G13D)
SEQUENCE: 184
AMDVGKSAI                                                                    9

SEQ ID NO: 185         moltype = AA   length = 9
FEATURE                Location/Qualifiers
source                 1..9
                       organism = synthetic construct
                       mol_type = protein
                       note = Seed: DVGKSALTI (KRAS G13D)
SEQUENCE: 185
DVGKSALTW                                                                    9

SEQ ID NO: 186         moltype = AA   length = 9
FEATURE                Location/Qualifiers
source                 1..9
                       organism = synthetic construct
                       mol_type = protein
                       note = Seed: AGDVGKSAL (KRAS G13D)
SEQUENCE: 186
ANDVGKSAL                                                                    9

SEQ ID NO: 187         moltype = AA   length = 9
FEATURE                Location/Qualifiers
source                 1..9
                       organism = synthetic construct
                       mol_type = protein
                       note = Seed: GACGVGKSA (KRAS G12C)
SEQUENCE: 187
GACGVGKSM                                                                    9

SEQ ID NO: 188         moltype = AA   length = 9
FEATURE                Location/Qualifiers
source                 1..9
```

```
                        organism = synthetic construct
                        mol_type = protein
                        note = Seed: AGDVGKSAL (KRAS G13D)
SEQUENCE: 188
AQDVGKSAL                                                                        9

SEQ ID NO: 189          moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 189
GSVGVGKSL                                                                        9

SEQ ID NO: 190          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 190
GGDGVGKSM                                                                        9

SEQ ID NO: 191          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 191
AGDVGKSAF                                                                        9

SEQ ID NO: 192          moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 192
GTVGVGKSY                                                                        9

SEQ ID NO: 193          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 193
GLDGVGKSF                                                                        9

SEQ ID NO: 194          moltype = AA  length = 9
FEATURE                 Location/Qualifiers
source                  1..9
                        organism = synthetic construct
                        mol_type = protein
                        note = Seed: LVVVGADGV (KRAS G12D)
SEQUENCE: 194
LQVVGADGV                                                                        9

SEQ ID NO: 195          moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 195
GARGVGKSL                                                                        9

SEQ ID NO: 196          moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 196
GSVGVGKSF                                                                        9

SEQ ID NO: 197          moltype = AA  length = 9
```

```
                            -continued

FEATURE                 Location/Qualifiers
source                  1..9
                        organism = synthetic construct
                        mol_type = protein
                        note = Seed: AGDVGKSAL (KRAS G13D)
SEQUENCE: 197
ACDVGKSAL                                                                 9

SEQ ID NO: 198          moltype = AA  length = 9
FEATURE                 Location/Qualifiers
source                  1..9
                        organism = synthetic construct
                        mol_type = protein
                        note = Seed: VVGAVGVGK (KRAS G12V)
SEQUENCE: 198
VAGAVGVGM                                                                 9

SEQ ID NO: 199          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 199
AEDVGKSAL                                                                 9

SEQ ID NO: 200          moltype = AA  length = 9
FEATURE                 Location/Qualifiers
source                  1..9
                        organism = synthetic construct
                        mol_type = protein
                        note = Seed: LVVVGADGV (KRAS G12D)
SEQUENCE: 200
LLVVGADGI                                                                 9

SEQ ID NO: 201          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 201
AEDVGKSAF                                                                 9

SEQ ID NO: 202          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 202
GLDGVGKSV                                                                 9

SEQ ID NO: 203          moltype = AA  length = 9
FEATURE                 Location/Qualifiers
source                  1..9
                        organism = synthetic construct
                        mol_type = protein
                        note = Seed: VVGAVGVGK (KRAS G12V)
SEQUENCE: 203
VAGAVGVGR                                                                 9

SEQ ID NO: 204          moltype = AA  length = 9
FEATURE                 Location/Qualifiers
source                  1..9
                        organism = synthetic construct
                        mol_type = protein
                        note = Seed: VVGAVGVGK (KRAS G12V)
SEQUENCE: 204
VAGAVGVGF                                                                 9

SEQ ID NO: 205          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 205
GLDGVGKSI                                                                 9
```

```
SEQ ID NO: 206          moltype = AA   length = 9
FEATURE                 Location/Qualifiers
source                  1..9
                        organism = synthetic construct
                        mol_type = protein
                        note = Seed: VVGACGVGK (KRAS G12C)
SEQUENCE: 206
VTGACGVGR                                                                    9

SEQ ID NO: 207          moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 207
AADVGKSAY                                                                    9

SEQ ID NO: 208          moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 208
GVRGVGKSY                                                                    9

SEQ ID NO: 209          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 209
GFDGVGKSL                                                                    9

SEQ ID NO: 210          moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 210
GVVGVGKSY                                                                    9

SEQ ID NO: 211          moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 211
GSRGVGKSF                                                                    9

SEQ ID NO: 212          moltype = AA   length = 9
FEATURE                 Location/Qualifiers
source                  1..9
                        organism = synthetic construct
                        mol_type = protein
                        note = Seed: LVVVGARGV (KRAS G12R)
SEQUENCE: 212
LMVVGARGI                                                                    9

SEQ ID NO: 213          moltype = AA   length = 9
FEATURE                 Location/Qualifiers
source                  1..9
                        organism = synthetic construct
                        mol_type = protein
                        note = Seed: GACGVGKSA (KRAS G12C)
SEQUENCE: 213
GACGVGKSF                                                                    9

SEQ ID NO: 214          moltype = AA   length = 9
FEATURE                 Location/Qualifiers
source                  1..9
                        organism = synthetic construct
                        mol_type = protein
                        note = Seed: GAVGVGKSA (KRAS G12V)
```

-continued

```
SEQUENCE: 214
GTVGVGKSF                                                                          9

SEQ ID NO: 215         moltype = AA  length = 9
FEATURE                Location/Qualifiers
source                 1..9
                       organism = synthetic construct
                       mol_type = protein
                       note = Seed: DVGKSALTI (KRAS G13D)
SEQUENCE: 215
DAGKSALTI                                                                          9

SEQ ID NO: 216         moltype = AA  length = 9
FEATURE                Location/Qualifiers
source                 1..9
                       organism = synthetic construct
                       mol_type = protein
                       note = Seed: AGDVGKSAL (KRAS G13D)
SEQUENCE: 216
AQDVGKSAM                                                                          9

SEQ ID NO: 217         moltype = AA  length = 9
FEATURE                Location/Qualifiers
source                 1..9
                       organism = synthetic construct
                       mol_type = protein
                       note = Seed: AGDVGKSAL (KRAS G13D)
SEQUENCE: 217
ANDVGKSAM                                                                          9

SEQ ID NO: 218         moltype = AA  length = 9
FEATURE                Location/Qualifiers
source                 1..9
                       organism = synthetic construct
                       mol_type = protein
                       note = Seed: AGDVGKSAL (KRAS G13D)
SEQUENCE: 218
AYDVGKSAY                                                                          9

SEQ ID NO: 219         moltype = AA  length = 9
FEATURE                Location/Qualifiers
source                 1..9
                       organism = synthetic construct
                       mol_type = protein
                       note = Seed: GARGVGKSA (KRAS G12R)
SEQUENCE: 219
GTRGVGKSY                                                                          9

SEQ ID NO: 220         moltype = AA  length = 9
FEATURE                Location/Qualifiers
source                 1..9
                       organism = synthetic construct
                       mol_type = protein
                       note = Seed: GAGDVGKSA (KRAS G13D)
SEQUENCE: 220
GPGDVGKSA                                                                          9

SEQ ID NO: 221         moltype = AA  length = 9
FEATURE                Location/Qualifiers
source                 1..9
                       organism = synthetic construct
                       mol_type = protein
                       note = Seed: GADGVGKSA (KRAS G12D)
SEQUENCE: 221
GMDGVGKSV                                                                          9

SEQ ID NO: 222         moltype = AA  length = 9
FEATURE                Location/Qualifiers
source                 1..9
                       organism = synthetic construct
                       mol_type = protein
                       note = Seed: GARGVGKSA (KRAS G12R)
SEQUENCE: 222
GVRGVGKSF                                                                          9

SEQ ID NO: 223         moltype = AA  length = 9
FEATURE                Location/Qualifiers
source                 1..9
                       organism = synthetic construct
```

```
                                         mol_type = protein
                                         note = Seed: VVGAVGVGK (KRAS G12V)
SEQUENCE: 223
VSGAVGVGR                                                                       9

SEQ ID NO: 224              moltype = AA   length = 9
FEATURE                     Location/Qualifiers
source                      1..9
                            organism = synthetic construct
                            mol_type = protein
                            note = Seed: GADGVGKSA (KRAS G12D)
SEQUENCE: 224
GFDGVGKSM                                                                       9

SEQ ID NO: 225              moltype = AA   length = 9
FEATURE                     Location/Qualifiers
source                      1..9
                            organism = synthetic construct
                            mol_type = protein
                            note = Seed: AGDVGKSAL (KRAS G13D)
SEQUENCE: 225
AMDVGKSAF                                                                       9

SEQ ID NO: 226              moltype = AA   length = 9
FEATURE                     Location/Qualifiers
source                      1..9
                            organism = synthetic construct
                            mol_type = protein
                            note = Seed: GADGVGKSA (KRAS G12D)
SEQUENCE: 226
GCDGVGKSL                                                                       9

SEQ ID NO: 227              moltype = AA   length = 9
FEATURE                     Location/Qualifiers
source                      1..9
                            organism = synthetic construct
                            mol_type = protein
                            note = Seed: GAGDVGKSA (KRAS G13D)
SEQUENCE: 227
GVGDVGKSY                                                                       9

SEQ ID NO: 228              moltype = AA   length = 9
FEATURE                     Location/Qualifiers
source                      1..9
                            organism = synthetic construct
                            mol_type = protein
                            note = Seed: GARGVGKSA (KRAS G12R)
SEQUENCE: 228
GTRGVGKSF                                                                       9

SEQ ID NO: 229              moltype = AA   length = 9
FEATURE                     Location/Qualifiers
source                      1..9
                            organism = synthetic construct
                            mol_type = protein
                            note = Seed: GARGVGKSA (KRAS G12R)
SEQUENCE: 229
GIRGVGKSY                                                                       9

SEQ ID NO: 230              moltype = AA   length = 9
FEATURE                     Location/Qualifiers
source                      1..9
                            organism = synthetic construct
                            mol_type = protein
                            note = Seed: GADGVGKSA (KRAS G12D)
SEQUENCE: 230
GMDGVGKSI                                                                       9

SEQ ID NO: 231              moltype = AA   length = 9
FEATURE                     Location/Qualifiers
source                      1..9
                            organism = synthetic construct
                            mol_type = protein
                            note = Seed: AGDVGKSAL (KRAS G13D)
SEQUENCE: 231
ACDVGKSAM                                                                       9

SEQ ID NO: 232              moltype = AA   length = 9
FEATURE                     Location/Qualifiers
```

```
source                   1..9
                         organism = synthetic construct
                         mol_type = protein
                         note = Seed: GAGDVGKSA (KRAS G13D)
SEQUENCE: 232
GSGDVGKSY                                                                      9

SEQ ID NO: 233           moltype = AA  length = 9
FEATURE                  Location/Qualifiers
source                   1..9
                         organism = synthetic construct
                         mol_type = protein
                         note = Seed: GAVGVGKSA (KRAS G12V)
SEQUENCE: 233
GAVGVGKSV                                                                      9

SEQ ID NO: 234           moltype = AA  length = 9
FEATURE                  Location/Qualifiers
source                   1..9
                         organism = synthetic construct
                         mol_type = protein
                         note = Seed: GAVGVGKSA (KRAS G12V)
SEQUENCE: 234
GSVGVGKSM                                                                      9

SEQ ID NO: 235           moltype = AA  length = 9
FEATURE                  Location/Qualifiers
source                   1..9
                         organism = synthetic construct
                         mol_type = protein
                         note = Seed: DVGKSALTI (KRAS G13D)
SEQUENCE: 235
DVGKSALTY                                                                      9

SEQ ID NO: 236           moltype = AA  length = 9
FEATURE                  Location/Qualifiers
source                   1..9
                         organism = synthetic construct
                         mol_type = protein
                         note = Seed: GAVGVGKSA (KRAS G12V)
SEQUENCE: 236
GVVGVGKSF                                                                      9

SEQ ID NO: 237           moltype = AA  length = 9
FEATURE                  Location/Qualifiers
source                   1..9
                         organism = synthetic construct
                         mol_type = protein
                         note = Seed: GAVGVGKSA (KRAS G12V)
SEQUENCE: 237
GIVGVGKSY                                                                      9

SEQ ID NO: 238           moltype = AA  length = 9
FEATURE                  Location/Qualifiers
source                   1..9
                         organism = synthetic construct
                         mol_type = protein
                         note = Seed: VVGACGVGK (KRAS G12C)
SEQUENCE: 238
VAGACGVGY                                                                      9

SEQ ID NO: 239           moltype = AA  length = 9
FEATURE                  Location/Qualifiers
source                   1..9
                         organism = synthetic construct
                         mol_type = protein
                         note = Seed: GACGVGKSA (KRAS G12C)
SEQUENCE: 239
GSCGVGKSY                                                                      9

SEQ ID NO: 240           moltype = AA  length = 9
FEATURE                  Location/Qualifiers
source                   1..9
                         organism = synthetic construct
                         mol_type = protein
                         note = Seed: GAVGVGKSA (KRAS G12V)
SEQUENCE: 240
GTVGVGKSL                                                                      9
```

-continued

```
SEQ ID NO: 241          moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 241
GAVGVGKSH                                                                          9

SEQ ID NO: 242          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 242
GMDGVGKSF                                                                          9

SEQ ID NO: 243          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 243
GQDGVGKSL                                                                          9

SEQ ID NO: 244          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 244
GCDGVGKSM                                                                          9

SEQ ID NO: 245          moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 245
GSGDVGKSF                                                                          9

SEQ ID NO: 246          moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 246
GTGDVGKSY                                                                          9

SEQ ID NO: 247          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 247
GGDGVGKSI                                                                          9

SEQ ID NO: 248          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 248
ACDVGKSAV                                                                          9

SEQ ID NO: 249          moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 249
```

```
GSRGVGKSM                                                                 9

SEQ ID NO: 251          moltype = AA  length = 9
FEATURE                 Location/Qualifiers
source                  1..9
                        organism = synthetic construct
                        mol_type = protein
                        note = Seed: VVGAVGVGK (KRAS G12V)
SEQUENCE: 250
VSGAVGVGK                                                                 9

SEQ ID NO: 251          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 251
GYDGVGKSF                                                                 9

SEQ ID NO: 252          moltype = AA  length = 9
FEATURE                 Location/Qualifiers
source                  1..9
                        organism = synthetic construct
                        mol_type = protein
                        note = Seed: DVGKSALTI (KRAS G13D)
SEQUENCE: 252
DTGKSALTF                                                                 9

SEQ ID NO: 253          moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 253
GPRGVGKSP                                                                 9

SEQ ID NO: 254          moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 254
GPVGVGKSL                                                                 9

SEQ ID NO: 255          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 255
GGDGVGKSF                                                                 9

SEQ ID NO: 256          moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 256
GPCGVGKSV                                                                 9

SEQ ID NO: 257          moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 257
GVGDVGKSF                                                                 9

SEQ ID NO: 258          moltype = AA  length = 9
FEATURE                 Location/Qualifiers
source                  1..9
                        organism = synthetic construct
                        mol_type = protein
```

```
                        note = Seed: GAGDVGKSA (KRAS G13D)
SEQUENCE: 258
GIGDVGKSY                                                                   9

SEQ ID NO: 259          moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 259
GGVGVGKSY                                                                   9

SEQ ID NO: 260          moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 260
GPRGVGKST                                                                   9

SEQ ID NO: 261          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 261
GGDGVGKSV                                                                   9

SEQ ID NO: 262          moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 262
ACDVGKSAF                                                                   9

SEQ ID NO: 263          moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 263
GAVGVGKSI                                                                   9

SEQ ID NO: 264          moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 264
GIRGVGKSF                                                                   9

SEQ ID NO: 265          moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 265
GTGDVGKSF                                                                   9

SEQ ID NO: 266          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 266
GNDGVGKSL                                                                   9

SEQ ID NO: 267          moltype = AA   length = 9
FEATURE                 Location/Qualifiers
source                  1..9
```

-continued

```
                          organism = synthetic construct
                          mol_type = protein
                          note = Seed: VVGARGVGK (KRAS G12R)
SEQUENCE: 267
VAGARGVGF                                                                        9

SEQ ID NO: 268            moltype = AA  length = 9
FEATURE                   Location/Qualifiers
source                    1..9
                          organism = synthetic construct
                          mol_type = protein
                          note = Seed: GACGVGKSA (KRAS G12C)
SEQUENCE: 268
GVCGVGKSY                                                                        9

SEQ ID NO: 269            moltype = AA  length = 9
FEATURE                   Location/Qualifiers
source                    1..9
                          organism = synthetic construct
                          mol_type = protein
                          note = Seed: GARGVGKSA (KRAS G12R)
SEQUENCE: 269
GVRGVGKSM                                                                        9

SEQ ID NO: 270            moltype = AA  length = 9
FEATURE                   Location/Qualifiers
source                    1..9
                          organism = synthetic construct
                          mol_type = protein
                          note = Seed: VVGARGVGK (KRAS G12R)
SEQUENCE: 270
VTGARGVGR                                                                        9

SEQ ID NO: 271            moltype = AA  length = 9
FEATURE                   Location/Qualifiers
source                    1..9
                          organism = synthetic construct
                          mol_type = protein
                          note = Seed: VVGAVGVGK (KRAS G12V)
SEQUENCE: 271
VAGAVGVGK                                                                        9

SEQ ID NO: 272            moltype = AA  length = 9
FEATURE                   Location/Qualifiers
source                    1..9
                          organism = synthetic construct
                          mol_type = protein
                          note = Seed: VVGADGVGK (KRAS G12D)
SEQUENCE: 272
VAGADGVGY                                                                        9

SEQ ID NO: 273            moltype = AA  length = 9
FEATURE                   Location/Qualifiers
source                    1..9
                          organism = synthetic construct
                          mol_type = protein
                          note = Seed: GADGVGKSA (KRAS G12D)
SEQUENCE: 273
GQDGVGKSM                                                                        9

SEQ ID NO: 274            moltype = AA  length = 9
FEATURE                   Location/Qualifiers
source                    1..9
                          organism = synthetic construct
                          mol_type = protein
                          note = Seed: GAVGVGKSA (KRAS G12V)
SEQUENCE: 274
GPVGVGKST                                                                        9

SEQ ID NO: 275            moltype = AA  length = 9
FEATURE                   Location/Qualifiers
source                    1..9
                          organism = synthetic construct
                          mol_type = protein
                          note = Seed: AGDVGKSAL (KRAS G13D)
SEQUENCE: 275
AEDVGKSAI                                                                        9

SEQ ID NO: 276            moltype = AA  length = 9
```

```
FEATURE              Location/Qualifiers
source               1..9
                     organism = synthetic construct
                     mol_type = protein
                     note = Seed: VVGAVGVGK (KRAS G12V)
SEQUENCE: 276
VIGAVGVGK                                                                        9

SEQ ID NO: 277       moltype = AA  length = 9
FEATURE              Location/Qualifiers
source               1..9
                     organism = synthetic construct
                     mol_type = protein
                     note = Seed: GAVGVGKSA (KRAS G12V)
SEQUENCE: 277
GVVGVGKSL                                                                        9

SEQ ID NO: 278       moltype = AA  length = 9
FEATURE              Location/Qualifiers
source               1..9
                     organism = synthetic construct
                     mol_type = protein
                     note = Seed: GAVGVGKSA (KRAS G12V)
SEQUENCE: 278
GVVGVGKSM                                                                        9

SEQ ID NO: 279       moltype = AA  length = 9
FEATURE              Location/Qualifiers
source               1..9
                     organism = synthetic construct
                     mol_type = protein
                     note = Seed: VVGARGVGK (KRAS G12R)
SEQUENCE: 279
VAGARGVGY                                                                        9

SEQ ID NO: 280       moltype = AA  length = 9
FEATURE              Location/Qualifiers
source               1..9
                     organism = synthetic construct
                     mol_type = protein
                     note = Seed: GAVGVGKSA (KRAS G12V)
SEQUENCE: 280
GTVGVGKSM                                                                        9

SEQ ID NO: 281       moltype = AA  length = 9
FEATURE              Location/Qualifiers
source               1..9
                     organism = synthetic construct
                     mol_type = protein
                     note = Seed: AGDVGKSAL (KRAS G13D)
SEQUENCE: 281
ACDVGKSAI                                                                        9

SEQ ID NO: 282       moltype = AA  length = 9
FEATURE              Location/Qualifiers
source               1..9
                     organism = synthetic construct
                     mol_type = protein
                     note = Seed: GARGVGKSA (KRAS G12R)
SEQUENCE: 282
GPRGVGKSC                                                                        9

SEQ ID NO: 283       moltype = AA  length = 9
FEATURE              Location/Qualifiers
source               1..9
                     organism = synthetic construct
                     mol_type = protein
                     note = Seed: LVVVGARGV (KRAS G12R)
SEQUENCE: 283
LLVVGARGI                                                                        9

SEQ ID NO: 284       moltype = AA  length = 9
FEATURE              Location/Qualifiers
source               1..9
                     organism = synthetic construct
                     mol_type = protein
                     note = Seed: GARGVGKSA (KRAS G12R)
SEQUENCE: 284
GVRGVGKSL                                                                        9
```

```
SEQ ID NO: 285           moltype = AA   length = 9
FEATURE                  Location/Qualifiers
source                   1..9
                         organism = synthetic construct
                         mol_type = protein
                         note = Seed: GACGVGKSA (KRAS G12C)
SEQUENCE: 285
GTCGVGKSY                                                                9

SEQ ID NO: 286           moltype = AA   length = 9
FEATURE                  Location/Qualifiers
source                   1..9
                         organism = synthetic construct
                         mol_type = protein
                         note = Seed: GAVGVGKSA (KRAS G12V)
SEQUENCE: 286
GPVGVGKSP                                                                9

SEQ ID NO: 287           moltype = AA   length = 9
FEATURE                  Location/Qualifiers
source                   1..9
                         organism = synthetic construct
                         mol_type = protein
                         note = Seed: VVGAVGVGK (KRAS G12V)
SEQUENCE: 287
VSGAVGVGY                                                                9

SEQ ID NO: 288           moltype = AA   length = 9
FEATURE                  Location/Qualifiers
source                   1..9
                         organism = synthetic construct
                         mol_type = protein
                         note = Seed: GADGVGKSA (KRAS G12D)
SEQUENCE: 288
GFDGVGKSV                                                                9

SEQ ID NO: 289           moltype = AA   length = 9
FEATURE                  Location/Qualifiers
source                   1..9
                         organism = synthetic construct
                         mol_type = protein
                         note = Seed: DVGKSALTI (KRAS G13D)
SEQUENCE: 289
DIGKSALTW                                                                9

SEQ ID NO: 290           moltype = AA   length = 9
FEATURE                  Location/Qualifiers
source                   1..9
                         organism = synthetic construct
                         mol_type = protein
                         note = Seed: GADGVGKSA (KRAS G12D)
SEQUENCE: 290
GYDGVGKSI                                                                9

SEQ ID NO: 291           moltype = AA   length = 9
FEATURE                  Location/Qualifiers
source                   1..9
                         organism = synthetic construct
                         mol_type = protein
                         note = Seed: GARGVGKSA (KRAS G12R)
SEQUENCE: 291
GARGVGKSV                                                                9

SEQ ID NO: 292           moltype = AA   length = 9
FEATURE                  Location/Qualifiers
source                   1..9
                         organism = synthetic construct
                         mol_type = protein
                         note = Seed: GADGVGKSA (KRAS G12D)
SEQUENCE: 292
GPDGVGKSA                                                                9

SEQ ID NO: 293           moltype = AA   length = 9
FEATURE                  Location/Qualifiers
source                   1..9
                         organism = synthetic construct
                         mol_type = protein
                         note = Seed: GARGVGKSA (KRAS G12R)
```

```
SEQUENCE: 293
GGRGVGKSY                                                                    9

SEQ ID NO: 294         moltype = AA   length = 9
FEATURE                Location/Qualifiers
source                 1..9
                       organism = synthetic construct
                       mol_type = protein
                       note = Seed: GARGVGKSA (KRAS G12R)
SEQUENCE: 294
GTRGVGKSM                                                                    9

SEQ ID NO: 295         moltype = AA   length = 9
FEATURE                Location/Qualifiers
source                 1..9
                       organism = synthetic construct
                       mol_type = protein
                       note = Seed: GAVGVGKSA (KRAS G12V)
SEQUENCE: 295
GIVGVGKSF                                                                    9

SEQ ID NO: 296         moltype = AA   length = 9
FEATURE                Location/Qualifiers
source                 1..9
                       organism = synthetic construct
                       mol_type = protein
                       note = Seed: AGDVGKSAL (KRAS G13D)
SEQUENCE: 296
AEDVGKSAV                                                                    9

SEQ ID NO: 297         moltype = AA   length = 9
FEATURE                Location/Qualifiers
source                 1..9
                       organism = synthetic construct
                       mol_type = protein
                       note = Seed: GAVGVGKSA (KRAS G12V)
SEQUENCE: 297
GPVGVGKSI                                                                    9

SEQ ID NO: 298         moltype = AA   length = 9
FEATURE                Location/Qualifiers
source                 1..9
                       organism = synthetic construct
                       mol_type = protein
                       note = Seed: AGDVGKSAL (KRAS G13D)
SEQUENCE: 298
ADDVGKSAF                                                                    9

SEQ ID NO: 299         moltype = AA   length = 9
FEATURE                Location/Qualifiers
source                 1..9
                       organism = synthetic construct
                       mol_type = protein
                       note = Seed: GACGVGKSA (KRAS G12C)
SEQUENCE: 299
GSCGVGKSF                                                                    9

SEQ ID NO: 300         moltype = AA   length = 9
FEATURE                Location/Qualifiers
source                 1..9
                       organism = synthetic construct
                       mol_type = protein
                       note = Seed: AGDVGKSAL (KRAS G13D)
SEQUENCE: 300
ARDVGKSAL                                                                    9

SEQ ID NO: 301         moltype = AA   length = 9
FEATURE                Location/Qualifiers
source                 1..9
                       organism = synthetic construct
                       mol_type = protein
                       note = Seed: GAGDVGKSA (KRAS G13D)
SEQUENCE: 301
GSGDVGKSM                                                                    9

SEQ ID NO: 302         moltype = AA   length = 9
FEATURE                Location/Qualifiers
source                 1..9
                       organism = synthetic construct
```

```
                            mol_type = protein
                            note = Seed: AGDVGKSAL (KRAS G13D)
SEQUENCE: 302
AQDVGKSAI                                                               9

SEQ ID NO: 303          moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 303
GVGDVGKSM                                                               9

SEQ ID NO: 304          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 304
GFDGVGKSF                                                               9

SEQ ID NO: 305          moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 305
GSRGVGKSL                                                               9

SEQ ID NO: 306          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 306
ANDVGKSAI                                                               9

SEQ ID NO: 307          moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 307
GPVGVGKSM                                                               9

SEQ ID NO: 308          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 308
GNDGVGKSM                                                               9

SEQ ID NO: 309          moltype = AA  length = 9
FEATURE                 Location/Qualifiers
source                  1..9
                        organism = synthetic construct
                        mol_type = protein
                        note = Seed: VVGAVGVGK (KRAS G12V)
SEQUENCE: 309
VLGAVGVGR                                                               9

SEQ ID NO: 310          moltype = AA  length = 9
FEATURE                 Location/Qualifiers
source                  1..9
                        organism = synthetic construct
                        mol_type = protein
                        note = Seed: LVVVGARGV (KRAS G12R)
SEQUENCE: 310
LMVVGARGL                                                               9

SEQ ID NO: 311          moltype = AA  length = 9
FEATURE                 Location/Qualifiers
```

```
                            -continued source                      1..9
                            organism = synthetic construct
                            mol_type = protein
                            note = Seed: AGDVGKSAL (KRAS G13D)
SEQUENCE: 311
ANDVGKSAV                                                                          9

SEQ ID NO: 312              moltype = AA   length = 9
FEATURE                     Location/Qualifiers
source                      1..9
                            organism = synthetic construct
                            mol_type = protein
                            note = Seed: GADGVGKSA (KRAS G12D)
SEQUENCE: 312
GWDGVGKSL                                                                          9

SEQ ID NO: 313              moltype = AA   length = 9
FEATURE                     Location/Qualifiers
source                      1..9
                            organism = synthetic construct
                            mol_type = protein
                            note = Seed: VVGACGVGK (KRAS G12C)
SEQUENCE: 313
VAGACGVGR                                                                          9

SEQ ID NO: 314              moltype = AA   length = 9
FEATURE                     Location/Qualifiers
source                      1..9
                            organism = synthetic construct
                            mol_type = protein
                            note = Seed: AGDVGKSAL (KRAS G13D)
SEQUENCE: 314
ADDVGKSAL                                                                          9

SEQ ID NO: 315              moltype = AA   length = 9
FEATURE                     Location/Qualifiers
source                      1..9
                            organism = synthetic construct
                            mol_type = protein
                            note = Seed: GACGVGKSA (KRAS G12C)
SEQUENCE: 315
GSCGVGKSL                                                                          9

SEQ ID NO: 316              moltype = AA   length = 9
FEATURE                     Location/Qualifiers
source                      1..9
                            organism = synthetic construct
                            mol_type = protein
                            note = Seed: DVGKSALTI (KRAS G13D)
SEQUENCE: 316
DAGKSALTL                                                                          9

SEQ ID NO: 317              moltype = AA   length = 9
FEATURE                     Location/Qualifiers
source                      1..9
                            organism = synthetic construct
                            mol_type = protein
                            note = Seed: AGDVGKSAL (KRAS G13D)
SEQUENCE: 317
AQDVGKSAV                                                                          9

SEQ ID NO: 318              moltype = AA   length = 9
FEATURE                     Location/Qualifiers
source                      1..9
                            organism = synthetic construct
                            mol_type = protein
                            note = Seed: VVGAGDVGK (KRAS G13D)
SEQUENCE: 318
VTGAGDVGR                                                                          9

SEQ ID NO: 319              moltype = AA   length = 9
FEATURE                     Location/Qualifiers
source                      1..9
                            organism = synthetic construct
                            mol_type = protein
                            note = Seed: VVGADGVGK (KRAS G12D)
SEQUENCE: 319
VTGADGVGR                                                                          9
```

-continued

| | | |
|---|---|---|
| SEQ ID NO: 320<br>FEATURE<br>source | moltype = AA   length = 9<br>Location/Qualifiers<br>1..9<br>organism = synthetic construct<br>mol_type = protein<br>note = Seed: VVGAVGVGK (KRAS G12V) | |
| SEQUENCE: 320<br>VTGAVGVGY | | 9 |
| SEQ ID NO: 321<br>FEATURE<br>source | moltype = AA   length = 9<br>Location/Qualifiers<br>1..9<br>organism = synthetic construct<br>mol_type = protein<br>note = Seed: VVGAVGVGK (KRAS G12V) | |
| SEQUENCE: 321<br>VVGAVGVGY | | 9 |
| SEQ ID NO: 322<br>FEATURE<br>source | moltype = AA   length = 9<br>Location/Qualifiers<br>1..9<br>organism = synthetic construct<br>mol_type = protein<br>note = Seed: VVGAVGVGK (KRAS G12V) | |
| SEQUENCE: 322<br>VIGAVGVGR | | 9 |
| SEQ ID NO: 323<br>FEATURE<br>source | moltype = AA   length = 9<br>Location/Qualifiers<br>1..9<br>organism = synthetic construct<br>mol_type = protein<br>note = Seed: GACGVGKSA (KRAS G12C) | |
| SEQUENCE: 323<br>GICGVGKSY | | 9 |
| SEQ ID NO: 324<br>FEATURE<br>source | moltype = AA   length = 9<br>Location/Qualifiers<br>1..9<br>organism = synthetic construct<br>mol_type = protein<br>note = Seed: VVGARGVGK (KRAS G12R) | |
| SEQUENCE: 324<br>VVGARGVGR | | 9 |
| SEQ ID NO: 325<br>FEATURE<br>source | moltype = AA   length = 9<br>Location/Qualifiers<br>1..9<br>organism = synthetic construct<br>mol_type = protein<br>note = Seed: GAGDVGKSA (KRAS G13D) | |
| SEQUENCE: 325<br>GIGDVGKSF | | 9 |
| SEQ ID NO: 326<br>FEATURE<br>source | moltype = AA   length = 9<br>Location/Qualifiers<br>1..9<br>organism = synthetic construct<br>mol_type = protein<br>note = Seed: VVGARGVGK (KRAS G12R) | |
| SEQUENCE: 326<br>VMGARGVGR | | 9 |
| SEQ ID NO: 327<br>FEATURE<br>source | moltype = AA   length = 9<br>Location/Qualifiers<br>1..9<br>organism = synthetic construct<br>mol_type = protein<br>note = Seed: VVGACGVGK (KRAS G12C) | |
| SEQUENCE: 327<br>VAGACGVGF | | 9 |
| SEQ ID NO: 328<br>FEATURE<br>source | moltype = AA   length = 9<br>Location/Qualifiers<br>1..9<br>organism = synthetic construct<br>mol_type = protein<br>note = Seed: AGDVGKSAL (KRAS G13D) | |
| SEQUENCE: 328 | | |

-continued

```
AQDVGKSAF                                                           9

SEQ ID NO: 329          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 329
AVDVGKSAY                                                           9

SEQ ID NO: 330          moltype = AA  length = 9
FEATURE                 Location/Qualifiers
source                  1..9
                        organism = synthetic construct
                        mol_type = protein
                        note = Seed: VVGAGDVGK (KRAS G13D)
SEQUENCE: 330
VAGAGDVGY                                                           9

SEQ ID NO: 331          moltype = AA  length = 9
FEATURE                 Location/Qualifiers
source                  1..9
                        organism = synthetic construct
                        mol_type = protein
                        note = Seed: DVGKSALTI (KRAS G13D)
SEQUENCE: 331
DPGKSALTV                                                           9

SEQ ID NO: 332          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 332
GCDGVGKSV                                                           9

SEQ ID NO: 333          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 333
GFDGVGKSI                                                           9

SEQ ID NO: 334          moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 334
GIRGVGKSM                                                           9

SEQ ID NO: 335          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 335
GCDGVGKSF                                                           9

SEQ ID NO: 336          moltype = AA  length = 9
FEATURE                 Location/Qualifiers
source                  1..9
                        organism = synthetic construct
                        mol_type = protein
                        note = Seed: VVGACGVGK (KRAS G12C)
SEQUENCE: 336
VAGACGVGL                                                           9

SEQ ID NO: 337          moltype = AA  length = 9
FEATURE                 Location/Qualifiers
source                  1..9
                        organism = synthetic construct
                        mol_type = protein
```

-continued

```
                        note = Seed: LVVVGACGV (KRAS G12C)
SEQUENCE: 337
LVVVGACGI                                                              9

SEQ ID NO: 338          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 338
ASDVGKSAY                                                              9

SEQ ID NO: 339          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 339
GYDGVGKSV                                                              9

SEQ ID NO: 340          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 340
ADDVGKSAM                                                              9

SEQ ID NO: 341          moltype = AA  length = 9
FEATURE                 Location/Qualifiers
source                  1..9
                        organism = synthetic construct
                        mol_type = protein
                        note = Seed: DVGKSALTI (KRAS G13D)
SEQUENCE: 341
DTGKSALTW                                                              9

SEQ ID NO: 342          moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 342
GPCGVGKSL                                                              9

SEQ ID NO: 343          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 343
GRDGVGKSL                                                              9

SEQ ID NO: 344          moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 344
GVCGVGKSF                                                              9

SEQ ID NO: 345          moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 345
GLRGVGKSY                                                              9

SEQ ID NO: 346          moltype = AA  length = 9
FEATURE                 Location/Qualifiers
source                  1..9
```

```
                        organism = synthetic construct
                        mol_type = protein
                        note = Seed: GACGVGKSA (KRAS G12C)
SEQUENCE: 346
GACGVGKSV                                                                      9

SEQ ID NO: 347          moltype = AA   length = 9
FEATURE                 Location/Qualifiers
source                  1..9
                        organism = synthetic construct
                        mol_type = protein
                        note = Seed: GACGVGKSA (KRAS G12C)
SEQUENCE: 347
GTCGVGKSF                                                                      9

SEQ ID NO: 348          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 348
GSDGVGKSY                                                                      9

SEQ ID NO: 349          moltype = AA   length = 9
FEATURE                 Location/Qualifiers
source                  1..9
                        organism = synthetic construct
                        mol_type = protein
                        note = Seed: GACGVGKSA (KRAS G12C)
SEQUENCE: 349
GACGVGKSI                                                                      9

SEQ ID NO: 350          moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 350
GTGDVGKSM                                                                      9

SEQ ID NO: 351          moltype = AA   length = 9
FEATURE                 Location/Qualifiers
source                  1..9
                        organism = synthetic construct
                        mol_type = protein
                        note = Seed: VVGARGVGK (KRAS G12R)
SEQUENCE: 351
VSGARGVGM                                                                      9

SEQ ID NO: 352          moltype = AA   length = 9
FEATURE                 Location/Qualifiers
source                  1..9
                        organism = synthetic construct
                        mol_type = protein
                        note = Seed: VVGADGVGK (KRAS G12D)
SEQUENCE: 352
VTGADGVGK                                                                      9

SEQ ID NO: 353          moltype = AA   length = 9
FEATURE                 Location/Qualifiers
source                  1..9
                        organism = synthetic construct
                        mol_type = protein
                        note = Seed: VVGAVGVGK (KRAS G12V)
SEQUENCE: 353
VLGAVGVGK                                                                      9

SEQ ID NO: 354          moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 354
ARDVGKSAY                                                                      9

SEQ ID NO: 355          moltype = AA   length = 9
```

-continued

| FEATURE | Location/Qualifiers |
| --- | --- |
| source | 1..9<br>organism = synthetic construct<br>mol_type = protein<br>note = Seed: GAGDVGKSA (KRAS G13D) |

SEQUENCE: 355
GSGDVGKSL                                                                 9

| SEQ ID NO: 356 | moltype = AA  length = 9 |
| --- | --- |
| FEATURE | Location/Qualifiers |
| source | 1..9<br>organism = synthetic construct<br>mol_type = protein<br>note = Seed: VVGAGDVGK (KRAS G13D) |

SEQUENCE: 356
VVGAGDVGR                                                                 9

| SEQ ID NO: 357 | moltype = AA  length = 9 |
| --- | --- |
| FEATURE | Location/Qualifiers |
| source | 1..9<br>organism = synthetic construct<br>mol_type = protein<br>note = Seed: GAGDVGKSA (KRAS G13D) |

SEQUENCE: 357
GPGDVGKSV                                                                 9

| SEQ ID NO: 358 | moltype = AA  length = 9 |
| --- | --- |
| FEATURE | Location/Qualifiers |
| source | 1..9<br>organism = synthetic construct<br>mol_type = protein<br>note = Seed: DVGKSALTI (KRAS G13D) |

SEQUENCE: 358
DTGKSALTY                                                                 9

| SEQ ID NO: 359 | moltype = AA  length = 9 |
| --- | --- |
| FEATURE | Location/Qualifiers |
| source | 1..9<br>organism = synthetic construct<br>mol_type = protein<br>note = Seed: AGDVGKSAL (KRAS G13D) |

SEQUENCE: 359
ARDVGKSAF                                                                 9

| SEQ ID NO: 360 | moltype = AA  length = 9 |
| --- | --- |
| FEATURE | Location/Qualifiers |
| source | 1..9<br>organism = synthetic construct<br>mol_type = protein<br>note = Seed: GACGVGKSA (KRAS G12C) |

SEQUENCE: 360
GSCGVGKSM                                                                 9

| SEQ ID NO: 361 | moltype = AA  length = 9 |
| --- | --- |
| FEATURE | Location/Qualifiers |
| source | 1..9<br>organism = synthetic construct<br>mol_type = protein<br>note = Seed: AGDVGKSAL (KRAS G13D) |

SEQUENCE: 361
ATDVGKSAY                                                                 9

| SEQ ID NO: 362 | moltype = AA  length = 9 |
| --- | --- |
| FEATURE | Location/Qualifiers |
| source | 1..9<br>organism = synthetic construct<br>mol_type = protein<br>note = Seed: GARGVGKSA (KRAS G12R) |

SEQUENCE: 362
GMRGVGKSY                                                                 9

| SEQ ID NO: 363 | moltype = AA  length = 9 |
| --- | --- |
| FEATURE | Location/Qualifiers |
| source | 1..9<br>organism = synthetic construct<br>mol_type = protein<br>note = Seed: GAGDVGKSA (KRAS G13D) |

SEQUENCE: 363
GAGDVGKSH                                                                 9

```
SEQ ID NO: 364          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 364
GCDGVGKSI                                                              9

SEQ ID NO: 365          moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 365
GARGVGKSI                                                              9

SEQ ID NO: 366          moltype = AA   length = 9
FEATURE                 Location/Qualifiers
source                  1..9
                        organism = synthetic construct
                        mol_type = protein
                        note = Seed: VVGADGVGK (KRAS G12D)
SEQUENCE: 366
VVGADGVGR                                                              9

SEQ ID NO: 367          moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 367
ANDVGKSAF                                                              9

SEQ ID NO: 368          moltype = AA   length = 9
FEATURE                 Location/Qualifiers
source                  1..9
                        organism = synthetic construct
                        mol_type = protein
                        note = Seed: VVGACGVGK (KRAS G12C)
SEQUENCE: 368
VSGACGVGK                                                              9

SEQ ID NO: 369          moltype = AA   length = 9
FEATURE                 Location/Qualifiers
source                  1..9
                        organism = synthetic construct
                        mol_type = protein
                        note = Seed: VVGAVGVGK (KRAS G12V)
SEQUENCE: 369
VSGAVGVGF                                                              9

SEQ ID NO: 370          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 370
GWDGVGKSM                                                              9

SEQ ID NO: 371          moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 371
GTRGVGKSL                                                              9

SEQ ID NO: 372          moltype = AA   length = 9
FEATURE                 Location/Qualifiers
source                  1..9
                        organism = synthetic construct
                        mol_type = protein
                        note = Seed: GAVGVGKSA (KRAS G12V)
```

```
SEQUENCE: 372
GIVGVGKSM                                                                          9

SEQ ID NO: 373           moltype = AA   length = 9
FEATURE                  Location/Qualifiers
source                   1..9
                         organism = synthetic construct
                         mol_type = protein
                         note = Seed: VVGACGVGK (KRAS G12C)
SEQUENCE: 373
VIGACGVGK                                                                          9

SEQ ID NO: 374           moltype = AA   length = 9
FEATURE                  Location/Qualifiers
source                   1..9
                         organism = synthetic construct
                         mol_type = protein
                         note = Seed: GAGDVGKSA (KRAS G13D)
SEQUENCE: 374
GAGDVGKSV                                                                          9

SEQ ID NO: 375           moltype = AA   length = 9
FEATURE                  Location/Qualifiers
source                   1..9
                         organism = synthetic construct
                         mol_type = protein
                         note = Seed: GAGDVGKSA (KRAS G13D)
SEQUENCE: 375
GGGDVGKSY                                                                          9

SEQ ID NO: 376           moltype = AA   length = 9
FEATURE                  Location/Qualifiers
source                   1..9
                         organism = synthetic construct
                         mol_type = protein
                         note = Seed: LVVVGACGV (KRAS G12C)
SEQUENCE: 376
LQVVGACGL                                                                          9

SEQ ID NO: 377           moltype = AA   length = 9
FEATURE                  Location/Qualifiers
source                   1..9
                         organism = synthetic construct
                         mol_type = protein
                         note = Seed: GAGDVGKSA (KRAS G13D)
SEQUENCE: 377
GVGDVGKSL                                                                          9

SEQ ID NO: 378           moltype = AA   length = 9
FEATURE                  Location/Qualifiers
source                   1..9
                         organism = synthetic construct
                         mol_type = protein
                         note = Seed: VVGADGVGK (KRAS G12D)
SEQUENCE: 378
VAGADGVGF                                                                          9

SEQ ID NO: 379           moltype = AA   length = 9
FEATURE                  Location/Qualifiers
source                   1..9
                         organism = synthetic construct
                         mol_type = protein
                         note = Seed: GARGVGKSA (KRAS G12R)
SEQUENCE: 379
GARGVGKSH                                                                          9

SEQ ID NO: 380           moltype = AA   length = 9
FEATURE                  Location/Qualifiers
source                   1..9
                         organism = synthetic construct
                         mol_type = protein
                         note = Seed: GADGVGKSA (KRAS G12D)
SEQUENCE: 380
GVDGVGKSY                                                                          9

SEQ ID NO: 381           moltype = AA   length = 9
FEATURE                  Location/Qualifiers
source                   1..9
                         organism = synthetic construct
```

```
                                    mol_type = protein
                                    note = Seed: VVGACGVGK (KRAS G12C)
SEQUENCE: 381
VAGACGVGM                                                                        9

SEQ ID NO: 382         moltype = AA  length = 9
FEATURE                Location/Qualifiers
source                 1..9
                       organism = synthetic construct
                       mol_type = protein
                       note = Seed: GACGVGKSA (KRAS G12C)
SEQUENCE: 382
GPCGVGKSM                                                                        9

SEQ ID NO: 383         moltype = AA  length = 9
FEATURE                Location/Qualifiers
source                 1..9
                       organism = synthetic construct
                       mol_type = protein
                       note = Seed: VVGADGVGK (KRAS G12D)
SEQUENCE: 383
VTGADGVGY                                                                        9

SEQ ID NO: 384         moltype = AA  length = 9
FEATURE                Location/Qualifiers
source                 1..9
                       organism = synthetic construct
                       mol_type = protein
                       note = Seed: AGDVGKSAL (KRAS G13D)
SEQUENCE: 384
AADVGKSAA                                                                        9

SEQ ID NO: 385         moltype = AA  length = 9
FEATURE                Location/Qualifiers
source                 1..9
                       organism = synthetic construct
                       mol_type = protein
                       note = Seed: GACGVGKSA (KRAS G12C)
SEQUENCE: 385
GGCGVGKSY                                                                        9

SEQ ID NO: 386         moltype = AA  length = 9
FEATURE                Location/Qualifiers
source                 1..9
                       organism = synthetic construct
                       mol_type = protein
                       note = Seed: GAVGVGKSA (KRAS G12V)
SEQUENCE: 386
GSVGVGKSH                                                                        9

SEQ ID NO: 387         moltype = AA  length = 9
FEATURE                Location/Qualifiers
source                 1..9
                       organism = synthetic construct
                       mol_type = protein
                       note = Seed: AGDVGKSAL (KRAS G13D)
SEQUENCE: 387
AADVGKSAC                                                                        9

SEQ ID NO: 388         moltype = AA  length = 9
FEATURE                Location/Qualifiers
source                 1..9
                       organism = synthetic construct
                       mol_type = protein
                       note = Seed: DVGKSALTI (KRAS G13D)
SEQUENCE: 388
DIGKSALTF                                                                        9

SEQ ID NO: 389         moltype = AA  length = 9
FEATURE                Location/Qualifiers
source                 1..9
                       organism = synthetic construct
                       mol_type = protein
                       note = Seed: VVGAVGVGK (KRAS G12V)
SEQUENCE: 389
VAGAVGVGH                                                                        9

SEQ ID NO: 390         moltype = AA  length = 9
FEATURE                Location/Qualifiers
```

| | | |
|---|---|---|
| source | 1..9<br>organism = synthetic construct<br>mol_type = protein<br>note = Seed: GARGVGKSA (KRAS G12R) | |
| SEQUENCE: 390<br>GQRGVGKSY | | 9 |
| SEQ ID NO: 391<br>FEATURE<br>source | moltype = AA length = 9<br>Location/Qualifiers<br>1..9<br>organism = synthetic construct<br>mol_type = protein<br>note = Seed: AGDVGKSAL (KRAS G13D) | |
| SEQUENCE: 391<br>AFDVGKSAY | | 9 |
| SEQ ID NO: 392<br>FEATURE<br>source | moltype = AA length = 9<br>Location/Qualifiers<br>1..9<br>organism = synthetic construct<br>mol_type = protein<br>note = Seed: VVGARGVGK (KRAS G12R) | |
| SEQUENCE: 392<br>VSGARGVGL | | 9 |
| SEQ ID NO: 393<br>FEATURE<br>source | moltype = AA length = 9<br>Location/Qualifiers<br>1..9<br>organism = synthetic construct<br>mol_type = protein<br>note = Seed: GACGVGKSA (KRAS G12C) | |
| SEQUENCE: 393<br>GPCGVGKSI | | 9 |
| SEQ ID NO: 394<br>FEATURE<br>source | moltype = AA length = 9<br>Location/Qualifiers<br>1..9<br>organism = synthetic construct<br>mol_type = protein<br>note = Seed: GAVGVGKSA (KRAS G12V) | |
| SEQUENCE: 394<br>GQVGVGKSY | | 9 |
| SEQ ID NO: 395<br>FEATURE<br>source | moltype = AA length = 9<br>Location/Qualifiers<br>1..9<br>organism = synthetic construct<br>mol_type = protein<br>note = Seed: VVGACGVGK (KRAS G12C) | |
| SEQUENCE: 395<br>VTGACGVGY | | 9 |
| SEQ ID NO: 396<br>FEATURE<br>source | moltype = AA length = 9<br>Location/Qualifiers<br>1..9<br>organism = synthetic construct<br>mol_type = protein<br>note = Seed: GACGVGKSA (KRAS G12C) | |
| SEQUENCE: 396<br>GPCGVGKSP | | 9 |
| SEQ ID NO: 397<br>FEATURE<br>source | moltype = AA length = 9<br>Location/Qualifiers<br>1..9<br>organism = synthetic construct<br>mol_type = protein<br>note = Seed: VVGACGVGK (KRAS G12C) | |
| SEQUENCE: 397<br>VSGACGVGR | | 9 |
| SEQ ID NO: 398<br>FEATURE<br>source | moltype = AA length = 9<br>Location/Qualifiers<br>1..9<br>organism = synthetic construct<br>mol_type = protein<br>note = Seed: GAGDVGKSA (KRAS G13D) | |
| SEQUENCE: 398<br>GIGDVGKSM | | 9 |

```
SEQ ID NO: 399         moltype = AA  length = 9
FEATURE                Location/Qualifiers
source                 1..9
                       organism = synthetic construct
                       mol_type = protein
                       note = Seed: LVVVGAVGV (KRAS G12V)
SEQUENCE: 399
LMVVGAVGM                                                                  9

SEQ ID NO: 400         moltype = AA  length = 9
FEATURE                Location/Qualifiers
source                 1..9
                       organism = synthetic construct
                       mol_type = protein
                       note = Seed: AGDVGKSAL (KRAS G13D)
SEQUENCE: 400
ARDVGKSAM                                                                  9

SEQ ID NO: 401         moltype = AA  length = 9
FEATURE                Location/Qualifiers
source                 1..9
                       organism = synthetic construct
                       mol_type = protein
                       note = Seed: LVVVGAVGV (KRAS G12V)
SEQUENCE: 401
LQVVGAVGL                                                                  9

SEQ ID NO: 402         moltype = AA  length = 9
FEATURE                Location/Qualifiers
source                 1..9
                       organism = synthetic construct
                       mol_type = protein
                       note = Seed: GACGVGKSA (KRAS G12C)
SEQUENCE: 402
GACGVGKSH                                                                  9

SEQ ID NO: 403         moltype = AA  length = 9
FEATURE                Location/Qualifiers
source                 1..9
                       organism = synthetic construct
                       mol_type = protein
                       note = Seed: GACGVGKSA (KRAS G12C)
SEQUENCE: 403
GVCGVGKSM                                                                  9

SEQ ID NO: 404         moltype = AA  length = 9
FEATURE                Location/Qualifiers
source                 1..9
                       organism = synthetic construct
                       mol_type = protein
                       note = Seed: LVVVGARGV (KRAS G12R)
SEQUENCE: 404
LLVVGARGL                                                                  9

SEQ ID NO: 405         moltype = AA  length = 9
FEATURE                Location/Qualifiers
source                 1..9
                       organism = synthetic construct
                       mol_type = protein
                       note = Seed: GACGVGKSA (KRAS G12C)
SEQUENCE: 405
GTCGVGKSL                                                                  9

SEQ ID NO: 406         moltype = AA  length = 9
FEATURE                Location/Qualifiers
source                 1..9
                       organism = synthetic construct
                       mol_type = protein
                       note = Seed: AGDVGKSAL (KRAS G13D)
SEQUENCE: 406
AFDVGKSAC                                                                  9

SEQ ID NO: 407         moltype = AA  length = 9
FEATURE                Location/Qualifiers
source                 1..9
                       organism = synthetic construct
                       mol_type = protein
                       note = Seed: GAVGVGKSA (KRAS G12V)
SEQUENCE: 407
```

```
GLVGVGKSY                                                                                9

SEQ ID NO: 408          moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 408
GMVGVGKSY                                                                                9

SEQ ID NO: 409          moltype = AA  length = 9
FEATURE                 Location/Qualifiers
source                  1..9
                        organism = synthetic construct
                        mol_type = protein
                        note = Seed: VVGARGVGK (KRAS G12R)
SEQUENCE: 409
VSGARGVGF                                                                                9

SEQ ID NO: 410          moltype = AA  length = 9
FEATURE                 Location/Qualifiers
source                  1..9
                        organism = synthetic construct
                        mol_type = protein
                        note = Seed: VVGACGVGK (KRAS G12C)
SEQUENCE: 410
VLGACGVGK                                                                                9

SEQ ID NO: 411          moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 411
GTCGVGKSM                                                                                9

SEQ ID NO: 412          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 412
GTDGVGKSY                                                                                9

SEQ ID NO: 413          moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 413
GGVGVGKSF                                                                                9

SEQ ID NO: 414          moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 414
GTGDVGKSL                                                                                9

SEQ ID NO: 415          moltype = AA  length = 9
FEATURE                 Location/Qualifiers
source                  1..9
                        organism = synthetic construct
                        mol_type = protein
                        note = Seed: LVVVGACGV (KRAS G12C)
SEQUENCE: 415
LIVVGACGI                                                                                9

SEQ ID NO: 416          moltype = AA  length = 9
FEATURE                 Location/Qualifiers
source                  1..9
                        organism = synthetic construct
                        mol_type = protein
```

|   |   |   |
|---|---|---|
| | note = Seed: VVGARGVGK (KRAS G12R) | |
| SEQUENCE: 416 VLGARGVGK | | 9 |
| SEQ ID NO: 417 FEATURE source | moltype = AA length = 9 Location/Qualifiers 1..9 organism = synthetic construct mol_type = protein note = Seed: LVVVGARGV (KRAS G12R) | |
| SEQUENCE: 417 LMVVGARGA | | 9 |
| SEQ ID NO: 418 FEATURE source | moltype = AA length = 9 Location/Qualifiers 1..9 organism = synthetic construct mol_type = protein note = Seed: GACGVGKSA (KRAS G12C) | |
| SEQUENCE: 418 GPCGVGKST | | 9 |
| SEQ ID NO: 419 FEATURE source | moltype = AA length = 9 Location/Qualifiers 1..9 organism = synthetic construct mol_type = protein note = Seed: VVGAVGVGK (KRAS G12V) | |
| SEQUENCE: 419 VIGAVGVGY | | 9 |
| SEQ ID NO: 420 FEATURE source | moltype = AA length = 9 Location/Qualifiers 1..9 organism = synthetic construct mol_type = protein note = Seed: GARGVGKSA (KRAS G12R) | |
| SEQUENCE: 420 GPRGVGKSS | | 9 |
| SEQ ID NO: 421 FEATURE source | moltype = AA length = 9 Location/Qualifiers 1..9 organism = synthetic construct mol_type = protein note = Seed: LVVVGACGV (KRAS G12C) | |
| SEQUENCE: 421 LAVVGACGV | | 9 |
| SEQ ID NO: 422 FEATURE source | moltype = AA length = 9 Location/Qualifiers 1..9 organism = synthetic construct mol_type = protein note = Seed: GARGVGKSA (KRAS G12R) | |
| SEQUENCE: 422 GIRGVGKSL | | 9 |
| SEQ ID NO: 423 FEATURE source | moltype = AA length = 9 Location/Qualifiers 1..9 organism = synthetic construct mol_type = protein note = Seed: AGDVGKSAL (KRAS G13D) | |
| SEQUENCE: 423 AYDVGKSAC | | 9 |
| SEQ ID NO: 424 FEATURE source | moltype = AA length = 9 Location/Qualifiers 1..9 organism = synthetic construct mol_type = protein note = Seed: LVVVGADGV (KRAS G12D) | |
| SEQUENCE: 424 LMVVGADGA | | 9 |
| SEQ ID NO: 425 FEATURE source | moltype = AA length = 9 Location/Qualifiers 1..9 | |

-continued

```
                        organism = synthetic construct
                        mol_type = protein
                        note = Seed: DVGKSALTI (KRAS G13D)
SEQUENCE: 425
DPGKSALTI                                                                    9

SEQ ID NO: 426          moltype = AA  length = 9
FEATURE                 Location/Qualifiers
source                  1..9
                        organism = synthetic construct
                        mol_type = protein
                        note = Seed: VVGAGDVGK (KRAS G13D)
SEQUENCE: 426
VTGAGDVGK                                                                    9

SEQ ID NO: 427          moltype = AA  length = 9
FEATURE                 Location/Qualifiers
source                  1..9
                        organism = synthetic construct
                        mol_type = protein
                        note = Seed: VVGACGVGK (KRAS G12C)
SEQUENCE: 427
VAGACGVGK                                                                    9

SEQ ID NO: 428          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 428
GADGVGKSC                                                                    9

SEQ ID NO: 429          moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 429
GICGVGKSF                                                                    9

SEQ ID NO: 430          moltype = AA  length = 9
FEATURE                 Location/Qualifiers
source                  1..9
                        organism = synthetic construct
                        mol_type = protein
                        note = Seed: VVGAVGVGK (KRAS G12V)
SEQUENCE: 430
VVGAVGVGF                                                                    9

SEQ ID NO: 431          moltype = AA  length = 9
FEATURE                 Location/Qualifiers
source                  1..9
                        organism = synthetic construct
                        mol_type = protein
                        note = Seed: VVGADGVGK (KRAS G12D)
SEQUENCE: 431
VAGADGVGL                                                                    9

SEQ ID NO: 432          moltype = AA  length = 9
FEATURE                 Location/Qualifiers
source                  1..9
                        organism = synthetic construct
                        mol_type = protein
                        note = Seed: VVGARGVGK (KRAS G12R)
SEQUENCE: 432
VSGARGVGY                                                                    9

SEQ ID NO: 433          moltype = AA  length = 9
FEATURE                 Location/Qualifiers
source                  1..9
                        organism = synthetic construct
                        mol_type = protein
                        note = Seed: LVVVGACGV (KRAS G12C)
SEQUENCE: 433
LVVVGACGL                                                                    9

SEQ ID NO: 434          moltype = AA  length = 9
```

```
FEATURE                     Location/Qualifiers
source                      1..9
                            organism = synthetic construct
                            mol_type = protein
                            note = Seed: AGDVGKSAL (KRAS G13D)
SEQUENCE: 434
AHDVGKSAL                                                                        9

SEQ ID NO: 435              moltype = AA  length = 9
FEATURE                     Location/Qualifiers
source                      1..9
                            organism = synthetic construct
                            mol_type = protein
                            note = Seed: GADGVGKSA (KRAS G12D)
SEQUENCE: 435
GRDGVGKSM                                                                        9

SEQ ID NO: 436              moltype = AA  length = 9
FEATURE                     Location/Qualifiers
source                      1..9
                            organism = synthetic construct
                            mol_type = protein
                            note = Seed: VVGAGDVGK (KRAS G13D)
SEQUENCE: 436
VTGAGDVGY                                                                        9

SEQ ID NO: 437              moltype = AA  length = 9
FEATURE                     Location/Qualifiers
source                      1..9
                            organism = synthetic construct
                            mol_type = protein
                            note = Seed: LVVVGACGV (KRAS G12C)
SEQUENCE: 437
LTVVGACGI                                                                        9

SEQ ID NO: 438              moltype = AA  length = 9
FEATURE                     Location/Qualifiers
source                      1..9
                            organism = synthetic construct
                            mol_type = protein
                            note = Seed: VVGARGVGK (KRAS G12R)
SEQUENCE: 438
VTGARGVGM                                                                        9

SEQ ID NO: 439              moltype = AA  length = 9
FEATURE                     Location/Qualifiers
source                      1..9
                            organism = synthetic construct
                            mol_type = protein
                            note = Seed: AGDVGKSAL (KRAS G13D)
SEQUENCE: 439
APDVGKSAL                                                                        9

SEQ ID NO: 440              moltype = AA  length = 9
FEATURE                     Location/Qualifiers
source                      1..9
                            organism = synthetic construct
                            mol_type = protein
                            note = Seed: GACGVGKSA (KRAS G12C)
SEQUENCE: 440
GVCGVGKSL                                                                        9

SEQ ID NO: 441              moltype = AA  length = 9
FEATURE                     Location/Qualifiers
source                      1..9
                            organism = synthetic construct
                            mol_type = protein
                            note = Seed: VVGAGDVGK (KRAS G13D)
SEQUENCE: 441
VAGAGDVGF                                                                        9

SEQ ID NO: 442              moltype = AA  length = 9
FEATURE                     Location/Qualifiers
source                      1..9
                            organism = synthetic construct
                            mol_type = protein
                            note = Seed: GAVGVGKSA (KRAS G12V)
SEQUENCE: 442
GIVGVGKSL                                                                        9
```

```
SEQ ID NO: 443          moltype = AA  length = 9
FEATURE                 Location/Qualifiers
source                  1..9
                        organism = synthetic construct
                        mol_type = protein
                        note = Seed: VVGAGDVGK (KRAS G13D)
SEQUENCE: 443
VAGAGDVGL                                                                9

SEQ ID NO: 444          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 444
AIDVGKSAY                                                                9

SEQ ID NO: 445          moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 445
GPVGVGKSC                                                                9

SEQ ID NO: 446          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 446
GHDGVGKSL                                                                9

SEQ ID NO: 447          moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 447
GPVGVGKSS                                                                9

SEQ ID NO: 448          moltype = AA  length = 9
FEATURE                 Location/Qualifiers
source                  1..9
                        organism = synthetic construct
                        mol_type = protein
                        note = Seed: VVGARGVGK (KRAS G12R)
SEQUENCE: 448
VTGARGVGL                                                                9

SEQ ID NO: 449          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 449
GQDGVGKSF                                                                9

SEQ ID NO: 450          moltype = AA  length = 9
FEATURE                 Location/Qualifiers
source                  1..9
                        organism = synthetic construct
                        mol_type = protein
                        note = Seed: VVGACGVGK (KRAS G12C)
SEQUENCE: 450
VLGACGVGR                                                                9

SEQ ID NO: 451          moltype = AA  length = 9
FEATURE                 Location/Qualifiers
source                  1..9
                        organism = synthetic construct
                        mol_type = protein
                        note = Seed: AGDVGKSAL (KRAS G13D)
```

-continued

```
SEQUENCE: 451
AHDVGKSAM                                                                        9

SEQ ID NO: 452          moltype = AA  length = 9
FEATURE                 Location/Qualifiers
source                  1..9
                        organism = synthetic construct
                        mol_type = protein
                        note = Seed: LVVVGACGV (KRAS G12C)
SEQUENCE: 452
LQVVGACGI                                                                        9

SEQ ID NO: 453          moltype = AA  length = 9
FEATURE                 Location/Qualifiers
source                  1..9
                        organism = synthetic construct
                        mol_type = protein
                        note = Seed: VVGARGVGK (KRAS G12R)
SEQUENCE: 453
VTGARGVGF                                                                        9

SEQ ID NO: 454          moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 454
GAGDVGKSI                                                                        9

SEQ ID NO: 455          moltype = AA  length = 9
FEATURE                 Location/Qualifiers
source                  1..9
                        organism = synthetic construct
                        mol_type = protein
                        note = Seed: VVGADGVGK (KRAS G12D)
SEQUENCE: 455
VAGADGVGM                                                                        9

SEQ ID NO: 456          moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 456
GQGDVGKSY                                                                        9

SEQ ID NO: 457          moltype = AA  length = 9
FEATURE                 Location/Qualifiers
source                  1..9
                        organism = synthetic construct
                        mol_type = protein
                        note = Seed: VVGARGVGK (KRAS G12R)
SEQUENCE: 457
VAGARGVGK                                                                        9

SEQ ID NO: 458          moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 458
GLGDVGKSY                                                                        9

SEQ ID NO: 459          moltype = AA  length = 9
FEATURE                 Location/Qualifiers
source                  1..9
                        organism = synthetic construct
                        mol_type = protein
                        note = Seed: VVGARGVGK (KRAS G12R)
SEQUENCE: 459
VLGARGVGR                                                                        9

SEQ ID NO: 460          moltype = AA  length = 9
FEATURE                 Location/Qualifiers
source                  1..9
                        organism = synthetic construct
```

```
                                  mol_type = protein
                                  note = Seed: GAVGVGKSA (KRAS G12V)
SEQUENCE: 460
GGVGVGKSM                                                                    9

SEQ ID NO: 461                    moltype = AA  length = 9
FEATURE                           Location/Qualifiers
source                            1..9
                                  organism = synthetic construct
                                  mol_type = protein
                                  note = Seed: GADGVGKSA (KRAS G12D)
SEQUENCE: 461
GQDGVGKSV                                                                    9

SEQ ID NO: 462                    moltype = AA  length = 9
FEATURE                           Location/Qualifiers
source                            1..9
                                  organism = synthetic construct
                                  mol_type = protein
                                  note = Seed: LVVVGAVGV (KRAS G12V)
SEQUENCE: 462
LQVVGAVGI                                                                    9

SEQ ID NO: 463                    moltype = AA  length = 9
FEATURE                           Location/Qualifiers
source                            1..9
                                  organism = synthetic construct
                                  mol_type = protein
                                  note = Seed: LVVVGAVGV (KRAS G12V)
SEQUENCE: 463
LVVVGAVGI                                                                    9

SEQ ID NO: 464                    moltype = AA  length = 9
FEATURE                           Location/Qualifiers
source                            1..9
                                  organism = synthetic construct
                                  mol_type = protein
                                  note = Seed: VVGAVGVGK (KRAS G12V)
SEQUENCE: 464
VTGAVGVGF                                                                    9

SEQ ID NO: 465                    moltype = AA  length = 9
FEATURE                           Location/Qualifiers
source                            1..9
                                  organism = synthetic construct
                                  mol_type = protein
                                  note = Seed: GARGVGKSA (KRAS G12R)
SEQUENCE: 465
GGRGVGKSF                                                                    9

SEQ ID NO: 466                    moltype = AA  length = 9
FEATURE                           Location/Qualifiers
source                            1..9
                                  organism = synthetic construct
                                  mol_type = protein
                                  note = Seed: GARGVGKSA (KRAS G12R)
SEQUENCE: 466
GLRGVGKSF                                                                    9

SEQ ID NO: 467                    moltype = AA  length = 9
FEATURE                           Location/Qualifiers
source                            1..9
                                  organism = synthetic construct
                                  mol_type = protein
                                  note = Seed: GAGDVGKSA (KRAS G13D)
SEQUENCE: 467
GMGDVGKSY                                                                    9

SEQ ID NO: 468                    moltype = AA  length = 9
FEATURE                           Location/Qualifiers
source                            1..9
                                  organism = synthetic construct
                                  mol_type = protein
                                  note = Seed: GADGVGKSA (KRAS G12D)
SEQUENCE: 468
GQDGVGKSI                                                                    9

SEQ ID NO: 469                    moltype = AA  length = 9
FEATURE                           Location/Qualifiers
```

```
                    source              1..9
                                        organism = synthetic construct
                                        mol_type = protein
                                        note = Seed: VVGAVGVGK (KRAS G12V)
SEQUENCE: 469
VSGAVGVGM                                                                           9

SEQ ID NO: 470      moltype = AA  length = 9
FEATURE             Location/Qualifiers
source              1..9
                    organism = synthetic construct
                    mol_type = protein
                    note = Seed: GAVGVGKSA (KRAS G12V)
SEQUENCE: 470
GPVGVGKSF                                                                           9

SEQ ID NO: 471      moltype = AA  length = 9
FEATURE             Location/Qualifiers
source              1..9
                    organism = synthetic construct
                    mol_type = protein
                    note = Seed: DVGKSALTI (KRAS G13D)
SEQUENCE: 471
DQGKSALTV                                                                           9

SEQ ID NO: 472      moltype = AA  length = 9
FEATURE             Location/Qualifiers
source              1..9
                    organism = synthetic construct
                    mol_type = protein
                    note = Seed: VVGARGVGK (KRAS G12R)
SEQUENCE: 472
VSGARGVGK                                                                           9

SEQ ID NO: 473      moltype = AA  length = 9
FEATURE             Location/Qualifiers
source              1..9
                    organism = synthetic construct
                    mol_type = protein
                    note = Seed: GADGVGKSA (KRAS G12D)
SEQUENCE: 473
GPDGVGKSL                                                                           9

SEQ ID NO: 474      moltype = AA  length = 9
FEATURE             Location/Qualifiers
source              1..9
                    organism = synthetic construct
                    mol_type = protein
                    note = Seed: VVGARGVGK (KRAS G12R)
SEQUENCE: 474
VAGARGVGR                                                                           9

SEQ ID NO: 475      moltype = AA  length = 9
FEATURE             Location/Qualifiers
source              1..9
                    organism = synthetic construct
                    mol_type = protein
                    note = Seed: GADGVGKSA (KRAS G12D)
SEQUENCE: 475
GPDGVGKSV                                                                           9

SEQ ID NO: 476      moltype = AA  length = 9
FEATURE             Location/Qualifiers
source              1..9
                    organism = synthetic construct
                    mol_type = protein
                    note = Seed: GADGVGKSA (KRAS G12D)
SEQUENCE: 476
GWDGVGKSF                                                                           9

SEQ ID NO: 477      moltype = AA  length = 9
FEATURE             Location/Qualifiers
source              1..9
                    organism = synthetic construct
                    mol_type = protein
                    note = Seed: GAVGVGKSA (KRAS G12V)
SEQUENCE: 477
GVVGVGKSH                                                                           9
```

```
SEQ ID NO: 478           moltype = AA  length = 9
FEATURE                  Location/Qualifiers
source                   1..9
                         organism = synthetic construct
                         mol_type = protein
                         note = Seed: VVGARGVGK (KRAS G12R)
SEQUENCE: 478
VIGARGVGK                                                                    9

SEQ ID NO: 479           moltype = AA  length = 9
FEATURE                  Location/Qualifiers
source                   1..9
                         organism = synthetic construct
                         mol_type = protein
                         note = Seed: DVGKSALTI (KRAS G13D)
SEQUENCE: 479
DSGKSALTV                                                                    9

SEQ ID NO: 480           moltype = AA  length = 9
FEATURE                  Location/Qualifiers
source                   1..9
                         organism = synthetic construct
                         mol_type = protein
                         note = Seed: DVGKSALTI (KRAS G13D)
SEQUENCE: 480
DAGKSALTF                                                                    9

SEQ ID NO: 481           moltype = AA  length = 9
FEATURE                  Location/Qualifiers
source                   1..9
                         organism = synthetic construct
                         mol_type = protein
                         note = Seed: GADGVGKSA (KRAS G12D)
SEQUENCE: 481
GNDGVGKSF                                                                    9

SEQ ID NO: 482           moltype = AA  length = 9
FEATURE                  Location/Qualifiers
source                   1..9
                         organism = synthetic construct
                         mol_type = protein
                         note = Seed: GADGVGKSA (KRAS G12D)
SEQUENCE: 482
GHDGVGKSM                                                                    9

SEQ ID NO: 483           moltype = AA  length = 9
FEATURE                  Location/Qualifiers
source                   1..9
                         organism = synthetic construct
                         mol_type = protein
                         note = Seed: GACGVGKSA (KRAS G12C)
SEQUENCE: 483
GICGVGKSM                                                                    9

SEQ ID NO: 484           moltype = AA  length = 9
FEATURE                  Location/Qualifiers
source                   1..9
                         organism = synthetic construct
                         mol_type = protein
                         note = Seed: AGDVGKSAL (KRAS G13D)
SEQUENCE: 484
ADDVGKSAI                                                                    9

SEQ ID NO: 485           moltype = AA  length = 9
FEATURE                  Location/Qualifiers
source                   1..9
                         organism = synthetic construct
                         mol_type = protein
                         note = Seed: GARGVGKSA (KRAS G12R)
SEQUENCE: 485
GMRGVGKSF                                                                    9

SEQ ID NO: 486           moltype = AA  length = 9
FEATURE                  Location/Qualifiers
source                   1..9
                         organism = synthetic construct
                         mol_type = protein
                         note = Seed: GARGVGKSA (KRAS G12R)
SEQUENCE: 486
```

```
GPRGVGKSG                                                                        9

SEQ ID NO: 487          moltype = AA  length = 9
FEATURE                 Location/Qualifiers
source                  1..9
                        organism = synthetic construct
                        mol_type = protein
                        note = Seed: LVVVGAVGV (KRAS G12V)
SEQUENCE: 487
LAVVGAVGV                                                                        9

SEQ ID NO: 488          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 488
ARDVGKSAI                                                                        9

SEQ ID NO: 489          moltype = AA  length = 9
FEATURE                 Location/Qualifiers
source                  1..9
                        organism = synthetic construct
                        mol_type = protein
                        note = Seed: LVVVGACGV (KRAS G12C)
SEQUENCE: 489
LIVVGACGL                                                                        9

SEQ ID NO: 490          moltype = AA  length = 9
FEATURE                 Location/Qualifiers
source                  1..9
                        organism = synthetic construct
                        mol_type = protein
                        note = Seed: LVVVGAVGV (KRAS G12V)
SEQUENCE: 490
LLVVGAVGM                                                                        9

SEQ ID NO: 491          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 491
GNDGVGKSI                                                                        9

SEQ ID NO: 492          moltype = AA  length = 9
FEATURE                 Location/Qualifiers
source                  1..9
                        organism = synthetic construct
                        mol_type = protein
                        note = Seed: VVGACGVGK (KRAS G12C)
SEQUENCE: 492
VSGACGVGY                                                                        9

SEQ ID NO: 493          moltype = AA  length = 9
FEATURE                 Location/Qualifiers
source                  1..9
                        organism = synthetic construct
                        mol_type = protein
                        note = Seed: DVGKSALTI (KRAS G13D)
SEQUENCE: 493
DAGKSALTW                                                                        9

SEQ ID NO: 494          moltype = AA  length = 9
FEATURE                 Location/Qualifiers
source                  1..9
                        organism = synthetic construct
                        mol_type = protein
                        note = Seed: VVGADGVGK (KRAS G12D)
SEQUENCE: 494
VSGADGVGY                                                                        9

SEQ ID NO: 495          moltype = AA  length = 9
FEATURE                 Location/Qualifiers
source                  1..9
                        organism = synthetic construct
                        mol_type = protein
```

-continued

| | | |
|---|---|---|
| | note = Seed: GAVGVGKSA (KRAS G12V) | |
| SEQUENCE: 495<br>GTVGVGKSH | | 9 |
| SEQ ID NO: 496<br>FEATURE<br>source | moltype = AA  length = 9<br>Location/Qualifiers<br>1..9<br>organism = synthetic construct<br>mol_type = protein<br>note = Seed: GARGVGKSA (KRAS G12R) | |
| SEQUENCE: 496<br>GVRGVGKSA | | 9 |
| SEQ ID NO: 497<br>FEATURE<br>source | moltype = AA  length = 9<br>Location/Qualifiers<br>1..9<br>organism = synthetic construct<br>mol_type = protein<br>note = Seed: LVVVGAGDV (KRAS G13D) | |
| SEQUENCE: 497<br>LMVVGAGDV | | 9 |
| SEQ ID NO: 498<br>FEATURE<br>source | moltype = AA  length = 9<br>Location/Qualifiers<br>1..9<br>organism = synthetic construct<br>mol_type = protein<br>note = Seed: VVGACGVGK (KRAS G12C) | |
| SEQUENCE: 498<br>VVGACGVGY | | 9 |
| SEQ ID NO: 499<br>FEATURE<br>source | moltype = AA  length = 9<br>Location/Qualifiers<br>1..9<br>organism = synthetic construct<br>mol_type = protein<br>note = Seed: DVGKSALTI (KRAS G13D) | |
| SEQUENCE: 499<br>DIGKSALTY | | 9 |
| SEQ ID NO: 500<br>FEATURE<br>source | moltype = AA  length = 9<br>Location/Qualifiers<br>1..9<br>organism = synthetic construct<br>mol_type = protein<br>note = Seed: GAVGVGKSA (KRAS G12V) | |
| SEQUENCE: 500<br>GSVGVGKSV | | 9 |
| SEQ ID NO: 501<br>FEATURE<br>source | moltype = AA  length = 9<br>Location/Qualifiers<br>1..9<br>organism = synthetic construct<br>mol_type = protein<br>note = Seed: GADGVGKSA (KRAS G12D) | |
| SEQUENCE: 501<br>GNDGVGKSV | | 9 |
| SEQ ID NO: 502<br>FEATURE<br>source | moltype = AA  length = 9<br>Location/Qualifiers<br>1..9<br>organism = synthetic construct<br>mol_type = protein<br>note = Seed: GADGVGKSA (KRAS G12D) | |
| SEQUENCE: 502<br>GRDGVGKSF | | 9 |
| SEQ ID NO: 503<br>FEATURE<br>source | moltype = AA  length = 9<br>Location/Qualifiers<br>1..9<br>organism = synthetic construct<br>mol_type = protein<br>note = Seed: VVGARGVGK (KRAS G12R) | |
| SEQUENCE: 503<br>VTGARGVGY | | 9 |
| SEQ ID NO: 504<br>FEATURE<br>source | moltype = AA  length = 9<br>Location/Qualifiers<br>1..9 | |

```
                        organism = synthetic construct
                        mol_type = protein
                        note = Seed: GAGDVGKSA (KRAS G13D)
SEQUENCE: 504
GIGDVGKSL                                                               9

SEQ ID NO: 505          moltype = AA  length = 9
FEATURE                 Location/Qualifiers
source                  1..9
                        organism = synthetic construct
                        mol_type = protein
                        note = Seed: LVVVGAVGV (KRAS G12V)
SEQUENCE: 505
LIVVGAVGI                                                               9

SEQ ID NO: 506          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 506
GIDGVGKSY                                                               9

SEQ ID NO: 507          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 507
GTDGVGKSC                                                               9

SEQ ID NO: 508          moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 508
GQCGVGKSY                                                               9

SEQ ID NO: 509          moltype = AA  length = 9
FEATURE                 Location/Qualifiers
source                  1..9
                        organism = synthetic construct
                        mol_type = protein
                        note = Seed: VVGAVGVGK (KRAS G12V)
SEQUENCE: 509
VGGAVGVGY                                                               9

SEQ ID NO: 510          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 510
AHDVGKSAF                                                               9

SEQ ID NO: 511          moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 511
GMVGVGKSF                                                               9

SEQ ID NO: 512          moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 512
GMCGVGKSY                                                               9

SEQ ID NO: 513          moltype = AA  length = 9
```

| FEATURE | Location/Qualifiers |
|---|---|
| source | 1..9<br>organism = synthetic construct<br>mol_type = protein<br>note = Seed: AGDVGKSAL (KRAS G13D) |

SEQUENCE: 513
AFDVGKSAW                                                                        9

| SEQ ID NO: 514 | moltype = AA length = 9 |
|---|---|
| FEATURE | Location/Qualifiers |
| source | 1..9<br>organism = synthetic construct<br>mol_type = protein<br>note = Seed: LVVVGAVGV (KRAS G12V) |

SEQUENCE: 514
LTVVGAVGI                                                                        9

| SEQ ID NO: 515 | moltype = AA length = 9 |
|---|---|
| FEATURE | Location/Qualifiers |
| source | 1..9<br>organism = synthetic construct<br>mol_type = protein<br>note = Seed: GACGVGKSA (KRAS G12C) |

SEQUENCE: 515
GLCGVGKSY                                                                        9

| SEQ ID NO: 516 | moltype = AA length = 9 |
|---|---|
| FEATURE | Location/Qualifiers |
| source | 1..9<br>organism = synthetic construct<br>mol_type = protein<br>note = Seed: DVGKSALTI (KRAS G13D) |

SEQUENCE: 516
DGGKSALTV                                                                        9

| SEQ ID NO: 517 | moltype = AA length = 9 |
|---|---|
| FEATURE | Location/Qualifiers |
| source | 1..9<br>organism = synthetic construct<br>mol_type = protein<br>note = Seed: GARGVGKSA (KRAS G12R) |

SEQUENCE: 517
GNRGVGKSY                                                                        9

| SEQ ID NO: 518 | moltype = AA length = 9 |
|---|---|
| FEATURE | Location/Qualifiers |
| source | 1..9<br>organism = synthetic construct<br>mol_type = protein<br>note = Seed: VVGAGDVGK (KRAS G13D) |

SEQUENCE: 518
VAGAGDVGR                                                                        9

| SEQ ID NO: 519 | moltype = AA length = 9 |
|---|---|
| FEATURE | Location/Qualifiers |
| source | 1..9<br>organism = synthetic construct<br>mol_type = protein<br>note = Seed: AGDVGKSAL (KRAS G13D) |

SEQUENCE: 519
APDVGKSAM                                                                        9

| SEQ ID NO: 520 | moltype = AA length = 9 |
|---|---|
| FEATURE | Location/Qualifiers |
| source | 1..9<br>organism = synthetic construct<br>mol_type = protein<br>note = Seed: AGDVGKSAL (KRAS G13D) |

SEQUENCE: 520
AHDVGKSAY                                                                        9

| SEQ ID NO: 521 | moltype = AA length = 9 |
|---|---|
| FEATURE | Location/Qualifiers |
| source | 1..9<br>organism = synthetic construct<br>mol_type = protein<br>note = Seed: VVGAGDVGK (KRAS G13D) |

SEQUENCE: 521
VAGAGDVGM                                                                        9

-continued

```
SEQ ID NO: 522            moltype = AA   length = 9
FEATURE                   Location/Qualifiers
source                    1..9
                          organism = synthetic construct
                          mol_type = protein
                          note = Seed: VVGACGVGK (KRAS G12C)
SEQUENCE: 522
VIGACGVGR                                                                  9

SEQ ID NO: 523            moltype = AA   length = 9
FEATURE                   Location/Qualifiers
source                    1..9
                          organism = synthetic construct
                          mol_type = protein
                          note = Seed: GADGVGKSA (KRAS G12D)
SEQUENCE: 523
GRDGVGKSI                                                                  9

SEQ ID NO: 524            moltype = AA   length = 9
FEATURE                   Location/Qualifiers
source                    1..9
                          organism = synthetic construct
                          mol_type = protein
                          note = Seed: VVGAVGVGK (KRAS G12V)
SEQUENCE: 524
VSGAVGVGL                                                                  9

SEQ ID NO: 525            moltype = AA   length = 9
FEATURE                   Location/Qualifiers
source                    1..9
                          organism = synthetic construct
                          mol_type = protein
                          note = Seed: LVVVGAVGV (KRAS G12V)
SEQUENCE: 525
LVVVGAVGL                                                                  9

SEQ ID NO: 526            moltype = AA   length = 9
FEATURE                   Location/Qualifiers
source                    1..9
                          organism = synthetic construct
                          mol_type = protein
                          note = Seed: VVGARGVGK (KRAS G12R)
SEQUENCE: 526
VIGARGVGR                                                                  9

SEQ ID NO: 527            moltype = AA   length = 9
FEATURE                   Location/Qualifiers
source                    1..9
                          organism = synthetic construct
                          mol_type = protein
                          note = Seed: GAGDVGKSA (KRAS G13D)
SEQUENCE: 527
GPGDVGKSL                                                                  9

SEQ ID NO: 528            moltype = AA   length = 9
FEATURE                   Location/Qualifiers
source                    1..9
                          organism = synthetic construct
                          mol_type = protein
                          note = Seed: GARGVGKSA (KRAS G12R)
SEQUENCE: 528
GSRGVGKSH                                                                  9

SEQ ID NO: 529            moltype = AA   length = 9
FEATURE                   Location/Qualifiers
source                    1..9
                          organism = synthetic construct
                          mol_type = protein
                          note = Seed: AGDVGKSAL (KRAS G13D)
SEQUENCE: 529
ARDVGKSAV                                                                  9

SEQ ID NO: 530            moltype = AA   length = 9
FEATURE                   Location/Qualifiers
source                    1..9
                          organism = synthetic construct
                          mol_type = protein
                          note = Seed: GAGDVGKSA (KRAS G13D)
```

```
SEQUENCE: 530
GPGDVGKSI                                                                                9

SEQ ID NO: 531         moltype = AA  length = 9
FEATURE                Location/Qualifiers
source                 1..9
                       organism = synthetic construct
                       mol_type = protein
                       note = Seed: GAGDVGKSA (KRAS G13D)
SEQUENCE: 531
GPGDVGKSP                                                                                9

SEQ ID NO: 532         moltype = AA  length = 9
FEATURE                Location/Qualifiers
source                 1..9
                       organism = synthetic construct
                       mol_type = protein
                       note = Seed: AGDVGKSAL (KRAS G13D)
SEQUENCE: 532
ATDVGKSAC                                                                                9

SEQ ID NO: 533         moltype = AA  length = 9
FEATURE                Location/Qualifiers
source                 1..9
                       organism = synthetic construct
                       mol_type = protein
                       note = Seed: VVGAGDVGK (KRAS G13D)
SEQUENCE: 533
VSGAGDVGY                                                                                9

SEQ ID NO: 534         moltype = AA  length = 9
FEATURE                Location/Qualifiers
source                 1..9
                       organism = synthetic construct
                       mol_type = protein
                       note = Seed: VVGADGVGK (KRAS G12D)
SEQUENCE: 534
VVGADGVGY                                                                                9

SEQ ID NO: 535         moltype = AA  length = 9
FEATURE                Location/Qualifiers
source                 1..9
                       organism = synthetic construct
                       mol_type = protein
                       note = Seed: GAVGVGKSA (KRAS G12V)
SEQUENCE: 535
GQVGVGKSF                                                                                9

SEQ ID NO: 536         moltype = AA  length = 9
FEATURE                Location/Qualifiers
source                 1..9
                       organism = synthetic construct
                       mol_type = protein
                       note = Seed: VVGADGVGK (KRAS G12D)
SEQUENCE: 536
VAGADGVGK                                                                                9

SEQ ID NO: 537         moltype = AA  length = 9
FEATURE                Location/Qualifiers
source                 1..9
                       organism = synthetic construct
                       mol_type = protein
                       note = Seed: DVGKSALTI (KRAS G13D)
SEQUENCE: 537
DVGKSALTV                                                                                9

SEQ ID NO: 538         moltype = AA  length = 9
FEATURE                Location/Qualifiers
source                 1..9
                       organism = synthetic construct
                       mol_type = protein
                       note = Seed: GAVGVGKSA (KRAS G12V)
SEQUENCE: 538
GNVGVGKSY                                                                                9

SEQ ID NO: 539         moltype = AA  length = 9
FEATURE                Location/Qualifiers
source                 1..9
                       organism = synthetic construct
```

```
                        mol_type = protein
                        note = Seed: GAVGVGKSA (KRAS G12V)
SEQUENCE: 539
GCVGVGKSY                                                               9

SEQ ID NO: 540          moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 540
GLVGVGKSF                                                               9

SEQ ID NO: 541          moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 541
GQRGVGKSF                                                               9

SEQ ID NO: 542          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 542
ADDVGKSAV                                                               9

SEQ ID NO: 543          moltype = AA  length = 9
FEATURE                 Location/Qualifiers
source                  1..9
                        organism = synthetic construct
                        mol_type = protein
                        note = Seed: LVVVGADGV (KRAS G12D)
SEQUENCE: 543
LQVVGADGL                                                               9

SEQ ID NO: 544          moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 544
GGGDVGKSF                                                               9

SEQ ID NO: 545          moltype = AA  length = 9
FEATURE                 Location/Qualifiers
source                  1..9
                        organism = synthetic construct
                        mol_type = protein
                        note = Seed: VVGARGVGK (KRAS G12R)
SEQUENCE: 545
VAGARGVGV                                                               9

SEQ ID NO: 546          moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 546
GSRGVGKSV                                                               9

SEQ ID NO: 547          moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 547
GCRGVGKSY                                                               9

SEQ ID NO: 548          moltype = AA  length = 9
FEATURE                 Location/Qualifiers
```

```
source                  1..9
                        organism = synthetic construct
                        mol_type = protein
                        note = Seed: GARGVGKSA (KRAS G12R)
SEQUENCE: 548
GGRGVGKSM                                                                       9

SEQ ID NO: 549          moltype = AA  length = 9
FEATURE                 Location/Qualifiers
source                  1..9
                        organism = synthetic construct
                        mol_type = protein
                        note = Seed: VVGAVGVGK (KRAS G12V)
SEQUENCE: 549
VPGAVGVGR                                                                       9

SEQ ID NO: 550          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 550
AADVGKSAW                                                                       9

SEQ ID NO: 551          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 551
ASDVGKSAC                                                                       9

SEQ ID NO: 552          moltype = AA  length = 9
FEATURE                 Location/Qualifiers
source                  1..9
                        organism = synthetic construct
                        mol_type = protein
                        note = Seed: LVVVGACGV (KRAS G12C)
SEQUENCE: 552
LSVVGACGV                                                                       9

SEQ ID NO: 553          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 553
GDDGVGKSL                                                                       9

SEQ ID NO: 554          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 554
GSDGVGKSC                                                                       9

SEQ ID NO: 555          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 555
GRDGVGKSV                                                                       9

SEQ ID NO: 556          moltype = AA  length = 9
FEATURE                 Location/Qualifiers
source                  1..9
                        organism = synthetic construct
                        mol_type = protein
                        note = Seed: VVGADGVGK (KRAS G12D)
SEQUENCE: 556
VAGADGVGR                                                                       9
```

```
SEQ ID NO: 557        moltype = AA   length = 9
FEATURE               Location/Qualifiers
source                1..9
                      organism = synthetic construct
                      mol_type = protein
                      note = Seed: VVGADGVGK (KRAS G12D)
SEQUENCE: 557
VMGADGVGK                                                                         9

SEQ ID NO: 558        moltype = AA   length = 9
FEATURE               Location/Qualifiers
source                1..9
                      organism = synthetic construct
                      mol_type = protein
                      note = Seed: GAGDVGKSA (KRAS G13D)
SEQUENCE: 558
GQGDVGKSF                                                                         9

SEQ ID NO: 559        moltype = AA   length = 9
FEATURE               Location/Qualifiers
source                1..9
                      organism = synthetic construct
                      mol_type = protein
                      note = Seed: AGDVGKSAL (KRAS G13D)
SEQUENCE: 559
AYDVGKSAW                                                                         9

SEQ ID NO: 560        moltype = AA   length = 9
FEATURE               Location/Qualifiers
source                1..9
                      organism = synthetic construct
                      mol_type = protein
                      note = Seed: LVVVGARGV (KRAS G12R)
SEQUENCE: 560
LQVVGARGV                                                                         9

SEQ ID NO: 561        moltype = AA   length = 9
FEATURE               Location/Qualifiers
source                1..9
                      organism = synthetic construct
                      mol_type = protein
                      note = Seed: AGDVGKSAL (KRAS G13D)
SEQUENCE: 561
ASDVGKSAA                                                                         9

SEQ ID NO: 562        moltype = AA   length = 9
FEATURE               Location/Qualifiers
source                1..9
                      organism = synthetic construct
                      mol_type = protein
                      note = Seed: AGDVGKSAL (KRAS G13D)
SEQUENCE: 562
AGDVGKSAY                                                                         9

SEQ ID NO: 563        moltype = AA   length = 9
FEATURE               Location/Qualifiers
source                1..9
                      organism = synthetic construct
                      mol_type = protein
                      note = Seed: VVGAVGVGK (KRAS G12V)
SEQUENCE: 563
VTGAVGVGM                                                                         9

SEQ ID NO: 564        moltype = AA   length = 9
FEATURE               Location/Qualifiers
source                1..9
                      organism = synthetic construct
                      mol_type = protein
                      note = Seed: VVGAVGVGK (KRAS G12V)
SEQUENCE: 564
VVGAVGVGM                                                                         9

SEQ ID NO: 565        moltype = AA   length = 9
FEATURE               Location/Qualifiers
source                1..9
                      organism = synthetic construct
                      mol_type = protein
                      note = Seed: LVVVGADGV (KRAS G12D)
SEQUENCE: 565
```

```
LLVVGADGA                                                                         9

SEQ ID NO: 566         moltype = AA   length = 9
FEATURE                Location/Qualifiers
source                 1..9
                       organism = synthetic construct
                       mol_type = protein
                       note = Seed: GAVGVGKSA (KRAS G12V)
SEQUENCE: 566
GAVGVGKSK                                                                         9

SEQ ID NO: 567         moltype = AA   length = 9
FEATURE                Location/Qualifiers
source                 1..9
                       organism = synthetic construct
                       mol_type = protein
                       note = Seed: GAGDVGKSA (KRAS G13D)
SEQUENCE: 567
GVGDVGKSH                                                                         9

SEQ ID NO: 568         moltype = AA   length = 9
FEATURE                Location/Qualifiers
source                 1..9
                       organism = synthetic construct
                       mol_type = protein
                       note = Seed: AGDVGKSAL (KRAS G13D)
SEQUENCE: 568
AEDVGKSAY                                                                         9

SEQ ID NO: 569         moltype = AA   length = 9
FEATURE                Location/Qualifiers
source                 1..9
                       organism = synthetic construct
                       mol_type = protein
                       note = Seed: GAGDVGKSA (KRAS G13D)
SEQUENCE: 569
GPGDVGKST                                                                         9

SEQ ID NO: 570         moltype = AA   length = 9
FEATURE                Location/Qualifiers
source                 1..9
                       organism = synthetic construct
                       mol_type = protein
                       note = Seed: GAVGVGKSA (KRAS G12V)
SEQUENCE: 570
GPVGVGKSG                                                                         9

SEQ ID NO: 571         moltype = AA   length = 9
FEATURE                Location/Qualifiers
source                 1..9
                       organism = synthetic construct
                       mol_type = protein
                       note = Seed: GADGVGKSA (KRAS G12D)
SEQUENCE: 571
GPDGVGKSM                                                                         9

SEQ ID NO: 572         moltype = AA   length = 9
FEATURE                Location/Qualifiers
source                 1..9
                       organism = synthetic construct
                       mol_type = protein
                       note = Seed: LVVVGAVGV (KRAS G12V)
SEQUENCE: 572
LIVVGAVGL                                                                         9

SEQ ID NO: 573         moltype = AA   length = 9
FEATURE                Location/Qualifiers
source                 1..9
                       organism = synthetic construct
                       mol_type = protein
                       note = Seed: VVGAGDVGK (KRAS G13D)
SEQUENCE: 573
VMGAGDVGK                                                                         9

SEQ ID NO: 574         moltype = AA   length = 9
FEATURE                Location/Qualifiers
source                 1..9
                       organism = synthetic construct
                       mol_type = protein
```

-continued

| | | |
|---|---|---|
| | note = Seed: GACGVGKSA (KRAS G12C) | |
| SEQUENCE: 574 | | |
| GPCGVGKSF | | 9 |
| SEQ ID NO: 575<br>FEATURE<br>source | moltype = AA  length = 9<br>Location/Qualifiers<br>1..9<br>organism = synthetic construct<br>mol_type = protein<br>note = Seed: DVGKSALTI (KRAS G13D) | |
| SEQUENCE: 575 | | |
| DVGKSALTL | | 9 |
| SEQ ID NO: 576<br>FEATURE<br>source | moltype = AA  length = 9<br>Location/Qualifiers<br>1..9<br>organism = synthetic construct<br>mol_type = protein<br>note = Seed: VVGAVGVGK (KRAS G12V) | |
| SEQUENCE: 576 | | |
| VTGAVGVGL | | 9 |
| SEQ ID NO: 577<br>FEATURE<br>source | moltype = AA  length = 9<br>Location/Qualifiers<br>1..9<br>organism = synthetic construct<br>mol_type = protein<br>note = Seed: AGDVGKSAL (KRAS G13D) | |
| SEQUENCE: 577 | | |
| AWDVGKSAC | | 9 |
| SEQ ID NO: 578<br>FEATURE<br>source | moltype = AA  length = 9<br>Location/Qualifiers<br>1..9<br>organism = synthetic construct<br>mol_type = protein<br>note = Seed: AGDVGKSAL (KRAS G13D) | |
| SEQUENCE: 578 | | |
| AEDVGKSAW | | 9 |
| SEQ ID NO: 579<br>FEATURE<br>source | moltype = AA  length = 9<br>Location/Qualifiers<br>1..9<br>organism = synthetic construct<br>mol_type = protein<br>note = Seed: DVGKSALTI (KRAS G13D) | |
| SEQUENCE: 579 | | |
| DQGKSALTI | | 9 |
| SEQ ID NO: 580<br>FEATURE<br>source | moltype = AA  length = 9<br>Location/Qualifiers<br>1..9<br>organism = synthetic construct<br>mol_type = protein<br>note = Seed: VVGAVGVGK (KRAS G12V) | |
| SEQUENCE: 580 | | |
| VYGAVGVGR | | 9 |
| SEQ ID NO: 581<br>FEATURE<br>source | moltype = AA  length = 9<br>Location/Qualifiers<br>1..9<br>organism = synthetic construct<br>mol_type = protein<br>note = Seed: GADGVGKSA (KRAS G12D) | |
| SEQUENCE: 581 | | |
| GSDGVGKSA | | 9 |
| SEQ ID NO: 582<br>FEATURE<br>source | moltype = AA  length = 9<br>Location/Qualifiers<br>1..9<br>organism = synthetic construct<br>mol_type = protein<br>note = Seed: VVGAVGVGK (KRAS G12V) | |
| SEQUENCE: 582 | | |
| VGGAVGVGK | | 9 |
| SEQ ID NO: 583<br>FEATURE<br>source | moltype = AA  length = 9<br>Location/Qualifiers<br>1..9 | |

```
                        organism = synthetic construct
                        mol_type = protein
                        note = Seed: GAGDVGKSA (KRAS G13D)
SEQUENCE: 583
GLGDVGKSF                                                                9

SEQ ID NO: 584          moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 584
GSVGVGKSI                                                                9

SEQ ID NO: 585          moltype = AA  length = 9
FEATURE                 Location/Qualifiers
source                  1..9
                        organism = synthetic construct
                        mol_type = protein
                        note = Seed: LVVVGACGV (KRAS G12C)
SEQUENCE: 585
LMVVGACGM                                                                9

SEQ ID NO: 586          moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 586
GAVGVGKSW                                                                9

SEQ ID NO: 587          moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 587
GMGDVGKSF                                                                9

SEQ ID NO: 588          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 588
AWDVGKSAY                                                                9

SEQ ID NO: 589          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 589
GADGVGKSW                                                                9

SEQ ID NO: 590          moltype = AA  length = 9
FEATURE                 Location/Qualifiers
source                  1..9
                        organism = synthetic construct
                        mol_type = protein
                        note = Seed: VVGAGDVGK (KRAS G13D)
SEQUENCE: 590
VAGAGDVGK                                                                9

SEQ ID NO: 591          moltype = AA  length = 9
FEATURE                 Location/Qualifiers
source                  1..9
                        organism = synthetic construct
                        mol_type = protein
                        note = Seed: LVVVGAVGV (KRAS G12V)
SEQUENCE: 591
LSVVGAVGV                                                                9

SEQ ID NO: 592          moltype = AA  length = 9
```

```
FEATURE                 Location/Qualifiers
source                  1..9
                        organism = synthetic construct
                        mol_type = protein
                        note = Seed: VVGAVGVGK (KRAS G12V)
SEQUENCE: 592
VIGAVGVGF                                                                      9

SEQ ID NO: 593          moltype = AA  length = 9
FEATURE                 Location/Qualifiers
source                  1..9
                        organism = synthetic construct
                        mol_type = protein
                        note = Seed: VVGARGVGK (KRAS G12R)
SEQUENCE: 593
VAGARGVGI                                                                      9

SEQ ID NO: 594          moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 594
GLRGVGKSM                                                                      9

SEQ ID NO: 595          moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 595
GIVGVGKSH                                                                      9

SEQ ID NO: 596          moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 596
GMVGVGKSM                                                                      9

SEQ ID NO: 597          moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 597
GSRGVGKSI                                                                      9

SEQ ID NO: 598          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 598
AADVGKSAT                                                                      9

SEQ ID NO: 599          moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 599
GGCGVGKSF                                                                      9

SEQ ID NO: 600          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 600
GGDGVGKSY                                                                      9
```

```
SEQ ID NO: 601            moltype = AA   length = 9
FEATURE                   Location/Qualifiers
source                    1..9
                          organism = synthetic construct
                          mol_type = protein
                          note = Seed: GAVGVGKSA (KRAS G12V)
SEQUENCE: 601
GAVGVGKSR                                                                 9

SEQ ID NO: 602            moltype = AA   length = 9
FEATURE                   Location/Qualifiers
source                    1..9
                          organism = synthetic construct
                          mol_type = protein
                          note = Seed: GADGVGKSA (KRAS G12D)
SEQUENCE: 602
GWDGVGKSI                                                                 9

SEQ ID NO: 603            moltype = AA   length = 9
FEATURE                   Location/Qualifiers
source                    1..9
                          organism = synthetic construct
                          mol_type = protein
                          note = Seed: DVGKSALTI (KRAS G13D)
SEQUENCE: 603
DSGKSALTI                                                                 9

SEQ ID NO: 604            moltype = AA   length = 9
FEATURE                   Location/Qualifiers
source                    1..9
                          organism = synthetic construct
                          mol_type = protein
                          note = Seed: AGDVGKSAL (KRAS G13D)
SEQUENCE: 604
AMDVGKSAY                                                                 9

SEQ ID NO: 605            moltype = AA   length = 9
FEATURE                   Location/Qualifiers
source                    1..9
                          organism = synthetic construct
                          mol_type = protein
                          note = Seed: GACGVGKSA (KRAS G12C)
SEQUENCE: 605
GICGVGKSL                                                                 9

SEQ ID NO: 606            moltype = AA   length = 9
FEATURE                   Location/Qualifiers
source                    1..9
                          organism = synthetic construct
                          mol_type = protein
                          note = Seed: GAGDVGKSA (KRAS G13D)
SEQUENCE: 606
GSGDVGKSH                                                                 9

SEQ ID NO: 607            moltype = AA   length = 9
FEATURE                   Location/Qualifiers
source                    1..9
                          organism = synthetic construct
                          mol_type = protein
                          note = Seed: VVGARGVGK (KRAS G12R)
SEQUENCE: 607
VSGARGVGR                                                                 9

SEQ ID NO: 608            moltype = AA   length = 9
FEATURE                   Location/Qualifiers
source                    1..9
                          organism = synthetic construct
                          mol_type = protein
                          note = Seed: LVVVGADGV (KRAS G12D)
SEQUENCE: 608
LVVVGADGL                                                                 9

SEQ ID NO: 609            moltype = AA   length = 9
FEATURE                   Location/Qualifiers
source                    1..9
                          organism = synthetic construct
                          mol_type = protein
                          note = Seed: GADGVGKSA (KRAS G12D)
```

```
SEQUENCE: 609
GHDGVGKSF                                                                      9

SEQ ID NO: 610        moltype = AA   length = 9
FEATURE               Location/Qualifiers
source                1..9
                      organism = synthetic construct
                      mol_type = protein
                      note = Seed: DVGKSALTI (KRAS G13D)
SEQUENCE: 610
DAGKSALTM                                                                      9

SEQ ID NO: 611        moltype = AA   length = 9
FEATURE               Location/Qualifiers
source                1..9
                      organism = synthetic construct
                      mol_type = protein
                      note = Seed: AGDVGKSAL (KRAS G13D)
SEQUENCE: 611
AQDVGKSAY                                                                      9

SEQ ID NO: 612        moltype = AA   length = 9
FEATURE               Location/Qualifiers
source                1..9
                      organism = synthetic construct
                      mol_type = protein
                      note = Seed: VVGACGVGK (KRAS G12C)
SEQUENCE: 612
VSGACGVGF                                                                      9

SEQ ID NO: 613        moltype = AA   length = 9
FEATURE               Location/Qualifiers
source                1..9
                      organism = synthetic construct
                      mol_type = protein
                      note = Seed: GAGDVGKSA (KRAS G13D)
SEQUENCE: 613
GPGDVGKSM                                                                      9

SEQ ID NO: 614        moltype = AA   length = 9
FEATURE               Location/Qualifiers
source                1..9
                      organism = synthetic construct
                      mol_type = protein
                      note = Seed: LVVVGAGDV (KRAS G13D)
SEQUENCE: 614
LLVVGAGDV                                                                      9

SEQ ID NO: 615        moltype = AA   length = 9
FEATURE               Location/Qualifiers
source                1..9
                      organism = synthetic construct
                      mol_type = protein
                      note = Seed: AGDVGKSAL (KRAS G13D)
SEQUENCE: 615
AADVGKSAH                                                                      9

SEQ ID NO: 616        moltype = AA   length = 9
FEATURE               Location/Qualifiers
source                1..9
                      organism = synthetic construct
                      mol_type = protein
                      note = Seed: VVGAVGVGK (KRAS G12V)
SEQUENCE: 616
VGGAVGVGR                                                                      9

SEQ ID NO: 617        moltype = AA   length = 9
FEATURE               Location/Qualifiers
source                1..9
                      organism = synthetic construct
                      mol_type = protein
                      note = Seed: GADGVGKSA (KRAS G12D)
SEQUENCE: 617
GWDGVGKSV                                                                      9

SEQ ID NO: 618        moltype = AA   length = 9
FEATURE               Location/Qualifiers
source                1..9
                      organism = synthetic construct
```

-continued

```
                            mol_type = protein
                            note = Seed: GARGVGKSA (KRAS G12R)
SEQUENCE: 618
GMRGVGKSM                                                              9

SEQ ID NO: 619              moltype = AA   length = 9
FEATURE                     Location/Qualifiers
source                      1..9
                            organism = synthetic construct
                            mol_type = protein
                            note = Seed: VVGAGDVGK (KRAS G13D)
SEQUENCE: 619
VSGAGDVGR                                                              9

SEQ ID NO: 620              moltype = AA   length = 9
FEATURE                     Location/Qualifiers
source                      1..9
                            organism = synthetic construct
                            mol_type = protein
                            note = Seed: GAVGVGKSA (KRAS G12V)
SEQUENCE: 620
GQVGVGKSM                                                              9

SEQ ID NO: 621              moltype = AA   length = 9
FEATURE                     Location/Qualifiers
source                      1..9
                            organism = synthetic construct
                            mol_type = protein
                            note = Seed: VVGADGVGK (KRAS G12D)
SEQUENCE: 621
VMGADGVGR                                                              9

SEQ ID NO: 622              moltype = AA   length = 9
FEATURE                     Location/Qualifiers
source                      1..9
                            organism = synthetic construct
                            mol_type = protein
                            note = Seed: GAVGVGKSA (KRAS G12V)
SEQUENCE: 622
GVVGVGKSK                                                              9

SEQ ID NO: 623              moltype = AA   length = 9
FEATURE                     Location/Qualifiers
source                      1..9
                            organism = synthetic construct
                            mol_type = protein
                            note = Seed: VVGADGVGK (KRAS G12D)
SEQUENCE: 623
VIGADGVGK                                                              9

SEQ ID NO: 624              moltype = AA   length = 9
FEATURE                     Location/Qualifiers
source                      1..9
                            organism = synthetic construct
                            mol_type = protein
                            note = Seed: GAVGVGKSA (KRAS G12V)
SEQUENCE: 624
GGVGVGKSL                                                              9

SEQ ID NO: 625              moltype = AA   length = 9
FEATURE                     Location/Qualifiers
source                      1..9
                            organism = synthetic construct
                            mol_type = protein
                            note = Seed: GAGDVGKSA (KRAS G13D)
SEQUENCE: 625
GNGDVGKSY                                                              9

SEQ ID NO: 626              moltype = AA   length = 9
FEATURE                     Location/Qualifiers
source                      1..9
                            organism = synthetic construct
                            mol_type = protein
                            note = Seed: GADGVGKSA (KRAS G12D)
SEQUENCE: 626
GADGVGKST                                                              9

SEQ ID NO: 627              moltype = AA   length = 9
FEATURE                     Location/Qualifiers
```

```
source                      1..9
                            organism = synthetic construct
                            mol_type = protein
                            note = Seed: AGDVGKSAL (KRAS G13D)
SEQUENCE: 627
AFDVGKSAA                                                                           9

SEQ ID NO: 628              moltype = AA  length = 9
FEATURE                     Location/Qualifiers
source                      1..9
                            organism = synthetic construct
                            mol_type = protein
                            note = Seed: DVGKSALTI (KRAS G13D)
SEQUENCE: 628
DAGKSALTY                                                                           9

SEQ ID NO: 629              moltype = AA  length = 9
FEATURE                     Location/Qualifiers
source                      1..9
                            organism = synthetic construct
                            mol_type = protein
                            note = Seed: GACGVGKSA (KRAS G12C)
SEQUENCE: 629
GNCGVGKSY                                                                           9

SEQ ID NO: 630              moltype = AA  length = 9
FEATURE                     Location/Qualifiers
source                      1..9
                            organism = synthetic construct
                            mol_type = protein
                            note = Seed: VVGADGVGK (KRAS G12D)
SEQUENCE: 630
VSGADGVGK                                                                           9

SEQ ID NO: 631              moltype = AA  length = 9
FEATURE                     Location/Qualifiers
source                      1..9
                            organism = synthetic construct
                            mol_type = protein
                            note = Seed: VVGAGDVGK (KRAS G13D)
SEQUENCE: 631
VMGAGDVGR                                                                           9

SEQ ID NO: 632              moltype = AA  length = 9
FEATURE                     Location/Qualifiers
source                      1..9
                            organism = synthetic construct
                            mol_type = protein
                            note = Seed: AGDVGKSAL (KRAS G13D)
SEQUENCE: 632
AKDVGKSAL                                                                           9

SEQ ID NO: 633              moltype = AA  length = 9
FEATURE                     Location/Qualifiers
source                      1..9
                            organism = synthetic construct
                            mol_type = protein
                            note = Seed: AGDVGKSAL (KRAS G13D)
SEQUENCE: 633
AIDVGKSAC                                                                           9

SEQ ID NO: 634              moltype = AA  length = 9
FEATURE                     Location/Qualifiers
source                      1..9
                            organism = synthetic construct
                            mol_type = protein
                            note = Seed: GACGVGKSA (KRAS G12C)
SEQUENCE: 634
GSCGVGKSH                                                                           9

SEQ ID NO: 635              moltype = AA  length = 9
FEATURE                     Location/Qualifiers
source                      1..9
                            organism = synthetic construct
                            mol_type = protein
                            note = Seed: GAGDVGKSA (KRAS G13D)
SEQUENCE: 635
GAGDVGKSK                                                                           9
```

```
SEQ ID NO: 636         moltype = AA   length = 9
FEATURE                Location/Qualifiers
source                 1..9
                       organism = synthetic construct
                       mol_type = protein
                       note = Seed: AGDVGKSAL (KRAS G13D)
SEQUENCE: 636
AYDVGKSAA                                                             9

SEQ ID NO: 637         moltype = AA   length = 9
FEATURE                Location/Qualifiers
source                 1..9
                       organism = synthetic construct
                       mol_type = protein
                       note = Seed: GACGVGKSA (KRAS G12C)
SEQUENCE: 637
GPCGVGKSC                                                             9

SEQ ID NO: 638         moltype = AA   length = 9
FEATURE                Location/Qualifiers
source                 1..9
                       organism = synthetic construct
                       mol_type = protein
                       note = Seed: VVGAVGVGK (KRAS G12V)
SEQUENCE: 638
VQGAVGVGR                                                             9

SEQ ID NO: 639         moltype = AA   length = 9
FEATURE                Location/Qualifiers
source                 1..9
                       organism = synthetic construct
                       mol_type = protein
                       note = Seed: LVVVGARGV (KRAS G12R)
SEQUENCE: 639
LLVVGARGA                                                             9

SEQ ID NO: 640         moltype = AA   length = 9
FEATURE                Location/Qualifiers
source                 1..9
                       organism = synthetic construct
                       mol_type = protein
                       note = Seed: GADGVGKSA (KRAS G12D)
SEQUENCE: 640
GQDGVGKSY                                                             9

SEQ ID NO: 641         moltype = AA   length = 9
FEATURE                Location/Qualifiers
source                 1..9
                       organism = synthetic construct
                       mol_type = protein
                       note = Seed: VVGAGDVGK (KRAS G13D)
SEQUENCE: 641
VVGAGDVGY                                                             9

SEQ ID NO: 642         moltype = AA   length = 9
FEATURE                Location/Qualifiers
source                 1..9
                       organism = synthetic construct
                       mol_type = protein
                       note = Seed: VVGADGVGK (KRAS G12D)
SEQUENCE: 642
VIGADGVGR                                                             9

SEQ ID NO: 643         moltype = AA   length = 9
FEATURE                Location/Qualifiers
source                 1..9
                       organism = synthetic construct
                       mol_type = protein
                       note = Seed: GADGVGKSA (KRAS G12D)
SEQUENCE: 643
GTDGVGKSA                                                             9

SEQ ID NO: 644         moltype = AA   length = 9
FEATURE                Location/Qualifiers
source                 1..9
                       organism = synthetic construct
                       mol_type = protein
                       note = Seed: VVGAVGVGK (KRAS G12V)
SEQUENCE: 644
```

VQGAVGVGK 9

SEQ ID NO: 645    moltype = AA  length = 9
FEATURE           Location/Qualifiers
source            1..9
                  organism = synthetic construct
                  mol_type = protein
                  note = Seed: GAGDVGKSA (KRAS G13D)
SEQUENCE: 645
GVGDVGKSK 9

SEQ ID NO: 646    moltype = AA  length = 9
FEATURE           Location/Qualifiers
source            1..9
                  organism = synthetic construct
                  mol_type = protein
                  note = Seed: GADGVGKSA (KRAS G12D)
SEQUENCE: 646
GVDGVGKSC 9

SEQ ID NO: 647    moltype = AA  length = 9
FEATURE           Location/Qualifiers
source            1..9
                  organism = synthetic construct
                  mol_type = protein
                  note = Seed: LVVVGACGV (KRAS G12C)
SEQUENCE: 647
LLVVGACGM 9

SEQ ID NO: 648    moltype = AA  length = 9
FEATURE           Location/Qualifiers
source            1..9
                  organism = synthetic construct
                  mol_type = protein
                  note = Seed: DVGKSALTI (KRAS G13D)
SEQUENCE: 648
DSGKSALTF 9

SEQ ID NO: 649    moltype = AA  length = 9
FEATURE           Location/Qualifiers
source            1..9
                  organism = synthetic construct
                  mol_type = protein
                  note = Seed: DVGKSALTI (KRAS G13D)
SEQUENCE: 649
DPGKSALTL 9

SEQ ID NO: 650    moltype = AA  length = 9
FEATURE           Location/Qualifiers
source            1..9
                  organism = synthetic construct
                  mol_type = protein
                  note = Seed: GADGVGKSA (KRAS G12D)
SEQUENCE: 650
GIDGVGKSC 9

SEQ ID NO: 651    moltype = AA  length = 9
FEATURE           Location/Qualifiers
source            1..9
                  organism = synthetic construct
                  mol_type = protein
                  note = Seed: GAVGVGKSA (KRAS G12V)
SEQUENCE: 651
GIVGVGKSK 9

SEQ ID NO: 652    moltype = AA  length = 9
FEATURE           Location/Qualifiers
source            1..9
                  organism = synthetic construct
                  mol_type = protein
                  note = Seed: GARGVGKSA (KRAS G12R)
SEQUENCE: 652
GVRGVGKSH 9

SEQ ID NO: 653    moltype = AA  length = 9
FEATURE           Location/Qualifiers
source            1..9
                  organism = synthetic construct
                  mol_type = protein

```
                        note = Seed: GADGVGKSA (KRAS G12D)
SEQUENCE: 653
GMDGVGKSY                                                              9

SEQ ID NO: 654          moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 654
GAGDVGKSR                                                              9

SEQ ID NO: 655          moltype = AA   length = 9
FEATURE                 Location/Qualifiers
source                  1..9
                        organism = synthetic construct
                        mol_type = protein
                        note = Seed: VVGAGDVGK (KRAS G13D)
SEQUENCE: 655
VIGAGDVGK                                                              9

SEQ ID NO: 656          moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 656
GERGVGKSY                                                              9

SEQ ID NO: 657          moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 657
GVGDVGKSR                                                              9

SEQ ID NO: 658          moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 658
GSVGVGKSK                                                              9

SEQ ID NO: 659          moltype = AA   length = 9
FEATURE                 Location/Qualifiers
source                  1..9
                        organism = synthetic construct
                        mol_type = protein
                        note = Seed: LVVVGADGV (KRAS G12D)
SEQUENCE: 659
LVVVGADGI                                                              9

SEQ ID NO: 660          moltype = AA   length = 9
FEATURE                 Location/Qualifiers
source                  1..9
                        organism = synthetic construct
                        mol_type = protein
                        note = Seed: LVVVGARGV (KRAS G12R)
SEQUENCE: 660
LIVVGARGV                                                              9

SEQ ID NO: 661          moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 661
GTVGVGKSV                                                              9

SEQ ID NO: 662          moltype = AA   length = 9
FEATURE                 Location/Qualifiers
source                  1..9
```

```
                                organism = synthetic construct
                                mol_type = protein
                                note = Seed: GACGVGKSA (KRAS G12C)
SEQUENCE: 662
GPCGVGKSS                                                                                 9

SEQ ID NO: 663                  moltype = AA   length = 9
FEATURE                         Location/Qualifiers
source                          1..9
                                organism = synthetic construct
                                mol_type = protein
                                note = Seed: GAVGVGKSA (KRAS G12V)
SEQUENCE: 663
GVVGVGKSR                                                                                 9

SEQ ID NO: 664                  moltype = AA   length = 9
FEATURE                         Location/Qualifiers
source                          1..9
                                organism = synthetic construct
                                mol_type = protein
                                note = Seed: AGDVGKSAL (KRAS G13D)
SEQUENCE: 664
APDVGKSAV                                                                                 9

SEQ ID NO: 665                  moltype = AA   length = 9
FEATURE                         Location/Qualifiers
source                          1..9
                                organism = synthetic construct
                                mol_type = protein
                                note = Seed: GADGVGKSA (KRAS G12D)
SEQUENCE: 665
GVDGVGKSR                                                                                 9

SEQ ID NO: 666                  moltype = AA   length = 9
FEATURE                         Location/Qualifiers
source                          1..9
                                organism = synthetic construct
                                mol_type = protein
                                note = Seed: GADGVGKSA (KRAS G12D)
SEQUENCE: 666
GDDGVGKSM                                                                                 9

SEQ ID NO: 667                  moltype = AA   length = 9
FEATURE                         Location/Qualifiers
source                          1..9
                                organism = synthetic construct
                                mol_type = protein
                                note = Seed: GAGDVGKSA (KRAS G13D)
SEQUENCE: 667
GGGDVGKSM                                                                                 9

SEQ ID NO: 668                  moltype = AA   length = 9
FEATURE                         Location/Qualifiers
source                          1..9
                                organism = synthetic construct
                                mol_type = protein
                                note = Seed: AGDVGKSAL (KRAS G13D)
SEQUENCE: 668
ALDVGKSAY                                                                                 9

SEQ ID NO: 669                  moltype = AA   length = 9
FEATURE                         Location/Qualifiers
source                          1..9
                                organism = synthetic construct
                                mol_type = protein
                                note = Seed: VVGADGVGK (KRAS G12D)
SEQUENCE: 669
VSGADGVGR                                                                                 9

SEQ ID NO: 670                  moltype = AA   length = 9
FEATURE                         Location/Qualifiers
source                          1..9
                                organism = synthetic construct
                                mol_type = protein
                                note = Seed: VVGAVGVGK (KRAS G12V)
SEQUENCE: 670
VRGAVGVGL                                                                                 9

SEQ ID NO: 671                  moltype = AA   length = 9
```

| | | |
|---|---|---|
| FEATURE | Location/Qualifiers | |
| source | 1..9<br>organism = synthetic construct<br>mol_type = protein<br>note = Seed: GADGVGKSA (KRAS G12D) | |
| SEQUENCE: 671<br>GADGVGKSH | | 9 |
| SEQ ID NO: 672<br>FEATURE<br>source | moltype = AA  length = 9<br>Location/Qualifiers<br>1..9<br>organism = synthetic construct<br>mol_type = protein<br>note = Seed: GAVGVGKSA (KRAS G12V) | |
| SEQUENCE: 672<br>GTVGVGKSI | | 9 |
| SEQ ID NO: 673<br>FEATURE<br>source | moltype = AA  length = 9<br>Location/Qualifiers<br>1..9<br>organism = synthetic construct<br>mol_type = protein<br>note = Seed: VVGACGVGK (KRAS G12C) | |
| SEQUENCE: 673<br>VIGACGVGY | | 9 |
| SEQ ID NO: 674<br>FEATURE<br>source | moltype = AA  length = 9<br>Location/Qualifiers<br>1..9<br>organism = synthetic construct<br>mol_type = protein<br>note = Seed: VVGAVGVGK (KRAS G12V) | |
| SEQUENCE: 674<br>VAGAVGVGI | | 9 |
| SEQ ID NO: 675<br>FEATURE<br>source | moltype = AA  length = 9<br>Location/Qualifiers<br>1..9<br>organism = synthetic construct<br>mol_type = protein<br>note = Seed: GARGVGKSA (KRAS G12R) | |
| SEQUENCE: 675<br>GVRGVGKSV | | 9 |
| SEQ ID NO: 676<br>FEATURE<br>source | moltype = AA  length = 9<br>Location/Qualifiers<br>1..9<br>organism = synthetic construct<br>mol_type = protein<br>note = Seed: AGDVGKSAL (KRAS G13D) | |
| SEQUENCE: 676<br>AVDVGKSAC | | 9 |
| SEQ ID NO: 677<br>FEATURE<br>source | moltype = AA  length = 9<br>Location/Qualifiers<br>1..9<br>organism = synthetic construct<br>mol_type = protein<br>note = Seed: GACGVGKSA (KRAS G12C) | |
| SEQUENCE: 677<br>GMCGVGKSF | | 9 |
| SEQ ID NO: 678<br>FEATURE<br>source | moltype = AA  length = 9<br>Location/Qualifiers<br>1..9<br>organism = synthetic construct<br>mol_type = protein<br>note = Seed: GADGVGKSA (KRAS G12D) | |
| SEQUENCE: 678<br>GADGVGKSK | | 9 |
| SEQ ID NO: 679<br>FEATURE<br>source | moltype = AA  length = 9<br>Location/Qualifiers<br>1..9<br>organism = synthetic construct<br>mol_type = protein<br>note = Seed: AGDVGKSAL (KRAS G13D) | |
| SEQUENCE: 679<br>APDVGKSAI | | 9 |

```
SEQ ID NO: 680          moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 680
GQRGVGKSM                                                                   9

SEQ ID NO: 681          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 681
GVDGVGKSK                                                                   9

SEQ ID NO: 682          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 682
GKDGVGKSL                                                                   9

SEQ ID NO: 683          moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 683
GLVGVGKSM                                                                   9

SEQ ID NO: 684          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 684
GADGVGKSR                                                                   9

SEQ ID NO: 685          moltype = AA   length = 9
FEATURE                 Location/Qualifiers
source                  1..9
                        organism = synthetic construct
                        mol_type = protein
                        note = Seed: VVGAGDVGK (KRAS G13D)
SEQUENCE: 685
VIGAGDVGR                                                                   9

SEQ ID NO: 686          moltype = AA   length = 9
FEATURE                 Location/Qualifiers
source                  1..9
                        organism = synthetic construct
                        mol_type = protein
                        note = Seed: VVGACGVGK (KRAS G12C)
SEQUENCE: 686
VVGACGVGF                                                                   9

SEQ ID NO: 687          moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 687
GVRGVGKSI                                                                   9

SEQ ID NO: 688          moltype = AA   length = 9
FEATURE                 Location/Qualifiers
source                  1..9
                        organism = synthetic construct
                        mol_type = protein
                        note = Seed: GAVGVGKSA (KRAS G12V)
```

```
SEQUENCE: 688
GIVGVGKSR                                                                              9

SEQ ID NO: 689         moltype = AA  length = 9
FEATURE                Location/Qualifiers
source                 1..9
                       organism = synthetic construct
                       mol_type = protein
                       note = Seed: GAGDVGKSA (KRAS G13D)
SEQUENCE: 689
GIGDVGKSR                                                                              9

SEQ ID NO: 690         moltype = AA  length = 9
FEATURE                Location/Qualifiers
source                 1..9
                       organism = synthetic construct
                       mol_type = protein
                       note = Seed: VVGAVGVGK (KRAS G12V)
SEQUENCE: 690
VAGAVGVGV                                                                              9

SEQ ID NO: 691         moltype = AA  length = 9
FEATURE                Location/Qualifiers
source                 1..9
                       organism = synthetic construct
                       mol_type = protein
                       note = Seed: GAVGVGKSA (KRAS G12V)
SEQUENCE: 691
GTVGVGKSK                                                                              9

SEQ ID NO: 692         moltype = AA  length = 9
FEATURE                Location/Qualifiers
source                 1..9
                       organism = synthetic construct
                       mol_type = protein
                       note = Seed: VVGAVGVGK (KRAS G12V)
SEQUENCE: 692
VMGAVGVGY                                                                              9

SEQ ID NO: 693         moltype = AA  length = 9
FEATURE                Location/Qualifiers
source                 1..9
                       organism = synthetic construct
                       mol_type = protein
                       note = Seed: GAGDVGKSA (KRAS G13D)
SEQUENCE: 693
GIGDVGKSK                                                                              9

SEQ ID NO: 694         moltype = AA  length = 9
FEATURE                Location/Qualifiers
source                 1..9
                       organism = synthetic construct
                       mol_type = protein
                       note = Seed: LVVVGADGV (KRAS G12D)
SEQUENCE: 694
LIVVGADGL                                                                              9

SEQ ID NO: 695         moltype = AA  length = 9
FEATURE                Location/Qualifiers
source                 1..9
                       organism = synthetic construct
                       mol_type = protein
                       note = Seed: GARGVGKSA (KRAS G12R)
SEQUENCE: 695
GARGVGKSW                                                                              9

SEQ ID NO: 696         moltype = AA  length = 9
FEATURE                Location/Qualifiers
source                 1..9
                       organism = synthetic construct
                       mol_type = protein
                       note = Seed: LVVVGACGV (KRAS G12C)
SEQUENCE: 696
LTVVGACGL                                                                              9

SEQ ID NO: 697         moltype = AA  length = 9
FEATURE                Location/Qualifiers
source                 1..9
                       organism = synthetic construct
```

```
                        mol_type = protein
                        note = Seed: GAGDVGKSA (KRAS G13D)
SEQUENCE: 697
GQGDVGKSM                                                               9

SEQ ID NO: 698          moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 698
ATDVGKSAA                                                               9

SEQ ID NO: 699          moltype = AA   length = 9
FEATURE                 Location/Qualifiers
source                  1..9
                        organism = synthetic construct
                        mol_type = protein
                        note = Seed: GACGVGKSA (KRAS G12C)
SEQUENCE: 699
GQCGVGKSF                                                               9

SEQ ID NO: 700          moltype = AA   length = 9
FEATURE                 Location/Qualifiers
source                  1..9
                        organism = synthetic construct
                        mol_type = protein
                        note = Seed: VVGADGVGK (KRAS G12D)
SEQUENCE: 700
VSGADGVGF                                                               9

SEQ ID NO: 701          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 701
GPDGVGKSI                                                               9

SEQ ID NO: 702          moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 702
GSVGVGKSR                                                               9

SEQ ID NO: 703          moltype = AA   length = 9
FEATURE                 Location/Qualifiers
source                  1..9
                        organism = synthetic construct
                        mol_type = protein
                        note = Seed: VVGAGDVGK (KRAS G13D)
SEQUENCE: 703
VLGAGDVGR                                                               9

SEQ ID NO: 704          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 704
GIDGVGKSR                                                               9

SEQ ID NO: 705          moltype = AA   length = 9
FEATURE                 Location/Qualifiers
source                  1..9
                        organism = synthetic construct
                        mol_type = protein
                        note = Seed: DVGKSALTI (KRAS G13D)
SEQUENCE: 705
DGGKSALTI                                                               9

SEQ ID NO: 706          moltype = AA   length = 9
FEATURE                 Location/Qualifiers
```

```
-continued source                    1..9
                          organism = synthetic construct
                          mol_type = protein
                          note = Seed: GARGVGKSA (KRAS G12R)
SEQUENCE: 706
GTRGVGKSH                                                                          9

SEQ ID NO: 707            moltype = AA   length = 9
FEATURE                   Location/Qualifiers
source                    1..9
                          organism = synthetic construct
                          mol_type = protein
                          note = Seed: GAGDVGKSA (KRAS G13D)
SEQUENCE: 707
GAGDVGKSW                                                                          9

SEQ ID NO: 708            moltype = AA   length = 9
FEATURE                   Location/Qualifiers
source                    1..9
                          organism = synthetic construct
                          mol_type = protein
                          note = Seed: DVGKSALTI (KRAS G13D)
SEQUENCE: 708
DSGKSALTW                                                                          9

SEQ ID NO: 709            moltype = AA   length = 9
FEATURE                   Location/Qualifiers
source                    1..9
                          organism = synthetic construct
                          mol_type = protein
                          note = Seed: VVGAGDVGK (KRAS G13D)
SEQUENCE: 709
VSGAGDVGK                                                                          9

SEQ ID NO: 710            moltype = AA   length = 9
FEATURE                   Location/Qualifiers
source                    1..9
                          organism = synthetic construct
                          mol_type = protein
                          note = Seed: GACGVGKSA (KRAS G12C)
SEQUENCE: 710
GGCGVGKSM                                                                          9

SEQ ID NO: 711            moltype = AA   length = 9
FEATURE                   Location/Qualifiers
source                    1..9
                          organism = synthetic construct
                          mol_type = protein
                          note = Seed: GARGVGKSA (KRAS G12R)
SEQUENCE: 711
GMRGVGKSL                                                                          9

SEQ ID NO: 712            moltype = AA   length = 9
FEATURE                   Location/Qualifiers
source                    1..9
                          organism = synthetic construct
                          mol_type = protein
                          note = Seed: GAVGVGKSA (KRAS G12V)
SEQUENCE: 712
GTVGVGKSR                                                                          9

SEQ ID NO: 713            moltype = AA   length = 9
FEATURE                   Location/Qualifiers
source                    1..9
                          organism = synthetic construct
                          mol_type = protein
                          note = Seed: GAGDVGKSA (KRAS G13D)
SEQUENCE: 713
GMGDVGKSM                                                                          9

SEQ ID NO: 714            moltype = AA   length = 9
FEATURE                   Location/Qualifiers
source                    1..9
                          organism = synthetic construct
                          mol_type = protein
                          note = Seed: VVGADGVGK (KRAS G12D)
SEQUENCE: 714
VLGADGVGK                                                                          9
```

```
SEQ ID NO: 715           moltype = AA   length = 9
FEATURE                  Location/Qualifiers
source                   1..9
                         organism = synthetic construct
                         mol_type = protein
                         note = Seed: GAVGVGKSA (KRAS G12V)
SEQUENCE: 715
GEVGVGKSY                                                                 9

SEQ ID NO: 716           moltype = AA   length = 9
FEATURE                  Location/Qualifiers
source                   1..9
                         organism = synthetic construct
                         mol_type = protein
                         note = Seed: VVGACGVGK (KRAS G12C)
SEQUENCE: 716
VAGACGVGH                                                                 9

SEQ ID NO: 717           moltype = AA   length = 9
FEATURE                  Location/Qualifiers
source                   1..9
                         organism = synthetic construct
                         mol_type = protein
                         note = Seed: LVVVGADGV (KRAS G12D)
SEQUENCE: 717
LQVVGADGI                                                                 9

SEQ ID NO: 718           moltype = AA   length = 9
FEATURE                  Location/Qualifiers
source                   1..9
                         organism = synthetic construct
                         mol_type = protein
                         note = Seed: VVGAVGVGK (KRAS G12V)
SEQUENCE: 718
VFGAVGVGR                                                                 9

SEQ ID NO: 719           moltype = AA   length = 9
FEATURE                  Location/Qualifiers
source                   1..9
                         organism = synthetic construct
                         mol_type = protein
                         note = Seed: DVGKSALTI (KRAS G13D)
SEQUENCE: 719
DQGKSALTL                                                                 9

SEQ ID NO: 720           moltype = AA   length = 9
FEATURE                  Location/Qualifiers
source                   1..9
                         organism = synthetic construct
                         mol_type = protein
                         note = Seed: GAVGVGKSA (KRAS G12V)
SEQUENCE: 720
GGVGVGKSK                                                                 9

SEQ ID NO: 721           moltype = AA   length = 9
FEATURE                  Location/Qualifiers
source                   1..9
                         organism = synthetic construct
                         mol_type = protein
                         note = Seed: GACGVGKSA (KRAS G12C)
SEQUENCE: 721
GLCGVGKSF                                                                 9

SEQ ID NO: 722           moltype = AA   length = 9
FEATURE                  Location/Qualifiers
source                   1..9
                         organism = synthetic construct
                         mol_type = protein
                         note = Seed: VVGADGVGK (KRAS G12D)
SEQUENCE: 722
VLGADGVGR                                                                 9

SEQ ID NO: 723           moltype = AA   length = 9
FEATURE                  Location/Qualifiers
source                   1..9
                         organism = synthetic construct
                         mol_type = protein
                         note = Seed: GAGDVGKSA (KRAS G13D)
SEQUENCE: 723
```

```
GLGDVGKSM                                                                            9

SEQ ID NO: 724         moltype = AA  length = 9
FEATURE                Location/Qualifiers
source                 1..9
                       organism = synthetic construct
                       mol_type = protein
                       note = Seed: VVGADGVGK (KRAS G12D)
SEQUENCE: 724
VGGADGVGK                                                                            9

SEQ ID NO: 725         moltype = AA  length = 9
FEATURE                Location/Qualifiers
source                 1..9
                       organism = synthetic construct
                       mol_type = protein
                       note = Seed: LVVVGARGV (KRAS G12R)
SEQUENCE: 725
LTVVGARGV                                                                            9

SEQ ID NO: 726         moltype = AA  length = 9
FEATURE                Location/Qualifiers
source                 1..9
                       organism = synthetic construct
                       mol_type = protein
                       note = Seed: AGDVGKSAL (KRAS G13D)
SEQUENCE: 726
ALDVGKSAC                                                                            9

SEQ ID NO: 727         moltype = AA  length = 9
FEATURE                Location/Qualifiers
source                 1..9
                       organism = synthetic construct
                       mol_type = protein
                       note = Seed: GACGVGKSA (KRAS G12C)
SEQUENCE: 727
GVCGVGKSH                                                                            9

SEQ ID NO: 728         moltype = AA  length = 9
FEATURE                Location/Qualifiers
source                 1..9
                       organism = synthetic construct
                       mol_type = protein
                       note = Seed: VVGAGDVGK (KRAS G13D)
SEQUENCE: 728
VLGAGDVGK                                                                            9

SEQ ID NO: 729         moltype = AA  length = 9
FEATURE                Location/Qualifiers
source                 1..9
                       organism = synthetic construct
                       mol_type = protein
                       note = Seed: LVVVGAVGV (KRAS G12V)
SEQUENCE: 729
LTVVGAVGL                                                                            9

SEQ ID NO: 730         moltype = AA  length = 9
FEATURE                Location/Qualifiers
source                 1..9
                       organism = synthetic construct
                       mol_type = protein
                       note = Seed: LVVVGADGV (KRAS G12D)
SEQUENCE: 730
LIVVGADGI                                                                            9

SEQ ID NO: 731         moltype = AA  length = 9
FEATURE                Location/Qualifiers
source                 1..9
                       organism = synthetic construct
                       mol_type = protein
                       note = Seed: VVGADGVGK (KRAS G12D)
SEQUENCE: 731
VGGADGVGR                                                                            9

SEQ ID NO: 732         moltype = AA  length = 9
FEATURE                Location/Qualifiers
source                 1..9
                       organism = synthetic construct
                       mol_type = protein
```

```
                              note = Seed: VVGADGVGK (KRAS G12D)
SEQUENCE: 732
VAGADGVGH                                                              9

SEQ ID NO: 733        moltype = AA   length = 9
FEATURE               Location/Qualifiers
source                1..9
                      organism = synthetic construct
                      mol_type = protein
                      note = Seed: DVGKSALTI (KRAS G13D)
SEQUENCE: 733
DLGKSALTW                                                              9

SEQ ID NO: 734        moltype = AA   length = 9
FEATURE               Location/Qualifiers
source                1..9
                      organism = synthetic construct
                      mol_type = protein
                      note = Seed: GADGVGKSA (KRAS G12D)
SEQUENCE: 734
GEDGVGKSL                                                              9

SEQ ID NO: 735        moltype = AA   length = 9
FEATURE               Location/Qualifiers
source                1..9
                      organism = synthetic construct
                      mol_type = protein
                      note = Seed: GAVGVGKSA (KRAS G12V)
SEQUENCE: 735
GGVGVGKSR                                                              9

SEQ ID NO: 736        moltype = AA   length = 9
FEATURE               Location/Qualifiers
source                1..9
                      organism = synthetic construct
                      mol_type = protein
                      note = Seed: GADGVGKSA (KRAS G12D)
SEQUENCE: 736
GLDGVGKSY                                                              9

SEQ ID NO: 737        moltype = AA   length = 9
FEATURE               Location/Qualifiers
source                1..9
                      organism = synthetic construct
                      mol_type = protein
                      note = Seed: GADGVGKSA (KRAS G12D)
SEQUENCE: 737
GIDGVGKSK                                                              9

SEQ ID NO: 738        moltype = AA   length = 9
FEATURE               Location/Qualifiers
source                1..9
                      organism = synthetic construct
                      mol_type = protein
                      note = Seed: GAGDVGKSA (KRAS G13D)
SEQUENCE: 738
GTGDVGKSH                                                              9

SEQ ID NO: 739        moltype = AA   length = 9
FEATURE               Location/Qualifiers
source                1..9
                      organism = synthetic construct
                      mol_type = protein
                      note = Seed: VVGADGVGK (KRAS G12D)
SEQUENCE: 739
VVGADGVGF                                                              9

SEQ ID NO: 740        moltype = AA   length = 9
FEATURE               Location/Qualifiers
source                1..9
                      organism = synthetic construct
                      mol_type = protein
                      note = Seed: LVVVGACGV (KRAS G12C)
SEQUENCE: 740
LTVVGACGA                                                              9

SEQ ID NO: 741        moltype = AA   length = 9
FEATURE               Location/Qualifiers
source                1..9
```

```
                        organism = synthetic construct
                        mol_type = protein
                        note = Seed: VVGADGVGK (KRAS G12D)
SEQUENCE: 741
VIGADGVGY                                                                            9

SEQ ID NO: 742          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 742
GYDGVGKSC                                                                            9

SEQ ID NO: 743          moltype = AA   length = 9
FEATURE                 Location/Qualifiers
source                  1..9
                        organism = synthetic construct
                        mol_type = protein
                        note = Seed: DVGKSALTI (KRAS G13D)
SEQUENCE: 743
DVGKSALTM                                                                            9

SEQ ID NO: 744          moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 744
AHDVGKSAI                                                                            9

SEQ ID NO: 745          moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 745
GSGDVGKSK                                                                            9

SEQ ID NO: 746          moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 746
GIGDVGKSH                                                                            9

SEQ ID NO: 747          moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 747
GTGDVGKSK                                                                            9

SEQ ID NO: 748          moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 748
GTGDVGKSR                                                                            9

SEQ ID NO: 749          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 749
GTDGVGKSR                                                                            9

SEQ ID NO: 750          moltype = AA   length = 9
```

| | | |
|---|---|---|
| FEATURE | Location/Qualifiers | |
| source | 1..9<br>organism = synthetic construct<br>mol_type = protein<br>note = Seed: GACGVGKSA (KRAS G12C) | |
| SEQUENCE: 750<br>GSCGVGKSV | | 9 |
| SEQ ID NO: 751<br>FEATURE<br>source | moltype = AA  length = 9<br>Location/Qualifiers<br>1..9<br>organism = synthetic construct<br>mol_type = protein<br>note = Seed: GARGVGKSA (KRAS G12R) | |
| SEQUENCE: 751<br>GGRGVGKSL | | 9 |
| SEQ ID NO: 752<br>FEATURE<br>source | moltype = AA  length = 9<br>Location/Qualifiers<br>1..9<br>organism = synthetic construct<br>mol_type = protein<br>note = Seed: VVGAGDVGK (KRAS G13D) | |
| SEQUENCE: 752<br>VGGAGDVGK | | 9 |
| SEQ ID NO: 753<br>FEATURE<br>source | moltype = AA  length = 9<br>Location/Qualifiers<br>1..9<br>organism = synthetic construct<br>mol_type = protein<br>note = Seed: GAVGVGKSA (KRAS G12V) | |
| SEQUENCE: 753<br>GVVGVGKSV | | 9 |
| SEQ ID NO: 754<br>FEATURE<br>source | moltype = AA  length = 9<br>Location/Qualifiers<br>1..9<br>organism = synthetic construct<br>mol_type = protein<br>note = Seed: GAGDVGKSA (KRAS G13D) | |
| SEQUENCE: 754<br>GSGDVGKSR | | 9 |
| SEQ ID NO: 755<br>FEATURE<br>source | moltype = AA  length = 9<br>Location/Qualifiers<br>1..9<br>organism = synthetic construct<br>mol_type = protein<br>note = Seed: VVGAVGVGK (KRAS G12V) | |
| SEQUENCE: 755<br>VPGAVGVGK | | 9 |
| SEQ ID NO: 756<br>FEATURE<br>source | moltype = AA  length = 9<br>Location/Qualifiers<br>1..9<br>organism = synthetic construct<br>mol_type = protein<br>note = Seed: LVVVGACGV (KRAS G12C) | |
| SEQUENCE: 756<br>LIVVGACGA | | 9 |
| SEQ ID NO: 757<br>FEATURE<br>source | moltype = AA  length = 9<br>Location/Qualifiers<br>1..9<br>organism = synthetic construct<br>mol_type = protein<br>note = Seed: GAGDVGKSA (KRAS G13D) | |
| SEQUENCE: 757<br>GCGDVGKSY | | 9 |
| SEQ ID NO: 758<br>FEATURE<br>source | moltype = AA  length = 9<br>Location/Qualifiers<br>1..9<br>organism = synthetic construct<br>mol_type = protein<br>note = Seed: AGDVGKSAL (KRAS G13D) | |
| SEQUENCE: 758<br>AWDVGKSAW | | 9 |

```
SEQ ID NO: 759         moltype = AA  length = 9
FEATURE                Location/Qualifiers
source                 1..9
                       organism = synthetic construct
                       mol_type = protein
                       note = Seed: GADGVGKSA (KRAS G12D)
SEQUENCE: 759
GTDGVGKSK                                                                      9

SEQ ID NO: 760         moltype = AA  length = 9
FEATURE                Location/Qualifiers
source                 1..9
                       organism = synthetic construct
                       mol_type = protein
                       note = Seed: VVGACGVGK (KRAS G12C)
SEQUENCE: 760
VPGACGVGR                                                                      9

SEQ ID NO: 761         moltype = AA  length = 9
FEATURE                Location/Qualifiers
source                 1..9
                       organism = synthetic construct
                       mol_type = protein
                       note = Seed: GARGVGKSA (KRAS G12R)
SEQUENCE: 761
GTRGVGKSV                                                                      9

SEQ ID NO: 762         moltype = AA  length = 9
FEATURE                Location/Qualifiers
source                 1..9
                       organism = synthetic construct
                       mol_type = protein
                       note = Seed: AGDVGKSAL (KRAS G13D)
SEQUENCE: 762
AIDVGKSAW                                                                      9

SEQ ID NO: 763         moltype = AA  length = 9
FEATURE                Location/Qualifiers
source                 1..9
                       organism = synthetic construct
                       mol_type = protein
                       note = Seed: GAVGVGKSA (KRAS G12V)
SEQUENCE: 763
GPVGVGKSY                                                                      9

SEQ ID NO: 764         moltype = AA  length = 9
FEATURE                Location/Qualifiers
source                 1..9
                       organism = synthetic construct
                       mol_type = protein
                       note = Seed: VVGAVGVGK (KRAS G12V)
SEQUENCE: 764
VVGAVGVGL                                                                      9

SEQ ID NO: 765         moltype = AA  length = 9
FEATURE                Location/Qualifiers
source                 1..9
                       organism = synthetic construct
                       mol_type = protein
                       note = Seed: GACGVGKSA (KRAS G12C)
SEQUENCE: 765
GVCGVGKSK                                                                      9

SEQ ID NO: 766         moltype = AA  length = 9
FEATURE                Location/Qualifiers
source                 1..9
                       organism = synthetic construct
                       mol_type = protein
                       note = Seed: GAGDVGKSA (KRAS G13D)
SEQUENCE: 766
GEGDVGKSY                                                                      9

SEQ ID NO: 767         moltype = AA  length = 9
FEATURE                Location/Qualifiers
source                 1..9
                       organism = synthetic construct
                       mol_type = protein
                       note = Seed: VVGAVGVGK (KRAS G12V)
```

```
SEQUENCE: 767
VQGAVGVGY                                                                       9

SEQ ID NO: 768         moltype = AA  length = 9
FEATURE                Location/Qualifiers
source                 1..9
                       organism = synthetic construct
                       mol_type = protein
                       note = Seed: VVGAVGVGK (KRAS G12V)
SEQUENCE: 768
VNGAVGVGK                                                                       9

SEQ ID NO: 769         moltype = AA  length = 9
FEATURE                Location/Qualifiers
source                 1..9
                       organism = synthetic construct
                       mol_type = protein
                       note = Seed: GACGVGKSA (KRAS G12C)
SEQUENCE: 769
GACGVGKSW                                                                       9

SEQ ID NO: 770         moltype = AA  length = 9
FEATURE                Location/Qualifiers
source                 1..9
                       organism = synthetic construct
                       mol_type = protein
                       note = Seed: GADGVGKSA (KRAS G12D)
SEQUENCE: 770
GGDGVGKSR                                                                       9

SEQ ID NO: 771         moltype = AA  length = 9
FEATURE                Location/Qualifiers
source                 1..9
                       organism = synthetic construct
                       mol_type = protein
                       note = Seed: GARGVGKSA (KRAS G12R)
SEQUENCE: 771
GPRGVGKSY                                                                       9

SEQ ID NO: 772         moltype = AA  length = 9
FEATURE                Location/Qualifiers
source                 1..9
                       organism = synthetic construct
                       mol_type = protein
                       note = Seed: GACGVGKSA (KRAS G12C)
SEQUENCE: 772
GACGVGKSK                                                                       9

SEQ ID NO: 773         moltype = AA  length = 9
FEATURE                Location/Qualifiers
source                 1..9
                       organism = synthetic construct
                       mol_type = protein
                       note = Seed: VVGAGDVGK (KRAS G13D)
SEQUENCE: 773
VSGAGDVGF                                                                       9

SEQ ID NO: 774         moltype = AA  length = 9
FEATURE                Location/Qualifiers
source                 1..9
                       organism = synthetic construct
                       mol_type = protein
                       note = Seed: GADGVGKSA (KRAS G12D)
SEQUENCE: 774
GHDGVGKSI                                                                       9

SEQ ID NO: 775         moltype = AA  length = 9
FEATURE                Location/Qualifiers
source                 1..9
                       organism = synthetic construct
                       mol_type = protein
                       note = Seed: VVGACGVGK (KRAS G12C)
SEQUENCE: 775
VYGACGVGR                                                                       9

SEQ ID NO: 776         moltype = AA  length = 9
FEATURE                Location/Qualifiers
source                 1..9
                       organism = synthetic construct
```

```
                            mol_type = protein
                            note = Seed: AGDVGKSAL (KRAS G13D)
SEQUENCE: 776
AMDVGKSAC                                                                    9

SEQ ID NO: 777              moltype = AA  length = 9
FEATURE                     Location/Qualifiers
source                      1..9
                            organism = synthetic construct
                            mol_type = protein
                            note = Seed: GACGVGKSA (KRAS G12C)
SEQUENCE: 777
GMCGVGKSM                                                                    9

SEQ ID NO: 778              moltype = AA  length = 9
FEATURE                     Location/Qualifiers
source                      1..9
                            organism = synthetic construct
                            mol_type = protein
                            note = Seed: GADGVGKSA (KRAS G12D)
SEQUENCE: 778
GSDGVGKSR                                                                    9

SEQ ID NO: 779              moltype = AA  length = 9
FEATURE                     Location/Qualifiers
source                      1..9
                            organism = synthetic construct
                            mol_type = protein
                            note = Seed: GARGVGKSA (KRAS G12R)
SEQUENCE: 779
GPRGVGKSW                                                                    9

SEQ ID NO: 780              moltype = AA  length = 9
FEATURE                     Location/Qualifiers
source                      1..9
                            organism = synthetic construct
                            mol_type = protein
                            note = Seed: GAVGVGKSA (KRAS G12V)
SEQUENCE: 780
GGVGVGKSH                                                                    9

SEQ ID NO: 781              moltype = AA  length = 9
FEATURE                     Location/Qualifiers
source                      1..9
                            organism = synthetic construct
                            mol_type = protein
                            note = Seed: VVGAVGVGK (KRAS G12V)
SEQUENCE: 781
VLGAVGVGY                                                                    9

SEQ ID NO: 782              moltype = AA  length = 9
FEATURE                     Location/Qualifiers
source                      1..9
                            organism = synthetic construct
                            mol_type = protein
                            note = Seed: GACGVGKSA (KRAS G12C)
SEQUENCE: 782
GQCGVGKSM                                                                    9

SEQ ID NO: 783              moltype = AA  length = 9
FEATURE                     Location/Qualifiers
source                      1..9
                            organism = synthetic construct
                            mol_type = protein
                            note = Seed: GAVGVGKSA (KRAS G12V)
SEQUENCE: 783
GVVGVGKSI                                                                    9

SEQ ID NO: 784              moltype = AA  length = 9
FEATURE                     Location/Qualifiers
source                      1..9
                            organism = synthetic construct
                            mol_type = protein
                            note = Seed: GAGDVGKSA (KRAS G13D)
SEQUENCE: 784
GVGDVGKSV                                                                    9

SEQ ID NO: 785              moltype = AA  length = 9
FEATURE                     Location/Qualifiers
```

-continued

```
source                          1..9
                                organism = synthetic construct
                                mol_type = protein
                                note = Seed: GADGVGKSA (KRAS G12D)
SEQUENCE: 785
GPDGVGKST                                                                        9

SEQ ID NO: 786                  moltype = AA   length = 9
FEATURE                         Location/Qualifiers
source                          1..9
                                organism = synthetic construct
                                mol_type = protein
                                note = Seed: AGDVGKSAL (KRAS G13D)
SEQUENCE: 786
AKDVGKSAM                                                                        9

SEQ ID NO: 787                  moltype = AA   length = 9
FEATURE                         Location/Qualifiers
source                          1..9
                                organism = synthetic construct
                                mol_type = protein
                                note = Seed: AGDVGKSAL (KRAS G13D)
SEQUENCE: 787
APDVGKSAF                                                                        9

SEQ ID NO: 788                  moltype = AA   length = 9
FEATURE                         Location/Qualifiers
source                          1..9
                                organism = synthetic construct
                                mol_type = protein
                                note = Seed: VVGAVGVGK (KRAS G12V)
SEQUENCE: 788
VNGAVGVGR                                                                        9

SEQ ID NO: 789                  moltype = AA   length = 9
FEATURE                         Location/Qualifiers
source                          1..9
                                organism = synthetic construct
                                mol_type = protein
                                note = Seed: VVGAGDVGK (KRAS G13D)
SEQUENCE: 789
VGGAGDVGR                                                                        9

SEQ ID NO: 790                  moltype = AA   length = 9
FEATURE                         Location/Qualifiers
source                          1..9
                                organism = synthetic construct
                                mol_type = protein
                                note = Seed: LVVVGACGV (KRAS G12C)
SEQUENCE: 790
LVVVGACGA                                                                        9

SEQ ID NO: 791                  moltype = AA   length = 9
FEATURE                         Location/Qualifiers
source                          1..9
                                organism = synthetic construct
                                mol_type = protein
                                note = Seed: AGDVGKSAL (KRAS G13D)
SEQUENCE: 791
AEDVGKSAC                                                                        9

SEQ ID NO: 792                  moltype = AA   length = 9
FEATURE                         Location/Qualifiers
source                          1..9
                                organism = synthetic construct
                                mol_type = protein
                                note = Seed: GAGDVGKSA (KRAS G13D)
SEQUENCE: 792
GPGDVGKSC                                                                        9

SEQ ID NO: 793                  moltype = AA   length = 9
FEATURE                         Location/Qualifiers
source                          1..9
                                organism = synthetic construct
                                mol_type = protein
                                note = Seed: AGDVGKSAL (KRAS G13D)
SEQUENCE: 793
AHDVGKSAV                                                                        9
```

| | | |
|---|---|---|
| SEQ ID NO: 794<br>FEATURE<br>source | moltype = AA   length = 9<br>Location/Qualifiers<br>1..9<br>organism = synthetic construct<br>mol_type = protein<br>note = Seed: DVGKSALTI (KRAS G13D) | |
| SEQUENCE: 794<br>DMGKSALTW | | 9 |
| SEQ ID NO: 795<br>FEATURE<br>source | moltype = AA   length = 9<br>Location/Qualifiers<br>1..9<br>organism = synthetic construct<br>mol_type = protein<br>note = Seed: GARGVGKSA (KRAS G12R) | |
| SEQUENCE: 795<br>GLRGVGKSL | | 9 |
| SEQ ID NO: 796<br>FEATURE<br>source | moltype = AA   length = 9<br>Location/Qualifiers<br>1..9<br>organism = synthetic construct<br>mol_type = protein<br>note = Seed: VVGAVGVGK (KRAS G12V) | |
| SEQUENCE: 796<br>VSGAVGVGH | | 9 |
| SEQ ID NO: 797<br>FEATURE<br>source | moltype = AA   length = 9<br>Location/Qualifiers<br>1..9<br>organism = synthetic construct<br>mol_type = protein<br>note = Seed: GADGVGKSA (KRAS G12D) | |
| SEQUENCE: 797<br>GDDGVGKSF | | 9 |
| SEQ ID NO: 798<br>FEATURE<br>source | moltype = AA   length = 9<br>Location/Qualifiers<br>1..9<br>organism = synthetic construct<br>mol_type = protein<br>note = Seed: GADGVGKSA (KRAS G12D) | |
| SEQUENCE: 798<br>GGDGVGKSK | | 9 |
| SEQ ID NO: 799<br>FEATURE<br>source | moltype = AA   length = 9<br>Location/Qualifiers<br>1..9<br>organism = synthetic construct<br>mol_type = protein<br>note = Seed: GAVGVGKSA (KRAS G12V) | |
| SEQUENCE: 799<br>GMVGVGKSL | | 9 |
| SEQ ID NO: 800<br>FEATURE<br>source | moltype = AA   length = 9<br>Location/Qualifiers<br>1..9<br>organism = synthetic construct<br>mol_type = protein<br>note = Seed: VVGACGVGK (KRAS G12C) | |
| SEQUENCE: 800<br>VGGACGVGK | | 9 |
| SEQ ID NO: 801<br>FEATURE<br>source | moltype = AA   length = 9<br>Location/Qualifiers<br>1..9<br>organism = synthetic construct<br>mol_type = protein<br>note = Seed: GADGVGKSA (KRAS G12D) | |
| SEQUENCE: 801<br>GSDGVGKSW | | 9 |
| SEQ ID NO: 802<br>FEATURE<br>source | moltype = AA   length = 9<br>Location/Qualifiers<br>1..9<br>organism = synthetic construct<br>mol_type = protein<br>note = Seed: GAVGVGKSA (KRAS G12V) | |
| SEQUENCE: 802 | | |

-continued

```
GCVGVGKSF                                                                9

SEQ ID NO: 803          moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 803
GSGDVGKSV                                                                9

SEQ ID NO: 804          moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 804
GTCGVGKSH                                                                9

SEQ ID NO: 805          moltype = AA  length = 9
FEATURE                 Location/Qualifiers
source                  1..9
                        organism = synthetic construct
                        mol_type = protein
                        note = Seed: VVGACGVGK (KRAS G12C)
SEQUENCE: 805
VFGACGVGR                                                                9

SEQ ID NO: 806          moltype = AA  length = 9
FEATURE                 Location/Qualifiers
source                  1..9
                        organism = synthetic construct
                        mol_type = protein
                        note = Seed: VVGACGVGK (KRAS G12C)
SEQUENCE: 806
VQGACGVGK                                                                9

SEQ ID NO: 807          moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 807
GSVGVGKSA                                                                9

SEQ ID NO: 808          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 808
GLDGVGKSR                                                                9

SEQ ID NO: 809          moltype = AA  length = 9
FEATURE                 Location/Qualifiers
source                  1..9
                        organism = synthetic construct
                        mol_type = protein
                        note = Seed: LVVVGADGV (KRAS G12D)
SEQUENCE: 809
LAVVGADGV                                                                9

SEQ ID NO: 810          moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 810
GECGVGKSY                                                                9

SEQ ID NO: 811          moltype = AA  length = 9
FEATURE                 Location/Qualifiers
source                  1..9
                        organism = synthetic construct
                        mol_type = protein
```

```
                        note = Seed: GADGVGKSA (KRAS G12D)
SEQUENCE: 811
GSDGVGKSK                                                                        9

SEQ ID NO: 812          moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 812
GGGDVGKSR                                                                        9

SEQ ID NO: 813          moltype = AA   length = 9
FEATURE                 Location/Qualifiers
source                  1..9
                        organism = synthetic construct
                        mol_type = protein
                        note = Seed: GACGVGKSA (KRAS G12C)
SEQUENCE: 813
GPCGVGKSG                                                                        9

SEQ ID NO: 814          moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 814
AIDVGKSAA                                                                        9

SEQ ID NO: 815          moltype = AA   length = 9
FEATURE                 Location/Qualifiers
source                  1..9
                        organism = synthetic construct
                        mol_type = protein
                        note = Seed: GACGVGKSA (KRAS G12C)
SEQUENCE: 815
GACGVGKSR                                                                        9

SEQ ID NO: 816          moltype = AA   length = 9
FEATURE                 Location/Qualifiers
source                  1..9
                        organism = synthetic construct
                        mol_type = protein
                        note = Seed: VVGAVGVGK (KRAS G12V)
SEQUENCE: 816
VDGAVGVGK                                                                        9

SEQ ID NO: 817          moltype = AA   length = 9
FEATURE                 Location/Qualifiers
source                  1..9
                        organism = synthetic construct
                        mol_type = protein
                        note = Seed: GACGVGKSA (KRAS G12C)
SEQUENCE: 817
GLCGVGKSM                                                                        9

SEQ ID NO: 818          moltype = AA   length = 9
FEATURE                 Location/Qualifiers
source                  1..9
                        organism = synthetic construct
                        mol_type = protein
                        note = Seed: GACGVGKSA (KRAS G12C)
SEQUENCE: 818
GSCGVGKSI                                                                        9

SEQ ID NO: 819          moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 819
GIRGVGKSH                                                                        9

SEQ ID NO: 820          moltype = AA   length = 9
FEATURE                 Location/Qualifiers
source                  1..9
```

```
                            organism = synthetic construct
                            mol_type = protein
                            note = Seed: GADGVGKSA (KRAS G12D)
SEQUENCE: 820
GLDGVGKSC                                                                       9

SEQ ID NO: 821              moltype = AA   length = 9
FEATURE                     Location/Qualifiers
source                      1..9
                            organism = synthetic construct
                            mol_type = protein
                            note = Seed: GAVGVGKSA (KRAS G12V)
SEQUENCE: 821
GNVGVGKSF                                                                       9

SEQ ID NO: 822              moltype = AA   length = 9
FEATURE                     Location/Qualifiers
source                      1..9
                            organism = synthetic construct
                            mol_type = protein
                            note = Seed: GADGVGKSA (KRAS G12D)
SEQUENCE: 822
GHDGVGKSV                                                                       9

SEQ ID NO: 823              moltype = AA   length = 9
FEATURE                     Location/Qualifiers
source                      1..9
                            organism = synthetic construct
                            mol_type = protein
                            note = Seed: GACGVGKSA (KRAS G12C)
SEQUENCE: 823
GICGVGKSK                                                                       9

SEQ ID NO: 824              moltype = AA   length = 9
FEATURE                     Location/Qualifiers
source                      1..9
                            organism = synthetic construct
                            mol_type = protein
                            note = Seed: GARGVGKSA (KRAS G12R)
SEQUENCE: 824
GTRGVGKSI                                                                       9

SEQ ID NO: 825              moltype = AA   length = 9
FEATURE                     Location/Qualifiers
source                      1..9
                            organism = synthetic construct
                            mol_type = protein
                            note = Seed: GACGVGKSA (KRAS G12C)
SEQUENCE: 825
GCCGVGKSY                                                                       9

SEQ ID NO: 826              moltype = AA   length = 9
FEATURE                     Location/Qualifiers
source                      1..9
                            organism = synthetic construct
                            mol_type = protein
                            note = Seed: GAVGVGKSA (KRAS G12V)
SEQUENCE: 826
GLVGVGKSK                                                                       9

SEQ ID NO: 827              moltype = AA   length = 9
FEATURE                     Location/Qualifiers
source                      1..9
                            organism = synthetic construct
                            mol_type = protein
                            note = Seed: VVGARGVGK (KRAS G12R)
SEQUENCE: 827
VYGARGVGR                                                                       9

SEQ ID NO: 828              moltype = AA   length = 9
FEATURE                     Location/Qualifiers
source                      1..9
                            organism = synthetic construct
                            mol_type = protein
                            note = Seed: DVGKSALTI (KRAS G13D)
SEQUENCE: 828
DSGKSALTY                                                                       9

SEQ ID NO: 829              moltype = AA   length = 9
```

| FEATURE | Location/Qualifiers |
|---|---|
| source | 1..9<br>organism = synthetic construct<br>mol_type = protein<br>note = Seed: VVGACGVGK (KRAS G12C) |

SEQUENCE: 829
VGGACGVGY                                                                9

| SEQ ID NO: 830 | moltype = AA  length = 9 |
|---|---|
| FEATURE | Location/Qualifiers |
| source | 1..9<br>organism = synthetic construct<br>mol_type = protein<br>note = Seed: GARGVGKSA (KRAS G12R) |

SEQUENCE: 830
GNRGVGKSF                                                                9

| SEQ ID NO: 831 | moltype = AA  length = 9 |
|---|---|
| FEATURE | Location/Qualifiers |
| source | 1..9<br>organism = synthetic construct<br>mol_type = protein<br>note = Seed: VVGADGVGK (KRAS G12D) |

SEQUENCE: 831
VTGADGVGF                                                                9

| SEQ ID NO: 832 | moltype = AA  length = 9 |
|---|---|
| FEATURE | Location/Qualifiers |
| source | 1..9<br>organism = synthetic construct<br>mol_type = protein<br>note = Seed: GACGVGKSA (KRAS G12C) |

SEQUENCE: 832
GVCGVGKSV                                                                9

| SEQ ID NO: 833 | moltype = AA  length = 9 |
|---|---|
| FEATURE | Location/Qualifiers |
| source | 1..9<br>organism = synthetic construct<br>mol_type = protein<br>note = Seed: GAGDVGKSA (KRAS G13D) |

SEQUENCE: 833
GGGDVGKSK                                                                9

| SEQ ID NO: 834 | moltype = AA  length = 9 |
|---|---|
| FEATURE | Location/Qualifiers |
| source | 1..9<br>organism = synthetic construct<br>mol_type = protein<br>note = Seed: GADGVGKSA (KRAS G12D) |

SEQUENCE: 834
GIDGVGKSW                                                                9

| SEQ ID NO: 835 | moltype = AA  length = 9 |
|---|---|
| FEATURE | Location/Qualifiers |
| source | 1..9<br>organism = synthetic construct<br>mol_type = protein<br>note = Seed: GADGVGKSA (KRAS G12D) |

SEQUENCE: 835
GVDGVGKSA                                                                9

| SEQ ID NO: 836 | moltype = AA  length = 9 |
|---|---|
| FEATURE | Location/Qualifiers |
| source | 1..9<br>organism = synthetic construct<br>mol_type = protein<br>note = Seed: AGDVGKSAL (KRAS G13D) |

SEQUENCE: 836
AVDVGKSAA                                                                9

| SEQ ID NO: 837 | moltype = AA  length = 9 |
|---|---|
| FEATURE | Location/Qualifiers |
| source | 1..9<br>organism = synthetic construct<br>mol_type = protein<br>note = Seed: AGDVGKSAL (KRAS G13D) |

SEQUENCE: 837
ASDVGKSAW                                                                9

```
SEQ ID NO: 838          moltype = AA   length = 9
FEATURE                 Location/Qualifiers
source                  1..9
                        organism = synthetic construct
                        mol_type = protein
                        note = Seed: VVGACGVGK (KRAS G12C)
SEQUENCE: 838
VSGACGVGM                                                                9

SEQ ID NO: 839          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 839
GLDGVGKSK                                                                9

SEQ ID NO: 840          moltype = AA   length = 9
FEATURE                 Location/Qualifiers
source                  1..9
                        organism = synthetic construct
                        mol_type = protein
                        note = Seed: GACGVGKSA (KRAS G12C)
SEQUENCE: 840
GVCGVGKSR                                                                9

SEQ ID NO: 841          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 841
GEDGVGKSM                                                                9

SEQ ID NO: 842          moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 842
GTGDVGKSV                                                                9

SEQ ID NO: 843          moltype = AA   length = 9
FEATURE                 Location/Qualifiers
source                  1..9
                        organism = synthetic construct
                        mol_type = protein
                        note = Seed: VVGACGVGK (KRAS G12C)
SEQUENCE: 843
VTGACGVGF                                                                9

SEQ ID NO: 844          moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 844
GIRGVGKSA                                                                9

SEQ ID NO: 845          moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 845
GLGDVGKSR                                                                9

SEQ ID NO: 846          moltype = AA   length = 9
FEATURE                 Location/Qualifiers
source                  1..9
                        organism = synthetic construct
                        mol_type = protein
                        note = Seed: VVGAGDVGK (KRAS G13D)
```

```
SEQUENCE: 846
VVGAGDVGF                                                                        9

SEQ ID NO: 847         moltype = AA  length = 9
FEATURE                Location/Qualifiers
source                 1..9
                       organism = synthetic construct
                       mol_type = protein
                       note = Seed: GAVGVGKSA (KRAS G12V)
SEQUENCE: 847
GNVGVGKSK                                                                        9

SEQ ID NO: 848         moltype = AA  length = 9
FEATURE                Location/Qualifiers
source                 1..9
                       organism = synthetic construct
                       mol_type = protein
                       note = Seed: GADGVGKSA (KRAS G12D)
SEQUENCE: 848
GPDGVGKSP                                                                        9

SEQ ID NO: 849         moltype = AA  length = 9
FEATURE                Location/Qualifiers
source                 1..9
                       organism = synthetic construct
                       mol_type = protein
                       note = Seed: LVVVGADGV (KRAS G12D)
SEQUENCE: 849
LMVVGADGM                                                                        9

SEQ ID NO: 850         moltype = AA  length = 9
FEATURE                Location/Qualifiers
source                 1..9
                       organism = synthetic construct
                       mol_type = protein
                       note = Seed: VVGACGVGK (KRAS G12C)
SEQUENCE: 850
VQGACGVGR                                                                        9

SEQ ID NO: 851         moltype = AA  length = 9
FEATURE                Location/Qualifiers
source                 1..9
                       organism = synthetic construct
                       mol_type = protein
                       note = Seed: VVGAVGVGK (KRAS G12V)
SEQUENCE: 851
VEGAVGVGK                                                                        9

SEQ ID NO: 852         moltype = AA  length = 9
FEATURE                Location/Qualifiers
source                 1..9
                       organism = synthetic construct
                       mol_type = protein
                       note = Seed: GACGVGKSA (KRAS G12C)
SEQUENCE: 852
GICGVGKSR                                                                        9

SEQ ID NO: 853         moltype = AA  length = 9
FEATURE                Location/Qualifiers
source                 1..9
                       organism = synthetic construct
                       mol_type = protein
                       note = Seed: AGDVGKSAL (KRAS G13D)
SEQUENCE: 853
AVDVGKSAW                                                                        9

SEQ ID NO: 854         moltype = AA  length = 9
FEATURE                Location/Qualifiers
source                 1..9
                       organism = synthetic construct
                       mol_type = protein
                       note = Seed: GARGVGKSA (KRAS G12R)
SEQUENCE: 854
GCRGVGKSF                                                                        9

SEQ ID NO: 855         moltype = AA  length = 9
FEATURE                Location/Qualifiers
source                 1..9
                       organism = synthetic construct
```

```
                        mol_type = protein
                        note = Seed: VVGARGVGK (KRAS G12R)
SEQUENCE: 855
VFGARGVGR                                                   9

SEQ ID NO: 856          moltype = AA  length = 9
FEATURE                 Location/Qualifiers
source                  1..9
                        organism = synthetic construct
                        mol_type = protein
                        note = Seed: DVGKSALTI (KRAS G13D)
SEQUENCE: 856
DAGKSALTC                                                   9

SEQ ID NO: 857          moltype = AA  length = 9
FEATURE                 Location/Qualifiers
source                  1..9
                        organism = synthetic construct
                        mol_type = protein
                        note = Seed: DVGKSALTI (KRAS G13D)
SEQUENCE: 857
DTGKSALTV                                                   9

SEQ ID NO: 858          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 858
AEDVGKSAA                                                   9

SEQ ID NO: 859          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 859
GYDGVGKSY                                                   9

SEQ ID NO: 860          moltype = AA  length = 9
FEATURE                 Location/Qualifiers
source                  1..9
                        organism = synthetic construct
                        mol_type = protein
                        note = Seed: VVGAVGVGK (KRAS G12V)
SEQUENCE: 860
VGGAVGVGF                                                   9

SEQ ID NO: 861          moltype = AA  length = 9
FEATURE                 Location/Qualifiers
source                  1..9
                        organism = synthetic construct
                        mol_type = protein
                        note = Seed: VVGARGVGK (KRAS G12R)
SEQUENCE: 861
VVGARGVGY                                                   9

SEQ ID NO: 862          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 862
ALDVGKSAW                                                   9

SEQ ID NO: 863          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 863
AVDVGKSAK                                                   9

SEQ ID NO: 864          moltype = AA  length = 9
FEATURE                 Location/Qualifiers
```

```
source                          1..9
                                organism = synthetic construct
                                mol_type = protein
                                note = Seed: GADGVGKSA (KRAS G12D)
SEQUENCE: 864
GIDGVGKSA                                                                          9

SEQ ID NO: 865                  moltype = AA  length = 9
FEATURE                         Location/Qualifiers
source                          1..9
                                organism = synthetic construct
                                mol_type = protein
                                note = Seed: VVGACGVGK (KRAS G12C)
SEQUENCE: 865
VGGACGVGR                                                                          9

SEQ ID NO: 866                  moltype = AA  length = 9
FEATURE                         Location/Qualifiers
source                          1..9
                                organism = synthetic construct
                                mol_type = protein
                                note = Seed: GAGDVGKSA (KRAS G13D)
SEQUENCE: 866
GLGDVGKSK                                                                          9

SEQ ID NO: 867                  moltype = AA  length = 9
FEATURE                         Location/Qualifiers
source                          1..9
                                organism = synthetic construct
                                mol_type = protein
                                note = Seed: GAVGVGKSA (KRAS G12V)
SEQUENCE: 867
GLVGVGKSR                                                                          9

SEQ ID NO: 868                  moltype = AA  length = 9
FEATURE                         Location/Qualifiers
source                          1..9
                                organism = synthetic construct
                                mol_type = protein
                                note = Seed: VVGAVGVGK (KRAS G12V)
SEQUENCE: 868
VIGAVGVGM                                                                          9

SEQ ID NO: 869                  moltype = AA  length = 9
FEATURE                         Location/Qualifiers
source                          1..9
                                organism = synthetic construct
                                mol_type = protein
                                note = Seed: GAVGVGKSA (KRAS G12V)
SEQUENCE: 869
GQVGVGKSL                                                                          9

SEQ ID NO: 870                  moltype = AA  length = 9
FEATURE                         Location/Qualifiers
source                          1..9
                                organism = synthetic construct
                                mol_type = protein
                                note = Seed: AGDVGKSAL (KRAS G13D)
SEQUENCE: 870
ATDVGKSAW                                                                          9

SEQ ID NO: 871                  moltype = AA  length = 9
FEATURE                         Location/Qualifiers
source                          1..9
                                organism = synthetic construct
                                mol_type = protein
                                note = Seed: DVGKSALTI (KRAS G13D)
SEQUENCE: 871
DIGKSALTV                                                                          9

SEQ ID NO: 872                  moltype = AA  length = 9
FEATURE                         Location/Qualifiers
source                          1..9
                                organism = synthetic construct
                                mol_type = protein
                                note = Seed: VVGARGVGK (KRAS G12R)
SEQUENCE: 872
VVGARGVGM                                                                          9
```

```
SEQ ID NO: 873        moltype = AA   length = 9
FEATURE               Location/Qualifiers
source                1..9
                      organism = synthetic construct
                      mol_type = protein
                      note = Seed: GARGVGKSA (KRAS G12R)
SEQUENCE: 873
GDRGVGKSY                                                                         9

SEQ ID NO: 874        moltype = AA   length = 9
FEATURE               Location/Qualifiers
source                1..9
                      organism = synthetic construct
                      mol_type = protein
                      note = Seed: GAVGVGKSA (KRAS G12V)
SEQUENCE: 874
GDVGVGKSK                                                                         9

SEQ ID NO: 875        moltype = AA   length = 9
FEATURE               Location/Qualifiers
source                1..9
                      organism = synthetic construct
                      mol_type = protein
                      note = Seed: GADGVGKSA (KRAS G12D)
SEQUENCE: 875
GVDGVGKSW                                                                         9

SEQ ID NO: 876        moltype = AA   length = 9
FEATURE               Location/Qualifiers
source                1..9
                      organism = synthetic construct
                      mol_type = protein
                      note = Seed: VVGADGVGK (KRAS G12D)
SEQUENCE: 876
VQGADGVGK                                                                         9

SEQ ID NO: 877        moltype = AA   length = 9
FEATURE               Location/Qualifiers
source                1..9
                      organism = synthetic construct
                      mol_type = protein
                      note = Seed: GADGVGKSA (KRAS G12D)
SEQUENCE: 877
GPDGVGKSF                                                                         9

SEQ ID NO: 878        moltype = AA   length = 9
FEATURE               Location/Qualifiers
source                1..9
                      organism = synthetic construct
                      mol_type = protein
                      note = Seed: GAGDVGKSA (KRAS G13D)
SEQUENCE: 878
GSGDVGKSI                                                                         9

SEQ ID NO: 879        moltype = AA   length = 9
FEATURE               Location/Qualifiers
source                1..9
                      organism = synthetic construct
                      mol_type = protein
                      note = Seed: GADGVGKSA (KRAS G12D)
SEQUENCE: 879
GMDGVGKSR                                                                         9

SEQ ID NO: 880        moltype = AA   length = 9
FEATURE               Location/Qualifiers
source                1..9
                      organism = synthetic construct
                      mol_type = protein
                      note = Seed: VVGARGVGK (KRAS G12R)
SEQUENCE: 880
VVGARGVGF                                                                         9

SEQ ID NO: 881        moltype = AA   length = 9
FEATURE               Location/Qualifiers
source                1..9
                      organism = synthetic construct
                      mol_type = protein
                      note = Seed: DVGKSALTI (KRAS G13D)
SEQUENCE: 881
```

```
DMGKSALTV                                                                        9

SEQ ID NO: 882         moltype = AA  length = 9
FEATURE                Location/Qualifiers
source                 1..9
                       organism = synthetic construct
                       mol_type = protein
                       note = Seed: VVGAGDVGK (KRAS G13D)
SEQUENCE: 882
VAGAGDVGH                                                                        9

SEQ ID NO: 883         moltype = AA  length = 9
FEATURE                Location/Qualifiers
source                 1..9
                       organism = synthetic construct
                       mol_type = protein
                       note = Seed: GAVGVGKSA (KRAS G12V)
SEQUENCE: 883
GAVGVGKSC                                                                        9

SEQ ID NO: 884         moltype = AA  length = 9
FEATURE                Location/Qualifiers
source                 1..9
                       organism = synthetic construct
                       mol_type = protein
                       note = Seed: VVGADGVGK (KRAS G12D)
SEQUENCE: 884
VSGADGVGM                                                                        9

SEQ ID NO: 885         moltype = AA  length = 9
FEATURE                Location/Qualifiers
source                 1..9
                       organism = synthetic construct
                       mol_type = protein
                       note = Seed: AGDVGKSAL (KRAS G13D)
SEQUENCE: 885
AVDVGKSAR                                                                        9

SEQ ID NO: 886         moltype = AA  length = 9
FEATURE                Location/Qualifiers
source                 1..9
                       organism = synthetic construct
                       mol_type = protein
                       note = Seed: VVGADGVGK (KRAS G12D)
SEQUENCE: 886
VQGADGVGR                                                                        9

SEQ ID NO: 887         moltype = AA  length = 9
FEATURE                Location/Qualifiers
source                 1..9
                       organism = synthetic construct
                       mol_type = protein
                       note = Seed: GARGVGKSA (KRAS G12R)
SEQUENCE: 887
GSRGVGKSA                                                                        9

SEQ ID NO: 888         moltype = AA  length = 9
FEATURE                Location/Qualifiers
source                 1..9
                       organism = synthetic construct
                       mol_type = protein
                       note = Seed: AGDVGKSAL (KRAS G13D)
SEQUENCE: 888
AYDVGKSAT                                                                        9

SEQ ID NO: 889         moltype = AA  length = 9
FEATURE                Location/Qualifiers
source                 1..9
                       organism = synthetic construct
                       mol_type = protein
                       note = Seed: VVGAVGVGK (KRAS G12V)
SEQUENCE: 889
VDGAVGVGR                                                                        9

SEQ ID NO: 890         moltype = AA  length = 9
FEATURE                Location/Qualifiers
source                 1..9
                       organism = synthetic construct
                       mol_type = protein
```

```
                                note = Seed: VVGAGDVGK (KRAS G13D)
SEQUENCE: 890
VIGAGDVGY                                                                9

SEQ ID NO: 891         moltype = AA   length = 9
FEATURE                Location/Qualifiers
source                 1..9
                       organism = synthetic construct
                       mol_type = protein
                       note = Seed: GADGVGKSA (KRAS G12D)
SEQUENCE: 891
GKDGVGKSM                                                                9

SEQ ID NO: 892         moltype = AA   length = 9
FEATURE                Location/Qualifiers
source                 1..9
                       organism = synthetic construct
                       mol_type = protein
                       note = Seed: GACGVGKSA (KRAS G12C)
SEQUENCE: 892
GSCGVGKSK                                                                9

SEQ ID NO: 893         moltype = AA   length = 9
FEATURE                Location/Qualifiers
source                 1..9
                       organism = synthetic construct
                       mol_type = protein
                       note = Seed: GAGDVGKSA (KRAS G13D)
SEQUENCE: 893
GNGDVGKSF                                                                9

SEQ ID NO: 894         moltype = AA   length = 9
FEATURE                Location/Qualifiers
source                 1..9
                       organism = synthetic construct
                       mol_type = protein
                       note = Seed: LVVVGACGV (KRAS G12C)
SEQUENCE: 894
LQVVGACGA                                                                9

SEQ ID NO: 895         moltype = AA   length = 9
FEATURE                Location/Qualifiers
source                 1..9
                       organism = synthetic construct
                       mol_type = protein
                       note = Seed: GAGDVGKSA (KRAS G13D)
SEQUENCE: 895
GVGDVGKSI                                                                9

SEQ ID NO: 896         moltype = AA   length = 9
FEATURE                Location/Qualifiers
source                 1..9
                       organism = synthetic construct
                       mol_type = protein
                       note = Seed: VVGADGVGK (KRAS G12D)
SEQUENCE: 896
VNGADGVGR                                                                9

SEQ ID NO: 897         moltype = AA   length = 9
FEATURE                Location/Qualifiers
source                 1..9
                       organism = synthetic construct
                       mol_type = protein
                       note = Seed: AGDVGKSAL (KRAS G13D)
SEQUENCE: 897
AKDVGKSAF                                                                9

SEQ ID NO: 898         moltype = AA   length = 9
FEATURE                Location/Qualifiers
source                 1..9
                       organism = synthetic construct
                       mol_type = protein
                       note = Seed: GAVGVGKSA (KRAS G12V)
SEQUENCE: 898
GQVGVGKSK                                                                9

SEQ ID NO: 899         moltype = AA   length = 9
FEATURE                Location/Qualifiers
source                 1..9
```

```
                              organism = synthetic construct
                              mol_type = protein
                              note = Seed: VVGAVGVGK (KRAS G12V)
SEQUENCE: 899
VRGAVGVGM                                                                       9

SEQ ID NO: 900                moltype = AA  length = 9
FEATURE                       Location/Qualifiers
source                        1..9
                              organism = synthetic construct
                              mol_type = protein
                              note = Seed: AGDVGKSAL (KRAS G13D)
SEQUENCE: 900
AWDVGKSAA                                                                       9

SEQ ID NO: 901                moltype = AA  length = 9
FEATURE                       Location/Qualifiers
source                        1..9
                              organism = synthetic construct
                              mol_type = protein
                              note = Seed: VVGARGVGK (KRAS G12R)
SEQUENCE: 901
VVGARGVGL                                                                       9

SEQ ID NO: 902                moltype = AA  length = 9
FEATURE                       Location/Qualifiers
source                        1..9
                              organism = synthetic construct
                              mol_type = protein
                              note = Seed: GAVGVGKSA (KRAS G12V)
SEQUENCE: 902
GLVGVGKSL                                                                       9

SEQ ID NO: 903                moltype = AA  length = 9
FEATURE                       Location/Qualifiers
source                        1..9
                              organism = synthetic construct
                              mol_type = protein
                              note = Seed: GACGVGKSA (KRAS G12C)
SEQUENCE: 903
GTCGVGKSK                                                                       9

SEQ ID NO: 904                moltype = AA  length = 9
FEATURE                       Location/Qualifiers
source                        1..9
                              organism = synthetic construct
                              mol_type = protein
                              note = Seed: GADGVGKSA (KRAS G12D)
SEQUENCE: 904
GSDGVGKST                                                                       9

SEQ ID NO: 905                moltype = AA  length = 9
FEATURE                       Location/Qualifiers
source                        1..9
                              organism = synthetic construct
                              mol_type = protein
                              note = Seed: GARGVGKSA (KRAS G12R)
SEQUENCE: 905
GQRGVGKSL                                                                       9

SEQ ID NO: 906                moltype = AA  length = 9
FEATURE                       Location/Qualifiers
source                        1..9
                              organism = synthetic construct
                              mol_type = protein
                              note = Seed: DVGKSALTI (KRAS G13D)
SEQUENCE: 906
DTGKSALTL                                                                       9

SEQ ID NO: 907                moltype = AA  length = 9
FEATURE                       Location/Qualifiers
source                        1..9
                              organism = synthetic construct
                              mol_type = protein
                              note = Seed: GADGVGKSA (KRAS G12D)
SEQUENCE: 907
GMDGVGKSC                                                                       9

SEQ ID NO: 908                moltype = AA  length = 9
```

```
FEATURE             Location/Qualifiers
source              1..9
                    organism = synthetic construct
                    mol_type = protein
                    note = Seed: GAVGVGKSA (KRAS G12V)
SEQUENCE: 908
GAVGVGKST                                                                      9

SEQ ID NO: 909      moltype = AA   length = 9
FEATURE             Location/Qualifiers
source              1..9
                    organism = synthetic construct
                    mol_type = protein
                    note = Seed: AGDVGKSAL (KRAS G13D)
SEQUENCE: 909
AIDVGKSAK                                                                      9

SEQ ID NO: 910      moltype = AA   length = 9
FEATURE             Location/Qualifiers
source              1..9
                    organism = synthetic construct
                    mol_type = protein
                    note = Seed: GACGVGKSA (KRAS G12C)
SEQUENCE: 910
GPCGVGKSY                                                                      9

SEQ ID NO: 911      moltype = AA   length = 9
FEATURE             Location/Qualifiers
source              1..9
                    organism = synthetic construct
                    mol_type = protein
                    note = Seed: AGDVGKSAL (KRAS G13D)
SEQUENCE: 911
AIDVGKSAR                                                                      9

SEQ ID NO: 912      moltype = AA   length = 9
FEATURE             Location/Qualifiers
source              1..9
                    organism = synthetic construct
                    mol_type = protein
                    note = Seed: GAGDVGKSA (KRAS G13D)
SEQUENCE: 912
GQGDVGKSL                                                                      9

SEQ ID NO: 913      moltype = AA   length = 9
FEATURE             Location/Qualifiers
source              1..9
                    organism = synthetic construct
                    mol_type = protein
                    note = Seed: VVGARGVGK (KRAS G12R)
SEQUENCE: 913
VQGARGVGR                                                                      9

SEQ ID NO: 914      moltype = AA   length = 9
FEATURE             Location/Qualifiers
source              1..9
                    organism = synthetic construct
                    mol_type = protein
                    note = Seed: GACGVGKSA (KRAS G12C)
SEQUENCE: 914
GICGVGKSH                                                                      9

SEQ ID NO: 915      moltype = AA   length = 9
FEATURE             Location/Qualifiers
source              1..9
                    organism = synthetic construct
                    mol_type = protein
                    note = Seed: GACGVGKSA (KRAS G12C)
SEQUENCE: 915
GVCGVGKSI                                                                      9

SEQ ID NO: 916      moltype = AA   length = 9
FEATURE             Location/Qualifiers
source              1..9
                    organism = synthetic construct
                    mol_type = protein
                    note = Seed: GADGVGKSA (KRAS G12D)
SEQUENCE: 916
GMDGVGKSK                                                                      9
```

-continued

| | |
|---|---|
| SEQ ID NO: 917<br>FEATURE<br>source | moltype = AA  length = 9<br>Location/Qualifiers<br>1..9<br>organism = synthetic construct<br>mol_type = protein<br>note = Seed: GAGDVGKSA (KRAS G13D) |
| SEQUENCE: 917<br>GFGDVGKSY | 9 |
| SEQ ID NO: 918<br>FEATURE<br>source | moltype = AA  length = 9<br>Location/Qualifiers<br>1..9<br>organism = synthetic construct<br>mol_type = protein<br>note = Seed: GADGVGKSA (KRAS G12D) |
| SEQUENCE: 918<br>GTDGVGKSW | 9 |
| SEQ ID NO: 919<br>FEATURE<br>source | moltype = AA  length = 9<br>Location/Qualifiers<br>1..9<br>organism = synthetic construct<br>mol_type = protein<br>note = Seed: LVVVGADGV (KRAS G12D) |
| SEQUENCE: 919<br>LLVVGADGM | 9 |
| SEQ ID NO: 920<br>FEATURE<br>source | moltype = AA  length = 9<br>Location/Qualifiers<br>1..9<br>organism = synthetic construct<br>mol_type = protein<br>note = Seed: AGDVGKSAL (KRAS G13D) |
| SEQUENCE: 920<br>AADVGKSAK | 9 |
| SEQ ID NO: 921<br>FEATURE<br>source | moltype = AA  length = 9<br>Location/Qualifiers<br>1..9<br>organism = synthetic construct<br>mol_type = protein<br>note = Seed: GAGDVGKSA (KRAS G13D) |
| SEQUENCE: 921<br>GTGDVGKSI | 9 |
| SEQ ID NO: 922<br>FEATURE<br>source | moltype = AA  length = 9<br>Location/Qualifiers<br>1..9<br>organism = synthetic construct<br>mol_type = protein<br>note = Seed: VVGAVGVGK (KRAS G12V) |
| SEQUENCE: 922<br>VFGAVGVGK | 9 |
| SEQ ID NO: 923<br>FEATURE<br>source | moltype = AA  length = 9<br>Location/Qualifiers<br>1..9<br>organism = synthetic construct<br>mol_type = protein<br>note = Seed: GACGVGKSA (KRAS G12C) |
| SEQUENCE: 923<br>GSCGVGKSR | 9 |
| SEQ ID NO: 924<br>FEATURE<br>source | moltype = AA  length = 9<br>Location/Qualifiers<br>1..9<br>organism = synthetic construct<br>mol_type = protein<br>note = Seed: GACGVGKSA (KRAS G12C) |
| SEQUENCE: 924<br>GTCGVGKSV | 9 |
| SEQ ID NO: 925<br>FEATURE<br>source | moltype = AA  length = 9<br>Location/Qualifiers<br>1..9<br>organism = synthetic construct<br>mol_type = protein<br>note = Seed: DVGKSALTI (KRAS G13D) |

```
SEQUENCE: 925
DAGKSALTA                                                                                           9

SEQ ID NO: 926              moltype = AA   length = 9
FEATURE                     Location/Qualifiers
source                      1..9
                            organism = synthetic construct
                            mol_type = protein
                            note = Seed: GACGVGKSA (KRAS G12C)
SEQUENCE: 926
GTCGVGKSR                                                                                           9

SEQ ID NO: 927              moltype = AA   length = 9
FEATURE                     Location/Qualifiers
source                      1..9
                            organism = synthetic construct
                            mol_type = protein
                            note = Seed: VVGAVGVGK (KRAS G12V)
SEQUENCE: 927
VYGAVGVGK                                                                                           9

SEQ ID NO: 928              moltype = AA   length = 9
FEATURE                     Location/Qualifiers
source                      1..9
                            organism = synthetic construct
                            mol_type = protein
                            note = Seed: GARGVGKSA (KRAS G12R)
SEQUENCE: 928
GIRGVGKSV                                                                                           9

SEQ ID NO: 929              moltype = AA   length = 9
FEATURE                     Location/Qualifiers
source                      1..9
                            organism = synthetic construct
                            mol_type = protein
                            note = Seed: VVGARGVGK (KRAS G12R)
SEQUENCE: 929
VSGARGVGV                                                                                           9

SEQ ID NO: 930              moltype = AA   length = 9
FEATURE                     Location/Qualifiers
source                      1..9
                            organism = synthetic construct
                            mol_type = protein
                            note = Seed: VVGAGDVGK (KRAS G13D)
SEQUENCE: 930
VNGAGDVGK                                                                                           9

SEQ ID NO: 931              moltype = AA   length = 9
FEATURE                     Location/Qualifiers
source                      1..9
                            organism = synthetic construct
                            mol_type = protein
                            note = Seed: VVGAGDVGK (KRAS G13D)
SEQUENCE: 931
VQGAGDVGK                                                                                           9

SEQ ID NO: 932              moltype = AA   length = 9
FEATURE                     Location/Qualifiers
source                      1..9
                            organism = synthetic construct
                            mol_type = protein
                            note = Seed: GADGVGKSA (KRAS G12D)
SEQUENCE: 932
GQDGVGKSK                                                                                           9

SEQ ID NO: 933              moltype = AA   length = 9
FEATURE                     Location/Qualifiers
source                      1..9
                            organism = synthetic construct
                            mol_type = protein
                            note = Seed: GAVGVGKSA (KRAS G12V)
SEQUENCE: 933
GNVGVGKSR                                                                                           9

SEQ ID NO: 934              moltype = AA   length = 9
FEATURE                     Location/Qualifiers
source                      1..9
                            organism = synthetic construct
```

```
                                              mol_type = protein
                                              note = Seed: GADGVGKSA (KRAS G12D)
SEQUENCE: 934
GNDGVGKSR                                                                    9

SEQ ID NO: 935          moltype = AA  length = 9
FEATURE                 Location/Qualifiers
source                  1..9
                        organism = synthetic construct
                        mol_type = protein
                        note = Seed: VVGAVGVGK (KRAS G12V)
SEQUENCE: 935
VAGAVGVGA                                                                    9

SEQ ID NO: 936          moltype = AA  length = 9
FEATURE                 Location/Qualifiers
source                  1..9
                        organism = synthetic construct
                        mol_type = protein
                        note = Seed: VVGADGVGK (KRAS G12D)
SEQUENCE: 936
VNGADGVGK                                                                    9

SEQ ID NO: 937          moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 937
GPGDVGKSY                                                                    9

SEQ ID NO: 938          moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 938
GGCGVGKSL                                                                    9

SEQ ID NO: 939          moltype = AA  length = 9
FEATURE                 Location/Qualifiers
source                  1..9
                        organism = synthetic construct
                        mol_type = protein
                        note = Seed: VVGAGDVGK (KRAS G13D)
SEQUENCE: 939
VQGAGDVGR                                                                    9

SEQ ID NO: 940          moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 940
GGCGVGKSR                                                                    9

SEQ ID NO: 941          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 941
GQDGVGKSR                                                                    9

SEQ ID NO: 942          moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 942
GGGDVGKSL                                                                    9

SEQ ID NO: 943          moltype = AA  length = 9
FEATURE                 Location/Qualifiers
```

```
source                          1..9
                                organism = synthetic construct
                                mol_type = protein
                                note = Seed: VVGAGDVGK (KRAS G13D)
SEQUENCE: 943
VTGAGDVGF                                                                        9

SEQ ID NO: 944                  moltype = AA  length = 9
FEATURE                         Location/Qualifiers
source                          1..9
                                organism = synthetic construct
                                mol_type = protein
                                note = Seed: VVGARGVGK (KRAS G12R)
SEQUENCE: 944
VSGARGVGI                                                                        9

SEQ ID NO: 945                  moltype = AA  length = 9
FEATURE                         Location/Qualifiers
source                          1..9
                                organism = synthetic construct
                                mol_type = protein
                                note = Seed: GARGVGKSA (KRAS G12R)
SEQUENCE: 945
GARGVGKSC                                                                        9

SEQ ID NO: 946                  moltype = AA  length = 9
FEATURE                         Location/Qualifiers
source                          1..9
                                organism = synthetic construct
                                mol_type = protein
                                note = Seed: AGDVGKSAL (KRAS G13D)
SEQUENCE: 946
ASDVGKSAT                                                                        9

SEQ ID NO: 947                  moltype = AA  length = 9
FEATURE                         Location/Qualifiers
source                          1..9
                                organism = synthetic construct
                                mol_type = protein
                                note = Seed: VVGAVGVGK (KRAS G12V)
SEQUENCE: 947
VVGAVGVGH                                                                        9

SEQ ID NO: 948                  moltype = AA  length = 9
FEATURE                         Location/Qualifiers
source                          1..9
                                organism = synthetic construct
                                mol_type = protein
                                note = Seed: GAVGVGKSA (KRAS G12V)
SEQUENCE: 948
GDVGVGKSR                                                                        9

SEQ ID NO: 949                  moltype = AA  length = 9
FEATURE                         Location/Qualifiers
source                          1..9
                                organism = synthetic construct
                                mol_type = protein
                                note = Seed: AGDVGKSAL (KRAS G13D)
SEQUENCE: 949
AFDVGKSAT                                                                        9

SEQ ID NO: 950                  moltype = AA  length = 9
FEATURE                         Location/Qualifiers
source                          1..9
                                organism = synthetic construct
                                mol_type = protein
                                note = Seed: VVGACGVGK (KRAS G12C)
SEQUENCE: 950
VVGACGVGM                                                                        9

SEQ ID NO: 951                  moltype = AA  length = 9
FEATURE                         Location/Qualifiers
source                          1..9
                                organism = synthetic construct
                                mol_type = protein
                                note = Seed: GARGVGKSA (KRAS G12R)
SEQUENCE: 951
GIRGVGKSI                                                                        9
```

| | | |
|---|---|---|
| SEQ ID NO: 952<br>FEATURE<br>source | moltype = AA length = 9<br>Location/Qualifiers<br>1..9<br>organism = synthetic construct<br>mol_type = protein<br>note = Seed: VVGAGDVGK (KRAS G13D) | |
| SEQUENCE: 952<br>VNGAGDVGR | | 9 |
| SEQ ID NO: 953<br>FEATURE<br>source | moltype = AA length = 9<br>Location/Qualifiers<br>1..9<br>organism = synthetic construct<br>mol_type = protein<br>note = Seed: GACGVGKSA (KRAS G12C) | |
| SEQUENCE: 953<br>GVCGVGKSA | | 9 |
| SEQ ID NO: 954<br>FEATURE<br>source | moltype = AA length = 9<br>Location/Qualifiers<br>1..9<br>organism = synthetic construct<br>mol_type = protein<br>note = Seed: VVGACGVGK (KRAS G12C) | |
| SEQUENCE: 954<br>VIGACGVGF | | 9 |
| SEQ ID NO: 955<br>FEATURE<br>source | moltype = AA length = 9<br>Location/Qualifiers<br>1..9<br>organism = synthetic construct<br>mol_type = protein<br>note = Seed: GACGVGKSA (KRAS G12C) | |
| SEQUENCE: 955<br>GGCGVGKSK | | 9 |
| SEQ ID NO: 956<br>FEATURE<br>source | moltype = AA length = 9<br>Location/Qualifiers<br>1..9<br>organism = synthetic construct<br>mol_type = protein<br>note = Seed: GARGVGKSA (KRAS G12R) | |
| SEQUENCE: 956<br>GFRGVGKSY | | 9 |
| SEQ ID NO: 957<br>FEATURE<br>source | moltype = AA length = 9<br>Location/Qualifiers<br>1..9<br>organism = synthetic construct<br>mol_type = protein<br>note = Seed: VVGAVGVGK (KRAS G12V) | |
| SEQUENCE: 957<br>VMGAVGVGF | | 9 |
| SEQ ID NO: 958<br>FEATURE<br>source | moltype = AA length = 9<br>Location/Qualifiers<br>1..9<br>organism = synthetic construct<br>mol_type = protein<br>note = Seed: VVGAGDVGK (KRAS G13D) | |
| SEQUENCE: 958<br>VPGAGDVGR | | 9 |
| SEQ ID NO: 959<br>FEATURE<br>source | moltype = AA length = 9<br>Location/Qualifiers<br>1..9<br>organism = synthetic construct<br>mol_type = protein<br>note = Seed: GARGVGKSA (KRAS G12R) | |
| SEQUENCE: 959<br>GPRGVGKSQ | | 9 |
| SEQ ID NO: 960<br>FEATURE<br>source | moltype = AA length = 9<br>Location/Qualifiers<br>1..9<br>organism = synthetic construct<br>mol_type = protein<br>note = Seed: GACGVGKSA (KRAS G12C) | |
| SEQUENCE: 960 | | |

-continued

```
GTCGVGKSI                                                                  9

SEQ ID NO: 961          moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 961
GNDGVGKSK                                                                  9

SEQ ID NO: 962          moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 962
GMGDVGKSL                                                                  9

SEQ ID NO: 963          moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 963
GLGDVGKSL                                                                  9

SEQ ID NO: 964          moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 964
GCVGVGKSM                                                                  9

SEQ ID NO: 965          moltype = AA   length = 9
FEATURE                 Location/Qualifiers
source                  1..9
                        organism = synthetic construct
                        mol_type = protein
                        note = Seed: VVGAVGVGK (KRAS G12V)
SEQUENCE: 965
VEGAVGVGR                                                                  9

SEQ ID NO: 966          moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 966
GDVGVGKSY                                                                  9

SEQ ID NO: 967          moltype = AA   length = 9
FEATURE                 Location/Qualifiers
source                  1..9
                        organism = synthetic construct
                        mol_type = protein
                        note = Seed: GACGVGKSA (KRAS G12C)
SEQUENCE: 967
GNCGVGKSF                                                                  9

SEQ ID NO: 968          moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 968
AADVGKSAR                                                                  9

SEQ ID NO: 969          moltype = AA   length = 9
FEATURE                 Location/Qualifiers
source                  1..9
                        organism = synthetic construct
                        mol_type = protein
```

```
                        note = Seed: GADGVGKSA (KRAS G12D)
SEQUENCE: 969
GNDGVGKSY                                                               9

SEQ ID NO: 970          moltype = AA   length = 9
FEATURE                 Location/Qualifiers
source                  1..9
                        organism = synthetic construct
                        mol_type = protein
                        note = Seed: LVVVGAVGV (KRAS G12V)
SEQUENCE: 970
LVVVGAVGA                                                               9

SEQ ID NO: 971          moltype = AA   length = 9
FEATURE                 Location/Qualifiers
source                  1..9
                        organism = synthetic construct
                        mol_type = protein
                        note = Seed: DVGKSALTI (KRAS G13D)
SEQUENCE: 971
DSGKSALTL                                                               9

SEQ ID NO: 972          moltype = AA   length = 9
FEATURE                 Location/Qualifiers
source                  1..9
                        organism = synthetic construct
                        mol_type = protein
                        note = Seed: VVGARGVGK (KRAS G12R)
SEQUENCE: 972
VPGARGVGR                                                               9

SEQ ID NO: 973          moltype = AA   length = 9
FEATURE                 Location/Qualifiers
source                  1..9
                        organism = synthetic construct
                        mol_type = protein
                        note = Seed: VVGACGVGK (KRAS G12C)
SEQUENCE: 973
VMGACGVGY                                                               9

SEQ ID NO: 974          moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 974
ADDVGKSAY                                                               9

SEQ ID NO: 975          moltype = AA   length = 9
FEATURE                 Location/Qualifiers
source                  1..9
                        organism = synthetic construct
                        mol_type = protein
                        note = Seed: VVGAGDVGK (KRAS G13D)
SEQUENCE: 975
VFGAGDVGK                                                               9

SEQ ID NO: 976          moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 976
GMVGVGKSK                                                               9

SEQ ID NO: 977          moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 977
GVVGVGKSA                                                               9

SEQ ID NO: 978          moltype = AA   length = 9
FEATURE                 Location/Qualifiers
source                  1..9
```

```
                        organism = synthetic construct
                        mol_type = protein
                        note = Seed: GADGVGKSA (KRAS G12D)
SEQUENCE: 978
GFDGVGKSC                                                                       9

SEQ ID NO: 979          moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 979
GPGDVGKSS                                                                       9

SEQ ID NO: 980          moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 980
GSVGVGKSW                                                                       9

SEQ ID NO: 981          moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 981
GDGDVGKSK                                                                       9

SEQ ID NO: 982          moltype = AA  length = 9
FEATURE                 Location/Qualifiers
source                  1..9
                        organism = synthetic construct
                        mol_type = protein
                        note = Seed: LVVGADGV (KRAS G12D)
SEQUENCE: 982
LTVVGADGL                                                                       9

SEQ ID NO: 983          moltype = AA  length = 9
FEATURE                 Location/Qualifiers
source                  1..9
                        organism = synthetic construct
                        mol_type = protein
                        note = Seed: DVGKSALTI (KRAS G13D)
SEQUENCE: 983
DIGKSALTI                                                                       9

SEQ ID NO: 984          moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 984
GFDGVGKSY                                                                       9

SEQ ID NO: 985          moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 985
ADDVGKSAW                                                                       9

SEQ ID NO: 986          moltype = AA  length = 9
FEATURE                 Location/Qualifiers
source                  1..9
                        organism = synthetic construct
                        mol_type = protein
                        note = Seed: LVVGAVGV (KRAS G12V)
SEQUENCE: 986
LIVVGAVGA                                                                       9

SEQ ID NO: 987          moltype = AA  length = 9
```

-continued

| FEATURE | Location/Qualifiers |
|---|---|
| source | 1..9<br>organism = synthetic construct<br>mol_type = protein<br>note = Seed: LVVVGAVGV (KRAS G12V) |

SEQUENCE: 987
LTVVGAVGA                                                              9

| SEQ ID NO: 988 | moltype = AA  length = 9 |
|---|---|
| FEATURE | Location/Qualifiers |
| source | 1..9<br>organism = synthetic construct<br>mol_type = protein<br>note = Seed: GARGVGKSA (KRAS G12R) |

SEQUENCE: 988
GERGVGKSF                                                              9

| SEQ ID NO: 989 | moltype = AA  length = 9 |
|---|---|
| FEATURE | Location/Qualifiers |
| source | 1..9<br>organism = synthetic construct<br>mol_type = protein<br>note = Seed: DVGKSALTI (KRAS G13D) |

SEQUENCE: 989
DTGKSALTI                                                              9

| SEQ ID NO: 990 | moltype = AA  length = 9 |
|---|---|
| FEATURE | Location/Qualifiers |
| source | 1..9<br>organism = synthetic construct<br>mol_type = protein<br>note = Seed: GAVGVGKSA (KRAS G12V) |

SEQUENCE: 990
GQVGVGKSR                                                              9

| SEQ ID NO: 991 | moltype = AA  length = 9 |
|---|---|
| FEATURE | Location/Qualifiers |
| source | 1..9<br>organism = synthetic construct<br>mol_type = protein<br>note = Seed: GAGDVGKSA (KRAS G13D) |

SEQUENCE: 991
GNGDVGKSK                                                              9

| SEQ ID NO: 992 | moltype = AA  length = 9 |
|---|---|
| FEATURE | Location/Qualifiers |
| source | 1..9<br>organism = synthetic construct<br>mol_type = protein<br>note = Seed: GAGDVGKSA (KRAS G13D) |

SEQUENCE: 992
GNGDVGKSR                                                              9

| SEQ ID NO: 993 | moltype = AA  length = 9 |
|---|---|
| FEATURE | Location/Qualifiers |
| source | 1..9<br>organism = synthetic construct<br>mol_type = protein<br>note = Seed: VVGADGVGK (KRAS G12D) |

SEQUENCE: 993
VMGADGVGY                                                              9

| SEQ ID NO: 994 | moltype = AA  length = 9 |
|---|---|
| FEATURE | Location/Qualifiers |
| source | 1..9<br>organism = synthetic construct<br>mol_type = protein<br>note = Seed: GAGDVGKSA (KRAS G13D) |

SEQUENCE: 994
GMGDVGKSR                                                              9

| SEQ ID NO: 995 | moltype = AA  length = 9 |
|---|---|
| FEATURE | Location/Qualifiers |
| source | 1..9<br>organism = synthetic construct<br>mol_type = protein<br>note = Seed: VVGADGVGK (KRAS G12D) |

SEQUENCE: 995
VDGADGVGK                                                              9

```
SEQ ID NO: 996            moltype = AA   length = 9
FEATURE                   Location/Qualifiers
source                    1..9
                          organism = synthetic construct
                          mol_type = protein
                          note = Seed: GACGVGKSA (KRAS G12C)
SEQUENCE: 996
GMCGVGKSL                                                                     9

SEQ ID NO: 997            moltype = AA   length = 9
FEATURE                   Location/Qualifiers
source                    1..9
                          organism = synthetic construct
                          mol_type = protein
                          note = Seed: VVGADGVGK (KRAS G12D)
SEQUENCE: 997
VPGADGVGR                                                                     9

SEQ ID NO: 998            moltype = AA   length = 9
FEATURE                   Location/Qualifiers
source                    1..9
                          organism = synthetic construct
                          mol_type = protein
                          note = Seed: AGDVGKSAL (KRAS G13D)
SEQUENCE: 998
ANDVGKSAY                                                                     9

SEQ ID NO: 999            moltype = AA   length = 9
FEATURE                   Location/Qualifiers
source                    1..9
                          organism = synthetic construct
                          mol_type = protein
                          note = Seed: AGDVGKSAL (KRAS G13D)
SEQUENCE: 999
AGDVGKSAK                                                                     9

SEQ ID NO: 1000           moltype = AA   length = 9
FEATURE                   Location/Qualifiers
source                    1..9
                          organism = synthetic construct
                          mol_type = protein
                          note = Seed: VVGADGVGK (KRAS G12D)
SEQUENCE: 1000
VPGADGVGK                                                                     9

SEQ ID NO: 1001           moltype = AA   length = 9
FEATURE                   Location/Qualifiers
source                    1..9
                          organism = synthetic construct
                          mol_type = protein
                          note = Seed: GAVGVGKSA (KRAS G12V)
SEQUENCE: 1001
GMVGVGKSH                                                                     9

SEQ ID NO: 1002           moltype = AA   length = 9
FEATURE                   Location/Qualifiers
source                    1..9
                          organism = synthetic construct
                          mol_type = protein
                          note = Seed: GADGVGKSA (KRAS G12D)
SEQUENCE: 1002
GPDGVGKSC                                                                     9

SEQ ID NO: 1003           moltype = AA   length = 9
FEATURE                   Location/Qualifiers
source                    1..9
                          organism = synthetic construct
                          mol_type = protein
                          note = Seed: VVGACGVGK (KRAS G12C)
SEQUENCE: 1003
VSGACGVGL                                                                     9

SEQ ID NO: 1004           moltype = AA   length = 9
FEATURE                   Location/Qualifiers
source                    1..9
                          organism = synthetic construct
                          mol_type = protein
                          note = Seed: GAGDVGKSA (KRAS G13D)
```

```
SEQUENCE: 1004
GEGDVGKSF                                                                                  9

SEQ ID NO: 1005         moltype = AA   length = 9
FEATURE                 Location/Qualifiers
source                  1..9
                        organism = synthetic construct
                        mol_type = protein
                        note = Seed: VVGACGVGK (KRAS G12C)
SEQUENCE: 1005
VLGACGVGY                                                                                  9

SEQ ID NO: 1006         moltype = AA   length = 9
FEATURE                 Location/Qualifiers
source                  1..9
                        organism = synthetic construct
                        mol_type = protein
                        note = Seed: VVGADGVGK (KRAS G12D)
SEQUENCE: 1006
VGGADGVGY                                                                                  9

SEQ ID NO: 1007         moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 1007
GMVGVGKSR                                                                                  9

SEQ ID NO: 1008         moltype = AA   length = 9
FEATURE                 Location/Qualifiers
source                  1..9
                        organism = synthetic construct
                        mol_type = protein
                        note = Seed: VVGAVGVGK (KRAS G12V)
SEQUENCE: 1008
VWGAVGVGR                                                                                  9

SEQ ID NO: 1009         moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 1009
GTDGVGKST                                                                                  9

SEQ ID NO: 1010         moltype = AA   length = 9
FEATURE                 Location/Qualifiers
source                  1..9
                        organism = synthetic construct
                        mol_type = protein
                        note = Seed: VVGADGVGK (KRAS G12D)
SEQUENCE: 1010
VLGADGVGY                                                                                  9

SEQ ID NO: 1011         moltype = AA   length = 9
FEATURE                 Location/Qualifiers
source                  1..9
                        organism = synthetic construct
                        mol_type = protein
                        note = Seed: VVGAGDVGK (KRAS G13D)
SEQUENCE: 1011
VSGAGDVGM                                                                                  9

SEQ ID NO: 1012         moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 1012
GMGDVGKSK                                                                                  9

SEQ ID NO: 1013         moltype = AA   length = 9
FEATURE                 Location/Qualifiers
source                  1..9
                        organism = synthetic construct
```

-continued

```
                         mol_type = protein
                         note = Seed: GAGDVGKSA (KRAS G13D)
SEQUENCE: 1013
GDGDVGKSR                                                        9

SEQ ID NO: 1014          moltype = AA  length = 9
FEATURE                  Location/Qualifiers
source                   1..9
                         organism = synthetic construct
                         mol_type = protein
                         note = Seed: VVGACGVGK (KRAS G12C)
SEQUENCE: 1014
VPGACGVGK                                                        9

SEQ ID NO: 1015          moltype = AA  length = 9
FEATURE                  Location/Qualifiers
source                   1..9
                         organism = synthetic construct
                         mol_type = protein
                         note = Seed: GADGVGKSA (KRAS G12D)
SEQUENCE: 1015
GYDGVGKSA                                                        9

SEQ ID NO: 1016          moltype = AA  length = 9
FEATURE                  Location/Qualifiers
source                   1..9
                         organism = synthetic construct
                         mol_type = protein
                         note = Seed: VVGADGVGK (KRAS G12D)
SEQUENCE: 1016
VFGADGVGK                                                        9

SEQ ID NO: 1017          moltype = AA  length = 9
FEATURE                  Location/Qualifiers
source                   1..9
                         organism = synthetic construct
                         mol_type = protein
                         note = Seed: VVGAVGVGK (KRAS G12V)
SEQUENCE: 1017
VQGAVGVGF                                                        9

SEQ ID NO: 1018          moltype = AA  length = 9
FEATURE                  Location/Qualifiers
source                   1..9
                         organism = synthetic construct
                         mol_type = protein
                         note = Seed: GAGDVGKSA (KRAS G13D)
SEQUENCE: 1018
GCGDVGKSF                                                        9

SEQ ID NO: 1019          moltype = AA  length = 9
FEATURE                  Location/Qualifiers
source                   1..9
                         organism = synthetic construct
                         mol_type = protein
                         note = Seed: AGDVGKSAL (KRAS G13D)
SEQUENCE: 1019
ARDVGKSAW                                                        9

SEQ ID NO: 1020          moltype = AA  length = 9
FEATURE                  Location/Qualifiers
source                   1..9
                         organism = synthetic construct
                         mol_type = protein
                         note = Seed: GARGVGKSA (KRAS G12R)
SEQUENCE: 1020
GGRGVGKSA                                                        9

SEQ ID NO: 1021          moltype = AA  length = 9
FEATURE                  Location/Qualifiers
source                   1..9
                         organism = synthetic construct
                         mol_type = protein
                         note = Seed: AGDVGKSAL (KRAS G13D)
SEQUENCE: 1021
AKDVGKSAY                                                        9

SEQ ID NO: 1022          moltype = AA  length = 9
FEATURE                  Location/Qualifiers
```

```
source                  1..9
                        organism = synthetic construct
                        mol_type = protein
                        note = Seed: VVGAVGVGK (KRAS G12V)
SEQUENCE: 1022
VRGAVGVGI                                                                        9

SEQ ID NO: 1023         moltype = AA  length = 9
FEATURE                 Location/Qualifiers
source                  1..9
                        organism = synthetic construct
                        mol_type = protein
                        note = Seed: VVGADGVGK (KRAS G12D)
SEQUENCE: 1023
VEGADGVGK                                                                        9

SEQ ID NO: 1024         moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 1024
GLCGVGKSR                                                                        9

SEQ ID NO: 1025         moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 1025
GDDGVGKSI                                                                        9

SEQ ID NO: 1026         moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 1026
GFVGVGKSY                                                                        9

SEQ ID NO: 1027         moltype = AA  length = 9
FEATURE                 Location/Qualifiers
source                  1..9
                        organism = synthetic construct
                        mol_type = protein
                        note = Seed: DVGKSALTI (KRAS G13D)
SEQUENCE: 1027
DTGKSALTM                                                                        9

SEQ ID NO: 1028         moltype = AA  length = 9
FEATURE                 Location/Qualifiers
source                  1..9
                        organism = synthetic construct
                        mol_type = protein
                        note = Seed: VVGARGVGK (KRAS G12R)
SEQUENCE: 1028
VIGARGVGY                                                                        9

SEQ ID NO: 1029         moltype = AA  length = 9
FEATURE                 Location/Qualifiers
source                  1..9
                        organism = synthetic construct
                        mol_type = protein
                        note = Seed: VVGAVGVGK (KRAS G12V)
SEQUENCE: 1029
VTGAVGVGH                                                                        9

SEQ ID NO: 1030         moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 1030
AGDVGKSAR                                                                        9
```

-continued

```
SEQ ID NO: 1031         moltype = AA   length = 9
FEATURE                 Location/Qualifiers
source                  1..9
                        organism = synthetic construct
                        mol_type = protein
                        note = Seed: GACGVGKSA (KRAS G12C)
SEQUENCE: 1031
GQCGVGKSL                                                                         9

SEQ ID NO: 1032         moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 1032
GNVGVGKSM                                                                         9

SEQ ID NO: 1033         moltype = AA   length = 9
FEATURE                 Location/Qualifiers
source                  1..9
                        organism = synthetic construct
                        mol_type = protein
                        note = Seed: VVGAGDVGK (KRAS G13D)
SEQUENCE: 1033
VMGAGDVGY                                                                         9

SEQ ID NO: 1034         moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 1034
GFDGVGKSK                                                                         9

SEQ ID NO: 1035         moltype = AA   length = 9
FEATURE                 Location/Qualifiers
source                  1..9
                        organism = synthetic construct
                        mol_type = protein
                        note = Seed: VVGAGDVGK (KRAS G13D)
SEQUENCE: 1035
VDGAGDVGK                                                                         9

SEQ ID NO: 1036         moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 1036
AQDVGKSAW                                                                         9

SEQ ID NO: 1037         moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 1037
GDDGVGKSK                                                                         9

SEQ ID NO: 1038         moltype = AA   length = 9
FEATURE                 Location/Qualifiers
source                  1..9
                        organism = synthetic construct
                        mol_type = protein
                        note = Seed: VVGARGVGK (KRAS G12R)
SEQUENCE: 1038
VTGARGVGI                                                                         9

SEQ ID NO: 1039         moltype = AA   length = 9
FEATURE                 Location/Qualifiers
source                  1..9
                        organism = synthetic construct
                        mol_type = protein
                        note = Seed: LVVVGADGV (KRAS G12D)
SEQUENCE: 1039
```

```
LSVVGADGV                                                                          9

SEQ ID NO: 1040         moltype = AA  length = 9
FEATURE                 Location/Qualifiers
source                  1..9
                        organism = synthetic construct
                        mol_type = protein
                        note = Seed: VVGADGVGK (KRAS G12D)
SEQUENCE: 1040
VVGADGVGM                                                                          9

SEQ ID NO: 1041         moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 1041
GNRGVGKSM                                                                          9

SEQ ID NO: 1042         moltype = AA  length = 9
FEATURE                 Location/Qualifiers
source                  1..9
                        organism = synthetic construct
                        mol_type = protein
                        note = Seed: VVGAVGVGK (KRAS G12V)
SEQUENCE: 1042
VGGAVGVGM                                                                          9

SEQ ID NO: 1043         moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 1043
GEVGVGKSK                                                                          9

SEQ ID NO: 1044         moltype = AA  length = 9
FEATURE                 Location/Qualifiers
source                  1..9
                        organism = synthetic construct
                        mol_type = protein
                        note = Seed: LVVVGAVGV (KRAS G12V)
SEQUENCE: 1044
LQVVGAVGA                                                                          9

SEQ ID NO: 1045         moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 1045
GPRGVGKSH                                                                          9

SEQ ID NO: 1046         moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 1046
GLDGVGKSW                                                                          9

SEQ ID NO: 1047         moltype = AA  length = 9
FEATURE                 Location/Qualifiers
source                  1..9
                        organism = synthetic construct
                        mol_type = protein
                        note = Seed: VVGARGVGK (KRAS G12R)
SEQUENCE: 1047
VTGARGVGV                                                                          9

SEQ ID NO: 1048         moltype = AA  length = 9
FEATURE                 Location/Qualifiers
source                  1..9
                        organism = synthetic construct
                        mol_type = protein
```

-continued

```
                        note = Seed: GAGDVGKSA (KRAS G13D)
SEQUENCE: 1048
GQGDVGKSR                                                                9

SEQ ID NO: 1049         moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 1049
GEDGVGKSF                                                                9

SEQ ID NO: 1050         moltype = AA   length = 9
FEATURE                 Location/Qualifiers
source                  1..9
                        organism = synthetic construct
                        mol_type = protein
                        note = Seed: VVGADGVGK (KRAS G12D)
SEQUENCE: 1050
VIGADGVGF                                                                9

SEQ ID NO: 1051         moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 1051
GQGDVGKSK                                                                9

SEQ ID NO: 1052         moltype = AA   length = 9
FEATURE                 Location/Qualifiers
source                  1..9
                        organism = synthetic construct
                        mol_type = protein
                        note = Seed: VVGARGVGK (KRAS G12R)
SEQUENCE: 1052
VGGARGVGY                                                                9

SEQ ID NO: 1053         moltype = AA   length = 9
FEATURE                 Location/Qualifiers
source                  1..9
                        organism = synthetic construct
                        mol_type = protein
                        note = Seed: VVGARGVGK (KRAS G12R)
SEQUENCE: 1053
VQGARGVGK                                                                9

SEQ ID NO: 1054         moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 1054
GKDGVGKSF                                                                9

SEQ ID NO: 1055         moltype = AA   length = 9
FEATURE                 Location/Qualifiers
source                  1..9
                        organism = synthetic construct
                        mol_type = protein
                        note = Seed: VVGAVGVGK (KRAS G12V)
SEQUENCE: 1055
VRGAVGVGV                                                                9

SEQ ID NO: 1056         moltype = AA   length = 9
FEATURE                 Location/Qualifiers
source                  1..9
                        organism = synthetic construct
                        mol_type = protein
                        note = Seed: VVGACGVGK (KRAS G12C)
SEQUENCE: 1056
VDGACGVGK                                                                9

SEQ ID NO: 1057         moltype = AA   length = 9
FEATURE                 Location/Qualifiers
source                  1..9
```

```
                            organism = synthetic construct
                            mol_type = protein
                            note = Seed: AGDVGKSAL (KRAS G13D)
SEQUENCE: 1057
ASDVGKSAK                                                                       9

SEQ ID NO: 1058             moltype = AA   length = 9
FEATURE                     Location/Qualifiers
source                      1..9
                            organism = synthetic construct
                            mol_type = protein
                            note = Seed: GAVGVGKSA (KRAS G12V)
SEQUENCE: 1058
GQVGVGKSH                                                                       9

SEQ ID NO: 1059             moltype = AA   length = 9
FEATURE                     Location/Qualifiers
source                      1..9
                            organism = synthetic construct
                            mol_type = protein
                            note = Seed: AGDVGKSAL (KRAS G13D)
SEQUENCE: 1059
ASDVGKSAR                                                                       9

SEQ ID NO: 1060             moltype = AA   length = 9
FEATURE                     Location/Qualifiers
source                      1..9
                            organism = synthetic construct
                            mol_type = protein
                            note = Seed: AGDVGKSAL (KRAS G13D)
SEQUENCE: 1060
ASDVGKSAH                                                                       9

SEQ ID NO: 1061             moltype = AA   length = 9
FEATURE                     Location/Qualifiers
source                      1..9
                            organism = synthetic construct
                            mol_type = protein
                            note = Seed: GAVGVGKSA (KRAS G12V)
SEQUENCE: 1061
GEVGVGKSF                                                                       9

SEQ ID NO: 1062             moltype = AA   length = 9
FEATURE                     Location/Qualifiers
source                      1..9
                            organism = synthetic construct
                            mol_type = protein
                            note = Seed: VVGAGDVGK (KRAS G13D)
SEQUENCE: 1062
VLGAGDVGY                                                                       9

SEQ ID NO: 1063             moltype = AA   length = 9
FEATURE                     Location/Qualifiers
source                      1..9
                            organism = synthetic construct
                            mol_type = protein
                            note = Seed: GARGVGKSA (KRAS G12R)
SEQUENCE: 1063
GARGVGKST                                                                       9

SEQ ID NO: 1064             moltype = AA   length = 9
FEATURE                     Location/Qualifiers
source                      1..9
                            organism = synthetic construct
                            mol_type = protein
                            note = Seed: DVGKSALTI (KRAS G13D)
SEQUENCE: 1064
DMGKSALTI                                                                       9

SEQ ID NO: 1065             moltype = AA   length = 9
FEATURE                     Location/Qualifiers
source                      1..9
                            organism = synthetic construct
                            mol_type = protein
                            note = Seed: LVVVGADGV (KRAS G12D)
SEQUENCE: 1065
LTVVGADGI                                                                       9

SEQ ID NO: 1066             moltype = AA   length = 9
```

-continued

| FEATURE | Location/Qualifiers |
|---|---|
| source | 1..9<br>organism = synthetic construct<br>mol_type = protein<br>note = Seed: GAVGVGKSA (KRAS G12V) |

SEQUENCE: 1066
GLVGVGKSH                                                                    9

SEQ ID NO: 1067   moltype = AA   length = 9
FEATURE           Location/Qualifiers
source            1..9
                  organism = synthetic construct
                  mol_type = protein
                  note = Seed: GACGVGKSA (KRAS G12C)
SEQUENCE: 1067
GLCGVGKSL                                                                    9

SEQ ID NO: 1068   moltype = AA   length = 9
FEATURE           Location/Qualifiers
source            1..9
                  organism = synthetic construct
                  mol_type = protein
                  note = Seed: VVGARGVGK (KRAS G12R)
SEQUENCE: 1068
VIGARGVGF                                                                    9

SEQ ID NO: 1069   moltype = AA   length = 9
FEATURE           Location/Qualifiers
source            1..9
                  organism = synthetic construct
                  mol_type = protein
                  note = Seed: GADGVGKSA (KRAS G12D)
SEQUENCE: 1069
GDDGVGKSR                                                                    9

SEQ ID NO: 1070   moltype = AA   length = 9
FEATURE           Location/Qualifiers
source            1..9
                  organism = synthetic construct
                  mol_type = protein
                  note = Seed: AGDVGKSAL (KRAS G13D)
SEQUENCE: 1070
AGDVGKSAA                                                                    9

SEQ ID NO: 1071   moltype = AA   length = 9
FEATURE           Location/Qualifiers
source            1..9
                  organism = synthetic construct
                  mol_type = protein
                  note = Seed: VVGARGVGK (KRAS G12R)
SEQUENCE: 1071
VAGARGVGW                                                                    9

SEQ ID NO: 1072   moltype = AA   length = 9
FEATURE           Location/Qualifiers
source            1..9
                  organism = synthetic construct
                  mol_type = protein
                  note = Seed: VVGADGVGK (KRAS G12D)
SEQUENCE: 1072
VTGADGVGM                                                                    9

SEQ ID NO: 1073   moltype = AA   length = 9
FEATURE           Location/Qualifiers
source            1..9
                  organism = synthetic construct
                  mol_type = protein
                  note = Seed: LVVVGACGV (KRAS G12C)
SEQUENCE: 1073
LMVVGACGT                                                                    9

SEQ ID NO: 1074   moltype = AA   length = 9
FEATURE           Location/Qualifiers
source            1..9
                  organism = synthetic construct
                  mol_type = protein
                  note = Seed: GADGVGKSA (KRAS G12D)
SEQUENCE: 1074
GPDGVGKSK                                                                    9

```
SEQ ID NO: 1075        moltype = AA  length = 9
FEATURE                Location/Qualifiers
source                 1..9
                       organism = synthetic construct
                       mol_type = protein
                       note = Seed: GACGVGKSA (KRAS G12C)
SEQUENCE: 1075
GECGVGKSF                                                                        9

SEQ ID NO: 1076        moltype = AA  length = 9
FEATURE                Location/Qualifiers
source                 1..9
                       organism = synthetic construct
                       mol_type = protein
                       note = Seed: GADGVGKSA (KRAS G12D)
SEQUENCE: 1076
GVDGVGKSH                                                                        9

SEQ ID NO: 1077        moltype = AA  length = 9
FEATURE                Location/Qualifiers
source                 1..9
                       organism = synthetic construct
                       mol_type = protein
                       note = Seed: AGDVGKSAL (KRAS G13D)
SEQUENCE: 1077
ALDVGKSAR                                                                        9

SEQ ID NO: 1078        moltype = AA  length = 9
FEATURE                Location/Qualifiers
source                 1..9
                       organism = synthetic construct
                       mol_type = protein
                       note = Seed: AGDVGKSAL (KRAS G13D)
SEQUENCE: 1078
ATDVGKSAK                                                                        9

SEQ ID NO: 1079        moltype = AA  length = 9
FEATURE                Location/Qualifiers
source                 1..9
                       organism = synthetic construct
                       mol_type = protein
                       note = Seed: GAGDVGKSA (KRAS G13D)
SEQUENCE: 1079
GVGDVGKSA                                                                        9

SEQ ID NO: 1080        moltype = AA  length = 9
FEATURE                Location/Qualifiers
source                 1..9
                       organism = synthetic construct
                       mol_type = protein
                       note = Seed: GADGVGKSA (KRAS G12D)
SEQUENCE: 1080
GRDGVGKSA                                                                        9

SEQ ID NO: 1081        moltype = AA  length = 9
FEATURE                Location/Qualifiers
source                 1..9
                       organism = synthetic construct
                       mol_type = protein
                       note = Seed: GACGVGKSA (KRAS G12C)
SEQUENCE: 1081
GLCGVGKSK                                                                        9

SEQ ID NO: 1082        moltype = AA  length = 9
FEATURE                Location/Qualifiers
source                 1..9
                       organism = synthetic construct
                       mol_type = protein
                       note = Seed: AGDVGKSAL (KRAS G13D)
SEQUENCE: 1082
AKDVGKSAI                                                                        9

SEQ ID NO: 1083        moltype = AA  length = 9
FEATURE                Location/Qualifiers
source                 1..9
                       organism = synthetic construct
                       mol_type = protein
                       note = Seed: AGDVGKSAL (KRAS G13D)
```

```
SEQUENCE: 1083
ARDVGKSAA                                                                    9

SEQ ID NO: 1084         moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 1084
GIVGVGKSV                                                                    9

SEQ ID NO: 1085         moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 1085
GDDGVGKSV                                                                    9

SEQ ID NO: 1086         moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 1086
GEDGVGKSY                                                                    9

SEQ ID NO: 1087         moltype = AA   length = 9
FEATURE                 Location/Qualifiers
source                  1..9
                        organism = synthetic construct
                        mol_type = protein
                        note = Seed: DVGKSALTI (KRAS G13D)
SEQUENCE: 1087
DGGKSALTL                                                                    9

SEQ ID NO: 1088         moltype = AA   length = 9
FEATURE                 Location/Qualifiers
source                  1..9
                        organism = synthetic construct
                        mol_type = protein
                        note = Seed: VVGACGVGK (KRAS G12C)
SEQUENCE: 1088
VYGACGVGK                                                                    9

SEQ ID NO: 1089         moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 1089
GIVGVGKSI                                                                    9

SEQ ID NO: 1090         moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 1090
GFVGVGKSK                                                                    9

SEQ ID NO: 1091         moltype = AA   length = 9
FEATURE                 Location/Qualifiers
source                  1..9
                        organism = synthetic construct
                        mol_type = protein
                        note = Seed: VVGACGVGK (KRAS G12C)
SEQUENCE: 1091
VNGACGVGK                                                                    9

SEQ ID NO: 1092         moltype = AA   length = 9
FEATURE                 Location/Qualifiers
source                  1..9
                        organism = synthetic construct
```

```
                              mol_type = protein
                              note = Seed: GAGDVGKSA (KRAS G13D)
SEQUENCE: 1092
GFGDVGKSK                                                              9

SEQ ID NO: 1093               moltype = AA   length = 9
FEATURE                       Location/Qualifiers
source                        1..9
                              organism = synthetic construct
                              mol_type = protein
                              note = Seed: AGDVGKSAL (KRAS G13D)
SEQUENCE: 1093
ATDVGKSAR                                                              9

SEQ ID NO: 1094               moltype = AA   length = 9
FEATURE                       Location/Qualifiers
source                        1..9
                              organism = synthetic construct
                              mol_type = protein
                              note = Seed: VVGAVGVGK (KRAS G12V)
SEQUENCE: 1094
VCGAVGVGK                                                              9

SEQ ID NO: 1095               moltype = AA   length = 9
FEATURE                       Location/Qualifiers
source                        1..9
                              organism = synthetic construct
                              mol_type = protein
                              note = Seed: GADGVGKSA (KRAS G12D)
SEQUENCE: 1095
GRDGVGKSC                                                              9

SEQ ID NO: 1096               moltype = AA   length = 9
FEATURE                       Location/Qualifiers
source                        1..9
                              organism = synthetic construct
                              mol_type = protein
                              note = Seed: GAVGVGKSA (KRAS G12V)
SEQUENCE: 1096
GAVGVGKSQ                                                              9

SEQ ID NO: 1097               moltype = AA   length = 9
FEATURE                       Location/Qualifiers
source                        1..9
                              organism = synthetic construct
                              mol_type = protein
                              note = Seed: VVGAVGVGK (KRAS G12V)
SEQUENCE: 1097
VYGAVGVGF                                                              9

SEQ ID NO: 1098               moltype = AA   length = 9
FEATURE                       Location/Qualifiers
source                        1..9
                              organism = synthetic construct
                              mol_type = protein
                              note = Seed: GAVGVGKSA (KRAS G12V)
SEQUENCE: 1098
GCVGVGKSK                                                              9

SEQ ID NO: 1099               moltype = AA   length = 9
FEATURE                       Location/Qualifiers
source                        1..9
                              organism = synthetic construct
                              mol_type = protein
                              note = Seed: VVGARGVGK (KRAS G12R)
SEQUENCE: 1099
VGGARGVGK                                                              9

SEQ ID NO: 1100               moltype = AA   length = 9
FEATURE                       Location/Qualifiers
source                        1..9
                              organism = synthetic construct
                              mol_type = protein
                              note = Seed: VVGADGVGK (KRAS G12D)
SEQUENCE: 1100
VDGADGVGR                                                              9

SEQ ID NO: 1101               moltype = AA   length = 9
FEATURE                       Location/Qualifiers
```

```
source                        1..9
                              organism = synthetic construct
                              mol_type = protein
                              note = Seed: VVGACGVGK (KRAS G12C)
SEQUENCE: 1101
VDGACGVGR                                                                        9

SEQ ID NO: 1102               moltype = AA   length = 9
FEATURE                       Location/Qualifiers
source                        1..9
                              organism = synthetic construct
                              mol_type = protein
                              note = Seed: GADGVGKSA (KRAS G12D)
SEQUENCE: 1102
GYDGVGKSK                                                                        9

SEQ ID NO: 1103               moltype = AA   length = 9
FEATURE                       Location/Qualifiers
source                        1..9
                              organism = synthetic construct
                              mol_type = protein
                              note = Seed: AGDVGKSAL (KRAS G13D)
SEQUENCE: 1103
ALDVGKSAK                                                                        9

SEQ ID NO: 1104               moltype = AA   length = 9
FEATURE                       Location/Qualifiers
source                        1..9
                              organism = synthetic construct
                              mol_type = protein
                              note = Seed: VVGAGDVGK (KRAS G13D)
SEQUENCE: 1104
VFGAGDVGR                                                                        9

SEQ ID NO: 1105               moltype = AA   length = 9
FEATURE                       Location/Qualifiers
source                        1..9
                              organism = synthetic construct
                              mol_type = protein
                              note = Seed: VVGAGDVGK (KRAS G13D)
SEQUENCE: 1105
VEGAGDVGK                                                                        9

SEQ ID NO: 1106               moltype = AA   length = 9
FEATURE                       Location/Qualifiers
source                        1..9
                              organism = synthetic construct
                              mol_type = protein
                              note = Seed: VVGADGVGK (KRAS G12D)
SEQUENCE: 1106
VFGADGVGR                                                                        9

SEQ ID NO: 1107               moltype = AA   length = 9
FEATURE                       Location/Qualifiers
source                        1..9
                              organism = synthetic construct
                              mol_type = protein
                              note = Seed: AGDVGKSAL (KRAS G13D)
SEQUENCE: 1107
ALDVGKSAA                                                                        9

SEQ ID NO: 1108               moltype = AA   length = 9
FEATURE                       Location/Qualifiers
source                        1..9
                              organism = synthetic construct
                              mol_type = protein
                              note = Seed: GADGVGKSA (KRAS G12D)
SEQUENCE: 1108
GSDGVGKSH                                                                        9

SEQ ID NO: 1109               moltype = AA   length = 9
FEATURE                       Location/Qualifiers
source                        1..9
                              organism = synthetic construct
                              mol_type = protein
                              note = Seed: VVGAVGVGK (KRAS G12V)
SEQUENCE: 1109
VRGAVGVGF                                                                        9
```

```
SEQ ID NO: 1110        moltype = AA   length = 9
FEATURE                Location/Qualifiers
source                 1..9
                       organism = synthetic construct
                       mol_type = protein
                       note = Seed: VVGAVGVGK (KRAS G12V)
SEQUENCE: 1110
VNGAVGVGY                                                                 9

SEQ ID NO: 1111        moltype = AA   length = 9
FEATURE                Location/Qualifiers
source                 1..9
                       organism = synthetic construct
                       mol_type = protein
                       note = Seed: GAGDVGKSA (KRAS G13D)
SEQUENCE: 1111
GIGDVGKSV                                                                 9

SEQ ID NO: 1112        moltype = AA   length = 9
FEATURE                Location/Qualifiers
source                 1..9
                       organism = synthetic construct
                       mol_type = protein
                       note = Seed: AGDVGKSAL (KRAS G13D)
SEQUENCE: 1112
ARDVGKSAC                                                                 9

SEQ ID NO: 1113        moltype = AA   length = 9
FEATURE                Location/Qualifiers
source                 1..9
                       organism = synthetic construct
                       mol_type = protein
                       note = Seed: GAVGVGKSA (KRAS G12V)
SEQUENCE: 1113
GCVGVGKSL                                                                 9

SEQ ID NO: 1114        moltype = AA   length = 9
FEATURE                Location/Qualifiers
source                 1..9
                       organism = synthetic construct
                       mol_type = protein
                       note = Seed: AGDVGKSAL (KRAS G13D)
SEQUENCE: 1114
AEDVGKSAT                                                                 9

SEQ ID NO: 1115        moltype = AA   length = 9
FEATURE                Location/Qualifiers
source                 1..9
                       organism = synthetic construct
                       mol_type = protein
                       note = Seed: GAVGVGKSA (KRAS G12V)
SEQUENCE: 1115
GPVGVGKSK                                                                 9

SEQ ID NO: 1116        moltype = AA   length = 9
FEATURE                Location/Qualifiers
source                 1..9
                       organism = synthetic construct
                       mol_type = protein
                       note = Seed: GAVGVGKSA (KRAS G12V)
SEQUENCE: 1116
GTVGVGKSW                                                                 9

SEQ ID NO: 1117        moltype = AA   length = 9
FEATURE                Location/Qualifiers
source                 1..9
                       organism = synthetic construct
                       mol_type = protein
                       note = Seed: VVGACGVGK (KRAS G12C)
SEQUENCE: 1117
VEGACGVGK                                                                 9

SEQ ID NO: 1118        moltype = AA   length = 9
FEATURE                Location/Qualifiers
source                 1..9
                       organism = synthetic construct
                       mol_type = protein
                       note = Seed: GACGVGKSA (KRAS G12C)
SEQUENCE: 1118
```

```
GDCGVGKSY                                                                            9

SEQ ID NO: 1119           moltype = AA  length = 9
FEATURE                   Location/Qualifiers
source                    1..9
                          organism = synthetic construct
                          mol_type = protein
                          note = Seed: DVGKSALTI (KRAS G13D)
SEQUENCE: 1119
DEGKSALTV                                                                            9

SEQ ID NO: 1120           moltype = AA  length = 9
FEATURE                   Location/Qualifiers
source                    1..9
                          organism = synthetic construct
                          mol_type = protein
                          note = Seed: DVGKSALTI (KRAS G13D)
SEQUENCE: 1120
DQGKSALTM                                                                            9

SEQ ID NO: 1121           moltype = AA  length = 9
FEATURE                   Location/Qualifiers
source                    1..9
                          organism = synthetic construct
                          mol_type = protein
                          note = Seed: GADGVGKSA (KRAS G12D)
SEQUENCE: 1121
GEDGVGKSK                                                                            9

SEQ ID NO: 1122           moltype = AA  length = 9
FEATURE                   Location/Qualifiers
source                    1..9
                          organism = synthetic construct
                          mol_type = protein
                          note = Seed: VVGACGVGK (KRAS G12C)
SEQUENCE: 1122
VFGACGVGK                                                                            9

SEQ ID NO: 1123           moltype = AA  length = 9
FEATURE                   Location/Qualifiers
source                    1..9
                          organism = synthetic construct
                          mol_type = protein
                          note = Seed: VVGAGDVGK (KRAS G13D)
SEQUENCE: 1123
VGGAGDVGY                                                                            9

SEQ ID NO: 1124           moltype = AA  length = 9
FEATURE                   Location/Qualifiers
source                    1..9
                          organism = synthetic construct
                          mol_type = protein
                          note = Seed: GAVGVGKSA (KRAS G12V)
SEQUENCE: 1124
GCVGVGKSR                                                                            9

SEQ ID NO: 1125           moltype = AA  length = 9
FEATURE                   Location/Qualifiers
source                    1..9
                          organism = synthetic construct
                          mol_type = protein
                          note = Seed: GADGVGKSA (KRAS G12D)
SEQUENCE: 1125
GFDGVGKSR                                                                            9

SEQ ID NO: 1126           moltype = AA  length = 9
FEATURE                   Location/Qualifiers
source                    1..9
                          organism = synthetic construct
                          mol_type = protein
                          note = Seed: VVGAGDVGK (KRAS G13D)
SEQUENCE: 1126
VDGAGDVGR                                                                            9

SEQ ID NO: 1127           moltype = AA  length = 9
FEATURE                   Location/Qualifiers
source                    1..9
                          organism = synthetic construct
                          mol_type = protein
```

```
                            note = Seed: VVGAVGVGK (KRAS G12V)
SEQUENCE: 1127
VAGAVGVGW                                                              9

SEQ ID NO: 1128         moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 1128
GFDGVGKSW                                                              9

SEQ ID NO: 1129         moltype = AA   length = 9
FEATURE                 Location/Qualifiers
source                  1..9
                        organism = synthetic construct
                        mol_type = protein
                        note = Seed: VVGAVGVGK (KRAS G12V)
SEQUENCE: 1129
VRGAVGVGY                                                              9

SEQ ID NO: 1130         moltype = AA   length = 9
FEATURE                 Location/Qualifiers
source                  1..9
                        organism = synthetic construct
                        mol_type = protein
                        note = Seed: VVGAVGVGK (KRAS G12V)
SEQUENCE: 1130
VIGAVGVGL                                                              9

SEQ ID NO: 1131         moltype = AA   length = 9
FEATURE                 Location/Qualifiers
source                  1..9
                        organism = synthetic construct
                        mol_type = protein
                        note = Seed: GACGVGKSA (KRAS G12C)
SEQUENCE: 1131
GICGVGKSV                                                              9

SEQ ID NO: 1132         moltype = AA   length = 9
FEATURE                 Location/Qualifiers
source                  1..9
                        organism = synthetic construct
                        mol_type = protein
                        note = Seed: VVGACGVGK (KRAS G12C)
SEQUENCE: 1132
VTGACGVGM                                                              9

SEQ ID NO: 1133         moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 1133
ACDVGKSAY                                                              9

SEQ ID NO: 1134         moltype = AA   length = 9
FEATURE                 Location/Qualifiers
source                  1..9
                        organism = synthetic construct
                        mol_type = protein
                        note = Seed: VVGAVGVGK (KRAS G12V)
SEQUENCE: 1134
VCGAVGVGR                                                              9

SEQ ID NO: 1135         moltype = AA   length = 9
FEATURE                 Location/Qualifiers
source                  1..9
                        organism = synthetic construct
                        mol_type = protein
                        note = Seed: VVGADGVGK (KRAS G12D)
SEQUENCE: 1135
VEGADGVGR                                                              9

SEQ ID NO: 1136         moltype = AA   length = 9
FEATURE                 Location/Qualifiers
source                  1..9
```

```
                          organism = synthetic construct
                          mol_type = protein
                          note = Seed: AGDVGKSAL (KRAS G13D)
SEQUENCE: 1136
AVDVGKSAH                                                          9

SEQ ID NO: 1137           moltype = AA  length = 9
FEATURE                   Location/Qualifiers
source                    1..9
                          organism = synthetic construct
                          mol_type = protein
                          note = Seed: GAGDVGKSA (KRAS G13D)
SEQUENCE: 1137
GDGDVGKSY                                                          9

SEQ ID NO: 1138           moltype = AA  length = 9
FEATURE                   Location/Qualifiers
source                    1..9
                          organism = synthetic construct
                          mol_type = protein
                          note = Seed: DVGKSALTI (KRAS G13D)
SEQUENCE: 1138
DPGKSALTM                                                          9

SEQ ID NO: 1139           moltype = AA  length = 9
FEATURE                   Location/Qualifiers
source                    1..9
                          organism = synthetic construct
                          mol_type = protein
                          note = Seed: GACGVGKSA (KRAS G12C)
SEQUENCE: 1139
GSCGVGKSA                                                          9

SEQ ID NO: 1140           moltype = AA  length = 9
FEATURE                   Location/Qualifiers
source                    1..9
                          organism = synthetic construct
                          mol_type = protein
                          note = Seed: GAGDVGKSA (KRAS G13D)
SEQUENCE: 1140
GSGDVGKSW                                                          9

SEQ ID NO: 1141           moltype = AA  length = 9
FEATURE                   Location/Qualifiers
source                    1..9
                          organism = synthetic construct
                          mol_type = protein
                          note = Seed: GACGVGKSA (KRAS G12C)
SEQUENCE: 1141
GDCGVGKSK                                                          9

SEQ ID NO: 1142           moltype = AA  length = 9
FEATURE                   Location/Qualifiers
source                    1..9
                          organism = synthetic construct
                          mol_type = protein
                          note = Seed: VVGAVGVGK (KRAS G12V)
SEQUENCE: 1142
VYGAVGVGM                                                          9

SEQ ID NO: 1143           moltype = AA  length = 9
FEATURE                   Location/Qualifiers
source                    1..9
                          organism = synthetic construct
                          mol_type = protein
                          note = Seed: VVGACGVGK (KRAS G12C)
SEQUENCE: 1143
VWGACGVGR                                                          9

SEQ ID NO: 1144           moltype = AA  length = 9
FEATURE                   Location/Qualifiers
source                    1..9
                          organism = synthetic construct
                          mol_type = protein
                          note = Seed: GAVGVGKSA (KRAS G12V)
SEQUENCE: 1144
GTVGVGKSA                                                          9

SEQ ID NO: 1145           moltype = AA  length = 9
```

```
FEATURE            Location/Qualifiers
source             1..9
                   organism = synthetic construct
                   mol_type = protein
                   note = Seed: GAGDVGKSA (KRAS G13D)
SEQUENCE: 1145
GSGDVGKSA                                                                        9

SEQ ID NO: 1146    moltype = AA   length = 9
FEATURE            Location/Qualifiers
source             1..9
                   organism = synthetic construct
                   mol_type = protein
                   note = Seed: DVGKSALTI (KRAS G13D)
SEQUENCE: 1146
DLGKSALTV                                                                        9

SEQ ID NO: 1147    moltype = AA   length = 9
FEATURE            Location/Qualifiers
source             1..9
                   organism = synthetic construct
                   mol_type = protein
                   note = Seed: AGDVGKSAL (KRAS G13D)
SEQUENCE: 1147
AQDVGKSAK                                                                        9

SEQ ID NO: 1148    moltype = AA   length = 9
FEATURE            Location/Qualifiers
source             1..9
                   organism = synthetic construct
                   mol_type = protein
                   note = Seed: AGDVGKSAL (KRAS G13D)
SEQUENCE: 1148
ATDVGKSAT                                                                        9

SEQ ID NO: 1149    moltype = AA   length = 9
FEATURE            Location/Qualifiers
source             1..9
                   organism = synthetic construct
                   mol_type = protein
                   note = Seed: VVGACGVGK (KRAS G12C)
SEQUENCE: 1149
VNGACGVGR                                                                        9

SEQ ID NO: 1150    moltype = AA   length = 9
FEATURE            Location/Qualifiers
source             1..9
                   organism = synthetic construct
                   mol_type = protein
                   note = Seed: GACGVGKSA (KRAS G12C)
SEQUENCE: 1150
GQCGVGKSK                                                                        9

SEQ ID NO: 1151    moltype = AA   length = 9
FEATURE            Location/Qualifiers
source             1..9
                   organism = synthetic construct
                   mol_type = protein
                   note = Seed: LVVGAVGV (KRAS G12V)
SEQUENCE: 1151
LMVVGAVGT                                                                        9

SEQ ID NO: 1152    moltype = AA   length = 9
FEATURE            Location/Qualifiers
source             1..9
                   organism = synthetic construct
                   mol_type = protein
                   note = Seed: VVGARGVGK (KRAS G12R)
SEQUENCE: 1152
VIGARGVGL                                                                        9

SEQ ID NO: 1153    moltype = AA   length = 9
FEATURE            Location/Qualifiers
source             1..9
                   organism = synthetic construct
                   mol_type = protein
                   note = Seed: VVGAVGVGK (KRAS G12V)
SEQUENCE: 1153
VYGAVGVGY                                                                        9
```

```
SEQ ID NO: 1154        moltype = AA  length = 9
FEATURE                Location/Qualifiers
source                 1..9
                       organism = synthetic construct
                       mol_type = protein
                       note = Seed: GACGVGKSA (KRAS G12C)
SEQUENCE: 1154
GNCGVGKSK                                                                    9

SEQ ID NO: 1155        moltype = AA  length = 9
FEATURE                Location/Qualifiers
source                 1..9
                       organism = synthetic construct
                       mol_type = protein
                       note = Seed: VVGACGVGK (KRAS G12C)
SEQUENCE: 1155
VTGACGVGL                                                                    9

SEQ ID NO: 1156        moltype = AA  length = 9
FEATURE                Location/Qualifiers
source                 1..9
                       organism = synthetic construct
                       mol_type = protein
                       note = Seed: VVGAVGVGK (KRAS G12V)
SEQUENCE: 1156
VHGAVGVGK                                                                    9

SEQ ID NO: 1157        moltype = AA  length = 9
FEATURE                Location/Qualifiers
source                 1..9
                       organism = synthetic construct
                       mol_type = protein
                       note = Seed: VVGARGVGK (KRAS G12R)
SEQUENCE: 1157
VGGARGVGM                                                                    9

SEQ ID NO: 1158        moltype = AA  length = 9
FEATURE                Location/Qualifiers
source                 1..9
                       organism = synthetic construct
                       mol_type = protein
                       note = Seed: VVGAGDVGK (KRAS G13D)
SEQUENCE: 1158
VPGAGDVGK                                                                    9

SEQ ID NO: 1159        moltype = AA  length = 9
FEATURE                Location/Qualifiers
source                 1..9
                       organism = synthetic construct
                       mol_type = protein
                       note = Seed: GAGDVGKSA (KRAS G13D)
SEQUENCE: 1159
GPGDVGKSF                                                                    9

SEQ ID NO: 1160        moltype = AA  length = 9
FEATURE                Location/Qualifiers
source                 1..9
                       organism = synthetic construct
                       mol_type = protein
                       note = Seed: VVGARGVGK (KRAS G12R)
SEQUENCE: 1160
VIGARGVGM                                                                    9

SEQ ID NO: 1161        moltype = AA  length = 9
FEATURE                Location/Qualifiers
source                 1..9
                       organism = synthetic construct
                       mol_type = protein
                       note = Seed: GARGVGKSA (KRAS G12R)
SEQUENCE: 1161
GPRGVGKSR                                                                    9

SEQ ID NO: 1162        moltype = AA  length = 9
FEATURE                Location/Qualifiers
source                 1..9
                       organism = synthetic construct
                       mol_type = protein
                       note = Seed: VVGARGVGK (KRAS G12R)
```

```
SEQUENCE: 1162
VFGARGVGY                                                                        9

SEQ ID NO: 1163          moltype = AA  length = 9
FEATURE                  Location/Qualifiers
source                   1..9
                         organism = synthetic construct
                         mol_type = protein
                         note = Seed: VVGACGVGK (KRAS G12C)
SEQUENCE: 1163
VQGACGVGY                                                                        9

SEQ ID NO: 1164          moltype = AA  length = 9
FEATURE                  Location/Qualifiers
source                   1..9
                         organism = synthetic construct
                         mol_type = protein
                         note = Seed: AGDVGKSAL (KRAS G13D)
SEQUENCE: 1164
ADDVGKSAK                                                                        9

SEQ ID NO: 1165          moltype = AA  length = 9
FEATURE                  Location/Qualifiers
source                   1..9
                         organism = synthetic construct
                         mol_type = protein
                         note = Seed: VVGADGVGK (KRAS G12D)
SEQUENCE: 1165
VSGADGVGL                                                                        9

SEQ ID NO: 1166          moltype = AA  length = 9
FEATURE                  Location/Qualifiers
source                   1..9
                         organism = synthetic construct
                         mol_type = protein
                         note = Seed: GADGVGKSA (KRAS G12D)
SEQUENCE: 1166
GLDGVGKSA                                                                        9

SEQ ID NO: 1167          moltype = AA  length = 9
FEATURE                  Location/Qualifiers
source                   1..9
                         organism = synthetic construct
                         mol_type = protein
                         note = Seed: VVGAGDVGK (KRAS G13D)
SEQUENCE: 1167
VYGAGDVGK                                                                        9

SEQ ID NO: 1168          moltype = AA  length = 9
FEATURE                  Location/Qualifiers
source                   1..9
                         organism = synthetic construct
                         mol_type = protein
                         note = Seed: VVGARGVGK (KRAS G12R)
SEQUENCE: 1168
VGGARGVGF                                                                        9

SEQ ID NO: 1169          moltype = AA  length = 9
FEATURE                  Location/Qualifiers
source                   1..9
                         organism = synthetic construct
                         mol_type = protein
                         note = Seed: GAGDVGKSA (KRAS G13D)
SEQUENCE: 1169
GVGDVGKSW                                                                        9

SEQ ID NO: 1170          moltype = AA  length = 9
FEATURE                  Location/Qualifiers
source                   1..9
                         organism = synthetic construct
                         mol_type = protein
                         note = Seed: VVGAVGVGK (KRAS G12V)
SEQUENCE: 1170
VCGAVGVGY                                                                        9

SEQ ID NO: 1171          moltype = AA  length = 9
FEATURE                  Location/Qualifiers
source                   1..9
                         organism = synthetic construct
```

```
                               mol_type = protein
                               note = Seed: VVGAGDVGK (KRAS G13D)
SEQUENCE: 1171
VVGAGDVGM                                                                9

SEQ ID NO: 1172                moltype = AA   length = 9
FEATURE                        Location/Qualifiers
source                         1..9
                               organism = synthetic construct
                               mol_type = protein
                               note = Seed: VVGARGVGK (KRAS G12R)
SEQUENCE: 1172
VGGARGVGR                                                                9

SEQ ID NO: 1173                moltype = AA   length = 9
FEATURE                        Location/Qualifiers
source                         1..9
                               organism = synthetic construct
                               mol_type = protein
                               note = Seed: GAGDVGKSA (KRAS G13D)
SEQUENCE: 1173
GNGDVGKSM                                                                9

SEQ ID NO: 1174                moltype = AA   length = 9
FEATURE                        Location/Qualifiers
source                         1..9
                               organism = synthetic construct
                               mol_type = protein
                               note = Seed: GADGVGKSA (KRAS G12D)
SEQUENCE: 1174
GKDGVGKSI                                                                9

SEQ ID NO: 1175                moltype = AA   length = 9
FEATURE                        Location/Qualifiers
source                         1..9
                               organism = synthetic construct
                               mol_type = protein
                               note = Seed: VVGARGVGK (KRAS G12R)
SEQUENCE: 1175
VMGARGVGY                                                                9

SEQ ID NO: 1176                moltype = AA   length = 9
FEATURE                        Location/Qualifiers
source                         1..9
                               organism = synthetic construct
                               mol_type = protein
                               note = Seed: VVGARGVGK (KRAS G12R)
SEQUENCE: 1176
VPGARGVGK                                                                9

SEQ ID NO: 1177                moltype = AA   length = 9
FEATURE                        Location/Qualifiers
source                         1..9
                               organism = synthetic construct
                               mol_type = protein
                               note = Seed: GAVGVGKSA (KRAS G12V)
SEQUENCE: 1177
GVVGVGKSW                                                                9

SEQ ID NO: 1178                moltype = AA   length = 9
FEATURE                        Location/Qualifiers
source                         1..9
                               organism = synthetic construct
                               mol_type = protein
                               note = Seed: VVGACGVGK (KRAS G12C)
SEQUENCE: 1178
VAGACGVGI                                                                9

SEQ ID NO: 1179                moltype = AA   length = 9
FEATURE                        Location/Qualifiers
source                         1..9
                               organism = synthetic construct
                               mol_type = protein
                               note = Seed: GARGVGKSA (KRAS G12R)
SEQUENCE: 1179
GCRGVGKSM                                                                9

SEQ ID NO: 1180                moltype = AA   length = 9
FEATURE                        Location/Qualifiers
```

```
                        -continued source                  1..9
                        organism = synthetic construct
                        mol_type = protein
                        note = Seed: AGDVGKSAL (KRAS G13D)
SEQUENCE: 1180
AMDVGKSAW                                                                       9

SEQ ID NO: 1181         moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 1181
ANDVGKSAK                                                                       9

SEQ ID NO: 1182         moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 1182
GAVGVGKSS                                                                       9

SEQ ID NO: 1183         moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 1183
GEDGVGKSI                                                                       9

SEQ ID NO: 1184         moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 1184
ANDVGKSAR                                                                       9

SEQ ID NO: 1185         moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 1185
GCDGVGKSY                                                                       9

SEQ ID NO: 1186         moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 1186
GEGDVGKSK                                                                       9

SEQ ID NO: 1187         moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 1187
AQDVGKSAR                                                                       9

SEQ ID NO: 1188         moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 1188
AGDVGKSAW                                                                       9
```

```
SEQ ID NO: 1189          moltype = AA   length = 9
FEATURE                  Location/Qualifiers
source                   1..9
                         organism = synthetic construct
                         mol_type = protein
                         note = Seed: AGDVGKSAL (KRAS G13D)
SEQUENCE: 1189
AGDVGKSAC                                                                  9

SEQ ID NO: 1190          moltype = AA   length = 9
FEATURE                  Location/Qualifiers
source                   1..9
                         organism = synthetic construct
                         mol_type = protein
                         note = Seed: GAGDVGKSA (KRAS G13D)
SEQUENCE: 1190
GPGDVGKSG                                                                  9

SEQ ID NO: 1191          moltype = AA   length = 9
FEATURE                  Location/Qualifiers
source                   1..9
                         organism = synthetic construct
                         mol_type = protein
                         note = Seed: GAGDVGKSA (KRAS G13D)
SEQUENCE: 1191
GAGDVGKSC                                                                  9

SEQ ID NO: 1192          moltype = AA   length = 9
FEATURE                  Location/Qualifiers
source                   1..9
                         organism = synthetic construct
                         mol_type = protein
                         note = Seed: GARGVGKSA (KRAS G12R)
SEQUENCE: 1192
GGRGVGKSH                                                                  9

SEQ ID NO: 1193          moltype = AA   length = 9
FEATURE                  Location/Qualifiers
source                   1..9
                         organism = synthetic construct
                         mol_type = protein
                         note = Seed: GARGVGKSA (KRAS G12R)
SEQUENCE: 1193
GSRGVGKSW                                                                  9

SEQ ID NO: 1194          moltype = AA   length = 9
FEATURE                  Location/Qualifiers
source                   1..9
                         organism = synthetic construct
                         mol_type = protein
                         note = Seed: GARGVGKSA (KRAS G12R)
SEQUENCE: 1194
GDRGVGKSF                                                                  9

SEQ ID NO: 1195          moltype = AA   length = 9
FEATURE                  Location/Qualifiers
source                   1..9
                         organism = synthetic construct
                         mol_type = protein
                         note = Seed: GACGVGKSA (KRAS G12C)
SEQUENCE: 1195
GNCGVGKSR                                                                  9

SEQ ID NO: 1196          moltype = AA   length = 9
FEATURE                  Location/Qualifiers
source                   1..9
                         organism = synthetic construct
                         mol_type = protein
                         note = Seed: VVGAGDVGK (KRAS G13D)
SEQUENCE: 1196
VEGAGDVGR                                                                  9

SEQ ID NO: 1197          moltype = AA   length = 9
FEATURE                  Location/Qualifiers
source                   1..9
                         organism = synthetic construct
                         mol_type = protein
                         note = Seed: VVGARGVGK (KRAS G12R)
SEQUENCE: 1197
```

VGGARGVGL 9

SEQ ID NO: 1198        moltype = AA  length = 9
FEATURE                Location/Qualifiers
source                 1..9
                       organism = synthetic construct
                       mol_type = protein
                       note = Seed: GAGDVGKSA (KRAS G13D)
SEQUENCE: 1198
GFGDVGKSR 9

SEQ ID NO: 1199        moltype = AA  length = 9
FEATURE                Location/Qualifiers
source                 1..9
                       organism = synthetic construct
                       mol_type = protein
                       note = Seed: GAGDVGKSA (KRAS G13D)
SEQUENCE: 1199
GPGDVGKSK 9

SEQ ID NO: 1200        moltype = AA  length = 9
FEATURE                Location/Qualifiers
source                 1..9
                       organism = synthetic construct
                       mol_type = protein
                       note = Seed: GACGVGKSA (KRAS G12C)
SEQUENCE: 1200
GFCGVGKSY 9

SEQ ID NO: 1201        moltype = AA  length = 9
FEATURE                Location/Qualifiers
source                 1..9
                       organism = synthetic construct
                       mol_type = protein
                       note = Seed: VVGADGVGK (KRAS G12D)
SEQUENCE: 1201
VYGADGVGK 9

SEQ ID NO: 1202        moltype = AA  length = 9
FEATURE                Location/Qualifiers
source                 1..9
                       organism = synthetic construct
                       mol_type = protein
                       note = Seed: GADGVGKSA (KRAS G12D)
SEQUENCE: 1202
GIDGVGKST 9

SEQ ID NO: 1203        moltype = AA  length = 9
FEATURE                Location/Qualifiers
source                 1..9
                       organism = synthetic construct
                       mol_type = protein
                       note = Seed: VVGAGDVGK (KRAS G13D)
SEQUENCE: 1203
VSGAGDVGL 9

SEQ ID NO: 1204        moltype = AA  length = 9
FEATURE                Location/Qualifiers
source                 1..9
                       organism = synthetic construct
                       mol_type = protein
                       note = Seed: VVGARGVGK (KRAS G12R)
SEQUENCE: 1204
VWGARGVGR 9

SEQ ID NO: 1205        moltype = AA  length = 9
FEATURE                Location/Qualifiers
source                 1..9
                       organism = synthetic construct
                       mol_type = protein
                       note = Seed: GADGVGKSA (KRAS G12D)
SEQUENCE: 1205
GVDGVGKST 9

SEQ ID NO: 1206        moltype = AA  length = 9
FEATURE                Location/Qualifiers
source                 1..9
                       organism = synthetic construct
                       mol_type = protein

```
                        note = Seed: GADGVGKSA (KRAS G12D)
SEQUENCE: 1206
GPDGVGKSS                                                                       9

SEQ ID NO: 1207         moltype = AA   length = 9
FEATURE                 Location/Qualifiers
source                  1..9
                        organism = synthetic construct
                        mol_type = protein
                        note = Seed: GACGVGKSA (KRAS G12C)
SEQUENCE: 1207
GNCGVGKSM                                                                       9

SEQ ID NO: 1208         moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 1208
GEDGVGKSR                                                                       9

SEQ ID NO: 1209         moltype = AA   length = 9
FEATURE                 Location/Qualifiers
source                  1..9
                        organism = synthetic construct
                        mol_type = protein
                        note = Seed: GACGVGKSA (KRAS G12C)
SEQUENCE: 1209
GQCGVGKSR                                                                       9

SEQ ID NO: 1210         moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 1210
GPDGVGKSY                                                                       9

SEQ ID NO: 1211         moltype = AA   length = 9
FEATURE                 Location/Qualifiers
source                  1..9
                        organism = synthetic construct
                        mol_type = protein
                        note = Seed: VVGACGVGK (KRAS G12C)
SEQUENCE: 1211
VEGACGVGR                                                                       9

SEQ ID NO: 1212         moltype = AA   length = 9
FEATURE                 Location/Qualifiers
source                  1..9
                        organism = synthetic construct
                        mol_type = protein
                        note = Seed: VVGAVGVGK (KRAS G12V)
SEQUENCE: 1212
VLGAVGVGF                                                                       9

SEQ ID NO: 1213         moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 1213
GPVGVGKSW                                                                       9

SEQ ID NO: 1214         moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 1214
GYDGVGKSW                                                                       9

SEQ ID NO: 1215         moltype = AA   length = 9
FEATURE                 Location/Qualifiers
source                  1..9
```

```
                        organism = synthetic construct
                        mol_type = protein
                        note = Seed: GACGVGKSA (KRAS G12C)
SEQUENCE: 1215
GICGVGKSI                                                           9

SEQ ID NO: 1216         moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 1216
GTRGVGKSA                                                           9

SEQ ID NO: 1217         moltype = AA  length = 9
FEATURE                 Location/Qualifiers
source                  1..9
                        organism = synthetic construct
                        mol_type = protein
                        note = Seed: VVGAVGVGK (KRAS G12V)
SEQUENCE: 1217
VWGAVGVGK                                                           9

SEQ ID NO: 1218         moltype = AA  length = 9
FEATURE                 Location/Qualifiers
source                  1..9
                        organism = synthetic construct
                        mol_type = protein
                        note = Seed: VVGARGVGK (KRAS G12R)
SEQUENCE: 1218
VFGARGVGF                                                           9

SEQ ID NO: 1219         moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 1219
GPVGVGKSR                                                           9

SEQ ID NO: 1220         moltype = AA  length = 9
FEATURE                 Location/Qualifiers
source                  1..9
                        organism = synthetic construct
                        mol_type = protein
                        note = Seed: VVGAVGVGK (KRAS G12V)
SEQUENCE: 1220
VDGAVGVGY                                                           9

SEQ ID NO: 1221         moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 1221
GGGDVGKSH                                                           9

SEQ ID NO: 1222         moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 1222
GGCGVGKSH                                                           9

SEQ ID NO: 1223         moltype = AA  length = 9
FEATURE                 Location/Qualifiers
source                  1..9
                        organism = synthetic construct
                        mol_type = protein
                        note = Seed: VVGAVGVGK (KRAS G12V)
SEQUENCE: 1223
VFGAVGVGF                                                           9

SEQ ID NO: 1224         moltype = AA  length = 9
```

```
FEATURE            Location/Qualifiers
source             1..9
                   organism = synthetic construct
                   mol_type = protein
                   note = Seed: VVGAGDVGK (KRAS G13D)
SEQUENCE: 1224
VIGAGDVGF                                                                         9

SEQ ID NO: 1225    moltype = AA   length = 9
FEATURE            Location/Qualifiers
source             1..9
                   organism = synthetic construct
                   mol_type = protein
                   note = Seed: AGDVGKSAL (KRAS G13D)
SEQUENCE: 1225
AKDVGKSAV                                                                         9

SEQ ID NO: 1226    moltype = AA   length = 9
FEATURE            Location/Qualifiers
source             1..9
                   organism = synthetic construct
                   mol_type = protein
                   note = Seed: GACGVGKSA (KRAS G12C)
SEQUENCE: 1226
GDCGVGKSR                                                                         9

SEQ ID NO: 1227    moltype = AA   length = 9
FEATURE            Location/Qualifiers
source             1..9
                   organism = synthetic construct
                   mol_type = protein
                   note = Seed: VVGARGVGK (KRAS G12R)
SEQUENCE: 1227
VDGARGVGK                                                                         9

SEQ ID NO: 1228    moltype = AA   length = 9
FEATURE            Location/Qualifiers
source             1..9
                   organism = synthetic construct
                   mol_type = protein
                   note = Seed: GARGVGKSA (KRAS G12R)
SEQUENCE: 1228
GPRGVGKSE                                                                         9

SEQ ID NO: 1229    moltype = AA   length = 9
FEATURE            Location/Qualifiers
source             1..9
                   organism = synthetic construct
                   mol_type = protein
                   note = Seed: AGDVGKSAL (KRAS G13D)
SEQUENCE: 1229
APDVGKSAY                                                                         9

SEQ ID NO: 1230    moltype = AA   length = 9
FEATURE            Location/Qualifiers
source             1..9
                   organism = synthetic construct
                   mol_type = protein
                   note = Seed: VVGAVGVGK (KRAS G12V)
SEQUENCE: 1230
VYGAVGVGL                                                                         9

SEQ ID NO: 1231    moltype = AA   length = 9
FEATURE            Location/Qualifiers
source             1..9
                   organism = synthetic construct
                   mol_type = protein
                   note = Seed: GAGDVGKSA (KRAS G13D)
SEQUENCE: 1231
GMGDVGKSH                                                                         9

SEQ ID NO: 1232    moltype = AA   length = 9
FEATURE            Location/Qualifiers
source             1..9
                   organism = synthetic construct
                   mol_type = protein
                   note = Seed: VVGADGVGK (KRAS G12D)
SEQUENCE: 1232
VTGADGVGL                                                                         9
```

```
SEQ ID NO: 1233              moltype = AA   length = 9
FEATURE                      Location/Qualifiers
source                       1..9
                             organism = synthetic construct
                             mol_type = protein
                             note = Seed: GAGDVGKSA (KRAS G13D)
SEQUENCE: 1233
GAGDVGKST                                                                    9

SEQ ID NO: 1234              moltype = AA   length = 9
FEATURE                      Location/Qualifiers
source                       1..9
                             organism = synthetic construct
                             mol_type = protein
                             note = Seed: GARGVGKSA (KRAS G12R)
SEQUENCE: 1234
GPRGVGKSK                                                                    9

SEQ ID NO: 1235              moltype = AA   length = 9
FEATURE                      Location/Qualifiers
source                       1..9
                             organism = synthetic construct
                             mol_type = protein
                             note = Seed: GADGVGKSA (KRAS G12D)
SEQUENCE: 1235
GCDGVGKSK                                                                    9

SEQ ID NO: 1236              moltype = AA   length = 9
FEATURE                      Location/Qualifiers
source                       1..9
                             organism = synthetic construct
                             mol_type = protein
                             note = Seed: GADGVGKSA (KRAS G12D)
SEQUENCE: 1236
GGDGVGKSC                                                                    9

SEQ ID NO: 1237              moltype = AA   length = 9
FEATURE                      Location/Qualifiers
source                       1..9
                             organism = synthetic construct
                             mol_type = protein
                             note = Seed: AGDVGKSAL (KRAS G13D)
SEQUENCE: 1237
ATDVGKSAH                                                                    9

SEQ ID NO: 1238              moltype = AA   length = 9
FEATURE                      Location/Qualifiers
source                       1..9
                             organism = synthetic construct
                             mol_type = protein
                             note = Seed: VVGADGVGK (KRAS G12D)
SEQUENCE: 1238
VQGADGVGY                                                                    9

SEQ ID NO: 1239              moltype = AA   length = 9
FEATURE                      Location/Qualifiers
source                       1..9
                             organism = synthetic construct
                             mol_type = protein
                             note = Seed: VVGAGDVGK (KRAS G13D)
SEQUENCE: 1239
VTGAGDVGM                                                                    9

SEQ ID NO: 1240              moltype = AA   length = 9
FEATURE                      Location/Qualifiers
source                       1..9
                             organism = synthetic construct
                             mol_type = protein
                             note = Seed: GAGDVGKSA (KRAS G13D)
SEQUENCE: 1240
GIGDVGKSI                                                                    9

SEQ ID NO: 1241              moltype = AA   length = 9
FEATURE                      Location/Qualifiers
source                       1..9
                             organism = synthetic construct
                             mol_type = protein
                             note = Seed: GACGVGKSA (KRAS G12C)
```

```
SEQUENCE: 1241
GMCGVGKSR                                                                              9

SEQ ID NO: 1242         moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 1242
AMDVGKSAR                                                                              9

SEQ ID NO: 1243         moltype = AA   length = 9
FEATURE                 Location/Qualifiers
source                  1..9
                        organism = synthetic construct
                        mol_type = protein
                        note = Seed: GACGVGKSA (KRAS G12C)
SEQUENCE: 1243
GCCGVGKSF                                                                              9

SEQ ID NO: 1244         moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 1244
AEDVGKSAK                                                                              9

SEQ ID NO: 1245         moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 1245
GEVGVGKSR                                                                              9

SEQ ID NO: 1246         moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 1246
GWDGVGKSK                                                                              9

SEQ ID NO: 1247         moltype = AA   length = 9
FEATURE                 Location/Qualifiers
source                  1..9
                        organism = synthetic construct
                        mol_type = protein
                        note = Seed: GACGVGKSA (KRAS G12C)
SEQUENCE: 1247
GSCGVGKSW                                                                              9

SEQ ID NO: 1248         moltype = AA   length = 9
FEATURE                 Location/Qualifiers
source                  1..9
                        organism = synthetic construct
                        mol_type = protein
                        note = Seed: VVGACGVGK (KRAS G12C)
SEQUENCE: 1248
VVGACGVGL                                                                              9

SEQ ID NO: 1249         moltype = AA   length = 9
FEATURE                 Location/Qualifiers
source                  1..9
                        organism = synthetic construct
                        mol_type = protein
                        note = Seed: VVGAVGVGK (KRAS G12V)
SEQUENCE: 1249
VSGAVGVGI                                                                              9

SEQ ID NO: 1250         moltype = AA   length = 9
FEATURE                 Location/Qualifiers
source                  1..9
                        organism = synthetic construct
```

```
                            mol_type = protein
                            note = Seed: AGDVGKSAL (KRAS G13D)
SEQUENCE: 1250
AIDVGKSAT                                                            9

SEQ ID NO: 1251             moltype = AA   length = 9
FEATURE                     Location/Qualifiers
source                      1..9
                            organism = synthetic construct
                            mol_type = protein
                            note = Seed: GADGVGKSA (KRAS G12D)
SEQUENCE: 1251
GTDGVGKSH                                                            9

SEQ ID NO: 1252             moltype = AA   length = 9
FEATURE                     Location/Qualifiers
source                      1..9
                            organism = synthetic construct
                            mol_type = protein
                            note = Seed: GARGVGKSA (KRAS G12R)
SEQUENCE: 1252
GARGVGKSR                                                            9

SEQ ID NO: 1253             moltype = AA   length = 9
FEATURE                     Location/Qualifiers
source                      1..9
                            organism = synthetic construct
                            mol_type = protein
                            note = Seed: VVGAVGVGK (KRAS G12V)
SEQUENCE: 1253
VSGAVGVGV                                                            9

SEQ ID NO: 1254             moltype = AA   length = 9
FEATURE                     Location/Qualifiers
source                      1..9
                            organism = synthetic construct
                            mol_type = protein
                            note = Seed: VVGARGVGK (KRAS G12R)
SEQUENCE: 1254
VYGARGVGK                                                            9

SEQ ID NO: 1255             moltype = AA   length = 9
FEATURE                     Location/Qualifiers
source                      1..9
                            organism = synthetic construct
                            mol_type = protein
                            note = Seed: AGDVGKSAL (KRAS G13D)
SEQUENCE: 1255
AMDVGKSAA                                                            9

SEQ ID NO: 1256             moltype = AA   length = 9
FEATURE                     Location/Qualifiers
source                      1..9
                            organism = synthetic construct
                            mol_type = protein
                            note = Seed: VVGARGVGK (KRAS G12R)
SEQUENCE: 1256
VLGARGVGY                                                            9

SEQ ID NO: 1257             moltype = AA   length = 9
FEATURE                     Location/Qualifiers
source                      1..9
                            organism = synthetic construct
                            mol_type = protein
                            note = Seed: GARGVGKSA (KRAS G12R)
SEQUENCE: 1257
GVRGVGKSW                                                            9

SEQ ID NO: 1258             moltype = AA   length = 9
FEATURE                     Location/Qualifiers
source                      1..9
                            organism = synthetic construct
                            mol_type = protein
                            note = Seed: GACGVGKSA (KRAS G12C)
SEQUENCE: 1258
GACGVGKST                                                            9

SEQ ID NO: 1259             moltype = AA   length = 9
FEATURE                     Location/Qualifiers
```

```
source                    1..9
                          organism = synthetic construct
                          mol_type = protein
                          note = Seed: GADGVGKSA (KRAS G12D)
SEQUENCE: 1259
GYDGVGKSR                                                                        9

SEQ ID NO: 1260           moltype = AA   length = 9
FEATURE                   Location/Qualifiers
source                    1..9
                          organism = synthetic construct
                          mol_type = protein
                          note = Seed: GADGVGKSA (KRAS G12D)
SEQUENCE: 1260
GCDGVGKSR                                                                        9

SEQ ID NO: 1261           moltype = AA   length = 9
FEATURE                   Location/Qualifiers
source                    1..9
                          organism = synthetic construct
                          mol_type = protein
                          note = Seed: GAVGVGKSA (KRAS G12V)
SEQUENCE: 1261
GGVGVGKSV                                                                        9

SEQ ID NO: 1262           moltype = AA   length = 9
FEATURE                   Location/Qualifiers
source                    1..9
                          organism = synthetic construct
                          mol_type = protein
                          note = Seed: VVGAVGVGK (KRAS G12V)
SEQUENCE: 1262
VFGAVGVGY                                                                        9

SEQ ID NO: 1263           moltype = AA   length = 9
FEATURE                   Location/Qualifiers
source                    1..9
                          organism = synthetic construct
                          mol_type = protein
                          note = Seed: VVGAVGVGK (KRAS G12V)
SEQUENCE: 1263
VIGAVGVGH                                                                        9

SEQ ID NO: 1264           moltype = AA   length = 9
FEATURE                   Location/Qualifiers
source                    1..9
                          organism = synthetic construct
                          mol_type = protein
                          note = Seed: VVGACGVGK (KRAS G12C)
SEQUENCE: 1264
VAGACGVGV                                                                        9

SEQ ID NO: 1265           moltype = AA   length = 9
FEATURE                   Location/Qualifiers
source                    1..9
                          organism = synthetic construct
                          mol_type = protein
                          note = Seed: AGDVGKSAL (KRAS G13D)
SEQUENCE: 1265
ADDVGKSAR                                                                        9

SEQ ID NO: 1266           moltype = AA   length = 9
FEATURE                   Location/Qualifiers
source                    1..9
                          organism = synthetic construct
                          mol_type = protein
                          note = Seed: DVGKSALTI (KRAS G13D)
SEQUENCE: 1266
DLGKSALTI                                                                        9

SEQ ID NO: 1267           moltype = AA   length = 9
FEATURE                   Location/Qualifiers
source                    1..9
                          organism = synthetic construct
                          mol_type = protein
                          note = Seed: AGDVGKSAL (KRAS G13D)
SEQUENCE: 1267
AQDVGKSAC                                                                        9
```

```
SEQ ID NO: 1268          moltype = AA   length = 9
FEATURE                  Location/Qualifiers
source                   1..9
                         organism = synthetic construct
                         mol_type = protein
                         note = Seed: GADGVGKSA (KRAS G12D)
SEQUENCE: 1268
GKDGVGKSV                                                                9

SEQ ID NO: 1269          moltype = AA   length = 9
FEATURE                  Location/Qualifiers
source                   1..9
                         organism = synthetic construct
                         mol_type = protein
                         note = Seed: GAGDVGKSA (KRAS G13D)
SEQUENCE: 1269
GCGDVGKSR                                                                9

SEQ ID NO: 1270          moltype = AA   length = 9
FEATURE                  Location/Qualifiers
source                   1..9
                         organism = synthetic construct
                         mol_type = protein
                         note = Seed: GADGVGKSA (KRAS G12D)
SEQUENCE: 1270
GPDGVGKSR                                                                9

SEQ ID NO: 1271          moltype = AA   length = 9
FEATURE                  Location/Qualifiers
source                   1..9
                         organism = synthetic construct
                         mol_type = protein
                         note = Seed: LVVVGAVGV (KRAS G12V)
SEQUENCE: 1271
LAVVGAVGL                                                                9

SEQ ID NO: 1272          moltype = AA   length = 9
FEATURE                  Location/Qualifiers
source                   1..9
                         organism = synthetic construct
                         mol_type = protein
                         note = Seed: GAGDVGKSA (KRAS G13D)
SEQUENCE: 1272
GCGDVGKSK                                                                9

SEQ ID NO: 1273          moltype = AA   length = 9
FEATURE                  Location/Qualifiers
source                   1..9
                         organism = synthetic construct
                         mol_type = protein
                         note = Seed: GAGDVGKSA (KRAS G13D)
SEQUENCE: 1273
GLGDVGKSH                                                                9

SEQ ID NO: 1274          moltype = AA   length = 9
FEATURE                  Location/Qualifiers
source                   1..9
                         organism = synthetic construct
                         mol_type = protein
                         note = Seed: LVVVGARGV (KRAS G12R)
SEQUENCE: 1274
LMVVGARGM                                                                9

SEQ ID NO: 1275          moltype = AA   length = 9
FEATURE                  Location/Qualifiers
source                   1..9
                         organism = synthetic construct
                         mol_type = protein
                         note = Seed: LVVVGARGV (KRAS G12R)
SEQUENCE: 1275
LLVVGARGM                                                                9

SEQ ID NO: 1276          moltype = AA   length = 9
FEATURE                  Location/Qualifiers
source                   1..9
                         organism = synthetic construct
                         mol_type = protein
                         note = Seed: AGDVGKSAL (KRAS G13D)
SEQUENCE: 1276
```

```
AMDVGKSAK                                                                        9

SEQ ID NO: 1277         moltype = AA  length = 9
FEATURE                 Location/Qualifiers
source                  1..9
                        organism = synthetic construct
                        mol_type = protein
                        note = Seed: LVVVGACGV (KRAS G12C)
SEQUENCE: 1277
LLVVGACGT                                                                        9

SEQ ID NO: 1278         moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 1278
GARGVGKSK                                                                        9

SEQ ID NO: 1279         moltype = AA  length = 9
FEATURE                 Location/Qualifiers
source                  1..9
                        organism = synthetic construct
                        mol_type = protein
                        note = Seed: VVGAGDVGK (KRAS G13D)
SEQUENCE: 1279
VTGAGDVGL                                                                        9

SEQ ID NO: 1280         moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 1280
GMDGVGKSW                                                                        9

SEQ ID NO: 1281         moltype = AA  length = 9
FEATURE                 Location/Qualifiers
source                  1..9
                        organism = synthetic construct
                        mol_type = protein
                        note = Seed: VVGARGVGK (KRAS G12R)
SEQUENCE: 1281
VDGARGVGR                                                                        9

SEQ ID NO: 1282         moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 1282
GFVGVGKSR                                                                        9

SEQ ID NO: 1283         moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 1283
GRDGVGKSY                                                                        9

SEQ ID NO: 1284         moltype = AA  length = 9
FEATURE                 Location/Qualifiers
source                  1..9
                        organism = synthetic construct
                        mol_type = protein
                        note = Seed: DVGKSALTI (KRAS G13D)
SEQUENCE: 1284
DIGKSALTL                                                                        9

SEQ ID NO: 1285         moltype = AA  length = 9
FEATURE                 Location/Qualifiers
source                  1..9
                        organism = synthetic construct
                        mol_type = protein
```

```
                           note = Seed: GAVGVGKSA (KRAS G12V)
SEQUENCE: 1285
GFVGVGKSF                                                              9

SEQ ID NO: 1286        moltype = AA   length = 9
FEATURE                Location/Qualifiers
source                 1..9
                       organism = synthetic construct
                       mol_type = protein
                       note = Seed: GADGVGKSA (KRAS G12D)
SEQUENCE: 1286
GADGVGKSS                                                              9

SEQ ID NO: 1287        moltype = AA   length = 9
FEATURE                Location/Qualifiers
source                 1..9
                       organism = synthetic construct
                       mol_type = protein
                       note = Seed: GAGDVGKSA (KRAS G13D)
SEQUENCE: 1287
GCGDVGKSM                                                              9

SEQ ID NO: 1288        moltype = AA   length = 9
FEATURE                Location/Qualifiers
source                 1..9
                       organism = synthetic construct
                       mol_type = protein
                       note = Seed: VVGADGVGK (KRAS G12D)
SEQUENCE: 1288
VSGADGVGH                                                              9

SEQ ID NO: 1289        moltype = AA   length = 9
FEATURE                Location/Qualifiers
source                 1..9
                       organism = synthetic construct
                       mol_type = protein
                       note = Seed: GAGDVGKSA (KRAS G13D)
SEQUENCE: 1289
GYGDVGKSY                                                              9

SEQ ID NO: 1290        moltype = AA   length = 9
FEATURE                Location/Qualifiers
source                 1..9
                       organism = synthetic construct
                       mol_type = protein
                       note = Seed: GAVGVGKSA (KRAS G12V)
SEQUENCE: 1290
GYVGVGKSK                                                              9

SEQ ID NO: 1291        moltype = AA   length = 9
FEATURE                Location/Qualifiers
source                 1..9
                       organism = synthetic construct
                       mol_type = protein
                       note = Seed: GACGVGKSA (KRAS G12C)
SEQUENCE: 1291
GFCGVGKSK                                                              9

SEQ ID NO: 1292        moltype = AA   length = 9
FEATURE                Location/Qualifiers
source                 1..9
                       organism = synthetic construct
                       mol_type = protein
                       note = Seed: GACGVGKSA (KRAS G12C)
SEQUENCE: 1292
GACGVGKSC                                                              9

SEQ ID NO: 1293        moltype = AA   length = 9
FEATURE                Location/Qualifiers
source                 1..9
                       organism = synthetic construct
                       mol_type = protein
                       note = Seed: VVGACGVGK (KRAS G12C)
SEQUENCE: 1293
VGGACGVGF                                                              9

SEQ ID NO: 1294        moltype = AA   length = 9
FEATURE                Location/Qualifiers
source                 1..9
```

```
                            organism = synthetic construct
                            mol_type = protein
                            note = Seed: GAGDVGKSA (KRAS G13D)
SEQUENCE: 1294
GFGDVGKSF                                                                    9

SEQ ID NO: 1295             moltype = AA   length = 9
FEATURE                     Location/Qualifiers
source                      1..9
                            organism = synthetic construct
                            mol_type = protein
                            note = Seed: GADGVGKSA (KRAS G12D)
SEQUENCE: 1295
GGDGVGKSA                                                                    9

SEQ ID NO: 1296             moltype = AA   length = 9
FEATURE                     Location/Qualifiers
source                      1..9
                            organism = synthetic construct
                            mol_type = protein
                            note = Seed: GADGVGKSA (KRAS G12D)
SEQUENCE: 1296
GWDGVGKSR                                                                    9

SEQ ID NO: 1297             moltype = AA   length = 9
FEATURE                     Location/Qualifiers
source                      1..9
                            organism = synthetic construct
                            mol_type = protein
                            note = Seed: GACGVGKSA (KRAS G12C)
SEQUENCE: 1297
GMCGVGKSK                                                                    9

SEQ ID NO: 1298             moltype = AA   length = 9
FEATURE                     Location/Qualifiers
source                      1..9
                            organism = synthetic construct
                            mol_type = protein
                            note = Seed: GAGDVGKSA (KRAS G13D)
SEQUENCE: 1298
GYGDVGKSK                                                                    9

SEQ ID NO: 1299             moltype = AA   length = 9
FEATURE                     Location/Qualifiers
source                      1..9
                            organism = synthetic construct
                            mol_type = protein
                            note = Seed: GACGVGKSA (KRAS G12C)
SEQUENCE: 1299
GECGVGKSK                                                                    9

SEQ ID NO: 1300             moltype = AA   length = 9
FEATURE                     Location/Qualifiers
source                      1..9
                            organism = synthetic construct
                            mol_type = protein
                            note = Seed: VVGAVGVGK (KRAS G12V)
SEQUENCE: 1300
VGGAVGVGL                                                                    9

SEQ ID NO: 1301             moltype = AA   length = 9
FEATURE                     Location/Qualifiers
source                      1..9
                            organism = synthetic construct
                            mol_type = protein
                            note = Seed: AGDVGKSAL (KRAS G13D)
SEQUENCE: 1301
AFDVGKSAK                                                                    9

SEQ ID NO: 1302             moltype = AA   length = 9
FEATURE                     Location/Qualifiers
source                      1..9
                            organism = synthetic construct
                            mol_type = protein
                            note = Seed: VVGADGVGK (KRAS G12D)
SEQUENCE: 1302
VVGADGVGL                                                                    9

SEQ ID NO: 1303             moltype = AA   length = 9
```

```
FEATURE                 Location/Qualifiers
source                  1..9
                        organism = synthetic construct
                        mol_type = protein
                        note = Seed: GARGVGKSA (KRAS G12R)
SEQUENCE: 1303
GERGVGKSM                                                                    9

SEQ ID NO: 1304         moltype = AA  length = 9
FEATURE                 Location/Qualifiers
source                  1..9
                        organism = synthetic construct
                        mol_type = protein
                        note = Seed: VVGAGDVGK (KRAS G13D)
SEQUENCE: 1304
VYGAGDVGR                                                                    9

SEQ ID NO: 1305         moltype = AA  length = 9
FEATURE                 Location/Qualifiers
source                  1..9
                        organism = synthetic construct
                        mol_type = protein
                        note = Seed: LVVVGACGV (KRAS G12C)
SEQUENCE: 1305
LAVVGACGL                                                                    9

SEQ ID NO: 1306         moltype = AA  length = 9
FEATURE                 Location/Qualifiers
source                  1..9
                        organism = synthetic construct
                        mol_type = protein
                        note = Seed: DVGKSALTI (KRAS G13D)
SEQUENCE: 1306
DMGKSALTL                                                                    9

SEQ ID NO: 1307         moltype = AA  length = 9
FEATURE                 Location/Qualifiers
source                  1..9
                        organism = synthetic construct
                        mol_type = protein
                        note = Seed: VVGADGVGK (KRAS G12D)
SEQUENCE: 1307
VYGADGVGR                                                                    9

SEQ ID NO: 1308         moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 1308
GARGVGKSP                                                                    9

SEQ ID NO: 1309         moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 1309
GHDGVGKSY                                                                    9

SEQ ID NO: 1310         moltype = AA  length = 9
FEATURE                 Location/Qualifiers
source                  1..9
                        organism = synthetic construct
                        mol_type = protein
                        note = Seed: VVGADGVGK (KRAS G12D)
SEQUENCE: 1310
VCGADGVGK                                                                    9

SEQ ID NO: 1311         moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 1311
GEDGVGKSV                                                                    9
```

```
SEQ ID NO: 1312          moltype = AA  length = 9
FEATURE                  Location/Qualifiers
source                   1..9
                         organism = synthetic construct
                         mol_type = protein
                         note = Seed: GAGDVGKSA (KRAS G13D)
SEQUENCE: 1312
GEGDVGKSR                                                                  9

SEQ ID NO: 1313          moltype = AA  length = 9
FEATURE                  Location/Qualifiers
source                   1..9
                         organism = synthetic construct
                         mol_type = protein
                         note = Seed: VVGAVGVGK (KRAS G12V)
SEQUENCE: 1313
VPGAVGVGY                                                                  9

SEQ ID NO: 1314          moltype = AA  length = 9
FEATURE                  Location/Qualifiers
source                   1..9
                         organism = synthetic construct
                         mol_type = protein
                         note = Seed: VVGADGVGK (KRAS G12D)
SEQUENCE: 1314
VCGADGVGR                                                                  9

SEQ ID NO: 1315          moltype = AA  length = 9
FEATURE                  Location/Qualifiers
source                   1..9
                         organism = synthetic construct
                         mol_type = protein
                         note = Seed: GAGDVGKSA (KRAS G13D)
SEQUENCE: 1315
GQGDVGKSH                                                                  9

SEQ ID NO: 1316          moltype = AA  length = 9
FEATURE                  Location/Qualifiers
source                   1..9
                         organism = synthetic construct
                         mol_type = protein
                         note = Seed: VVGAGDVGK (KRAS G13D)
SEQUENCE: 1316
VCGAGDVGK                                                                  9

SEQ ID NO: 1317          moltype = AA  length = 9
FEATURE                  Location/Qualifiers
source                   1..9
                         organism = synthetic construct
                         mol_type = protein
                         note = Seed: GARGVGKSA (KRAS G12R)
SEQUENCE: 1317
GLRGVGKSH                                                                  9

SEQ ID NO: 1318          moltype = AA  length = 9
FEATURE                  Location/Qualifiers
source                   1..9
                         organism = synthetic construct
                         mol_type = protein
                         note = Seed: GARGVGKSA (KRAS G12R)
SEQUENCE: 1318
GMRGVGKSH                                                                  9

SEQ ID NO: 1319          moltype = AA  length = 9
FEATURE                  Location/Qualifiers
source                   1..9
                         organism = synthetic construct
                         mol_type = protein
                         note = Seed: GADGVGKSA (KRAS G12D)
SEQUENCE: 1319
GMDGVGKSA                                                                  9

SEQ ID NO: 1320          moltype = AA  length = 9
FEATURE                  Location/Qualifiers
source                   1..9
                         organism = synthetic construct
                         mol_type = protein
                         note = Seed: VVGADGVGK (KRAS G12D)
```

```
SEQUENCE: 1320
VAGADGVGI                                                                                    9

SEQ ID NO: 1321         moltype = AA  length = 9
FEATURE                 Location/Qualifiers
source                  1..9
                        organism = synthetic construct
                        mol_type = protein
                        note = Seed: DVGKSALTI (KRAS G13D)
SEQUENCE: 1321
DEGKSALTI                                                                                    9

SEQ ID NO: 1322         moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 1322
AVDVGKSAT                                                                                    9

SEQ ID NO: 1323         moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 1323
AADVGKSAS                                                                                    9

SEQ ID NO: 1324         moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 1324
GARGVGKSQ                                                                                    9

SEQ ID NO: 1325         moltype = AA  length = 9
FEATURE                 Location/Qualifiers
source                  1..9
                        organism = synthetic construct
                        mol_type = protein
                        note = Seed: LVVVGACGV (KRAS G12C)
SEQUENCE: 1325
LAVVGACGI                                                                                    9

SEQ ID NO: 1326         moltype = AA  length = 9
FEATURE                 Location/Qualifiers
source                  1..9
                        organism = synthetic construct
                        mol_type = protein
                        note = Seed: VVGACGVGK (KRAS G12C)
SEQUENCE: 1326
VIGACGVGM                                                                                    9

SEQ ID NO: 1327         moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 1327
GWDGVGKSY                                                                                    9

SEQ ID NO: 1328         moltype = AA  length = 9
FEATURE                 Location/Qualifiers
source                  1..9
                        organism = synthetic construct
                        mol_type = protein
                        note = Seed: VVGADGVGK (KRAS G12D)
SEQUENCE: 1328
VHGADGVGK                                                                                    9

SEQ ID NO: 1329         moltype = AA  length = 9
FEATURE                 Location/Qualifiers
source                  1..9
                        organism = synthetic construct
```

```
                            mol_type = protein
                            note = Seed: GARGVGKSA (KRAS G12R)
SEQUENCE: 1329
GQRGVGKSH                                                          9

SEQ ID NO: 1330         moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 1330
GAVGVGKSP                                                          9

SEQ ID NO: 1331         moltype = AA  length = 9
FEATURE                 Location/Qualifiers
source                  1..9
                        organism = synthetic construct
                        mol_type = protein
                        note = Seed: VVGADGVGK (KRAS G12D)
SEQUENCE: 1331
VAGADGVGV                                                          9

SEQ ID NO: 1332         moltype = AA  length = 9
FEATURE                 Location/Qualifiers
source                  1..9
                        organism = synthetic construct
                        mol_type = protein
                        note = Seed: VVGAGDVGK (KRAS G13D)
SEQUENCE: 1332
VQGAGDVGY                                                          9

SEQ ID NO: 1333         moltype = AA  length = 9
FEATURE                 Location/Qualifiers
source                  1..9
                        organism = synthetic construct
                        mol_type = protein
                        note = Seed: VVGAVGVGK (KRAS G12V)
SEQUENCE: 1333
VEGAVGVGY                                                          9

SEQ ID NO: 1334         moltype = AA  length = 9
FEATURE                 Location/Qualifiers
source                  1..9
                        organism = synthetic construct
                        mol_type = protein
                        note = Seed: VVGACGVGK (KRAS G12C)
SEQUENCE: 1334
VDGACGVGY                                                          9

SEQ ID NO: 1335         moltype = AA  length = 9
FEATURE                 Location/Qualifiers
source                  1..9
                        organism = synthetic construct
                        mol_type = protein
                        note = Seed: VVGAVGVGK (KRAS G12V)
SEQUENCE: 1335
VFGAVGVGM                                                          9

SEQ ID NO: 1336         moltype = AA  length = 9
FEATURE                 Location/Qualifiers
source                  1..9
                        organism = synthetic construct
                        mol_type = protein
                        note = Seed: LVVVGAVGV (KRAS G12V)
SEQUENCE: 1336
LAVVGAVGI                                                          9

SEQ ID NO: 1337         moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 1337
GFDGVGKSA                                                          9

SEQ ID NO: 1338         moltype = AA  length = 9
FEATURE                 Location/Qualifiers
```

```
                       -continued
source              1..9
                    organism = synthetic construct
                    mol_type = protein
                    note = Seed: GAGDVGKSA (KRAS G13D)
SEQUENCE: 1338
GTGDVGKSW                                                                      9

SEQ ID NO: 1339     moltype = AA  length = 9
FEATURE             Location/Qualifiers
source              1..9
                    organism = synthetic construct
                    mol_type = protein
                    note = Seed: VVGADGVGK (KRAS G12D)
SEQUENCE: 1339
VWGADGVGK                                                                      9

SEQ ID NO: 1340     moltype = AA  length = 9
FEATURE             Location/Qualifiers
source              1..9
                    organism = synthetic construct
                    mol_type = protein
                    note = Seed: GADGVGKSA (KRAS G12D)
SEQUENCE: 1340
GGDGVGKSW                                                                      9

SEQ ID NO: 1341     moltype = AA  length = 9
FEATURE             Location/Qualifiers
source              1..9
                    organism = synthetic construct
                    mol_type = protein
                    note = Seed: VVGARGVGK (KRAS G12R)
SEQUENCE: 1341
VEGARGVGK                                                                      9

SEQ ID NO: 1342     moltype = AA  length = 9
FEATURE             Location/Qualifiers
source              1..9
                    organism = synthetic construct
                    mol_type = protein
                    note = Seed: VVGAVGVGK (KRAS G12V)
SEQUENCE: 1342
VTGAVGVGV                                                                      9

SEQ ID NO: 1343     moltype = AA  length = 9
FEATURE             Location/Qualifiers
source              1..9
                    organism = synthetic construct
                    mol_type = protein
                    note = Seed: GAGDVGKSA (KRAS G13D)
SEQUENCE: 1343
GEGDVGKSM                                                                      9

SEQ ID NO: 1344     moltype = AA  length = 9
FEATURE             Location/Qualifiers
source              1..9
                    organism = synthetic construct
                    mol_type = protein
                    note = Seed: DVGKSALTI (KRAS G13D)
SEQUENCE: 1344
DLGKSALTF                                                                      9

SEQ ID NO: 1345     moltype = AA  length = 9
FEATURE             Location/Qualifiers
source              1..9
                    organism = synthetic construct
                    mol_type = protein
                    note = Seed: GADGVGKSA (KRAS G12D)
SEQUENCE: 1345
GPDGVGKSG                                                                      9

SEQ ID NO: 1346     moltype = AA  length = 9
FEATURE             Location/Qualifiers
source              1..9
                    organism = synthetic construct
                    mol_type = protein
                    note = Seed: GAVGVGKSA (KRAS G12V)
SEQUENCE: 1346
GWVGVGKSK                                                                      9
```

```
SEQ ID NO: 1347            moltype = AA  length = 9
FEATURE                    Location/Qualifiers
source                     1..9
                           organism = synthetic construct
                           mol_type = protein
                           note = Seed: GAGDVGKSA (KRAS G13D)

SEQUENCE: 1347
GWGDVGKSK                                                                  9

SEQ ID NO: 1348            moltype = AA  length = 9
FEATURE                    Location/Qualifiers
source                     1..9
                           organism = synthetic construct
                           mol_type = protein
                           note = Seed: VVGAGDVGK (KRAS G13D)

SEQUENCE: 1348
VHGAGDVGK                                                                  9

SEQ ID NO: 1349            moltype = AA  length = 9
FEATURE                    Location/Qualifiers
source                     1..9
                           organism = synthetic construct
                           mol_type = protein
                           note = Seed: VVGAGDVGK (KRAS G13D)

SEQUENCE: 1349
VWGAGDVGK                                                                  9

SEQ ID NO: 1350            moltype = AA  length = 9
FEATURE                    Location/Qualifiers
source                     1..9
                           organism = synthetic construct
                           mol_type = protein
                           note = Seed: VVGAVGVGK (KRAS G12V)

SEQUENCE: 1350
VTGAVGVGI                                                                  9

SEQ ID NO: 1351            moltype = AA  length = 9
FEATURE                    Location/Qualifiers
source                     1..9
                           organism = synthetic construct
                           mol_type = protein
                           note = Seed: VVGARGVGK (KRAS G12R)

SEQUENCE: 1351
VFGARGVGK                                                                  9

SEQ ID NO: 1352            moltype = AA  length = 9
FEATURE                    Location/Qualifiers
source                     1..9
                           organism = synthetic construct
                           mol_type = protein
                           note = Seed: DVGKSALTI (KRAS G13D)

SEQUENCE: 1352
DMGKSALTF                                                                  9

SEQ ID NO: 1353            moltype = AA  length = 9
FEATURE                    Location/Qualifiers
source                     1..9
                           organism = synthetic construct
                           mol_type = protein
                           note = Seed: GACGVGKSA (KRAS G12C)

SEQUENCE: 1353
GMCGVGKSH                                                                  9

SEQ ID NO: 1354            moltype = AA  length = 9
FEATURE                    Location/Qualifiers
source                     1..9
                           organism = synthetic construct
                           mol_type = protein
                           note = Seed: VVGADGVGK (KRAS G12D)

SEQUENCE: 1354
VVGADGVGH                                                                  9

SEQ ID NO: 1355            moltype = AA  length = 9
FEATURE                    Location/Qualifiers
source                     1..9
                           organism = synthetic construct
                           mol_type = protein
                           note = Seed: GAVGVGKSA (KRAS G12V)

SEQUENCE: 1355
```

-continued

```
GYVGVGKSY                                                                          9

SEQ ID NO: 1356         moltype = AA  length = 9
FEATURE                 Location/Qualifiers
source                  1..9
                        organism = synthetic construct
                        mol_type = protein
                        note = Seed: LVVVGARGV (KRAS G12R)
SEQUENCE: 1356
LIVVGARGL                                                                          9

SEQ ID NO: 1357         moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 1357
GYRGVGKSY                                                                          9

SEQ ID NO: 1358         moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 1358
GDVGVGKSF                                                                          9

SEQ ID NO: 1359         moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 1359
GVCGVGKSW                                                                          9

SEQ ID NO: 1360         moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 1360
AEDVGKSAR                                                                          9

SEQ ID NO: 1361         moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 1361
GIDGVGKSH                                                                          9

SEQ ID NO: 1362         moltype = AA  length = 9
FEATURE                 Location/Qualifiers
source                  1..9
                        organism = synthetic construct
                        mol_type = protein
                        note = Seed: VVGACGVGK (KRAS G12C)
SEQUENCE: 1362
VSGACGVGH                                                                          9

SEQ ID NO: 1363         moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 1363
GEVGVGKSM                                                                          9

SEQ ID NO: 1364         moltype = AA  length = 9
FEATURE                 Location/Qualifiers
source                  1..9
                        organism = synthetic construct
                        mol_type = protein
```

```
                        -continued note = Seed: VVGAGDVGK (KRAS G13D)
SEQUENCE: 1364
VCGAGDVGR                                                                   9

SEQ ID NO: 1365         moltype = AA   length = 9
FEATURE                 Location/Qualifiers
source                  1..9
                        organism = synthetic construct
                        mol_type = protein
                        note = Seed: GACGVGKSA (KRAS G12C)
SEQUENCE: 1365
GQCGVGKSH                                                                   9

SEQ ID NO: 1366         moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 1366
AFDVGKSAR                                                                   9

SEQ ID NO: 1367         moltype = AA   length = 9
FEATURE                 Location/Qualifiers
source                  1..9
                        organism = synthetic construct
                        mol_type = protein
                        note = Seed: VVGARGVGK (KRAS G12R)
SEQUENCE: 1367
VDGARGVGY                                                                   9

SEQ ID NO: 1368         moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 1368
GMRGVGKSA                                                                   9

SEQ ID NO: 1369         moltype = AA   length = 9
FEATURE                 Location/Qualifiers
source                  1..9
                        organism = synthetic construct
                        mol_type = protein
                        note = Seed: AGDVGKSAL (KRAS G13D)
SEQUENCE: 1369
ADDVGKSAC                                                                   9

SEQ ID NO: 1370         moltype = AA   length = 9
FEATURE                 Location/Qualifiers
source                  1..9
                        organism = synthetic construct
                        mol_type = protein
                        note = Seed: VVGAVGVGK (KRAS G12V)
SEQUENCE: 1370
VQGAVGVGM                                                                   9

SEQ ID NO: 1371         moltype = AA   length = 9
FEATURE                 Location/Qualifiers
source                  1..9
                        organism = synthetic construct
                        mol_type = protein
                        note = Seed: LVVVGAVGV (KRAS G12V)
SEQUENCE: 1371
LIVVGAVGM                                                                   9

SEQ ID NO: 1372         moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 1372
GPGDVGKSR                                                                   9

SEQ ID NO: 1373         moltype = AA   length = 9
FEATURE                 Location/Qualifiers
source                  1..9
```

```
                          organism = synthetic construct
                          mol_type = protein
                          note = Seed: VVGACGVGK (KRAS G12C)
SEQUENCE: 1373
VTGACGVGH                                                                      9

SEQ ID NO: 1374           moltype = AA  length = 9
FEATURE                   Location/Qualifiers
source                    1..9
                          organism = synthetic construct
                          mol_type = protein
                          note = Seed: VVGARGVGK (KRAS G12R)
SEQUENCE: 1374
VMGARGVGF                                                                      9

SEQ ID NO: 1375           moltype = AA  length = 9
FEATURE                   Location/Qualifiers
source                    1..9
                          organism = synthetic construct
                          mol_type = protein
                          note = Seed: DVGKSALTI (KRAS G13D)
SEQUENCE: 1375
DIGKSALTM                                                                      9

SEQ ID NO: 1376           moltype = AA  length = 9
FEATURE                   Location/Qualifiers
source                    1..9
                          organism = synthetic construct
                          mol_type = protein
                          note = Seed: VVGARGVGK (KRAS G12R)
SEQUENCE: 1376
VNGARGVGK                                                                      9

SEQ ID NO: 1377           moltype = AA  length = 9
FEATURE                   Location/Qualifiers
source                    1..9
                          organism = synthetic construct
                          mol_type = protein
                          note = Seed: GADGVGKSA (KRAS G12D)
SEQUENCE: 1377
GWDGVGKSC                                                                      9

SEQ ID NO: 1378           moltype = AA  length = 9
FEATURE                   Location/Qualifiers
source                    1..9
                          organism = synthetic construct
                          mol_type = protein
                          note = Seed: GADGVGKSA (KRAS G12D)
SEQUENCE: 1378
GQDGVGKSW                                                                      9

SEQ ID NO: 1379           moltype = AA  length = 9
FEATURE                   Location/Qualifiers
source                    1..9
                          organism = synthetic construct
                          mol_type = protein
                          note = Seed: VVGACGVGK (KRAS G12C)
SEQUENCE: 1379
VMGACGVGF                                                                      9

SEQ ID NO: 1380           moltype = AA  length = 9
FEATURE                   Location/Qualifiers
source                    1..9
                          organism = synthetic construct
                          mol_type = protein
                          note = Seed: GARGVGKSA (KRAS G12R)
SEQUENCE: 1380
GLRGVGKSA                                                                      9

SEQ ID NO: 1381           moltype = AA  length = 9
FEATURE                   Location/Qualifiers
source                    1..9
                          organism = synthetic construct
                          mol_type = protein
                          note = Seed: GAGDVGKSA (KRAS G13D)
SEQUENCE: 1381
GAGDVGKSQ                                                                      9

SEQ ID NO: 1382           moltype = AA  length = 9
```

| | | |
|---|---|---|
| FEATURE | Location/Qualifiers | |
| source | 1..9 | |
| | organism = synthetic construct | |
| | mol_type = protein | |
| | note = Seed: VVGAVGVGK (KRAS G12V) | |
| SEQUENCE: 1382 | | |
| VHGAVGVGR | | 9 |
| | | |
| SEQ ID NO: 1383 | moltype = AA  length = 9 | |
| FEATURE | Location/Qualifiers | |
| source | 1..9 | |
| | organism = synthetic construct | |
| | mol_type = protein | |
| | note = Seed: AGDVGKSAL (KRAS G13D) | |
| SEQUENCE: 1383 | | |
| AYDVGKSAK | | 9 |
| | | |
| SEQ ID NO: 1384 | moltype = AA  length = 9 | |
| FEATURE | Location/Qualifiers | |
| source | 1..9 | |
| | organism = synthetic construct | |
| | mol_type = protein | |
| | note = Seed: GARGVGKSA (KRAS G12R) | |
| SEQUENCE: 1384 | | |
| GPRGVGKSN | | 9 |
| | | |
| SEQ ID NO: 1385 | moltype = AA  length = 9 | |
| FEATURE | Location/Qualifiers | |
| source | 1..9 | |
| | organism = synthetic construct | |
| | mol_type = protein | |
| | note = Seed: GAVGVGKSA (KRAS G12V) | |
| SEQUENCE: 1385 | | |
| GIVGVGKSW | | 9 |
| | | |
| SEQ ID NO: 1386 | moltype = AA  length = 9 | |
| FEATURE | Location/Qualifiers | |
| source | 1..9 | |
| | organism = synthetic construct | |
| | mol_type = protein | |
| | note = Seed: GARGVGKSA (KRAS G12R) | |
| SEQUENCE: 1386 | | |
| GFRGVGKSF | | 9 |
| | | |
| SEQ ID NO: 1387 | moltype = AA  length = 9 | |
| FEATURE | Location/Qualifiers | |
| source | 1..9 | |
| | organism = synthetic construct | |
| | mol_type = protein | |
| | note = Seed: GADGVGKSA (KRAS G12D) | |
| SEQUENCE: 1387 | | |
| GCDGVGKSA | | 9 |
| | | |
| SEQ ID NO: 1388 | moltype = AA  length = 9 | |
| FEATURE | Location/Qualifiers | |
| source | 1..9 | |
| | organism = synthetic construct | |
| | mol_type = protein | |
| | note = Seed: AGDVGKSAL (KRAS G13D) | |
| SEQUENCE: 1388 | | |
| ADDVGKSAA | | 9 |
| | | |
| SEQ ID NO: 1389 | moltype = AA  length = 9 | |
| FEATURE | Location/Qualifiers | |
| source | 1..9 | |
| | organism = synthetic construct | |
| | mol_type = protein | |
| | note = Seed: GAVGVGKSA (KRAS G12V) | |
| SEQUENCE: 1389 | | |
| GQVGVGKSW | | 9 |
| | | |
| SEQ ID NO: 1390 | moltype = AA  length = 9 | |
| FEATURE | Location/Qualifiers | |
| source | 1..9 | |
| | organism = synthetic construct | |
| | mol_type = protein | |
| | note = Seed: GAVGVGKSA (KRAS G12V) | |
| SEQUENCE: 1390 | | |
| GGVGVGKSI | | 9 |

```
SEQ ID NO: 1391            moltype = AA   length = 9
FEATURE                    Location/Qualifiers
source                     1..9
                           organism = synthetic construct
                           mol_type = protein
                           note = Seed: GAGDVGKSA (KRAS G13D)
SEQUENCE: 1391
GIGDVGKSW                                                                  9

SEQ ID NO: 1392            moltype = AA   length = 9
FEATURE                    Location/Qualifiers
source                     1..9
                           organism = synthetic construct
                           mol_type = protein
                           note = Seed: LVVVGAGDV (KRAS G13D)
SEQUENCE: 1392
LMVVGAGDL                                                                  9

SEQ ID NO: 1393            moltype = AA   length = 9
FEATURE                    Location/Qualifiers
source                     1..9
                           organism = synthetic construct
                           mol_type = protein
                           note = Seed: VVGADGVGK (KRAS G12D)
SEQUENCE: 1393
VGGADGVGF                                                                  9

SEQ ID NO: 1394            moltype = AA   length = 9
FEATURE                    Location/Qualifiers
source                     1..9
                           organism = synthetic construct
                           mol_type = protein
                           note = Seed: GACGVGKSA (KRAS G12C)
SEQUENCE: 1394
GLCGVGKSH                                                                  9

SEQ ID NO: 1395            moltype = AA   length = 9
FEATURE                    Location/Qualifiers
source                     1..9
                           organism = synthetic construct
                           mol_type = protein
                           note = Seed: LVVVGARGV (KRAS G12R)
SEQUENCE: 1395
LQVVGARGL                                                                  9

SEQ ID NO: 1396            moltype = AA   length = 9
FEATURE                    Location/Qualifiers
source                     1..9
                           organism = synthetic construct
                           mol_type = protein
                           note = Seed: VVGAGDVGK (KRAS G13D)
SEQUENCE: 1396
VAGAGDVGI                                                                  9

SEQ ID NO: 1397            moltype = AA   length = 9
FEATURE                    Location/Qualifiers
source                     1..9
                           organism = synthetic construct
                           mol_type = protein
                           note = Seed: GACGVGKSA (KRAS G12C)
SEQUENCE: 1397
GTCGVGKSW                                                                  9

SEQ ID NO: 1398            moltype = AA   length = 9
FEATURE                    Location/Qualifiers
source                     1..9
                           organism = synthetic construct
                           mol_type = protein
                           note = Seed: LVVVGADGV (KRAS G12D)
SEQUENCE: 1398
LVVVGADGA                                                                  9

SEQ ID NO: 1399            moltype = AA   length = 9
FEATURE                    Location/Qualifiers
source                     1..9
                           organism = synthetic construct
                           mol_type = protein
                           note = Seed: GACGVGKSA (KRAS G12C)
```

```
SEQUENCE: 1399
GTCGVGKSA                                                                           9

SEQ ID NO: 1400         moltype = AA   length = 9
FEATURE                 Location/Qualifiers
source                  1..9
                        organism = synthetic construct
                        mol_type = protein
                        note = Seed: GADGVGKSA (KRAS G12D)
SEQUENCE: 1400
GHDGVGKSK                                                                           9

SEQ ID NO: 1401         moltype = AA   length = 9
FEATURE                 Location/Qualifiers
source                  1..9
                        organism = synthetic construct
                        mol_type = protein
                        note = Seed: GAVGVGKSA (KRAS G12V)
SEQUENCE: 1401
GNVGVGKSL                                                                           9

SEQ ID NO: 1402         moltype = AA   length = 9
FEATURE                 Location/Qualifiers
source                  1..9
                        organism = synthetic construct
                        mol_type = protein
                        note = Seed: VVGARGVGK (KRAS G12R)
SEQUENCE: 1402
VFGARGVGM                                                                           9

SEQ ID NO: 1403         moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 1403
GNRGVGKSL                                                                           9

SEQ ID NO: 1404         moltype = AA   length = 9
FEATURE                 Location/Qualifiers
source                  1..9
                        organism = synthetic construct
                        mol_type = protein
                        note = Seed: GACGVGKSA (KRAS G12C)
SEQUENCE: 1404
GPCGVGKSW                                                                           9

SEQ ID NO: 1405         moltype = AA   length = 9
FEATURE                 Location/Qualifiers
source                  1..9
                        organism = synthetic construct
                        mol_type = protein
                        note = Seed: GAGDVGKSA (KRAS G13D)
SEQUENCE: 1405
GTGDVGKSA                                                                           9

SEQ ID NO: 1406         moltype = AA   length = 9
FEATURE                 Location/Qualifiers
source                  1..9
                        organism = synthetic construct
                        mol_type = protein
                        note = Seed: LVVVGAVGV (KRAS G12V)
SEQUENCE: 1406
LSVVGAVGL                                                                           9

SEQ ID NO: 1407         moltype = AA   length = 9
FEATURE                 Location/Qualifiers
source                  1..9
                        organism = synthetic construct
                        mol_type = protein
                        note = Seed: DVGKSALTI (KRAS G13D)
SEQUENCE: 1407
DMGKSALTY                                                                           9

SEQ ID NO: 1408         moltype = AA   length = 9
FEATURE                 Location/Qualifiers
source                  1..9
                        organism = synthetic construct
```

```
                                mol_type = protein
                                note = Seed: GACGVGKSA (KRAS G12C)
SEQUENCE: 1408
GECGVGKSM                                                                       9

SEQ ID NO: 1409                 moltype = AA   length = 9
FEATURE                         Location/Qualifiers
source                          1..9
                                organism = synthetic construct
                                mol_type = protein
                                note = Seed: GADGVGKSA (KRAS G12D)
SEQUENCE: 1409
GADGVGKSP                                                                       9

SEQ ID NO: 1410                 moltype = AA   length = 9
FEATURE                         Location/Qualifiers
source                          1..9
                                organism = synthetic construct
                                mol_type = protein
                                note = Seed: VVGAVGVGK (KRAS G12V)
SEQUENCE: 1410
VGGAVGVGH                                                                       9

SEQ ID NO: 1411                 moltype = AA   length = 9
FEATURE                         Location/Qualifiers
source                          1..9
                                organism = synthetic construct
                                mol_type = protein
                                note = Seed: GARGVGKSA (KRAS G12R)
SEQUENCE: 1411
GARGVGKSS                                                                       9

SEQ ID NO: 1412                 moltype = AA   length = 9
FEATURE                         Location/Qualifiers
source                          1..9
                                organism = synthetic construct
                                mol_type = protein
                                note = Seed: GACGVGKSA (KRAS G12C)
SEQUENCE: 1412
GPCGVGKSK                                                                       9

SEQ ID NO: 1413                 moltype = AA   length = 9
FEATURE                         Location/Qualifiers
source                          1..9
                                organism = synthetic construct
                                mol_type = protein
                                note = Seed: GACGVGKSA (KRAS G12C)
SEQUENCE: 1413
GPCGVGKSR                                                                       9

SEQ ID NO: 1414                 moltype = AA   length = 9
FEATURE                         Location/Qualifiers
source                          1..9
                                organism = synthetic construct
                                mol_type = protein
                                note = Seed: VVGADGVGK (KRAS G12D)
SEQUENCE: 1414
VDGADGVGY                                                                       9

SEQ ID NO: 1415                 moltype = AA   length = 9
FEATURE                         Location/Qualifiers
source                          1..9
                                organism = synthetic construct
                                mol_type = protein
                                note = Seed: VVGARGVGK (KRAS G12R)
SEQUENCE: 1415
VMGARGVGM                                                                       9

SEQ ID NO: 1416                 moltype = AA   length = 9
FEATURE                         Location/Qualifiers
source                          1..9
                                organism = synthetic construct
                                mol_type = protein
                                note = Seed: GAVGVGKSA (KRAS G12V)
SEQUENCE: 1416
GPVGVGKSQ                                                                       9

SEQ ID NO: 1417                 moltype = AA   length = 9
FEATURE                         Location/Qualifiers
```

```
source                  1..9
                        organism = synthetic construct
                        mol_type = protein
                        note = Seed: VVGARGVGK (KRAS G12R)
SEQUENCE: 1417
VMGARGVGL                                                                    9

SEQ ID NO: 1418         moltype = AA   length = 9
FEATURE                 Location/Qualifiers
source                  1..9
                        organism = synthetic construct
                        mol_type = protein
                        note = Seed: VVGAVGVGK (KRAS G12V)
SEQUENCE: 1418
VFGAVGVGL                                                                    9

SEQ ID NO: 1419         moltype = AA   length = 9
FEATURE                 Location/Qualifiers
source                  1..9
                        organism = synthetic construct
                        mol_type = protein
                        note = Seed: VVGADGVGK (KRAS G12D)
SEQUENCE: 1419
VWGADGVGR                                                                    9

SEQ ID NO: 1420         moltype = AA   length = 9
FEATURE                 Location/Qualifiers
source                  1..9
                        organism = synthetic construct
                        mol_type = protein
                        note = Seed: DVGKSALTI (KRAS G13D)
SEQUENCE: 1420
DNGKSALTV                                                                    9

SEQ ID NO: 1421         moltype = AA   length = 9
FEATURE                 Location/Qualifiers
source                  1..9
                        organism = synthetic construct
                        mol_type = protein
                        note = Seed: VVGACGVGK (KRAS G12C)
SEQUENCE: 1421
VNGACGVGY                                                                    9

SEQ ID NO: 1422         moltype = AA   length = 9
FEATURE                 Location/Qualifiers
source                  1..9
                        organism = synthetic construct
                        mol_type = protein
                        note = Seed: VVGAGDVGK (KRAS G13D)
SEQUENCE: 1422
VVGAGDVGL                                                                    9

SEQ ID NO: 1423         moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 1423
GCRGVGKSL                                                                    9

SEQ ID NO: 1424         moltype = AA   length = 9
FEATURE                 Location/Qualifiers
source                  1..9
                        organism = synthetic construct
                        mol_type = protein
                        note = Seed: VVGARGVGK (KRAS G12R)
SEQUENCE: 1424
VLGARGVGF                                                                    9

SEQ ID NO: 1425         moltype = AA   length = 9
FEATURE                 Location/Qualifiers
source                  1..9
                        organism = synthetic construct
                        mol_type = protein
                        note = Seed: GARGVGKSA (KRAS G12R)
SEQUENCE: 1425
GIRGVGKSW                                                                    9
```

-continued

| | | |
|---|---|---|
| SEQ ID NO: 1426<br>FEATURE<br>source | moltype = AA   length = 9<br>Location/Qualifiers<br>1..9<br>organism = synthetic construct<br>mol_type = protein<br>note = Seed: VVGACGVGK (KRAS G12C) | |
| SEQUENCE: 1426<br>VCGACGVGK | | 9 |
| SEQ ID NO: 1427<br>FEATURE<br>source | moltype = AA   length = 9<br>Location/Qualifiers<br>1..9<br>organism = synthetic construct<br>mol_type = protein<br>note = Seed: VVGAVGVGK (KRAS G12V) | |
| SEQUENCE: 1427<br>VMGAVGVGL | | 9 |
| SEQ ID NO: 1428<br>FEATURE<br>source | moltype = AA   length = 9<br>Location/Qualifiers<br>1..9<br>organism = synthetic construct<br>mol_type = protein<br>note = Seed: GARGVGKSA (KRAS G12R) | |
| SEQUENCE: 1428<br>GGRGVGKSV | | 9 |
| SEQ ID NO: 1429<br>FEATURE<br>source | moltype = AA   length = 9<br>Location/Qualifiers<br>1..9<br>organism = synthetic construct<br>mol_type = protein<br>note = Seed: AGDVGKSAL (KRAS G13D) | |
| SEQUENCE: 1429<br>AADVGKSAP | | 9 |
| SEQ ID NO: 1430<br>FEATURE<br>source | moltype = AA   length = 9<br>Location/Qualifiers<br>1..9<br>organism = synthetic construct<br>mol_type = protein<br>note = Seed: VVGAGDVGK (KRAS G13D) | |
| SEQUENCE: 1430<br>VWGAGDVGR | | 9 |
| SEQ ID NO: 1431<br>FEATURE<br>source | moltype = AA   length = 9<br>Location/Qualifiers<br>1..9<br>organism = synthetic construct<br>mol_type = protein<br>note = Seed: VVGAVGVGK (KRAS G12V) | |
| SEQUENCE: 1431<br>VLGAVGVGL | | 9 |
| SEQ ID NO: 1432<br>FEATURE<br>source | moltype = AA   length = 9<br>Location/Qualifiers<br>1..9<br>organism = synthetic construct<br>mol_type = protein<br>note = Seed: VVGARGVGK (KRAS G12R) | |
| SEQUENCE: 1432<br>VTGARGVGH | | 9 |
| SEQ ID NO: 1433<br>FEATURE<br>source | moltype = AA   length = 9<br>Location/Qualifiers<br>1..9<br>organism = synthetic construct<br>mol_type = protein<br>note = Seed: VVGAVGVGK (KRAS G12V) | |
| SEQUENCE: 1433<br>VMGAVGVGM | | 9 |
| SEQ ID NO: 1434<br>FEATURE<br>source | moltype = AA   length = 9<br>Location/Qualifiers<br>1..9<br>organism = synthetic construct<br>mol_type = protein<br>note = Seed: GAVGVGKSA (KRAS G12V) | |
| SEQUENCE: 1434 | | |

```
GHVGVGKSK                                                                            9

SEQ ID NO: 1435         moltype = AA  length = 9
FEATURE                 Location/Qualifiers
source                  1..9
                        organism = synthetic construct
                        mol_type = protein
                        note = Seed: VVGAVGVGK (KRAS G12V)
SEQUENCE: 1435
VAGAVGVGQ                                                                            9

SEQ ID NO: 1436         moltype = AA  length = 9
FEATURE                 Location/Qualifiers
source                  1..9
                        organism = synthetic construct
                        mol_type = protein
                        note = Seed: GADGVGKSA (KRAS G12D)
SEQUENCE: 1436
GRDGVGKSW                                                                            9

SEQ ID NO: 1437         moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 1437
GIGDVGKSA                                                                            9

SEQ ID NO: 1438         moltype = AA  length = 9
FEATURE                 Location/Qualifiers
source                  1..9
                        organism = synthetic construct
                        mol_type = protein
                        note = Seed: DVGKSALTI (KRAS G13D)
SEQUENCE: 1438
DCGKSALTV                                                                            9

SEQ ID NO: 1439         moltype = AA  length = 9
FEATURE                 Location/Qualifiers
source                  1..9
                        organism = synthetic construct
                        mol_type = protein
                        note = Seed: VVGACGVGK (KRAS G12C)
SEQUENCE: 1439
VVGACGVGH                                                                            9

SEQ ID NO: 1440         moltype = AA  length = 9
FEATURE                 Location/Qualifiers
source                  1..9
                        organism = synthetic construct
                        mol_type = protein
                        note = Seed: DVGKSALTI (KRAS G13D)
SEQUENCE: 1440
DLGKSALTY                                                                            9

SEQ ID NO: 1441         moltype = AA  length = 9
FEATURE                 Location/Qualifiers
source                  1..9
                        organism = synthetic construct
                        mol_type = protein
                        note = Seed: GACGVGKSA (KRAS G12C)
SEQUENCE: 1441
GYCGVGKSK                                                                            9

SEQ ID NO: 1442         moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 1442
ACDVGKSAC                                                                            9

SEQ ID NO: 1443         moltype = AA  length = 9
FEATURE                 Location/Qualifiers
source                  1..9
                        organism = synthetic construct
                        mol_type = protein
```

```
                        note = Seed: GADGVGKSA (KRAS G12D)
SEQUENCE: 1443
GDDGVGKSY                                                                9

SEQ ID NO: 1444         moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 1444
GPVGVGKSE                                                                9

SEQ ID NO: 1445         moltype = AA  length = 9
FEATURE                 Location/Qualifiers
source                  1..9
                        organism = synthetic construct
                        mol_type = protein
                        note = Seed: VVGADGVGK (KRAS G12D)
SEQUENCE: 1445
VIGADGVGM                                                                9

SEQ ID NO: 1446         moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 1446
ACDVGKSAA                                                                9

SEQ ID NO: 1447         moltype = AA  length = 9
FEATURE                 Location/Qualifiers
source                  1..9
                        organism = synthetic construct
                        mol_type = protein
                        note = Seed: VVGADGVGK (KRAS G12D)
SEQUENCE: 1447
VNGADGVGY                                                                9

SEQ ID NO: 1448         moltype = AA  length = 9
FEATURE                 Location/Qualifiers
source                  1..9
                        organism = synthetic construct
                        mol_type = protein
                        note = Seed: GAVGVGKSA (KRAS G12V)
SEQUENCE: 1448
GFVGVGKSM                                                                9

SEQ ID NO: 1449         moltype = AA  length = 9
FEATURE                 Location/Qualifiers
source                  1..9
                        organism = synthetic construct
                        mol_type = protein
                        note = Seed: VVGARGVGK (KRAS G12R)
SEQUENCE: 1449
VNGARGVGR                                                                9

SEQ ID NO: 1450         moltype = AA  length = 9
FEATURE                 Location/Qualifiers
source                  1..9
                        organism = synthetic construct
                        mol_type = protein
                        note = Seed: VVGARGVGK (KRAS G12R)
SEQUENCE: 1450
VLGARGVGM                                                                9

SEQ ID NO: 1451         moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 1451
GQGDVGKSW                                                                9

SEQ ID NO: 1452         moltype = AA  length = 9
FEATURE                 Location/Qualifiers
source                  1..9
```

```
                            organism = synthetic construct
                            mol_type = protein
                            note = Seed: LVVVGADGV (KRAS G12D)
SEQUENCE: 1452
LIVVGADGA                                                              9

SEQ ID NO: 1453             moltype = AA  length = 9
FEATURE                     Location/Qualifiers
source                      1..9
                            organism = synthetic construct
                            mol_type = protein
                            note = Seed: GAVGVGKSA (KRAS G12V)
SEQUENCE: 1453
GIVGVGKSA                                                              9

SEQ ID NO: 1454             moltype = AA  length = 9
FEATURE                     Location/Qualifiers
source                      1..9
                            organism = synthetic construct
                            mol_type = protein
                            note = Seed: VVGACGVGK (KRAS G12C)
SEQUENCE: 1454
VHGACGVGK                                                              9

SEQ ID NO: 1455             moltype = AA  length = 9
FEATURE                     Location/Qualifiers
source                      1..9
                            organism = synthetic construct
                            mol_type = protein
                            note = Seed: LVVVGAGDV (KRAS G13D)
SEQUENCE: 1455
LIVVGAGDV                                                              9

SEQ ID NO: 1456             moltype = AA  length = 9
FEATURE                     Location/Qualifiers
source                      1..9
                            organism = synthetic construct
                            mol_type = protein
                            note = Seed: VVGAGDVGK (KRAS G13D)
SEQUENCE: 1456
VAGAGDVGV                                                              9

SEQ ID NO: 1457             moltype = AA  length = 9
FEATURE                     Location/Qualifiers
source                      1..9
                            organism = synthetic construct
                            mol_type = protein
                            note = Seed: GACGVGKSA (KRAS G12C)
SEQUENCE: 1457
GDCGVGKSF                                                              9

SEQ ID NO: 1458             moltype = AA  length = 9
FEATURE                     Location/Qualifiers
source                      1..9
                            organism = synthetic construct
                            mol_type = protein
                            note = Seed: GACGVGKSA (KRAS G12C)
SEQUENCE: 1458
GFCGVGKSR                                                              9

SEQ ID NO: 1459             moltype = AA  length = 9
FEATURE                     Location/Qualifiers
source                      1..9
                            organism = synthetic construct
                            mol_type = protein
                            note = Seed: GACGVGKSA (KRAS G12C)
SEQUENCE: 1459
GECGVGKSR                                                              9

SEQ ID NO: 1460             moltype = AA  length = 9
FEATURE                     Location/Qualifiers
source                      1..9
                            organism = synthetic construct
                            mol_type = protein
                            note = Seed: GARGVGKSA (KRAS G12R)
SEQUENCE: 1460
GTRGVGKSW                                                              9

SEQ ID NO: 1461             moltype = AA  length = 9
```

```
FEATURE              Location/Qualifiers
source               1..9
                     organism = synthetic construct
                     mol_type = protein
                     note = Seed: GAGDVGKSA (KRAS G13D)
SEQUENCE: 1461
GDGDVGKSF                                                                    9

SEQ ID NO: 1462      moltype = AA  length = 9
FEATURE              Location/Qualifiers
source               1..9
                     organism = synthetic construct
                     mol_type = protein
                     note = Seed: GAVGVGKSA (KRAS G12V)
SEQUENCE: 1462
GNVGVGKSH                                                                    9

SEQ ID NO: 1463      moltype = AA  length = 9
FEATURE              Location/Qualifiers
source               1..9
                     organism = synthetic construct
                     mol_type = protein
                     note = Seed: GACGVGKSA (KRAS G12C)
SEQUENCE: 1463
GICGVGKSA                                                                    9

SEQ ID NO: 1464      moltype = AA  length = 9
FEATURE              Location/Qualifiers
source               1..9
                     organism = synthetic construct
                     mol_type = protein
                     note = Seed: VVGACGVGK (KRAS G12C)
SEQUENCE: 1464
VWGACGVGK                                                                    9

SEQ ID NO: 1465      moltype = AA  length = 9
FEATURE              Location/Qualifiers
source               1..9
                     organism = synthetic construct
                     mol_type = protein
                     note = Seed: GACGVGKSA (KRAS G12C)
SEQUENCE: 1465
GCCGVGKSM                                                                    9

SEQ ID NO: 1466      moltype = AA  length = 9
FEATURE              Location/Qualifiers
source               1..9
                     organism = synthetic construct
                     mol_type = protein
                     note = Seed: LVVGAGDV (KRAS G13D)
SEQUENCE: 1466
LMVVGAGDI                                                                    9

SEQ ID NO: 1467      moltype = AA  length = 9
FEATURE              Location/Qualifiers
source               1..9
                     organism = synthetic construct
                     mol_type = protein
                     note = Seed: VVGACGVGK (KRAS G12C)
SEQUENCE: 1467
VAGACGVGW                                                                    9

SEQ ID NO: 1468      moltype = AA  length = 9
FEATURE              Location/Qualifiers
source               1..9
                     organism = synthetic construct
                     mol_type = protein
                     note = Seed: GAGDVGKSA (KRAS G13D)
SEQUENCE: 1468
GYGDVGKSR                                                                    9

SEQ ID NO: 1469      moltype = AA  length = 9
FEATURE              Location/Qualifiers
source               1..9
                     organism = synthetic construct
                     mol_type = protein
                     note = Seed: LVVGARGV (KRAS G12R)
SEQUENCE: 1469
LQVVGARGI                                                                    9
```

-continued

```
SEQ ID NO: 1470            moltype = AA   length = 9
FEATURE                    Location/Qualifiers
source                     1..9
                           organism = synthetic construct
                           mol_type = protein
                           note = Seed: LVVVGAVGV (KRAS G12V)
SEQUENCE: 1470
LLVVGAVGT                                                                    9

SEQ ID NO: 1471            moltype = AA   length = 9
FEATURE                    Location/Qualifiers
source                     1..9
                           organism = synthetic construct
                           mol_type = protein
                           note = Seed: VVGAGDVGK (KRAS G13D)
SEQUENCE: 1471
VSGAGDVGH                                                                    9

SEQ ID NO: 1472            moltype = AA   length = 9
FEATURE                    Location/Qualifiers
source                     1..9
                           organism = synthetic construct
                           mol_type = protein
                           note = Seed: AGDVGKSAL (KRAS G13D)
SEQUENCE: 1472
AIDVGKSAH                                                                    9

SEQ ID NO: 1473            moltype = AA   length = 9
FEATURE                    Location/Qualifiers
source                     1..9
                           organism = synthetic construct
                           mol_type = protein
                           note = Seed: VVGARGVGK (KRAS G12R)
SEQUENCE: 1473
VSGARGVGW                                                                    9

SEQ ID NO: 1474            moltype = AA   length = 9
FEATURE                    Location/Qualifiers
source                     1..9
                           organism = synthetic construct
                           mol_type = protein
                           note = Seed: GACGVGKSA (KRAS G12C)
SEQUENCE: 1474
GACGVGKSQ                                                                    9

SEQ ID NO: 1475            moltype = AA   length = 9
FEATURE                    Location/Qualifiers
source                     1..9
                           organism = synthetic construct
                           mol_type = protein
                           note = Seed: VVGACGVGK (KRAS G12C)
SEQUENCE: 1475
VQGACGVGF                                                                    9

SEQ ID NO: 1476            moltype = AA   length = 9
FEATURE                    Location/Qualifiers
source                     1..9
                           organism = synthetic construct
                           mol_type = protein
                           note = Seed: VVGACGVGK (KRAS G12C)
SEQUENCE: 1476
VCGACGVGY                                                                    9

SEQ ID NO: 1477            moltype = AA   length = 9
FEATURE                    Location/Qualifiers
source                     1..9
                           organism = synthetic construct
                           mol_type = protein
                           note = Seed: VVGADGVGK (KRAS G12D)
SEQUENCE: 1477
VCGADGVGY                                                                    9

SEQ ID NO: 1478            moltype = AA   length = 9
FEATURE                    Location/Qualifiers
source                     1..9
                           organism = synthetic construct
                           mol_type = protein
                           note = Seed: LVVVGAGDV (KRAS G13D)
```

```
SEQUENCE: 1478
LLVVGAGDL                                                                                    9

SEQ ID NO: 1479          moltype = AA   length = 9
FEATURE                  Location/Qualifiers
source                   1..9
                         organism = synthetic construct
                         mol_type = protein
                         note = Seed: AGDVGKSAL (KRAS G13D)
SEQUENCE: 1479
ACDVGKSAW                                                                                    9

SEQ ID NO: 1480          moltype = AA   length = 9
FEATURE                  Location/Qualifiers
source                   1..9
                         organism = synthetic construct
                         mol_type = protein
                         note = Seed: LVVVGADGV (KRAS G12D)
SEQUENCE: 1480
LAVVGADGL                                                                                    9

SEQ ID NO: 1481          moltype = AA   length = 9
FEATURE                  Location/Qualifiers
source                   1..9
                         organism = synthetic construct
                         mol_type = protein
                         note = Seed: VVGAVGVGK (KRAS G12V)
SEQUENCE: 1481
VCGAVGVGF                                                                                    9

SEQ ID NO: 1482          moltype = AA   length = 9
FEATURE                  Location/Qualifiers
source                   1..9
                         organism = synthetic construct
                         mol_type = protein
                         note = Seed: VVGADGVGK (KRAS G12D)
SEQUENCE: 1482
VHGADGVGR                                                                                    9

SEQ ID NO: 1483          moltype = AA   length = 9
FEATURE                  Location/Qualifiers
source                   1..9
                         organism = synthetic construct
                         mol_type = protein
                         note = Seed: GACGVGKSA (KRAS G12C)
SEQUENCE: 1483
GCCGVGKSK                                                                                    9

SEQ ID NO: 1484          moltype = AA   length = 9
FEATURE                  Location/Qualifiers
source                   1..9
                         organism = synthetic construct
                         mol_type = protein
                         note = Seed: AGDVGKSAL (KRAS G13D)
SEQUENCE: 1484
AWDVGKSAT                                                                                    9

SEQ ID NO: 1485          moltype = AA   length = 9
FEATURE                  Location/Qualifiers
source                   1..9
                         organism = synthetic construct
                         mol_type = protein
                         note = Seed: LVVVGACGV (KRAS G12C)
SEQUENCE: 1485
LSVVGACGI                                                                                    9

SEQ ID NO: 1486          moltype = AA   length = 9
FEATURE                  Location/Qualifiers
source                   1..9
                         organism = synthetic construct
                         mol_type = protein
                         note = Seed: GACGVGKSA (KRAS G12C)
SEQUENCE: 1486
GCCGVGKSR                                                                                    9

SEQ ID NO: 1487          moltype = AA   length = 9
FEATURE                  Location/Qualifiers
source                   1..9
                         organism = synthetic construct
```

```
                              mol_type = protein
                              note = Seed: LVVVGAVGV (KRAS G12V)
SEQUENCE: 1487
LSVVGAVGI                                                              9

SEQ ID NO: 1488               moltype = AA   length = 9
FEATURE                       Location/Qualifiers
source                        1..9
                              organism = synthetic construct
                              mol_type = protein
                              note = Seed: AGDVGKSAL (KRAS G13D)
SEQUENCE: 1488
AYDVGKSAR                                                              9

SEQ ID NO: 1489               moltype = AA   length = 9
FEATURE                       Location/Qualifiers
source                        1..9
                              organism = synthetic construct
                              mol_type = protein
                              note = Seed: VVGARGVGK (KRAS G12R)
SEQUENCE: 1489
VLGARGVGL                                                              9

SEQ ID NO: 1490               moltype = AA   length = 9
FEATURE                       Location/Qualifiers
source                        1..9
                              organism = synthetic construct
                              mol_type = protein
                              note = Seed: LVVVGAVGV (KRAS G12V)
SEQUENCE: 1490
LQVVGAVGM                                                              9

SEQ ID NO: 1491               moltype = AA   length = 9
FEATURE                       Location/Qualifiers
source                        1..9
                              organism = synthetic construct
                              mol_type = protein
                              note = Seed: LVVVGAVGV (KRAS G12V)
SEQUENCE: 1491
LTVVGAVGM                                                              9

SEQ ID NO: 1492               moltype = AA   length = 9
FEATURE                       Location/Qualifiers
source                        1..9
                              organism = synthetic construct
                              mol_type = protein
                              note = Seed: VVGADGVGK (KRAS G12D)
SEQUENCE: 1492
VTGADGVGH                                                              9

SEQ ID NO: 1493               moltype = AA   length = 9
FEATURE                       Location/Qualifiers
source                        1..9
                              organism = synthetic construct
                              mol_type = protein
                              note = Seed: VVGADGVGK (KRAS G12D)
SEQUENCE: 1493
VQGADGVGF                                                              9

SEQ ID NO: 1494               moltype = AA   length = 9
FEATURE                       Location/Qualifiers
source                        1..9
                              organism = synthetic construct
                              mol_type = protein
                              note = Seed: GADGVGKSA (KRAS G12D)
SEQUENCE: 1494
GYDGVGKST                                                              9

SEQ ID NO: 1495               moltype = AA   length = 9
FEATURE                       Location/Qualifiers
source                        1..9
                              organism = synthetic construct
                              mol_type = protein
                              note = Seed: VVGACGVGK (KRAS G12C)
SEQUENCE: 1495
VIGACGVGL                                                              9

SEQ ID NO: 1496               moltype = AA   length = 9
FEATURE                       Location/Qualifiers
```

```
source                  1..9
                        organism = synthetic construct
                        mol_type = protein
                        note = Seed: VVGAVGVGK (KRAS G12V)
SEQUENCE: 1496
VLGAVGVGM                                                                        9

SEQ ID NO: 1497         moltype = AA  length = 9
FEATURE                 Location/Qualifiers
source                  1..9
                        organism = synthetic construct
                        mol_type = protein
                        note = Seed: LVVVGACGV (KRAS G12C)
SEQUENCE: 1497
LSVVGACGL                                                                        9

SEQ ID NO: 1498         moltype = AA  length = 9
FEATURE                 Location/Qualifiers
source                  1..9
                        organism = synthetic construct
                        mol_type = protein
                        note = Seed: VVGAGDVGK (KRAS G13D)
SEQUENCE: 1498
VNGAGDVGY                                                                        9

SEQ ID NO: 1499         moltype = AA  length = 9
FEATURE                 Location/Qualifiers
source                  1..9
                        organism = synthetic construct
                        mol_type = protein
                        note = Seed: VVGADGVGK (KRAS G12D)
SEQUENCE: 1499
VMGADGVGF                                                                        9

SEQ ID NO: 1500         moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 1500
GWGDVGKSR                                                                        9

SEQ ID NO: 1501         moltype = AA  length = 9
FEATURE                 Location/Qualifiers
source                  1..9
                        organism = synthetic construct
                        mol_type = protein
                        note = Seed: AGDVGKSAL (KRAS G13D)
SEQUENCE: 1501
AWDVGKSAK                                                                        9

SEQ ID NO: 1502         moltype = AA  length = 9
FEATURE                 Location/Qualifiers
source                  1..9
                        organism = synthetic construct
                        mol_type = protein
                        note = Seed: GAGDVGKSA (KRAS G13D)
SEQUENCE: 1502
GNGDVGKSL                                                                        9

SEQ ID NO: 1503         moltype = AA  length = 9
FEATURE                 Location/Qualifiers
source                  1..9
                        organism = synthetic construct
                        mol_type = protein
                        note = Seed: VVGAVGVGK (KRAS G12V)
SEQUENCE: 1503
VSGAVGVGW                                                                        9

SEQ ID NO: 1504         moltype = AA  length = 9
FEATURE                 Location/Qualifiers
source                  1..9
                        organism = synthetic construct
                        mol_type = protein
                        note = Seed: GARGVGKSA (KRAS G12R)
SEQUENCE: 1504
GQRGVGKSV                                                                        9
```

-continued

```
SEQ ID NO: 1505          moltype = AA   length = 9
FEATURE                  Location/Qualifiers
source                   1..9
                         organism = synthetic construct
                         mol_type = protein
                         note = Seed: VVGARGVGK (KRAS G12R)
SEQUENCE: 1505
VFGARGVGL                                                                 9

SEQ ID NO: 1506          moltype = AA   length = 9
FEATURE                  Location/Qualifiers
source                   1..9
                         organism = synthetic construct
                         mol_type = protein
                         note = Seed: VVGACGVGK (KRAS G12C)
SEQUENCE: 1506
VGGACGVGM                                                                 9

SEQ ID NO: 1507          moltype = AA   length = 9
FEATURE                  Location/Qualifiers
source                   1..9
                         organism = synthetic construct
                         mol_type = protein
                         note = Seed: DVGKSALTI (KRAS G13D)
SEQUENCE: 1507
DLGKSALTL                                                                 9

SEQ ID NO: 1508          moltype = AA   length = 9
FEATURE                  Location/Qualifiers
source                   1..9
                         organism = synthetic construct
                         mol_type = protein
                         note = Seed: GARGVGKSA (KRAS G12R)
SEQUENCE: 1508
GVRGVGKSC                                                                 9

SEQ ID NO: 1509          moltype = AA   length = 9
FEATURE                  Location/Qualifiers
source                   1..9
                         organism = synthetic construct
                         mol_type = protein
                         note = Seed: LVVVGACGV (KRAS G12C)
SEQUENCE: 1509
LQVVGACGM                                                                 9

SEQ ID NO: 1510          moltype = AA   length = 9
FEATURE                  Location/Qualifiers
source                   1..9
                         organism = synthetic construct
                         mol_type = protein
                         note = Seed: VVGARGVGK (KRAS G12R)
SEQUENCE: 1510
VYGARGVGY                                                                 9

SEQ ID NO: 1511          moltype = AA   length = 9
FEATURE                  Location/Qualifiers
source                   1..9
                         organism = synthetic construct
                         mol_type = protein
                         note = Seed: VVGADGVGK (KRAS G12D)
SEQUENCE: 1511
VYGADGVGY                                                                 9

SEQ ID NO: 1512          moltype = AA   length = 9
FEATURE                  Location/Qualifiers
source                   1..9
                         organism = synthetic construct
                         mol_type = protein
                         note = Seed: GACGVGKSA (KRAS G12C)
SEQUENCE: 1512
GGCGVGKSV                                                                 9

SEQ ID NO: 1513          moltype = AA   length = 9
FEATURE                  Location/Qualifiers
source                   1..9
                         organism = synthetic construct
                         mol_type = protein
                         note = Seed: VVGARGVGK (KRAS G12R)
SEQUENCE: 1513
```

```
VEGARGVGR                                                                        9

SEQ ID NO: 1514        moltype = AA  length = 9
FEATURE                Location/Qualifiers
source                 1..9
                       organism = synthetic construct
                       mol_type = protein
                       note = Seed: VVGACGVGK (KRAS G12C)
SEQUENCE: 1514
VCGACGVGR                                                                        9

SEQ ID NO: 1515        moltype = AA  length = 9
FEATURE                Location/Qualifiers
source                 1..9
                       organism = synthetic construct
                       mol_type = protein
                       note = Seed: GARGVGKSA (KRAS G12R)
SEQUENCE: 1515
GGRGVGKSI                                                                        9

SEQ ID NO: 1516        moltype = AA  length = 9
FEATURE                Location/Qualifiers
source                 1..9
                       organism = synthetic construct
                       mol_type = protein
                       note = Seed: GACGVGKSA (KRAS G12C)
SEQUENCE: 1516
GYCGVGKSY                                                                        9

SEQ ID NO: 1517        moltype = AA  length = 9
FEATURE                Location/Qualifiers
source                 1..9
                       organism = synthetic construct
                       mol_type = protein
                       note = Seed: AGDVGKSAL (KRAS G13D)
SEQUENCE: 1517
APDVGKSAK                                                                        9

SEQ ID NO: 1518        moltype = AA  length = 9
FEATURE                Location/Qualifiers
source                 1..9
                       organism = synthetic construct
                       mol_type = protein
                       note = Seed: DVGKSALTI (KRAS G13D)
SEQUENCE: 1518
DEGKSALTL                                                                        9

SEQ ID NO: 1519        moltype = AA  length = 9
FEATURE                Location/Qualifiers
source                 1..9
                       organism = synthetic construct
                       mol_type = protein
                       note = Seed: GARGVGKSA (KRAS G12R)
SEQUENCE: 1519
GERGVGKSL                                                                        9

SEQ ID NO: 1520        moltype = AA  length = 9
FEATURE                Location/Qualifiers
source                 1..9
                       organism = synthetic construct
                       mol_type = protein
                       note = Seed: GADGVGKSA (KRAS G12D)
SEQUENCE: 1520
GCDGVGKSW                                                                        9

SEQ ID NO: 1521        moltype = AA  length = 9
FEATURE                Location/Qualifiers
source                 1..9
                       organism = synthetic construct
                       mol_type = protein
                       note = Seed: GAGDVGKSA (KRAS G13D)
SEQUENCE: 1521
GWGDVGKSY                                                                        9

SEQ ID NO: 1522        moltype = AA  length = 9
FEATURE                Location/Qualifiers
source                 1..9
                       organism = synthetic construct
                       mol_type = protein
```

```
                        note = Seed: AGDVGKSAL (KRAS G13D)
SEQUENCE: 1522
ACDVGKSAK                                                                    9

SEQ ID NO: 1523         moltype = AA   length = 321
FEATURE                 Location/Qualifiers
source                  1..321
                        organism = synthetic construct
                        mol_type = protein
SEQUENCE: 1523
MRVTAPRTLI LLLSGALALT ETWAGSGGSG GGGSGGGADG VGKSMGGSGG GGSGGLMVVG       60
ADGVGGSGGG GSGGGAVGVG KSLGGSGGGG SGGLMVVGAV GVGGSGGGGS GGVTGARGVG      120
KGGSGGGGSG GEYKFVVLGT VGHGKSGGSG GGGSGGEYKI VVAGNVGIGK SGGSGGGGSG      180
GEYKFVVFGS DGAGKSGGSG GGGSGGMTEY KFVVSGADGI GKSALTGGSG GGGSGGMTEY      240
KFVVIGNRGV GKSALTGGSL GGGGSGIVGI VAGLAVLAVV VIGAVVATVM CRRKSSGGKG      300
GSYSQAASSD SAQGSDVSLT A                                                321
```